(12) United States Patent
Asefa et al.

(10) Patent No.: US 9,174,203 B2
(45) Date of Patent: Nov. 3, 2015

(54) SELECTIVE AND EFFICIENT BIFUNCTIONAL AND TRIFUNCTIONAL NANOPOROUS CATALYSTS AND METHODS OF SYNTHESIS THEREOF

(76) Inventors: Tewodros Asefa, Somerset, NJ (US); Krishna K. Sharma, Cambridge, MA (US)

( * ) Notice: Subject to any disclaimer, the term of this patent is extended or adjusted under 35 U.S.C. 154(b) by 76 days.

(21) Appl. No.: 12/857,400

(22) Filed: Aug. 16, 2010

(65) Prior Publication Data

US 2011/0196164 A1    Aug. 11, 2011

Related U.S. Application Data

(63) Continuation of application No. 12/188,224, filed on Aug. 8, 2008, now abandoned.

(60) Provisional application No. 60/954,619, filed on Aug. 8, 2007.

(51) Int. Cl.
| | |
|---|---|
| *C07F 7/18* | (2006.01) |
| *B01D 53/02* | (2006.01) |
| *B01D 53/40* | (2006.01) |
| *B01J 20/32* | (2006.01) |
| *B32B 3/26* | (2006.01) |
| *B32B 5/14* | (2006.01) |
| *B01J 29/03* | (2006.01) |
| *B01J 31/02* | (2006.01) |
| *C07C 205/14* | (2006.01) |

(52) U.S. Cl.
CPC .......... *B01J 29/0308* (2013.01); *B01J 31/0254* (2013.01); *C07C 205/14* (2013.01)

(58) Field of Classification Search
None
See application file for complete search history.

(56) References Cited

U.S. PATENT DOCUMENTS

2008/0193734 A1    8/2008 Whitnall et al.
2008/0276804 A1*  11/2008 Sayari et al. .................. 95/285

FOREIGN PATENT DOCUMENTS

WO    WO 2006/037888    *  4/2006 ............ C08F 220/28

OTHER PUBLICATIONS

Singh et al. Journal of catalysis, 244, 52-64, 2006.*
Cauvel et al. in J. Org. Chem. 1997, 62, 749-751.
Rao et al. in Angew. Chem. Int. Ed. 1997, 36, 2661-2663.
McKittrick et al. in J. Am. Chem. Soc. 2004, 126, 3052-3053.
Hicks et al. in Chem. Mater. 2006, 18, 5022-5032.
Bass et al. in J. Am. Chem. Soc. 2006, 128, 3737-3747.
Zeidan et al. in Angew. Chem. Int. ed. 2006, 45, 6332-6335.
Lim in J. Am. Chem. Soc. 1997, 119, 4090-4091.
Zapilko in Chem. Eur. J. 2007, 13, 3169-3176.
Huh et al. in J. Am. Chem. Soc. 2004, 126,1010-1011.
Choudary et al. in J. Molecular Catal. A. 1999, 42, 361-365.
Huh et al. in Angew. Chem. Int. Ed. 2005, 44, 1826-1830.
Huh et al. in Chem. Mater. 2003, 15, 4247-4256.
Demicheli et al. in Tetrahedron Lett. 2001, 42, 2401-2403.
Office Action of Feb. 16, 2010 in U.S. Appl. No. 12/188,224.

(Continued)

*Primary Examiner* — Yun Qian
(74) *Attorney, Agent, or Firm* — John M. Hammond; Patent Innovations LLC

(57) ABSTRACT

Selective and efficient multifunctional nanoporous catalysts containing spatially distributed organoamine and silanol groups, and methods of preparation thereof. The catalysts have been observed to be very highly efficient in catalysis of the Henry reaction.

7 Claims, 106 Drawing Sheets

(56) References Cited

OTHER PUBLICATIONS

Yokoi et al., "Amino-functionalized mesoporous silica as base catalyst and adsorbent," Applied Catalysis A: General 421-422 (2012) 14-37. File name 20120506 12-857400_IDS_NPL_cite1.

Gu et al., "A new approach to synthesis of periodic mesoporous organosilicas: taking advantage of self-assembly and reactivity of organic precursors," J. Mater Chem., 2011, 21, 6389. File name 20120506 12-857400_IDS_NPL_cite2.

Sayari et al., "Applications of Pore-Expanded Mesoporous Silicas. 3. Triamine Silane Grafting for Enhanced CO2 Adsorption," Ind. Eng. Chem. Res. 2006, 45, 3248-3255, published Mar. 22, 2006, EFS file name 20130908_12-857400_IDS_NPL_cite1.pdf.

Shi et al, "On the Synergetic Catalytic Effect in Heterogeneous Nanocomposite Catalysts," (Chem. Rev. 2013, 113, 2139-2181), on pp. 2159-2160, EFS file name 20130908_12-857400_IDS_NPL_cite2.pdf.

Shang et al., A comparative study of aminopropyl-functionalized SBA-15 prepared by grafting in different solvents, Reac. Kinet. Mech. Cat. (2011) 103:181-190, EFS file name 20130908_12-857400_IDS_NPL_cite3.pdf.

Yu et al., "Synergic catalytic effects in confined spaces," Chem. Commun., 2012, 48, 4933-4940, EFS file name 20130908_12-857400_IDS_NPL_cite4.pdf.

Yoshitake et al., "Grafting of paired 3-aminopropyltrialkoxy silanes onto mesoporous silica and adsorptions of isomers of benzenedialdehydes," Phys.Chem. Chem. Phys., 2013,15, 3946-3954, EFS file name 20130908_12-857400_IDS_NPL_cite5.pdf.

Diaz et al., "Catalysis using multifunctional organosiliceous hybrid materials," Chem. Soc. Rev., 2013, 4083-4097, EFS file name 20130908_12-857400_IDS_NPL_cite6.pdf.

Brunelli et al., "Cooperative Catalysis with Acid-Base Bifunctional Mesoporous Silica: Impact of Grafting and Co-condensation Synthesis Methods on Material Structure and Catalytic Properties," Chem. Mater. 2012, 24, 2433-2442, EFS file name 20130908_12-857400_IDS_NPL_cite7.pdf.

Lang et al., "Preparation and synergetic catalytic effects of amino-functionalized MCM-41 Catalysts," Science China, 2012, 55:6, 1167-1174, EFS file name 20130908_12-857400_IDS_NPL_cite8.pdf.

* cited by examiner

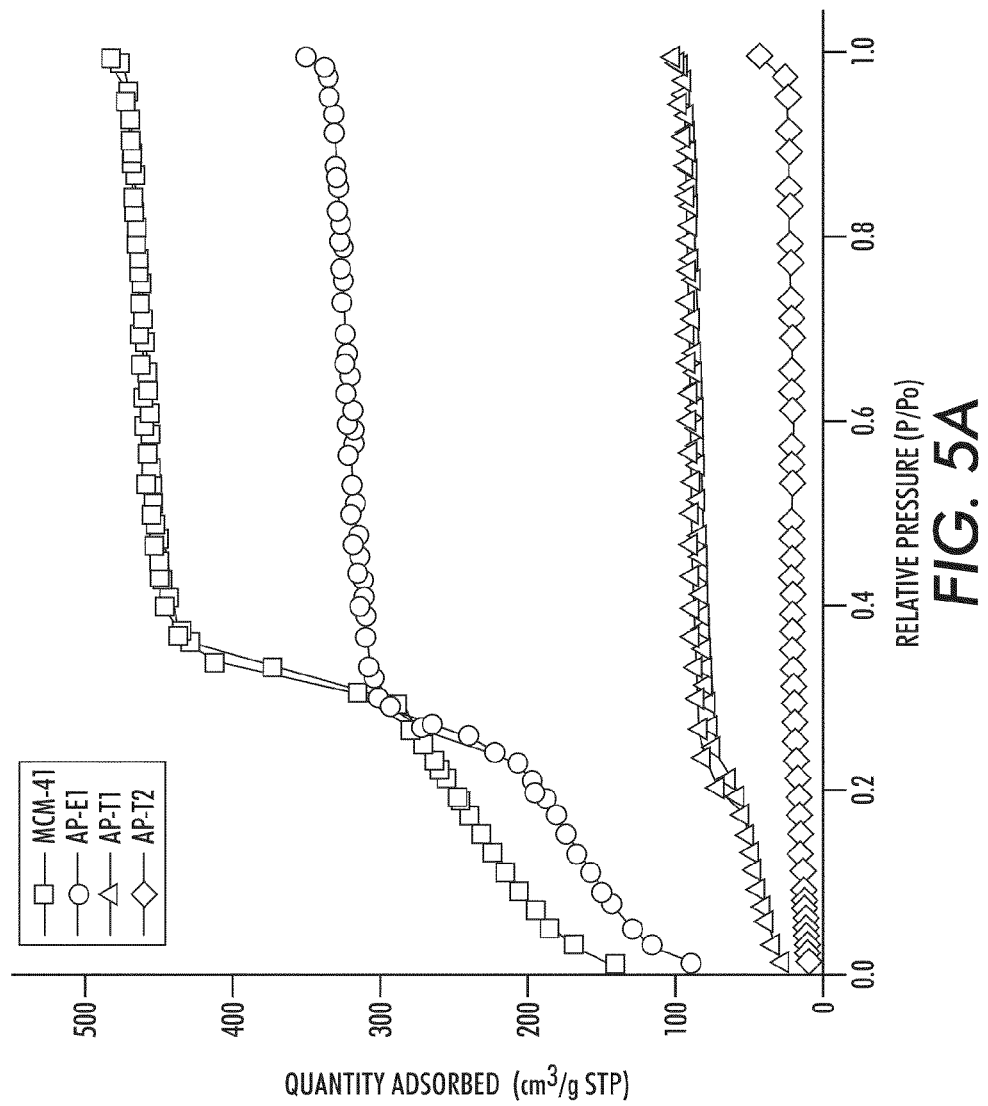

SELECTIVE AND EFFICIENT BIFUNCTIONAL AND TRIFUNCTIONAL NANOPOROUS CATALYSTS AND METHODS OF SYNTHESIS THEREOF

CROSS-REFERENCE TO RELATED PATENT APPLICATIONS

This application is a continuation application of U.S. application Ser. No. 12/188,224, filed Aug. 8, 2008, now abandoned which claims priority from U.S. provisional patent application Ser. No. 60/954,619 filed Aug. 8, 2007, the disclosures of which are incorporated herein by reference in their entireties.

STATEMENT REGARDING FEDERALLY SPONSORED RESEARCH OR DEVELOPMENT

Inventions described herein were developed under National Science Foundation Agreement No. CHE-0645348. The United States Government has certain rights in these inventions.

This invention relates to postgrafting of spatially isolated catalytic groups on mesoporous materials to produce nanoporous catalysts, and more particularly to selective and efficient multifunctional nanoporous catalysts, and their methods of preparation.

BACKGROUND OF THE INVENTION

1. Field of the Invention

Selective and efficient multifunctional nanoporous catalysts and methods of preparation thereof.

2. Description of Related Art

Multi-step and efficient synergistic catalytic processes to various types of biomolecules by biological catalysts (enzymes) are very common in living organisms. Many notable examples of such enzymatic and antibody catalytic processes involve acid-base cooperative or efficient bifunctional catalysts. By mimicking these extraordinary abilities of nature, some conventional homogeneous bifunctional acid-base catalysts have been synthesized, such as those disclosed by Breslow et al. in *J. Am. Chem. Soc.* 1993, 115, 10988-10989. However, the efficiency and selectivity of these catalysts, which often depend on the relative separation distances between the acid and base catalytic sites, are often poor because the materials lack a continuous range of acidic and basic catalytic sites. Hence, a considerable amount of recent effort has been directed towards the synthesis of heterogeneous solid-state, acid-base catalysts having well-controlled, high concentrations of acidic and basic catalytic sites.

A family of mesoporous materials, which were first reported in 1992, has been widely and effectively used as hosts for a variety of catalytically active functional groups, including acidic and basic sites, to produce efficient heterogeneous catalysts. By postgrafting of the residual surface silanol groups of the mesoporous materials with organosilanes, high surface area and tunable nanopores containing solid-acid and solid-base mesoporous catalysts for reactions such as Knoevenagel condensation, catalytic oxidation, and Michael addition have been synthesized, as reported by Cauvel et al. in *J. Org. Chem.* 1997, 62, 749-751; and Rao et al. in *Angew. Chem. Int. Ed.* 1997, 36, 2661-2663. However, to the best of the applicants' knowledge, almost all postgrafting syntheses of catalysts reported to date are typically done by stirring mesoporous materials with excess organosilanes in non-polar solvents such as toluene or cyclohexane at reflux temperature, 112° C.

Postgrafting of organosilanes onto mesoporous materials in toluene in reflux indeed allows an effective inclusion of densely populated or high concentrations of covalently bound organic functional groups, including organoamines. However, this synthetic approach also has drawbacks as it grafts most of the surface silanol groups of the materials. The latter groups, which can act as weak acids, generally increase the efficiencies of a number of organoamine catalyzed reactions such as the Henry reaction and nitroaldol condensations. Furthermore, the presence of densely populated organic groups reduces the surface areas and pore volumes of the materials. Therefore, densely populated organoamine catalysts synthesized in toluene are typically accompanied by loss of catalytic efficiency. For instance, metallocene catalytic groups immobilized on densely populated postgrafted organoamine synthesized in toluene have lower catalytic efficiency for polymerization reactions than corresponding samples containing sparsely populated metallocene groups, as reported by McKittrick et al. in *J. Am. Chem. Soc.* 2004, 126, 3052-3053; and Hicks et al. in *Chem. Mater.* 2006, 18, 5022-5032. However, the synthesis of the latter materials involves a lengthy multi-step procedure consisting of preparation of bulky imine containing organosilanes and postgrafting the groups in toluene to form densely populated imine functionalized mesoporous materials. Upon subsequent hydrolysis of the bulky imine groups, spatially ordered organoamines and silanol groups are formed.

Recently, Katz et al. described the synthesis of organoamine functionalized silica gel catalysts containing silanol groups in *J. Am. Chem. Soc.* 2006, 128, 3737-3747. These bifunctional catalysts showed increased efficiency and selectivity for the Michael and Henry reactions compared to the corresponding materials without silanols. However, the surface area of silica gel is low, the number of the bifunctional groups in the material is limited, and the distribution of the two groups is difficult to control. Davis et al. have also reported the synthesis of sulphonic acid and organoamine bifunctionalized catalysts for nitroaldol reaction by self-assembly in *Angew. Chem. Int. Ed.* 2006, 45, 6332-6335. However, these materials have a low number of randomly distributed acid and base groups.

What is needed to address these problems is a catalyst material that can be synthesized by a simple, straightforward process, that has both acidic and basic functionality, and that has a high efficiency with respect to catalyzed reaction rate and yield.

Additionally, many pharmaceutical and industrial catalytic processes involve multiple, similar reactants and competitive reactions while a product from one of the reactants or reactions is only needed. The production of specific products by selectively catalyzing a specific reactant or reaction in a mixture of similarly reactive compounds or from competitive reactions is often necessary for the efficient production of various fine chemicals and industrial materials in high yields. Consequently, the development of selective catalysts and the efficient catalysis of one specific reactant have remained important research areas in catalysis and materials science; however, achieving these goals is often met with considerable challenges. For instance, by using the differences in the sizes and shapes of the reactants and their mass transport into the catalytic sites on solid zeolite porous supports, many selective catalysts have been synthesized. However, due to the narrow pore-sizes of zeolites, selective catalytic reactions of only smaller molecules are possible.

The recent advances in the synthesis of organic- and organometallic-functionalized mesoporous metal oxides and imprinted polymeric and imprinted metal oxide nanostructured materials have opened up synthetic strategies to novel selective catalysts. While the nanoporous structures in mesoporous materials enable size and shape selectivity as in zeolites, the higher pore diameters and the large surface areas in mesoporous materials further allow surface immobilization of large numbers of various organic groups to tune the surface properties and pore-diameters of the materials without severely clogging the pores as in zeolites. Functionalization of these materials with organic groups of specific hydrophobicity or hydrophilicity modifies the immediate dielectric environment of the catalytic site and enables reactant of matching polarity to access the catalytic sites and undergo preferential catalytic reactions. For instance, by co-condensation of two organosilanes, Lim and co-workers report in *J. Am. Chem. Soc.* 1997, 119, 4090-4091 the synthesis of bifunctional mesoporous organosilica materials that are selective to hydrophobic groups. These materials, however, achieved the required selectivity with a maximum of 50% yields in over 24 h and selectivity only for hydrophobic reactants. Co-condensation procedures in synthesis of mesoporous organosilica often results in poorly ordered mesostructures, which might be one of the reasons for the low yield of the Henry product by these materials. Very recently, Anwander and co-workers synthesized functionalized mesoporous silicas with two steps grafting in non-polar solvent, cyclohexane, to pore-size engineer cage like pores of SBA-15 materials for size-selective catalytic transformations, as disclosed in *Chem. Eur. J.* 2007, 13, 3169-3176. They used various sized long chain alkyl dimethylaminosilanes and organoaluminum compounds and they demonstrate aluminum-catalyzed Meerwein-Ponndorf-Verley reduction of differently sized aromatic aldehydes (benzaldehyde and 1-pyrenecarboxyaldehyde).

What is needed to address the problems where a single reaction pathway and product is desired from multiple pathways and products is a multifunctional catalyst that has tunable selectivity and that is simple and straightforward to synthesize.

SUMMARY OF THE INVENTION

The present invention meets certain previously stated needs by providing multifunctional catalysts containing spatially distributed acid and base groups grafted to a substrate. The substrate is preferably a mesoporous substrate with a high degree of porosity and a high surface area; however, other substrates such as silica microspheres or silica gels may also be used with similar outcomes of obtaining "spatially distributed" groups. The respective acid and base groups are preferably silanol groups and organoamine groups. The substrate is preferably a form of mesoporous silica. These catalysts have been observed to be very highly efficient in catalysis of the Henry reaction. Additionally, certain catalysts are provided which have tunable selectivity for hydrophilic or hydrophobic reactants. Additionally, certain catalysts are provided which have optimized cooperative acid-base bifunctionality.

In accordance with the present invention, there is further provided methods of synthesizing such catalysts. In one embodiment, the synthesis was achieved by carrying out a simple, one-step postgrafting of excess aminoorganosilanes under reflux onto mesoporous silica in a polar-protic solvent, ethanol, at a lower temperature, 78° C., than is typically used in prior art synthetic methods. In another embodiment, the synthesis was achieved by postgrafting lesser amounts of aminoorganosilanes in toluene in shorter reacting time than prior art synthetic methods, at 78° C.

In other embodiments, the synthesis of catalysts of high efficiency may be accomplished by postgrafting of organoamine groups on the mesoporous substrate at a density of between about 6 and about 15 percent of the available silicon sites. In another embodiment, the synthesis may be accomplished by performing the organoamine postgrafting reaction in a polar-protic solvent. The solvent may be a low molecular weight alcohol, such as methanol, ethanol, and preferably isopropanol. In another embodiment, the synthesis may be accomplished by performing the organoamine postgrafting reaction in a dipolar-aprotic solvent, mainly acetonitrile. In another embodiment, the synthesis be accomplished by performing the organoamine postgrafting reaction in acetone.

In other embodiments, synthesis methods for selective, efficient trifunctional nanoporous catalysts for hydrophilic or hydrophobic reactants in the Henry reaction are provided in accordance with the invention. In these syntheses, two or more organofunctional groups may be judiciously chosen and co-placed in spatial-isolation and in different relative concentrations on the channel walls of mesoporous materials, leaving large numbers of residual silanols. In one embodiment, this was achieved by grafting a mixture of organosilanes onto prior-made mesoporous silica in isopropanol in one-pot. In another embodiment, sequential grafting of a first organosilane in isopropanol is performed, followed by a second organosilane in isopropanol or toluene. This has been demonstrated for 3-aminopropyl groups and a secondary functional group, which included ureidopropyl, 3-mercaptopropyl, or methyl groups. While 3-aminopropyl groups introduced solid base catalytic sites, the latter groups and the residual silanol groups on the materials controllably modified the catalyst's surface to either hydrophilic or hydrophobic, depending upon the particular grafted second group. By virtue of grafting in isopropanol and the site-isolated multifunctional groups it produced, the resulting materials afforded high catalytic efficiency with nearly 100% conversion of various p-substituted benzaldehydes within 15-30 minutes in the Henry reaction and tunable, time-dependent selectivities to hydrophilic or hydrophobic reactants in mixtures of p-substituted benzaldehydes with ratios as high as 7:1. This is a significant achievement compared to examples of previously reported selective catalysts, which showed selectivity only for hydrophobic reactants and with the highest yield of 50% in 24 h and maximum selectivity of 2.6:1.0, as reported by Huh, et al. in *J. Am. Chem. Soc.* 2004, 126, 1010-1011, for example. The applicants' synthetic approach is simple, generic, versatile, and can be extended to other reactants and reactions by judiciously choosing and grafting multiple organic groups in site-isolation on nanoporous materials, as will be described subsequently in this specification.

In additional embodiments of the invention, optimized cooperative acid-base bifunctional mesoporous catalysts for the Henry reaction are provided. The applicants have discovered that the site-isolation and relative concentrations of the bifunctional groups can be controlled by simple, one-step, facile grafting of organoamines on mesoporous silica at various temperatures using ethanol and toluene as solvents; and that the separation distances between the functional groups can be controlled by using shorter and longer organoamines, i.e. grafting organoamines of specifically chosen lengths. In accordance with the invention, organomonoamine- and organodiamine-functionalized samples with various degrees of site-isolation, relative concentrations of the bifunctional groups, and separation distances are provided, as well as a preparation method therefor comprising a simple, one-step, facile grafting of organosilanes on mesoporous silica at various temperatures using ethanol and toluene solvents.

The advantages of these catalysts having spatially distributed organoamines and silanols was demonstrated in one embodiment by synthesizing 3-aminopropyl functionalized mesoporous materials. One catalyst of the present invention resulted in a four fold increased catalytic efficiency or turnover number for the Henry reaction, as compared to prior art mesoporous silica catalysts that have been prepared in toluene in reflux. This catalyst material afforded a 99.4% yield for one example of the Henry reaction within 15 minutes. To the best of the applicants' knowledge, this is the highest catalytic efficiency of any mesoporous catalyst reported for the Henry reaction.

One aspect of the invention is based on the discovery of several techniques for synthesizing catalysts comprised of spatially distributed acid and base functional groups on mesoporous silica. The techniques enable the provision of selective and highly efficient multifunctional nanoporous catalysts.

BRIEF DESCRIPTION OF THE DRAWINGS

The invention will be described by reference to the following drawings, in which like numerals refer to like elements, and in which:

FIG. 5A is a composite graph of the $N_2$ adsorption isotherms for the MCM-41, AP-E1, AP-T1, and AP-T2 materials;

FIGS. 32a-32n are a series of plots for corresponding to the respective FIGS. 32A-32N, showing the ratio of % yield versus time for one reactant over another reactant and the time at which the maximum ratio of the % yield occurred;

FIGS. 34a-34l are a series of plots for corresponding to the respective FIGS. 34A-34L, showing the ratio of % yield versus time for one reactant over another reactant and the time at which the maximum ratio of the % yield occurred;

FIGS. 35a-35e are a series of plots for corresponding to the respective FIGS. 35A-35E, showing the ratio of % yield versus time for one reactant over another reactant and the time at which the maximum ratio of the % yield occurred;

FIGS. 41C-4J are the individual isotherms and pore-size distribution data for the AAP-E1, AAP-T1, AP-EE1, AP-ET1, AP-EE2, AP-ET2, AP-E1A, and AP-E1B materials;

Figure 1:
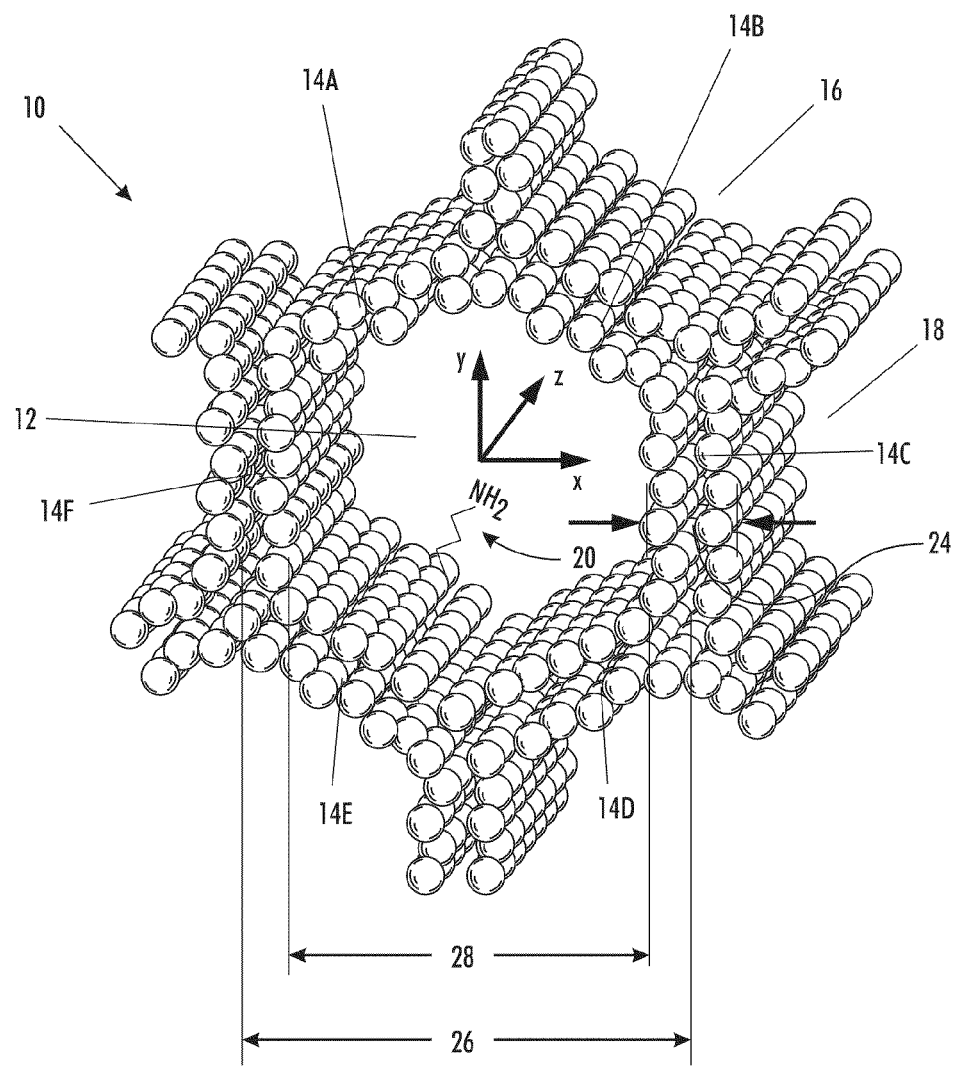
FIG. 1 is a three-dimensional schematic illustration of one exemplary mesoporous material to which the present invention is applicable.

The present invention will be described in connection with certain preferred embodiments. However, it will be understood that there is no intent to limit the invention to the embodiments described. On the contrary, the intent is to cover all alternatives, modifications, and equivalents as may be included within the spirit and scope of the invention as defined by the appended claims.

DESCRIPTION OF THE PREFERRED EMBODIMENTS

For a general understanding of the present invention, reference is made to the drawings. In the drawings, like reference numerals have been used throughout to designate identical elements. In describing the present invention, a variety of terms are used in the description.

As used herein, the term "catalyst" is meant to indicate a substance that increases the rate of a chemical reaction while not being consumed in the reaction.

As used herein, the term "selective," when used in reference to a catalyst, is meant to indicate the capability of the catalyst to cause the production of specific products by selectively catalyzing a specific reactant or reaction in a mixture of similarly reactive compounds or from competitive reactions. This capability may be the result of the geometry of the catalyst substrate in combination with the species of chemical groups grafted to the substrate and/or their density on the substrate and/or their locations and/or their relative proportions on the substrate.

As used herein, the term "mesoporous material" is meant to indicate a material containing pores between about 2 and about 50 nanometers across the pore (i.e. in diameter if the pores are substantially circular in cross-section).

As used herein, the term "postgrafting" when used in reference to a functional chemical group and a mesoporous material is meant to indicate the bonding of that group to the surface of the mesoporous material.

As used herein, the term "turnover number" when used in reference to a catalyst of a chemical reaction is meant to indicate the number of moles of reactant that a mole of catalyst can convert to product before becoming inactivated.

As used herein, the term "ambient conditions" when used in reference to a chemical synthesis is meant to indicate the typical conditions in a laboratory, i.e. a temperature of about 20 to 30 degrees Centigrade (° C.) and atmospheric pressure.

As used herein, the term "spatially distributed," when used in reference to functional groups attached to the mesopores of a catalyst material, is meant to indicate a density of distribution of the functional groups that is less than the maximum possible attainable density of distribution. The terms "spatially distributed," "spatially isolated," and "site-isolated" are used interchangeably herein.

In accordance with the present invention, multifunctional catalysts are provided containing spatially distributed acid and base groups grafted to a substrate. Various substrates may be used upon which the acid and base groups are provided, including but not limited to, e.g., silica microspheres or silica gels. A preferred class of substrates having a high degree of porosity and a high surface area are mesoporous substrates. FIG. 1 is a three-dimensional schematic illustration of one exemplary mesoporous substrate material to which the present invention is applicable. Mesoporous material 10 is known in the art as Mobile Crystalline Material 41, or MCM-41, which is a silicate material. MCM-41 is ordered to some degree, and is comprised of arrays of non intersecting hexagonal channels or pores, such as pore 12. In FIG. 1, the longitudinal axis of pore 12 is disposed along the z axis. The six walls 14A-14F of pore 12 provide the generally hexagonal shape of pore 12, and each of walls 14A-14F may form part of the wall of an adjacent hexagonal pore. In the illustration of FIG. 1, the hexagonal pores repeat in the X-Y plane with longitudinal axes in the Z direction. Portions of these adjacent pores, for example, pores 16 and 18 are also shown in FIG. 1. To an approximation, pore 12 has a wall thickness 24 equal to the unit cell diameter 26 minus the pore diameter 28.

The walls of the channels are amorphous $SiO_2$. For the sake of simplicity of illustration, the hydrogen atoms which form the silanol groups on the pore walls are not shown in FIG. 1. In the methods of the present invention, certain functional groups, such as the aminopropyl group 20 are postgrafted to the walls 14A-14E in controlled and spatially isolated arrangements to make the catalysts of the present invention, as will be explained herein. It is to be understood that although the pore 12 and adjacent pores of material 10 appear to be of a relatively shallow depth, these pores may extend a considerable distance further along the z axis. Additionally such pores are not necessarily disposed straight along the z axis and may deviate therefrom.

Various embodiment of the invention will be described herein. In general, selective and efficient multifunctional nanoporous catalysts comprising acid and/or base functional groups that are postgrafted within the pores of a mesoporous substrate with controlled spatial distributions are provided in accordance with the invention. Additionally, synthetic methods for making such catalysts are provided.

Spatially Distributed Organoamine Groups on Mesoporous Silica: General Description and Examples In certain embodiments of the invention, catalysts are provided which are comprised of spatially distributed organoamine groups on mesoporous silica. Synthesis of these catalysts was achieved by reacting excess aminoorganosilanes in ethanol; or in an alternative embodiment by postgrafting lower amounts of aminoorganosilanes in toluene for a short reaction time. Despite the lower number of catalytic sites, the resulting reaction products that have increased cooperative properties and higher surface areas gave the most enhanced catalytic properties in examples of the Henry reaction. The applicants have confirmed that such one-pot synthetic methods allow the preparation of spatially isolated bifunctional catalysts, which, to the best of the applicants' knowledge, until now were only achieved through lengthy multi-step, costly methods. In contrast, this scheme of the synthetic methods of the present invention is a very simple, one step versatile procedure as compared to those previously reported procedures of which the applicants are aware.

The following description provides examples of the applicants' catalysts that are comprised of spatially distributed organoamine groups on mesoporous silica, and their methods of preparation. It is to be understood that the instant catalysts described herein are exemplary, and that many other variants are to be construed as being within the scope of the invention. For example, other forms of mesoporous materials may be used instead of or in addition to the MCM-41 material, including but not limited to SBA-15.

In one embodiment, bifunctional, spatially isolated organoamine and silanol groups were postgrafted to the mesoporous silicate MCM-41. The MCM-41 was synthesized as follows: 2.0 g (5.5 mmol) cetyltrimethylammonium bromide (CTAB) was mixed with 480 g (26.7 mmol) of millipore water and 7 mL, 2.0 M NaOH solution. The solution was stirred for 30 minutes at 80° C. before the addition of 11.3 mL (50.6 mmol) tetraethoxysilane into it. The mixture was stirred moderately for 2 hours at 80° C. The solution was filtered and the precipitate was washed with 40 mL millipore water four times, followed by ethanol and dried under air for 4 hours. The CTAB surfactant was extracted by stirring 1 g of the sample in a solution of 0.5 mL of HCl and 150 mL of ethanol at 50° C. for 5 h. The resulting mesoporous material was filtered and washed again with millipore water and 40 mL ethanol. The extracted MCM-41 was then dried under vacuum for 3-4 hours and kept in an oven at 80° C. to remove physisorbed water prior before postgrafting. As used herein, the term "millipore water" is meant to indicate water that has been purified to a resistivity of at least 18 megaohms.

Figure 2:
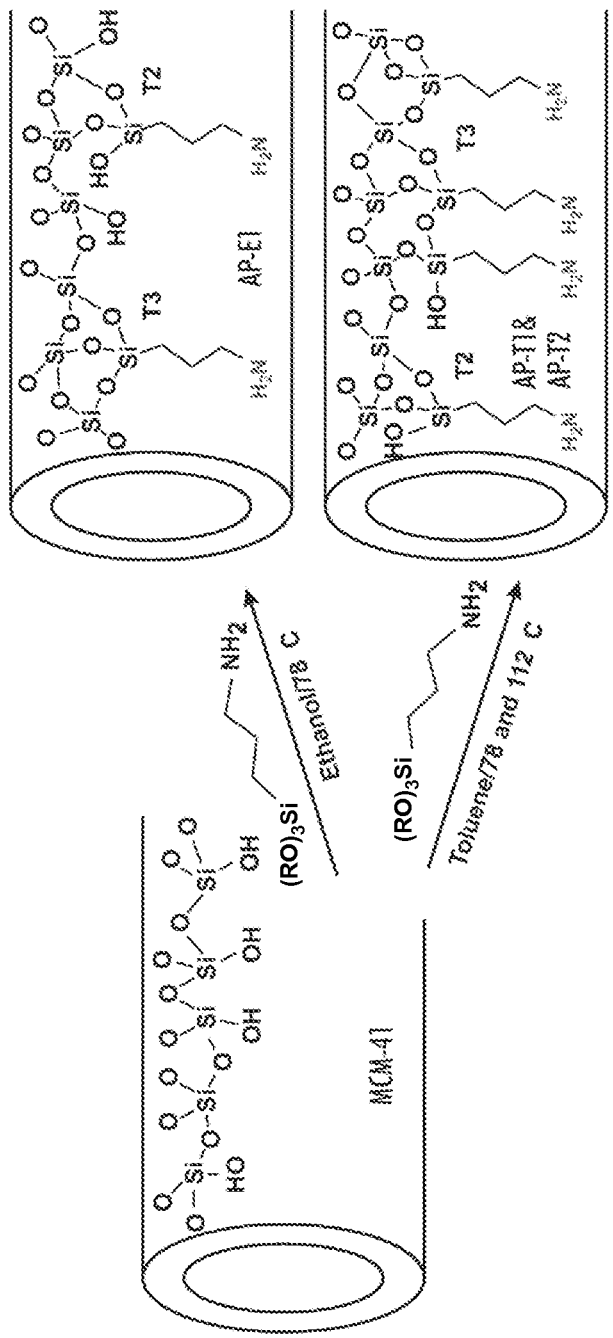
FIG. 2 is an illustration that summarizes the reaction schemes for converting the mesoporous material of FIG. 1 into certain catalysts of the invention.

The chosen organoamine group was the 3-aminopropyl group. The postgrafting was performed by stirring an excess amount of 3-aminopropytrimethoxysilane with MCM-41 in ethanol under reflux at 78° C. for 6 hours. The solution was filtered and the precipitate was washed with dichloromethane (200 mL) and ethanol (500 mL) and then dried in air to produce a first catalyst named and further referred to herein as "AP-E1." To obtain a first control sample, an excess amount of the same organosilane was postgrafted onto MCM-41 in toluene at 78° C. The solution was filtered and the precipitate washed as described above. The first control sample is named and further referred to herein as "AP-T1." To obtain a second control sample, an excess amount of the same organosilane was postgrafted onto MCM-41 in refluxing toluene at 112° C. The solution was filtered and the precipitate washed as described above. The second control sample is named and further referred to herein as "AP-T2." FIG. 2 is an illustration that summarizes the reaction schemes for converting the mesoporous material of FIG. 1 into AP-E1, AP-T1, and AP-T2. Additionally, Table 1 lists structural information for these materials.

TABLE 1

Structural information of MCM-41, AP-E1, AP-T1 and AP-T2.

| Sample | Surface Area (m$^2$/g) | Pore Volume (cm$^3$/g) | Unit Cell, $a_0$, (Å)$^a$ | Pore Diameter (Å) | Wall Thickness (Å)$^b$ |
|---|---|---|---|---|---|
| MCM-41 | 1030 | 0.88 | 44.3 | 34.1 | 10.2 |
| AP-E1 | 906 | 0.71 | 44.4 | 31.4 | 13.0 |
| AP-T1 | 260 | 0.20 | 45.6 | 31.5 | 14.1 |
| AP-T2 | 60 | 0.07 | 44.4 | 30.6 | 13.8 |

$^a a_o = 2d_{100}/3^{1/2}$ (Å) for 2-D hexagonally ordered materials
$^b$Wall thickness = Unit Cell − Pore Diameter.

Alternative postgrafting synthesis methods to produce aminopropyl functionalized mesoporous materials with spatially isolated aminopropyl and silanol groups were also performed. Samples having catalytic properties similar to those of AP-E1 were prepared in toluene by carefully controlling the synthesis conditions. Several samples were synthesized by decreasing the concentrations of aminorganosilanes and/or decreasing the postgrafting reaction times. Table 2 lists these samples C-I, along with additional samples of AP-E1 (A) and AP-T1 (B).

Figure 10A:
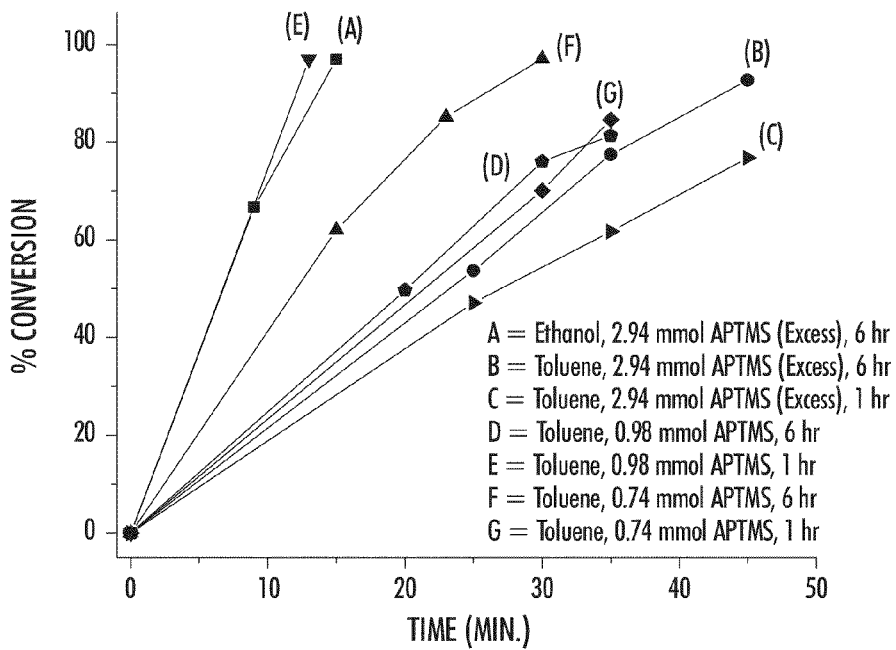
FIGS. 10A and 10B are graphs of the efficacy of catalyst samples that were synthesized by decreasing the concentrations of aminorganosilanes and/or decreasing the postgrafting reaction times of the synthesis.
Figure 10B:
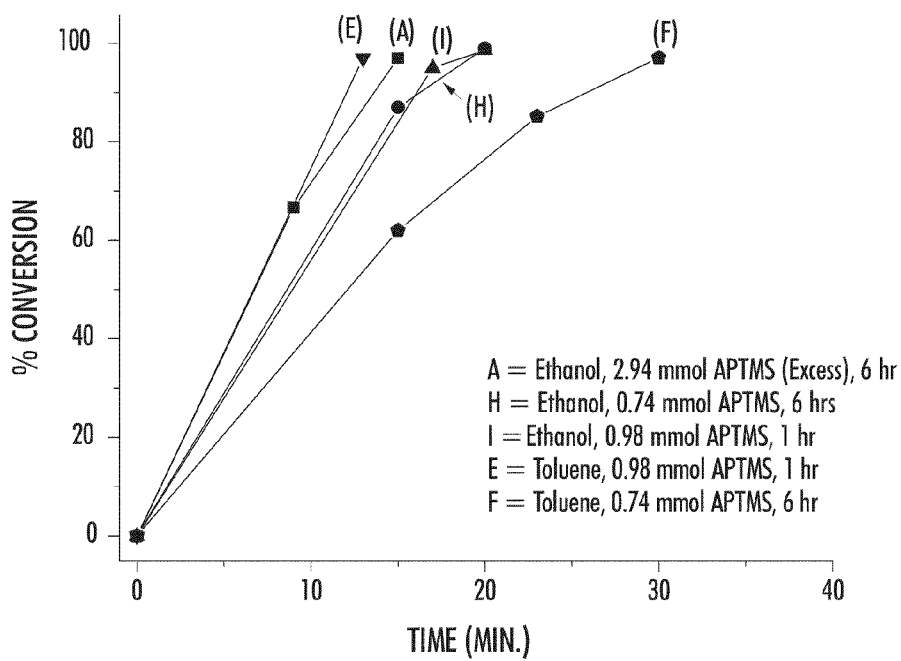

By way of example, sample E of Table 2 was synthesized by stirring 500 mg, pre-dried MCM-41 in 0.27 g (1.21 mmol) of 3-aminopropyltrimethoxysilane (APTMS) in 250 mL toluene at about 78° C. for 1 hr. The solution was filtered and the precipitate was washed with dichloromethane (200 mL) and ethanol (500 mL) and then dried in air. Similarly, other samples including the original parent materials investigated (sample A, AP-E1, and sample B, AP-T1) were also synthesized again as control samples. All of these samples were prepared at 78° C. Their efficacy in the catalysis of a Henry reaction was also investigated. The results are compiled in Table 2 and FIGS. 10A and 10B and will be described subsequently herein.

The materials of Table 1 and Table 2 were characterized by a variety of analytical instruments. A brief description of the individual analytical techniques will be provided here, followed by a summary of the data and results of each technique.

Figure 3A:
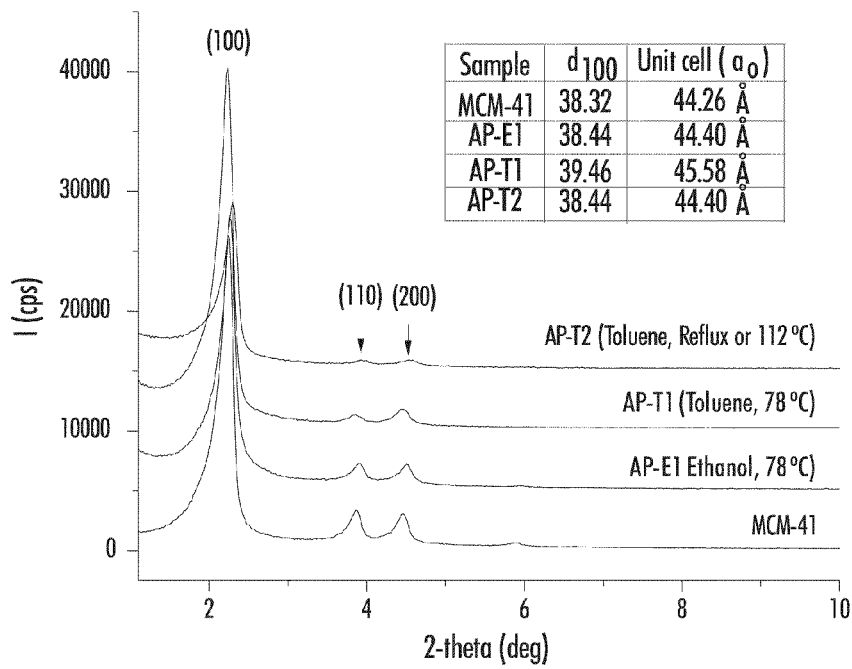
FIG. 3A is a graph of powder X-ray diffraction patterns of a mesoporous silicate material MCM-41, one exemplary catalyst AP-E1 of the invention, and two control catalyst samples AP-T1, and AP-T2.
Figure 3B:
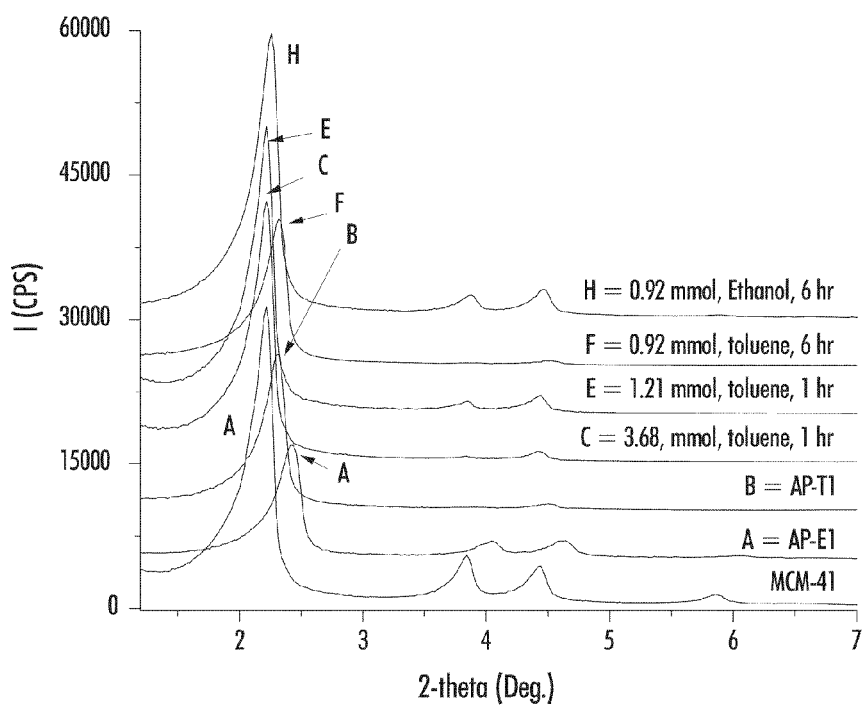
FIG. 3B is a graph of powder X-ray diffraction patterns of a mesoporous silicate material, the catalyst AP-E1 and the control samples of FIG. 2A, and additional catalysts synthesized by postgrafting a lesser amount of 3-aminopropyltrimethoxysilane (APTMS) in toluene and/or in shorter postgrafting reaction times.

Powder X-ray diffraction (XRD) measurements were made using a Scintag powder diffractometer. FIG. 3A depicts the powder X-ray diffraction patterns of MCM-41 and the organoamine functionalized catalyst samples AP-E1, AP-T1, and AP-T2. FIG. 3B is a graph of powder X-ray diffraction patterns of the materials of FIG. 3A, as well as additional catalysts of the invention.

Figure 4A:
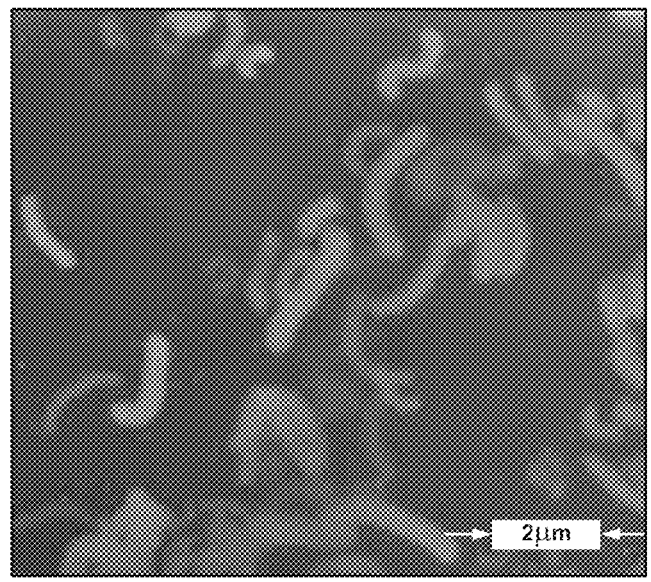
FIG. 4A and FIG. 4B are transmission electron microscopy images of the catalyst AP-E1.
Figure 4B:
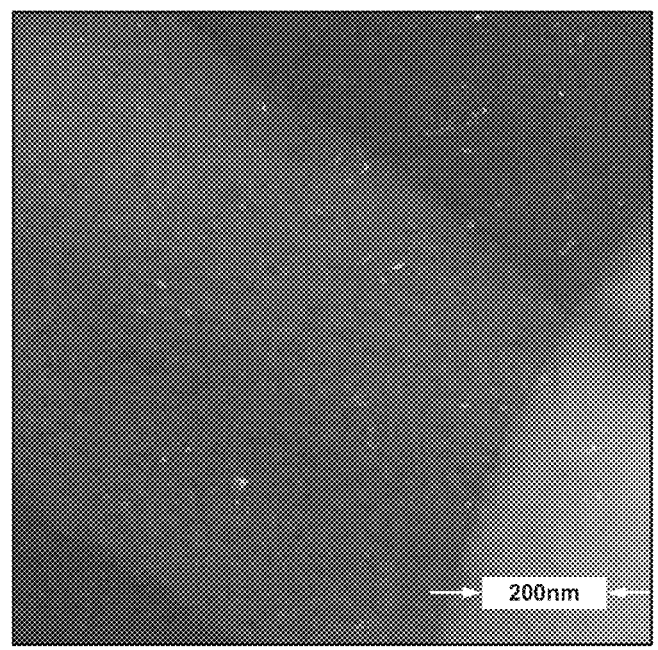

Transmission electron microscopy (TEM) was performed using a JEOL 2010 instrument. FIG. 4A and FIG. 4B are transmission electron microscopy images of catalyst AP-E1 at two different scales of magnification.

Figure 5B:
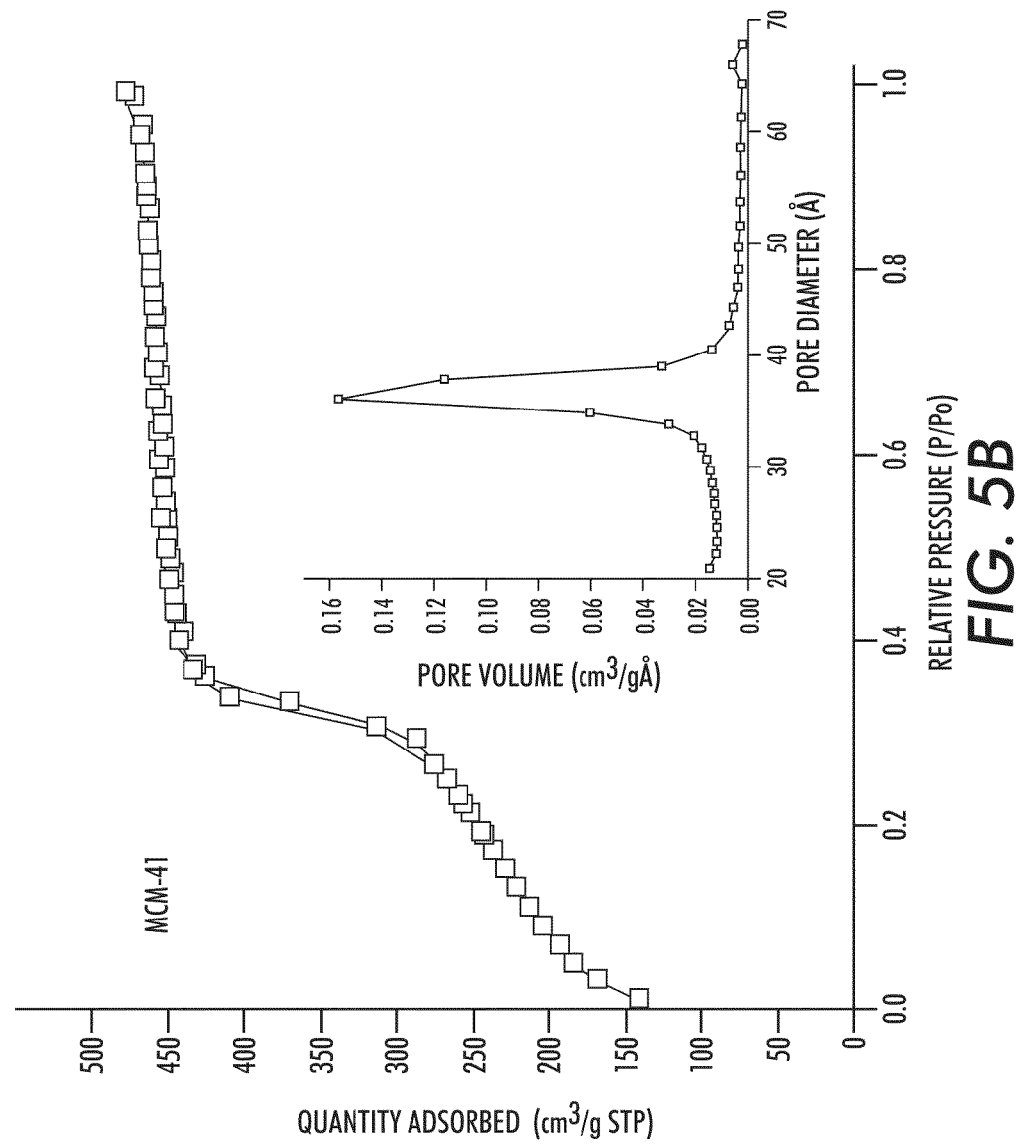
FIGS. 5B-5E are the individual isotherms and pore-size distribution data for the MCM-41, AP-E1, AP-T1, and AP-T2 materials.
Figure 5C:
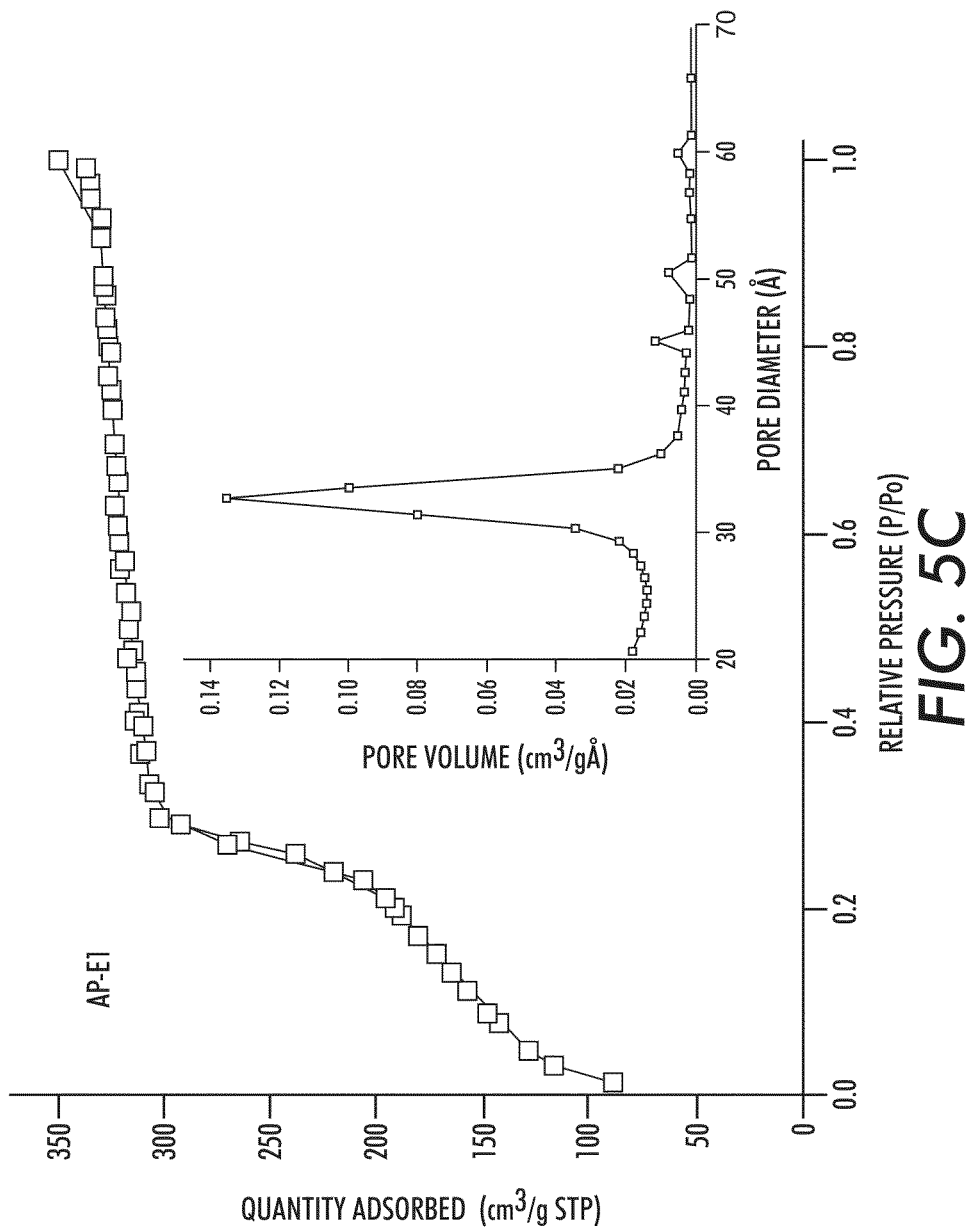
Figure 5D:
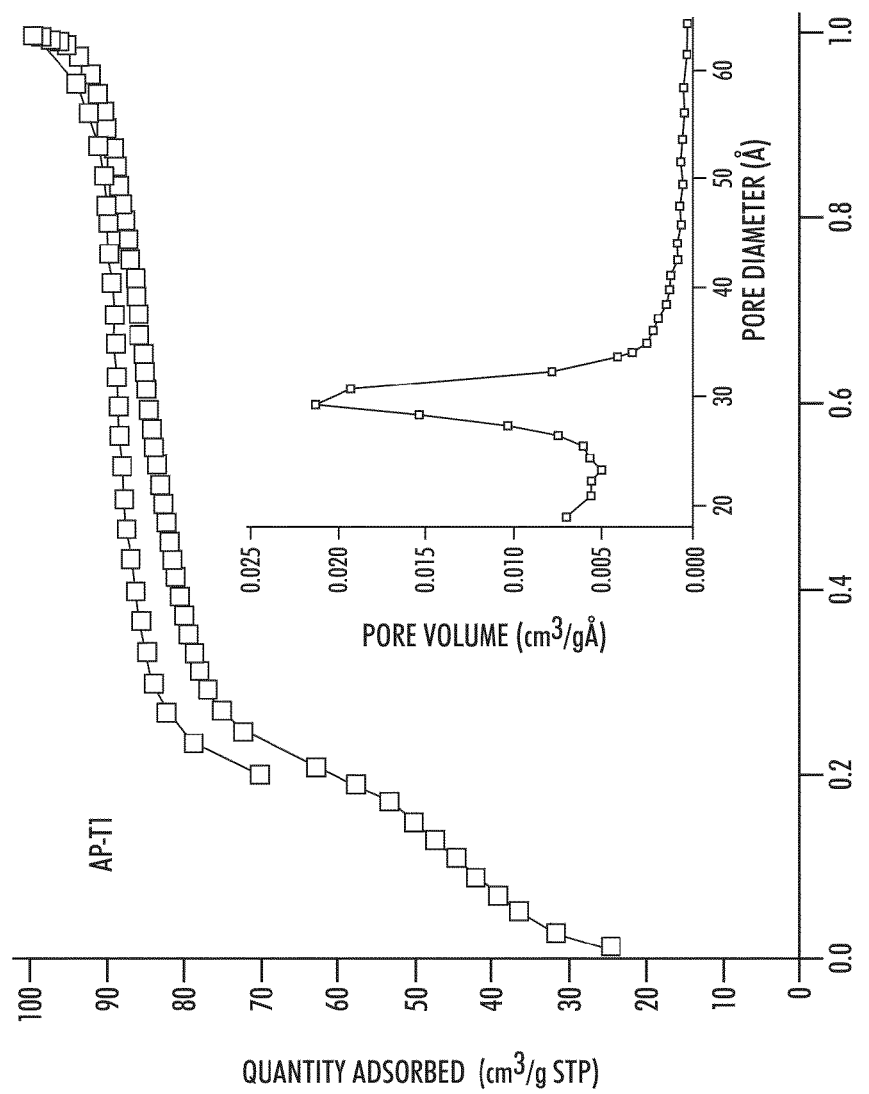
Figure 5E:
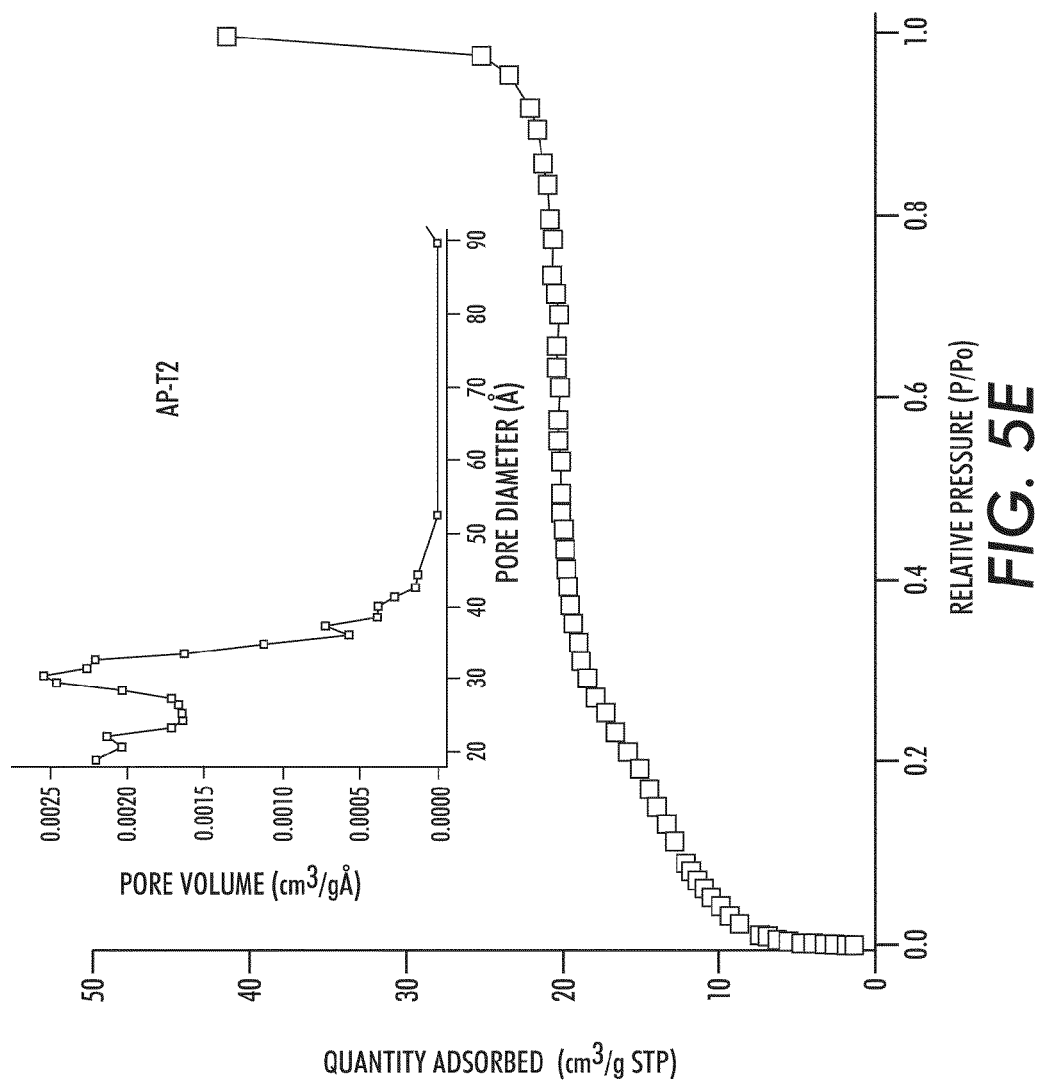

Nitrogen ($N_2$) gas adsorption measurements were obtained with a Micromeritics ASAP 2020 volumetric adsorption analyzer at 77 Kelvin. Prior to the measurements, the samples were outgassed at 160° C. for about 4 hours under vacuum, or until the pressure reached less than 6 μm Hg. FIG. 5A is a composite graph of the $N_2$ adsorption isotherms for the MCM-41, AP-E1, AP-T1, and AP-T2 materials, and FIGS. 5B-5E are the individual isotherms for the materials. The respective corresponding pore size distributions for each sample are also shown in these Figures.

Figure 6A:
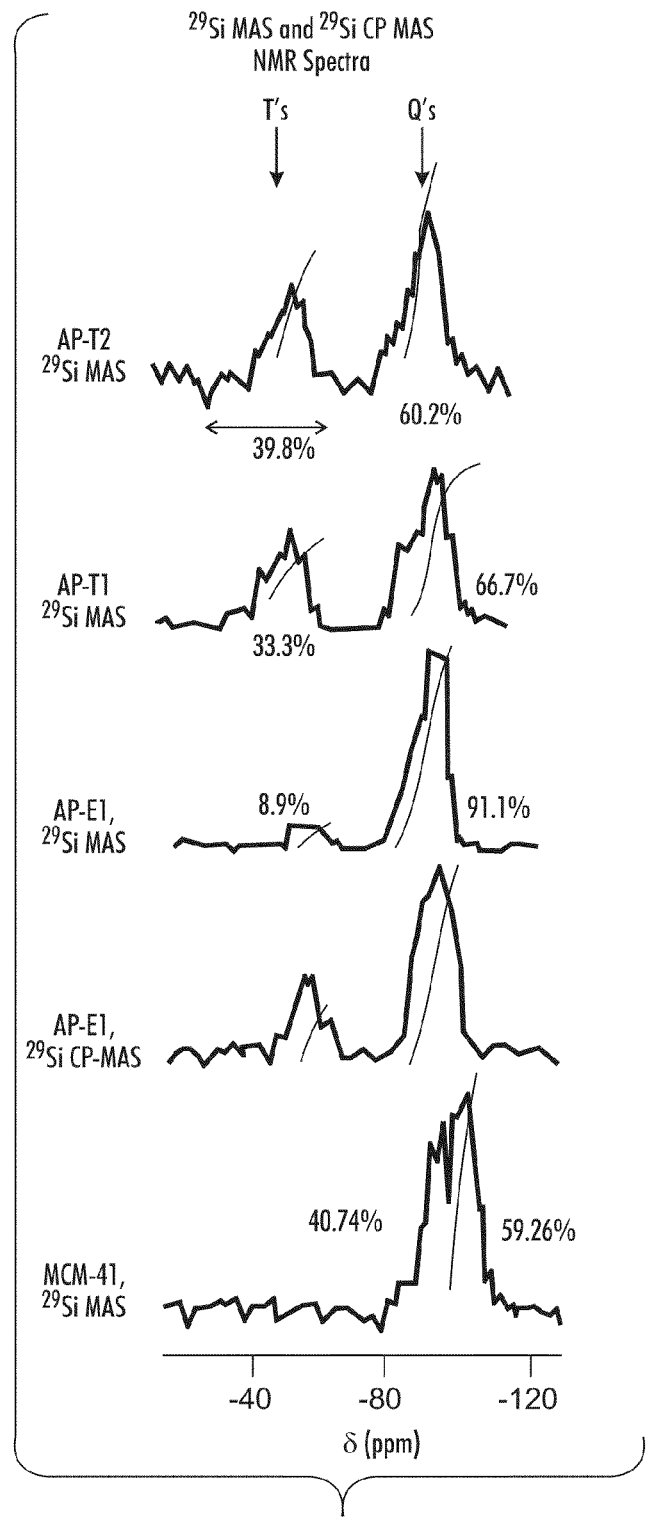
FIG. 6A is a graph of the $^{29}Si$ spectra obtained for the MCM-41, AP-E1, AP-T1, and AP-T2 materials.

Solid-state $^{29}$Si MAS, $^{29}$Si CP-MAS and $^{13}$C CP-MAS NMR spectra of the materials were measured with a 300 MHz Bruker Avance NMR spectrometer. ("CP" refers to "cross polarization," and "MAS" refers to "magic angle spinning." Both terms are well known in Nuclear Magnetic Resonance spectroscopy art.) FIG. 6A shows the $^{29}$Si spectra obtained

TABLE 2

Synthesis, composition and catalytic properties of mesoporous catalysts with spatially isolated organoamine groups synthesized by postgrafting a lesser amount of 3-aminopropyltrimethoxysilane (APTMS) in toluene and/or in shorter postgrafting reaction times.

| Sample | Solvent | APTMS | Post-grafting Time (hr)$^a$ | Weight loss (%) (100-600° C.)$^b$ | % Conversion in 12 min | % Conversion in 25 min | Time (min) for 100% Conversion |
|---|---|---|---|---|---|---|---|
| A (AP-E1) | Ethanol | 3.68 mmol (Excess) | 6 | 11.2 | 80 | 100 | 16 |
| B (AP-T1) | Toluene | 3.68 mmol (Excess) | 6 | 13.2 | 25 | 50 | 54 |
| C | Toluene | 3.68 mmol (Excess) | 1 | 16.1 | 22 | 45 | 74$^c$ |
| D | Toluene | 1.21 mmol | 6 | 13.5 | 29 | 59 | 42$^c$ |
| E$^d$ | Toluene | 1.21 mmol | 1 | 14.5 | 89 | 100 | 15 |
| F | Toluene | 0.92 mmol | 6 | 15.4 | 49 | 85 | 33$^c$ |
| G | Toluene | 0.92 mmol | 1 | 14.2 | 26 | 55 | 38$^c$ |
| H | Ethanol | 0.92 mmol | 6 | 11.0 | 66 | 100 | 22 |
| I | Ethanol | 1.21 mmol | 1 | 10.5 | 65 | 100 | 22 |

Figure 6B:
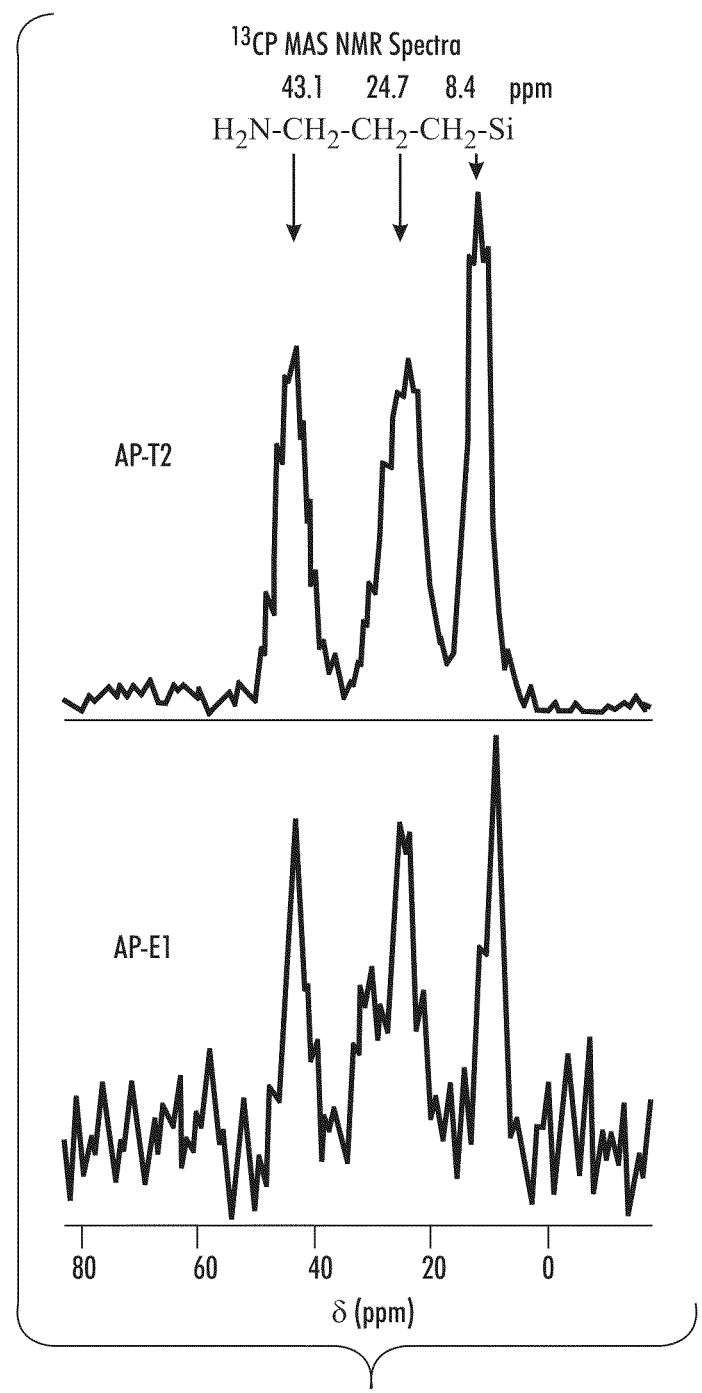
FIG. 6B is a graph of the $^{13}C$ spectra obtained for the AP-E1 and AP-T2 materials.

$^a$The postgrafting temperature was set to be 78° C. for all the samples.
$^b$The weight loss corresponds to the loss of organoamine groups and loss of water due to condensation of silanol groups.
$^c$Obtained by extrapolation of the graph (not shown) of thermogravimetric data for the sample.
$^d$This sample showed comparable high catalytic efficiency as postgrafted sample in ethanol (AP-E1).

for the four samples, and FIG. 6B shows the $^{13}$C spectra obtained for the AP-E1 and AP-T2 materials.

Figure 7:
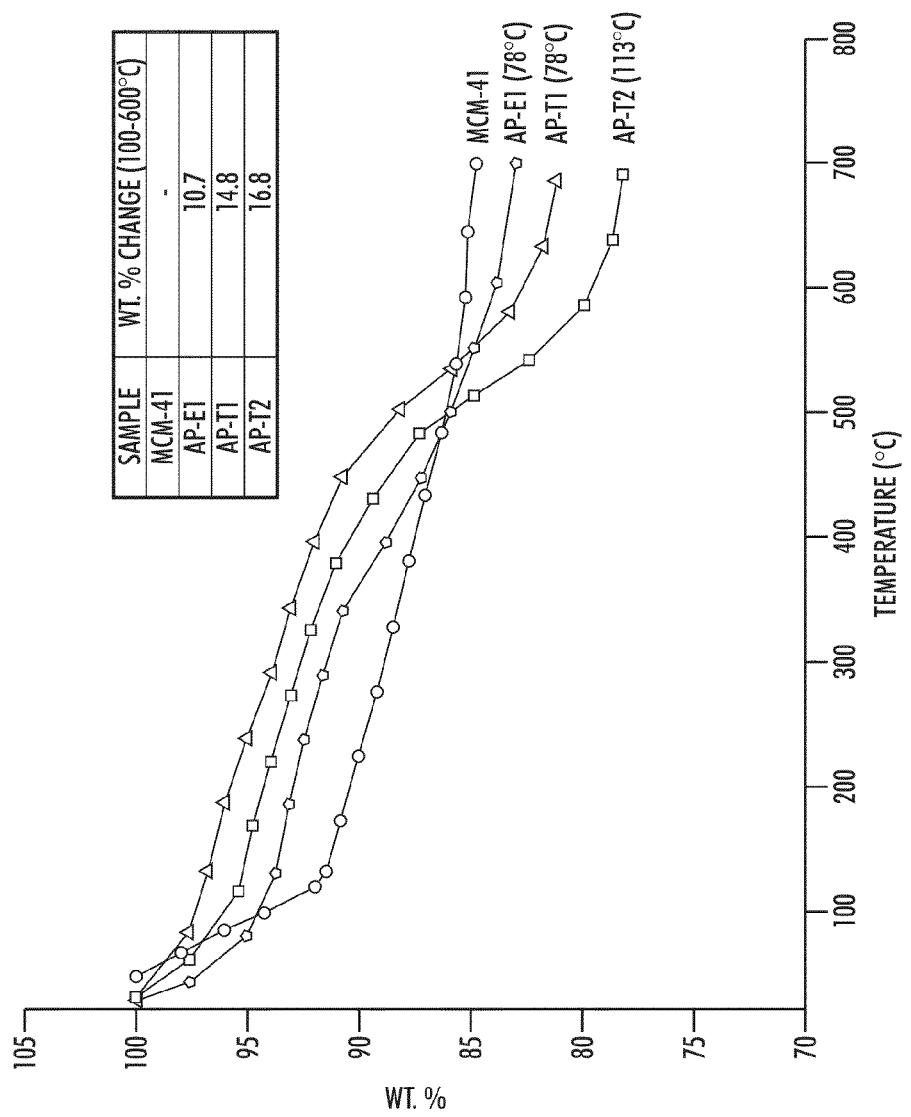
FIG. 7 is a graph of the thermogravimetric analyses of the MCM-41, AP-E1, AP-T1, and AP-T2 materials over the range from about 25 to about 700° C.

Thermogravimetric analysis (TGA) was carried out with a Q-500 Quantachrome instrument manufactured and sold by TA-Instruments. As is well known to those skilled in the art, TGA is a type of testing that is performed on samples to determine changes in weight in relation to change in temperature. FIG. 7 is a graph of the thermogravimetric analyses of the MCM-41, AP-E1, AP-T1, and AP-T2 materials over the range from about 25 to about 700° C.

Turning now to the results of these material analyses, and referring first to FIG. 3A, the table inset shows $d_{100}$ and unit cell ($a_o$) values of the samples, wherein $a_o = 2d_{100}/3^{1/2}$ (Å) for 2-D hexagonally ordered materials. The XRD patterns of all the samples showed a sharp peak corresponding to (100) peak as well as at least two more Bragg reflections corresponding to (110) and (200) peaks indicating that the materials have highly hexagonally ordered mesostructures, which remained intact during postgrafting. The peaks were indexed to give unit cells sizes of about 4.4-4.5 nanometers, which barely changed during postgrafting.

Referring to FIG. 3B and Table 2, all of the samples showed well ordered mesoporous structures. It is worth noting however that, samples postgrafted in ethanol (for instance, A and H) showed slightly more intense Bragg reflections compared to samples grafted in toluene for the same period of time at the same temperature (B and F). This clearly indicates the higher organoamine grafting in the channels of toluene product and the lower electron contrast between the mesoporous channels and walls. The XRD pattern also reveals that samples grafted with shorter postgrafting times or with more amount of organosilane showed slightly more intense peaks compared to samples postgrafted with longer time or with less amount of organosilane.

Referring to the TEM images of catalyst AP-E1 of FIG. 4A and FIG. 4B, the dimensional scales of these images are indicated in the respective lower right corners. Other TEM images (not shown) of the materials before postgrafting (i.e. starting material MCM-41) and after postgrafting (i.e. various catalyst product samples) also showed well-ordered mesoporous structures. These images showed clear channel structures similar to the channels 22 in the catalyst sample shown in FIG. 13B.

Referring to FIGS. 5A-5E, the gas adsorption measurements of all the materials exhibited BDDT (Brunauer, Deming, Deming, and Teller) Type IV isotherms, which are characteristic of mesoporous materials. Furthermore, their BET (Brunauer-Emmett-Teller) surface areas range between 1,030-1,060 m$^2$/g depending on grafting density, while their BJH (Barrett-Joyner-Halenda) pore size distributions are monodisperse.

Referring in particular to the individual pore size distribution plots of FIGS. 5B-5E, it can be seen that the distributions indicate monodisperse pore diameters, and that the capillary condensation step and the pore volume decreases in the order of MCM-41>AP-E1>AP-T1>AP-T2. This result is consistent with more grafting of organoamine groups in the mesoporous structures. The decrease of surface areas and pore volumes upon grafting of organic groups is previously known. Despite the observed significant decrease in pore volume and surface area, AP-T2 has still a well-ordered mesostructure as shown by its Type IV isotherm (FIG. 5E) and its intense peaks in its X-ray diffraction pattern (FIG. 3A).

Referring to FIG. 6A, by integration of the $^{29}$Si MAS spectra, the composition of the mesoporous materials MCM-41, AP-E1, AP-T1, and AP-T2 and the mmol NH$_2$/g for each material were obtained. In each of the following paragraphs, the numbers in the bracket indicate % silica and % organosilica for each material that were obtained by integrating the $^{29}$Si MAS spectra.

The composition of the MCM-41 can be represented as:

The compositions of AP-E1, AP-T1, and AP-T2 can be represented as:

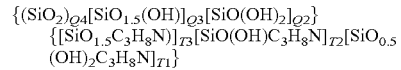

From the integration values:
For MCM-41:

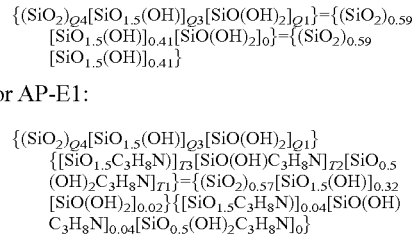

For AP-E1:

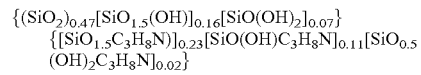

From the above, the mmol NH$_2$/g sample was calculated to be 1.32 mmol NH$_2$/g.

For AP-T1:

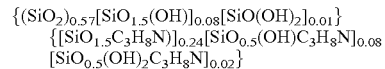

From the above, the mmol NH$_2$/g sample was calculated to be: 4.1 mmol NH$_2$/g.

For AP-T2:

$\{(SiO_2)_{0.57}[SiO_{1.5}(OH)]_{0.08}[SiO(OH)_2]_{0.01}\}$
$\{[SiO_{1.5}C_3H_8N]_{0.24}[SiO_{0.5}(OH)C_3H_8N]_{0.08}$
$[SiO_{0.5}(OH)_2C_3H_8N]_{0.02}\}$

From the above, the mmol NH$_2$/g sample was calculated to be: 4.3 mmol NH$_2$/g.

Referring to FIG. 7, the thermogravimetric traces for the MCM-41, AP-E1, AP-T1, and AP-T2 materials indicated a weight loss before 100° C. in all the samples due to the loss of physisorbed water. However, the weight loss of the samples between 100-600° C., which corresponds to the loss of organoamine groups and some condensed water, showed a trend. The AP-E1 showed the lowest weight loss followed by AP-T1 and then AP-T2; i.e. 10.7, 14.8 and 16.8%, respectively. Considering the removal of silanol groups from the materials during postgrafting, which is the highest in AP-T2, and which therefore results in the lowest weight loss due to condensation of water on TGA traces, the applicants believe that these weight loss differences due to the organoamine between 100-600° C. for AP-E1, AP-T1 and AP-T2 are more significant.

These results were further corroborated with the solid-state NMR spectroscopy results shown in FIGS. 6A and 6B and described previously herein. The $^{29}$Si MAS NMR of FIG. 6A qualitatively and quantitatively confirmed the presence of the highest organoamine groups in AP-T2 (4.3 mmol/g), followed by AP-T1 (4.1 mmol/g), and then AP-E1 (1.3 mmol/g). Similarly, the $^{13}$C CP-MAS NMR of FIG. 5B showed peaks corresponding to aminopropyl groups at 43.1, 24.7, and 8.4 ppm after postgrafting. The intensities of these peaks were higher for AP-T2, followed by AP-T1, and AP-E1, consistent with the TGA and $^{29}$Si MAS NMR results. Both the TGA and solid-state NMR results have confirmed AP-E1 to have a lesser number of organoamine groups and more silanols, that are likely to be spatially distributed, compared to AP-T1 and AP-T2, which have densely populated organoamines and fewer silanols.

Referring again to FIG. 2, the lesser amount of aminopropyl groups postgrafted to a pore wall of the AP-E1 material as compared to a pore wall of AP-T1 or AP-T2 is illustrated qualitatively. Accordingly, the aminopropyl groups are spatially distributed less densely in the pores of AP-E1. The significance of this discovery will be explained subsequently herein.

In order to demonstrate the usefulness of the bifunctional materials with spatially isolated organoamine and silanol groups, the applicants have performed the Henry reaction using the materials A-I of Table 2 as catalysts. In general, the Henry reaction is an aldol type reaction between an aldehyde and nitromethane. The nucleophilic addition step is base catalyzed and may be followed by an elimination reaction with removal of water when an acidic alpha proton is present. The reaction product is a beta-hydroxy nitro-compound or a nitroethylene compound.

Many organoamine functionalized mesoporous materials synthesized in reflux in toluene are reported to catalyze the Henry reaction. However, to the best of the applicants' knowledge, the highest yield and turnover-number (TON) values reported to date with such samples have been 96% yield in 1 hr reaction time with 50 mg catalyst and 2.5 mmol of reactant, as disclosed by Demicheli et al. in *Tetrahedron Lett.* 2001, 42, 2401-2403; and Choudary, et al in *J. Mol. Catal. A* 1999, 142, 361-365.

In the present application, the Henry reaction between p-hydroxy benzaldehyde and nitromethane at 90° C. was carried out, resulting in the formation of nitrostyrene. Typically, 20 mg of a particular aminofunctionalized mesoporous sample was added into a mixture of 122 mg (1 mmol) p-hydroxybenzaldehyde and 10 mL of nitromethane. The reaction mixture was stirred at 90° C. under nitrogen and aliquots of the reaction product were taken with a filter syringe and characterized by solution $^1$H NMR spectroscopy and GC-MS over the course of the reactions. The percent yield and conversion were determined by using $^1$H NMR spectra measured in deutrated acetone.

Figure 8:
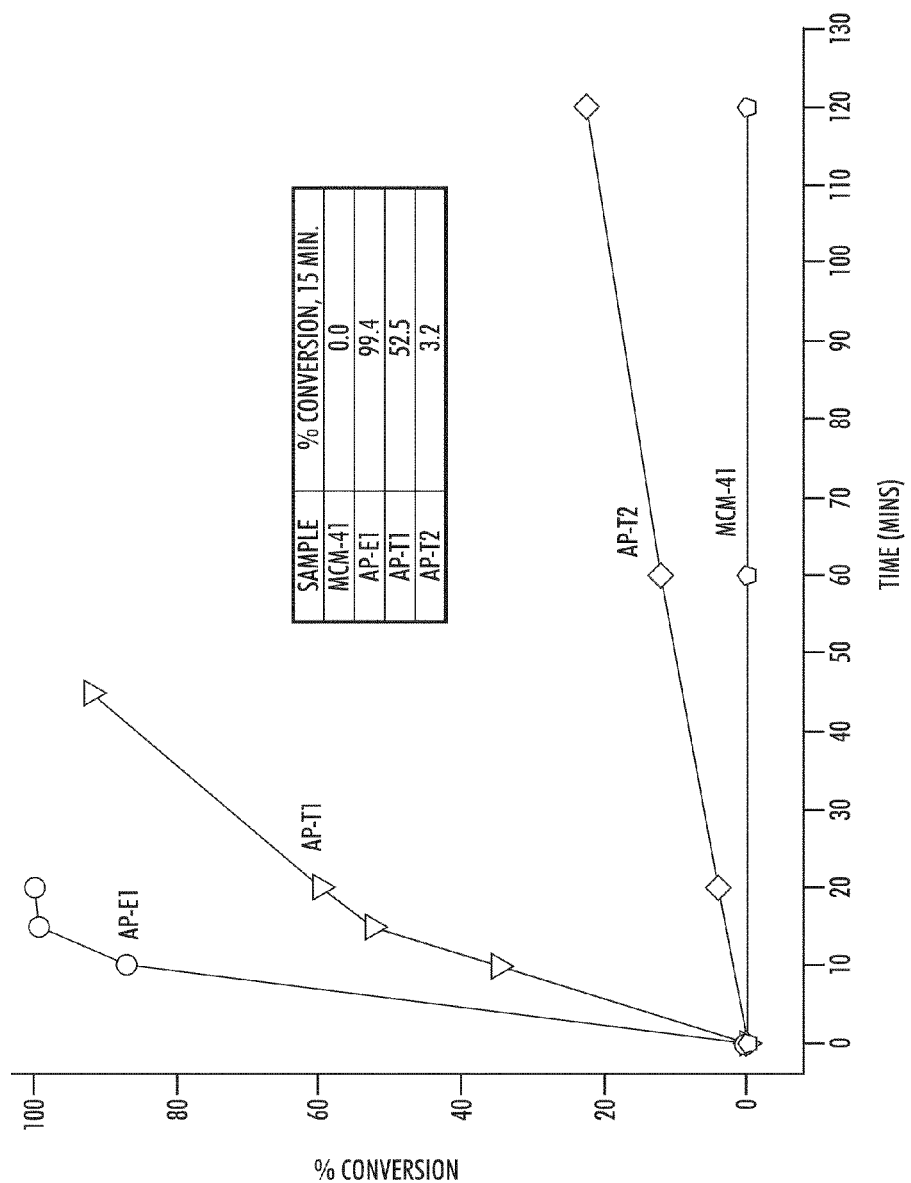
FIG. 8 is a graph of the efficacy of the catalyst AP-E1 of the invention and the control catalyst samples AP-T1 and AP-T2 in catalyzing the Henry reaction.

FIG. 8 is a graph of the efficacy of the resulting catalyst AP-E1 of the invention and the control catalyst samples AP-T1 and AP-T2 in catalyzing this Henry reaction. Performing the reaction with AP-E1 as a catalyst unexpectedly gave a yield of 99.4% in about 15 minutes. In contrast, the same amounts of AP-T1 and AP-T2 afforded yields of 52.4 and 8.4%, respectively, in 15 minutes. This is at least a two-fold increase in yield. A four-fold increase in turn-over-number for AP-E1 compared to AP-T1 and AP-T2 was also observed. To the best of the applicants' knowledge, it is the highest efficiency compared to any mesoporous catalyst reported in the literature for the Henry reaction. These results are unexpected, given the fact that AP-E1 has less organoamine groups per unit mass than both AP-T1 and AP-T2, and considering that mesostructures in all the samples remained intact as shown by XRD and TEM.

Figure 9A:
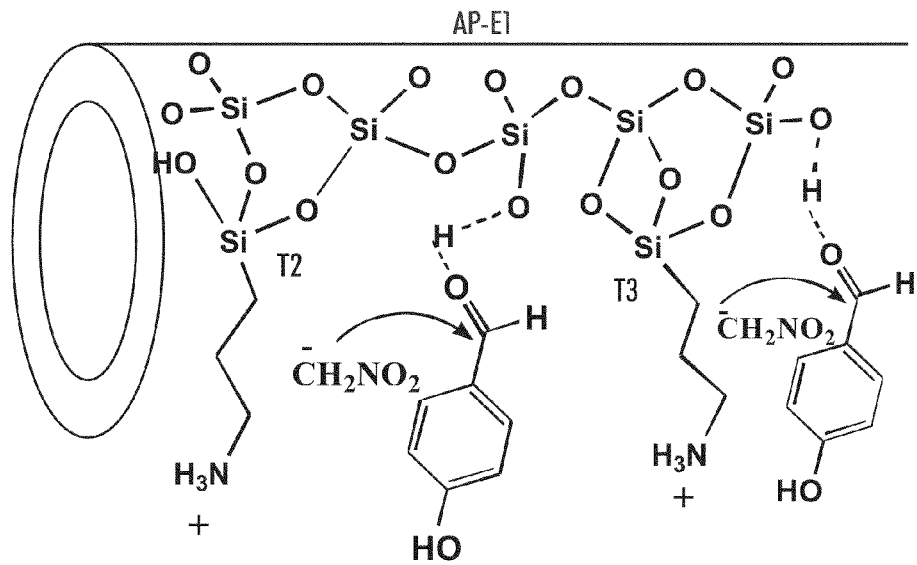
FIG. 9A is an illustration of a possible mechanism for the catalysis of the Henry reaction by the applicants' AP-E1 catalyst material.
Figure 9B:
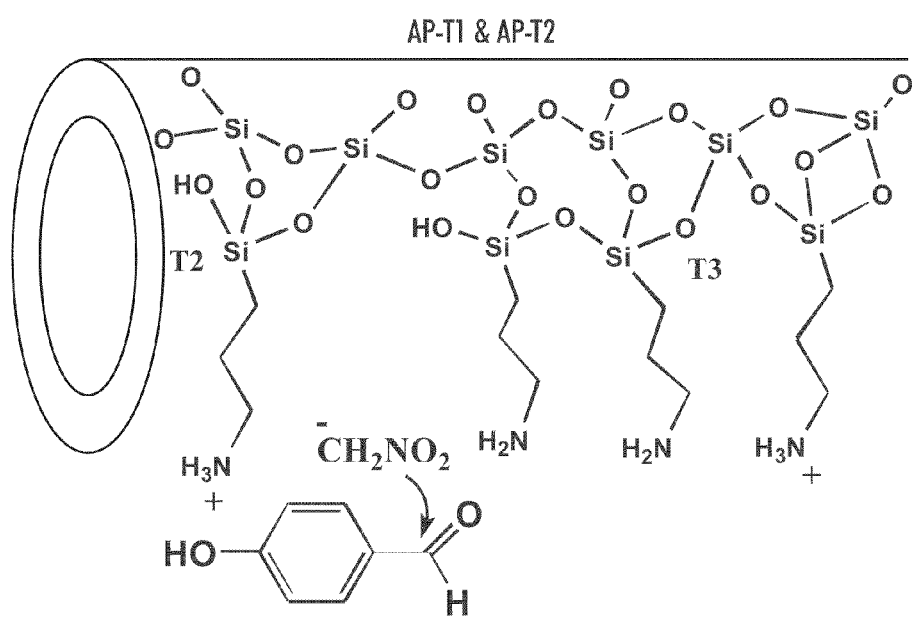
FIG. 9B is an illustration of a possible mechanism for the catalysis of the Henry reaction by the control catalyst materials AP-T1 and AP-T2.

Without wishing to be bound to any particular theory, the applicants believe that the enhanced catalytic efficiency by AP-E1 compared to AP-T1 and AP-T2 may be due to two reasons:

1. The higher number of silanols in AP-E1, as compared to the materials AP-T1 or AP-T2, can activate the carbonyl group of benzaldehyde to undergo the nitroaldol reaction more efficiently. The corresponding reaction mechanisms for AP-E1, and AP-T1 or AP-T2, are illustrated in FIGS. 9A and 9B, respectively. Referring in particular to FIG. 9A, the applicants believe that the significant number of spatially isolated silanol groups present in AP-E1 activates the carbonyl group of benzaldehyde for nucleophilic attack.

2. The higher surface area of AP-E1 due to its low organoamine grafting density compared to AP-T1 and AP-T2 may also have contributed to the differences in catalytic efficiency.

Similar studies of postgrafting organodiamine groups that the applicants have conducted using ethanol and toluene also showed increased efficiency for samples synthesized in ethanol compared to corresponding samples synthesized and grafted in toluene. The postgrafting of the remaining silanols of the ethanol product (or AP-E1) with more organic groups using toluene resulted in significant reduction in catalytic efficiency, further confirming the importance of spatially isolated organoamine and silanols for increased efficiency. Detailed synthesis of these materials and their catalytic properties are described subsequently in this specification.

Again, without wishing to be bound to any particular theory, the applicants hypothesize that postgrafting of spatially distributed organoamines with ethanol occurs because of the competition for the aminoorganosilane by ethanol (a polar protic solvent having a dielectric constant=24 D), and the hydrophilic surface silanols. Because of the absence of hydrogen bonding between the organoamines and toluene (a nonpolar solvent having a dielectric constant=2.4 D), the aminoorganosilanes aggregate and preferentially interact with the surface silanols. Aggregation of aminoorganosilanes in toluene has been previously proposed to cause grafting of very densely populated organic groups by Hicks et al. in *Chem. Mater.* 2006, 18, 5022-5032.

However, by lowering the concentration of aminoorganosilane and shortening the reaction times, the applicants have also synthesized similar site isolated samples that have efficient catalytic properties in toluene at lower temperature. The synthesis and the catalytic performance of these site isolated samples C-I are summarized in Table 2. Additionally, FIGS. 10A and 10B graphically show the efficacy of these catalyst samples C-I, along with samples A (AP-E1) and B (AP-T1) for comparison. It can be seen that the best result was achieved by sample E, in which the concentration of aminoorganosilane was reduced to 1.21 mmol, and the reaction time was shortened to one hour.

In summary, most of the prior art grafting of organosilanes has been performed in non-polar solvents, mainly toluene. In one embodiment, the applicants have synthesized organic functionalized mesoporous materials by grafting organosilanes in a polar solvent, ethanol. Although the applicants' approach resulted in less numbers of immobilized organic groups compared to the corresponding grafting in toluene, it produced materials with better structures such as higher surface area and site-isolated organocatalytic sites and consequently, much improved catalytic properties.

Despite this successful strategy, to the best the applicants' knowledge, the grafting of organosilanes in many other polar and non-polar solvents with different dielectric constants and the correlations between the solvents' properties and the structures and catalytic properties of the resulting materials have not been systematically investigated. The applicants have performed such an investigation, resulting in further embodiments of the invention which are described in the immediately following section of this specification.

Figure 11:
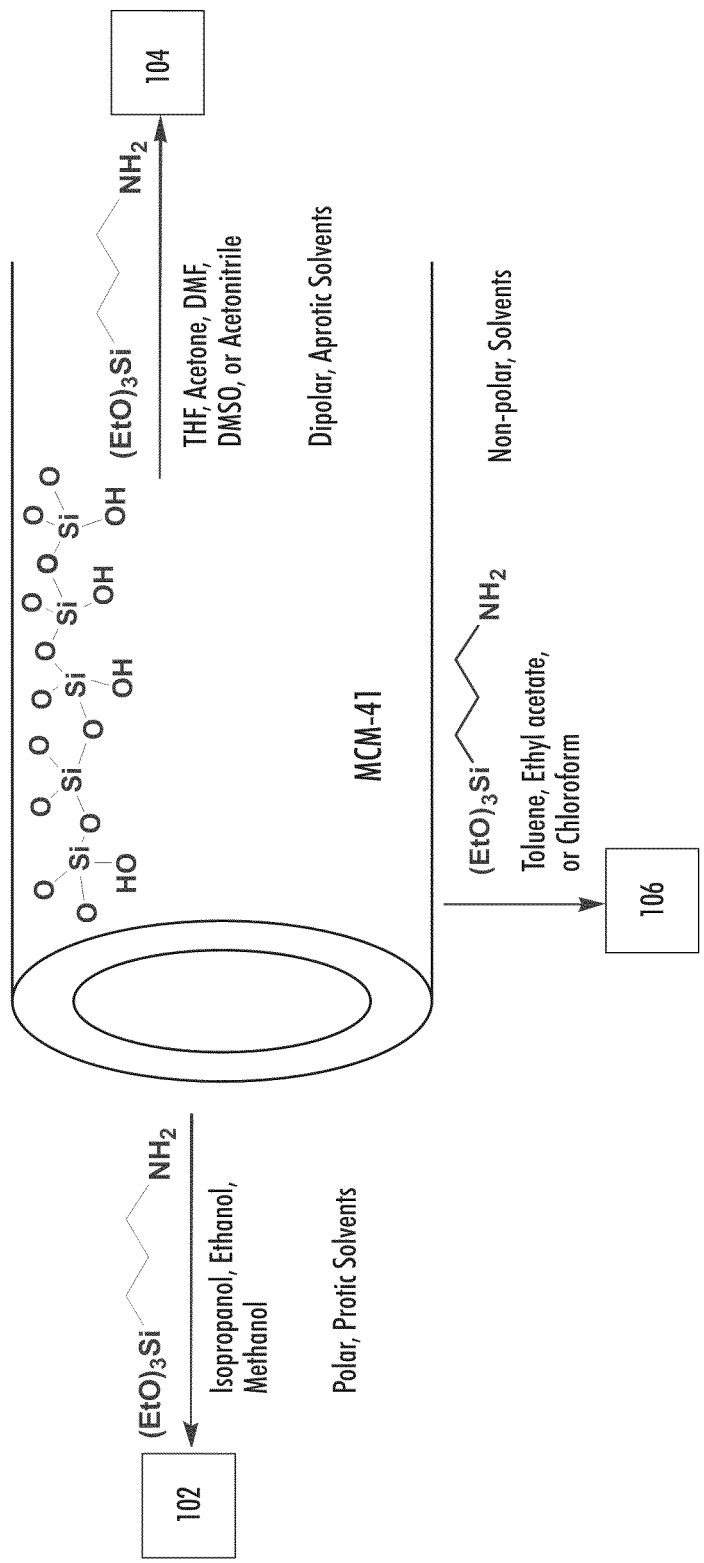
FIG. 11 is an illustration summarizing reaction schemes for converting a mesoporous material into certain catalysts, wherein various different types of solvents are used as the reaction medium.

Improvements in Grafting Spatially Distributed Organoamine Groups on Mesoporous Silica by Optimal Solvent Selection: General Description and Examples In performing this investigation, the applicants have discovered a generic correlation between the properties of solvents used for grafting and the percentages of grafted organic groups, the structures of the resulting materials, and their catalytic properties. The investigation was carried out by grafting 3-aminopropyl group, which is among the most common types of organic groups to be grafted onto mesoporous materials, under reflux in various polar protic, polar aprotic, and non-polar solvents. FIG. 11 is an illustration summarizing reaction schemes for converting mesoporous material into catalysts, wherein these different types of solvents are used as the reaction medium. Reactions performed with polar protic solvents produce catalyst products 102, reactions performed with dipolar aprotic solvents produce catalyst products 104, and reactions performed with nonpolar solvents produce catalyst products 106. The percentages of grafted organic groups, structures, and catalytic properties of these products will be described subsequently herein.

In particular, the applicants have discovered correlations between the polarity and dielectric constants of solvents used for grafting 3-aminopropyltrimethoxysilane, and the concentration of grafted organic groups, the degree of site-isolation of the 3-aminopropyl functional groups and the catalytic properties of the resulting materials for the Henry reaction. We have observed that polar protic solvents with low dielectric constants used as the grafting reaction medium result in small concentrations of grafted organic groups and higher surface areas but more efficient catalytic properties. In contrast, the use of dipolar protic solvent or non-polar solvent media result in a range of grafting concentrations of organic functional groups and lower surface areas, as well as a range of catalytic properties from "poor" to "efficient," which will be further quantified herein. These differences were further found to be strongly dependent on the dielectric constant of the solvents. Solvents that have higher dielectric constants were found to decrease the grafting density. Without wishing to be bound to a particular theory, the applicants believe that this phenomenon may possibly be due to the increased Coulombs interactive force between the protonated aminopropylsilane cation and deprotonated silanol anions.

In this solvent medium investigation, MCM-41 was used as the mesoporous silica substrate material. The MCM-41 was synthesized and kept in an oven to remove most of its physisorbed water prior to grafting, as described previously herein. The postgrafting reactions were also performed in a manner similar to that described previously herein. Briefly, 3-aminopropyltrimethoxysilane was refluxed with parent mesoporous silica (MCM-41) in the particular polar protic, dipolar aprotic, or non-polar solvent under nitrogen for 6 hours. The relative populations of the 3-aminopropyl group and the structures and the catalytic properties of the materials for the Henry (nitroaldol) reaction were then investigated. The techniques of powder x-ray diffraction, transmission electron microscopy, nitrogen gas adsorption, solid state $^{29}$Si MAS, $^{29}$Si CP-MAS and $^{13}$C CP-MAS NMR, and thermogravimetric analysis were used to characterize the samples as described previously. Details of these analytical techniques will thus not be repeated here; instead, only the results will be presented.

Figure 12A:
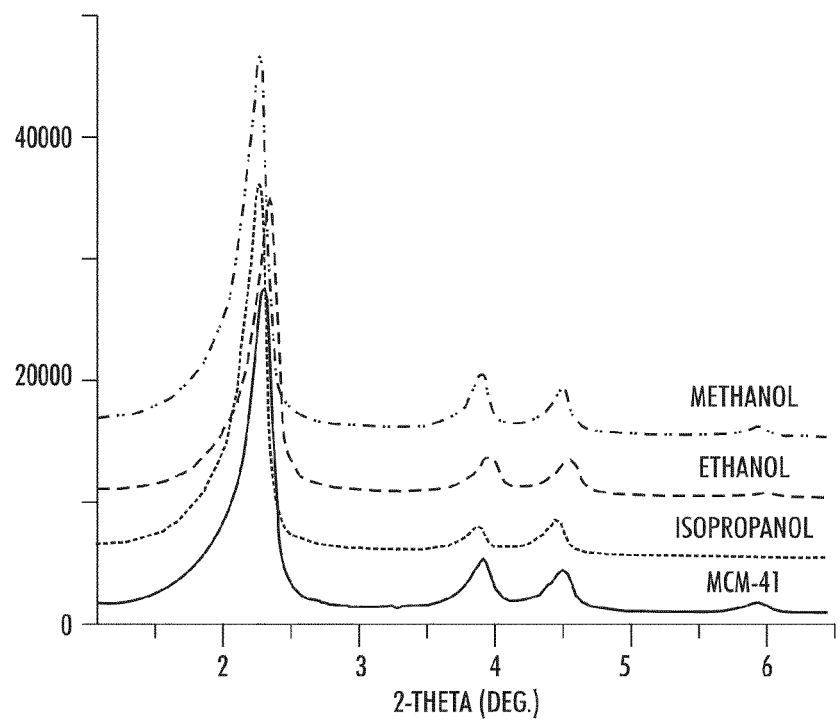
FIG. 12A is a graph of powder X-ray diffraction patterns of certain catalysts prepared in polar protic solvents.
Figure 12B:
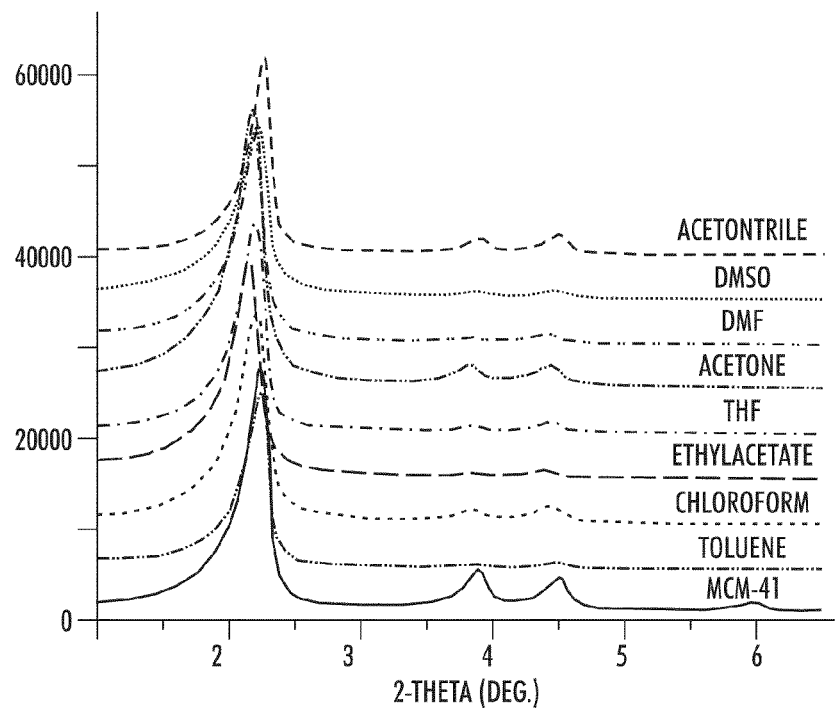
FIG. 12B is a graph of powder X-ray diffraction patterns of certain catalysts prepared in dipolar protic solvents or in non-polar solvents.
Figure 13A:
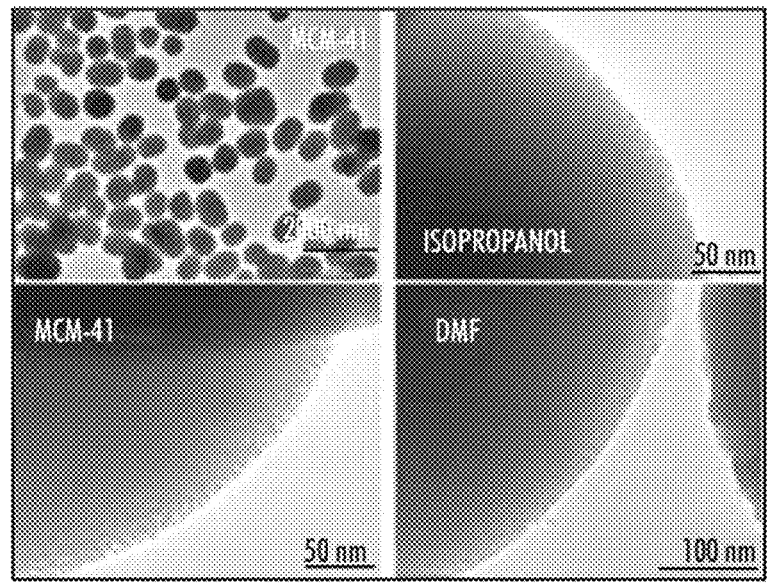
FIG. 13A is a set of transmission electron microscopy images of the MCM-41 starting material, and catalysts prepared in isopropanol and in dimethyl formamide.
Figure 13B:
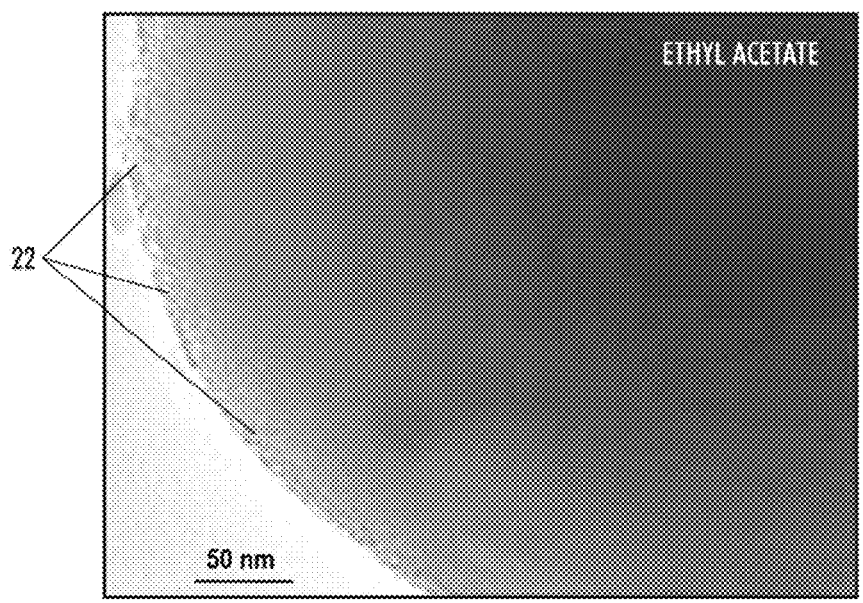
FIG. 13B is a set of transmission electron microscopy images of a catalyst prepared in ethyl acetate.
Figure 14A:
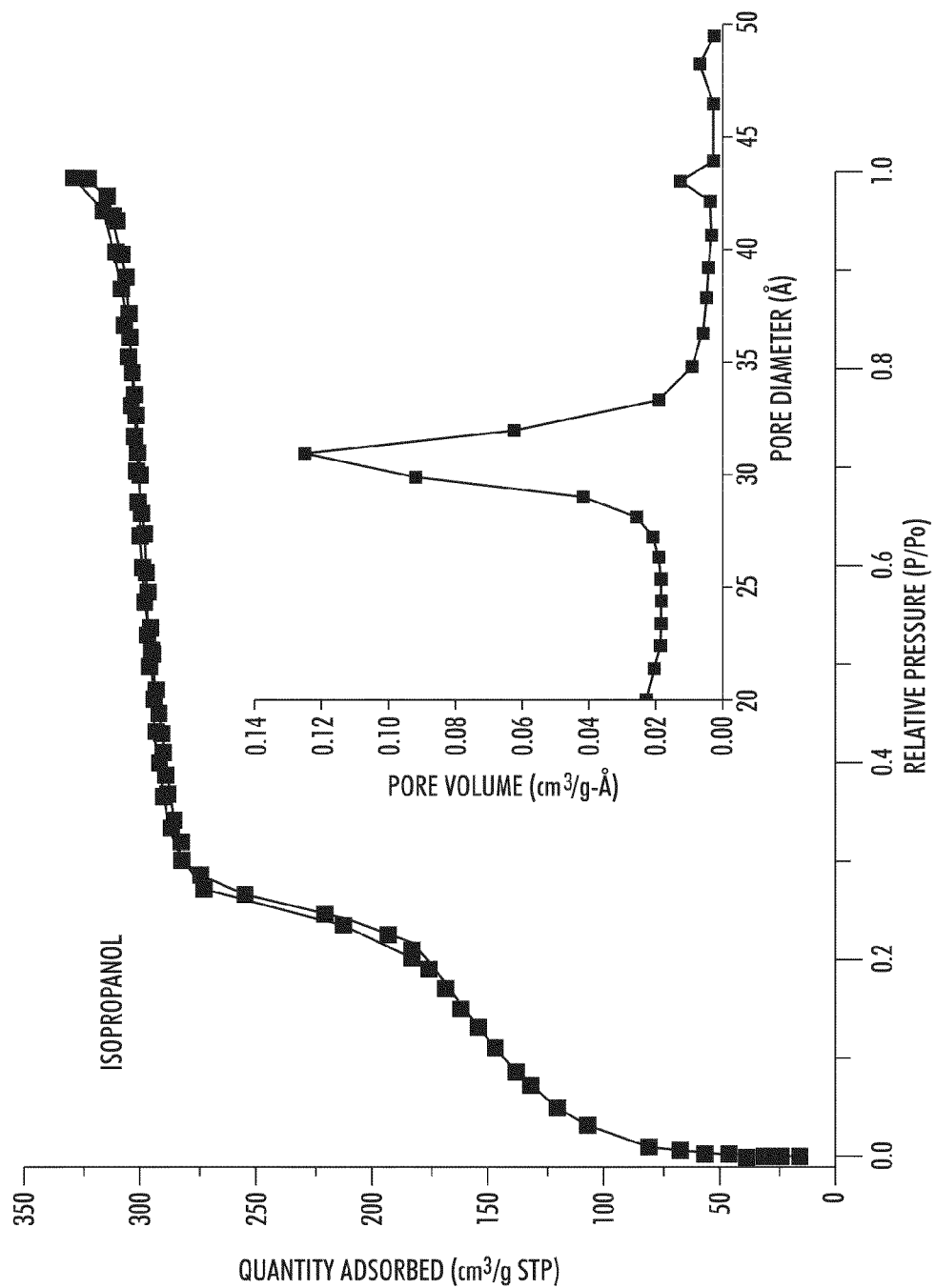
FIGS. 14A-14C are nitrogen gas adsorption isotherms and pore-size distribution data for 3-aminopropyl-grafted mesoporous samples grafted in polar protic solvents.
Figure 14B:
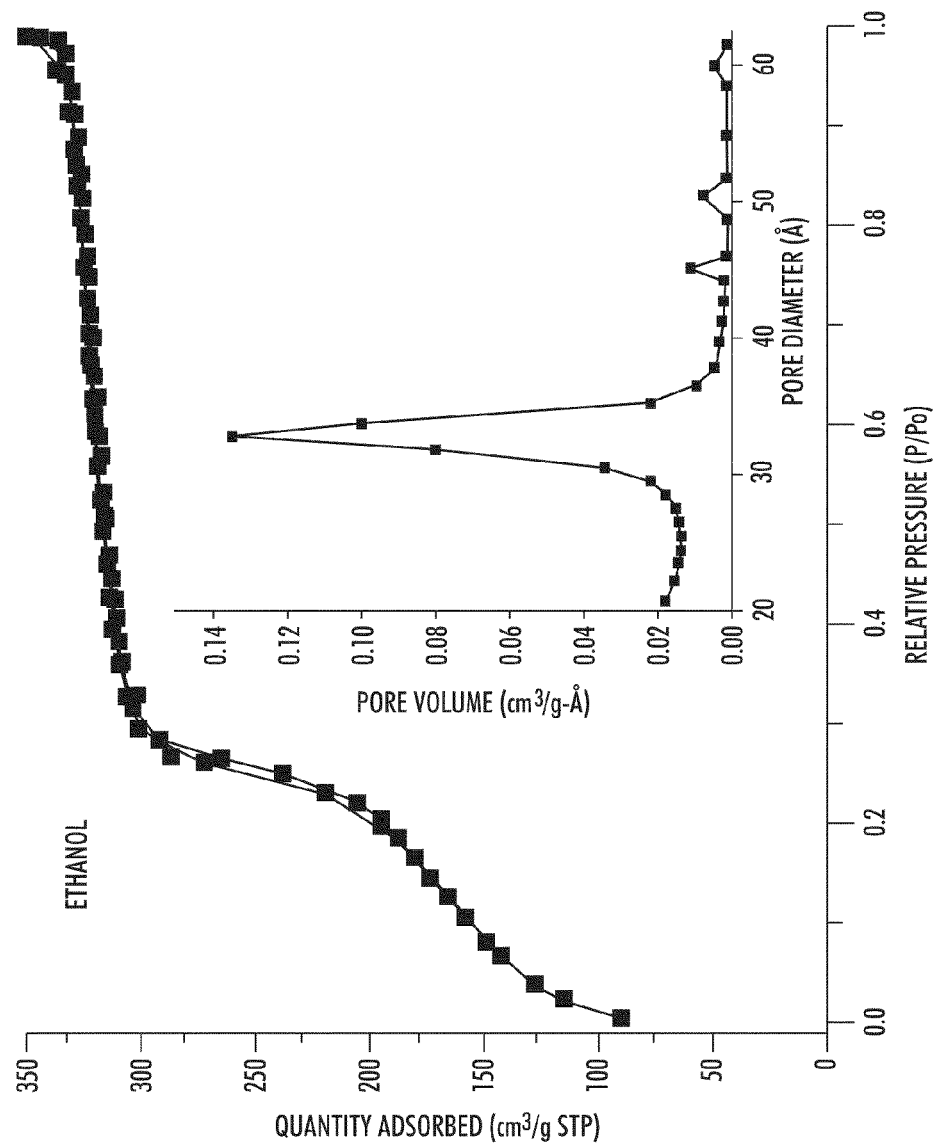
Figure 14C:
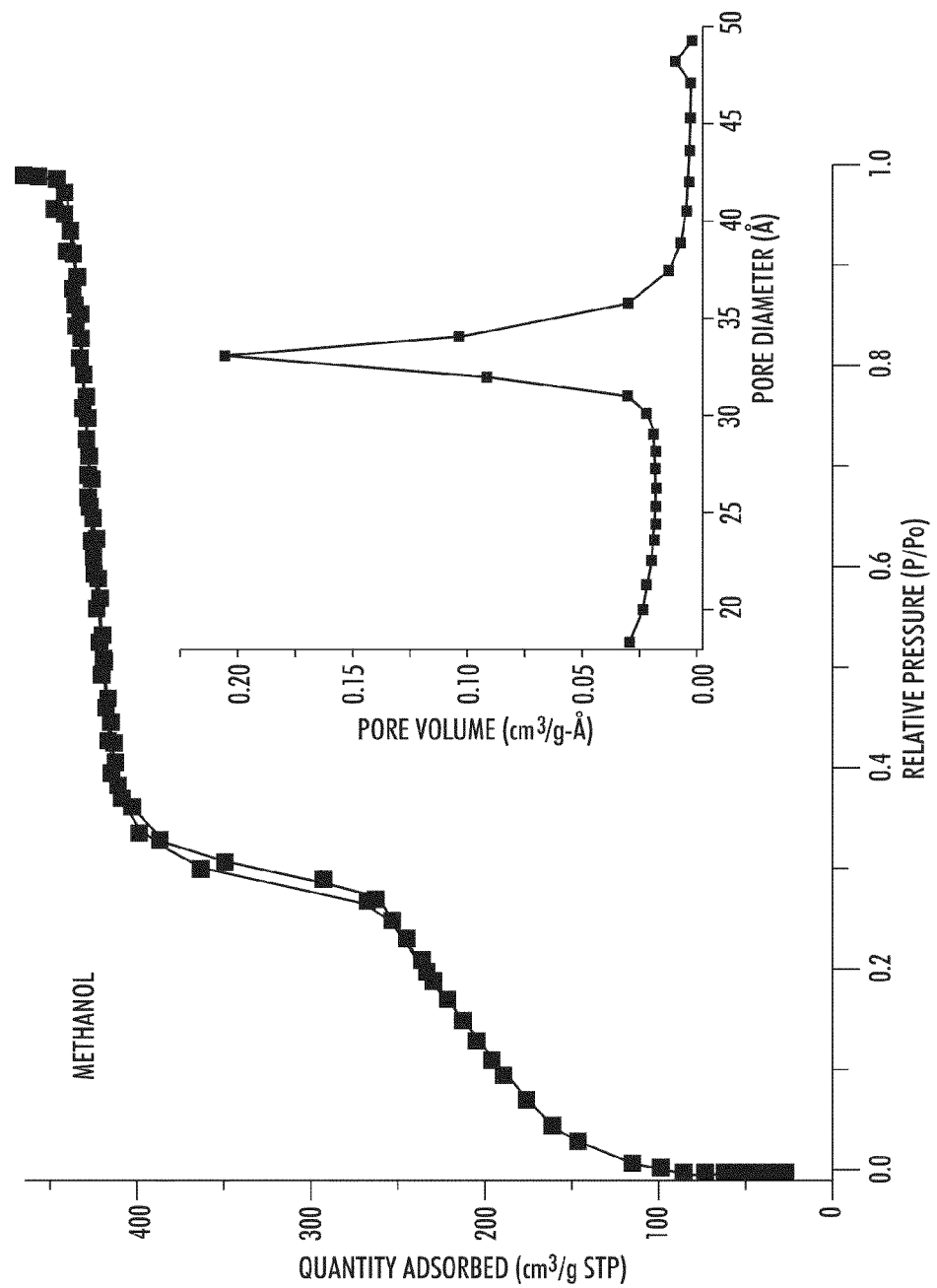
Figure 15A:
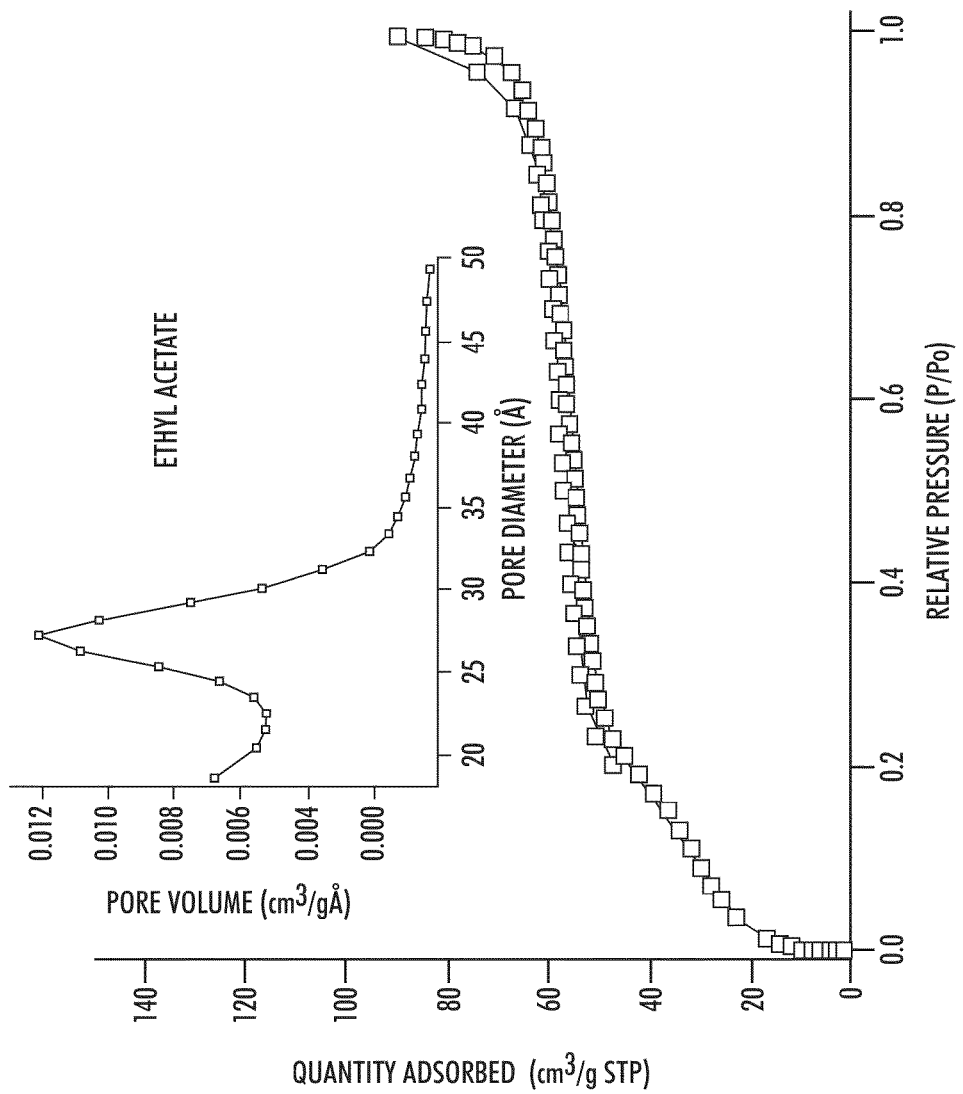
FIGS. 15A-15F are nitrogen gas adsorption isotherms and pore-size distribution data for 3-aminopropyl-grafted mesoporous samples grafted in dipolar aprotic solvents.
Figure 15B:
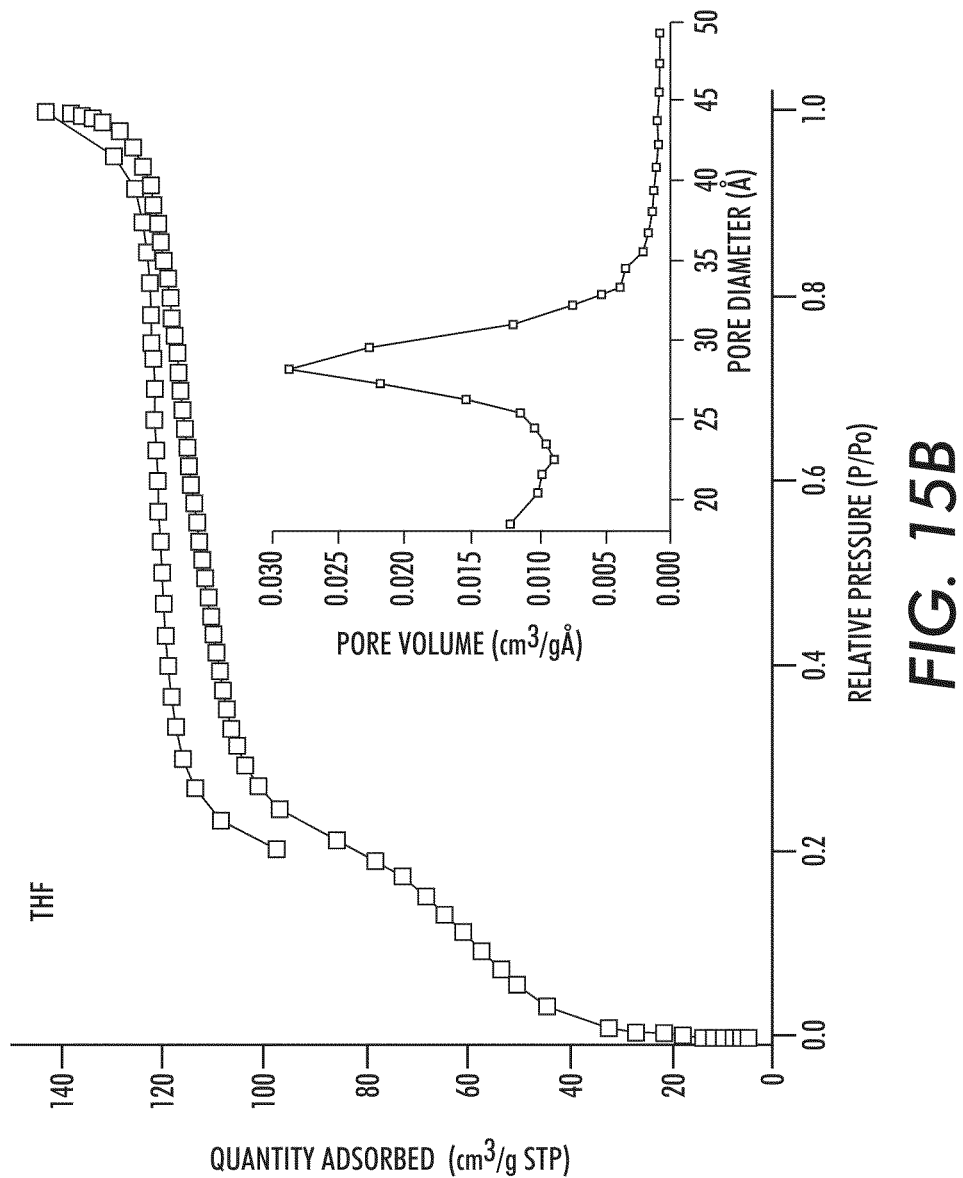
Figure 15C:
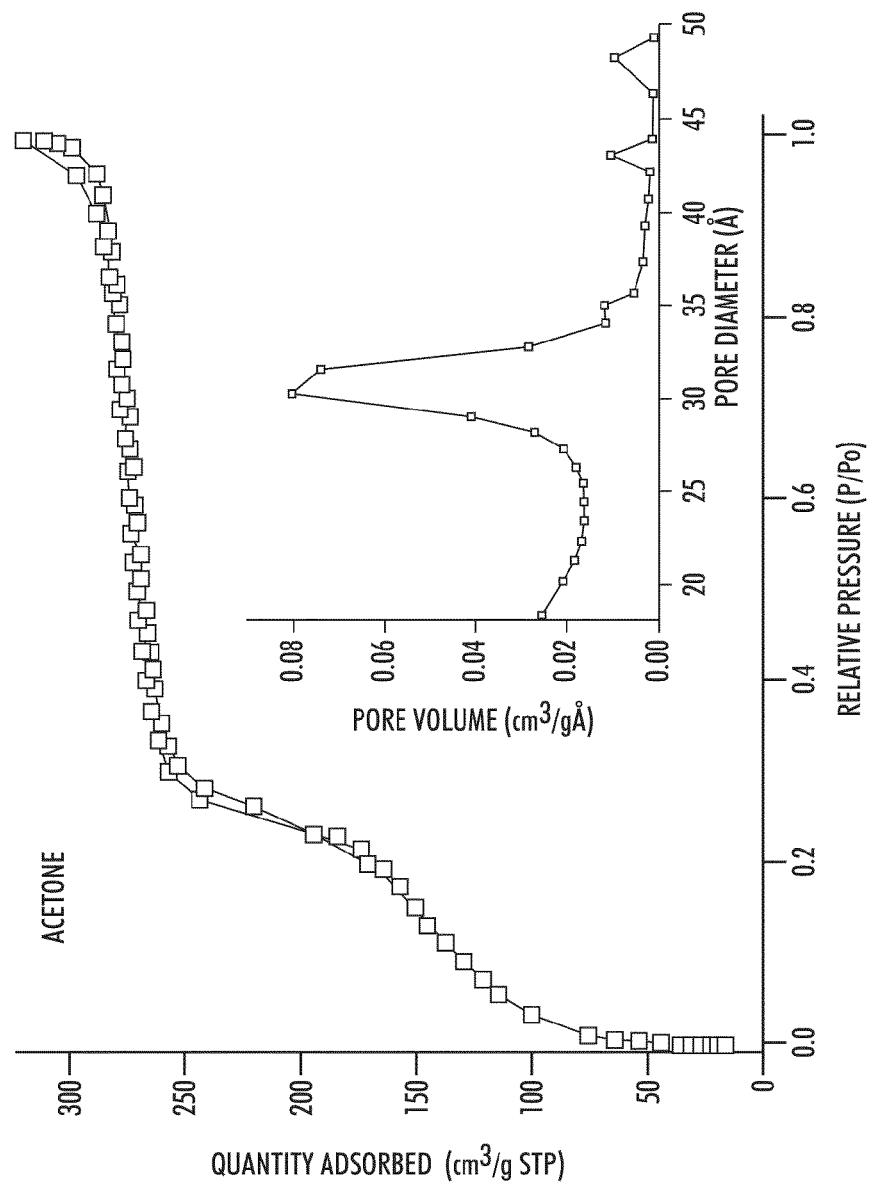
Figure 15D:
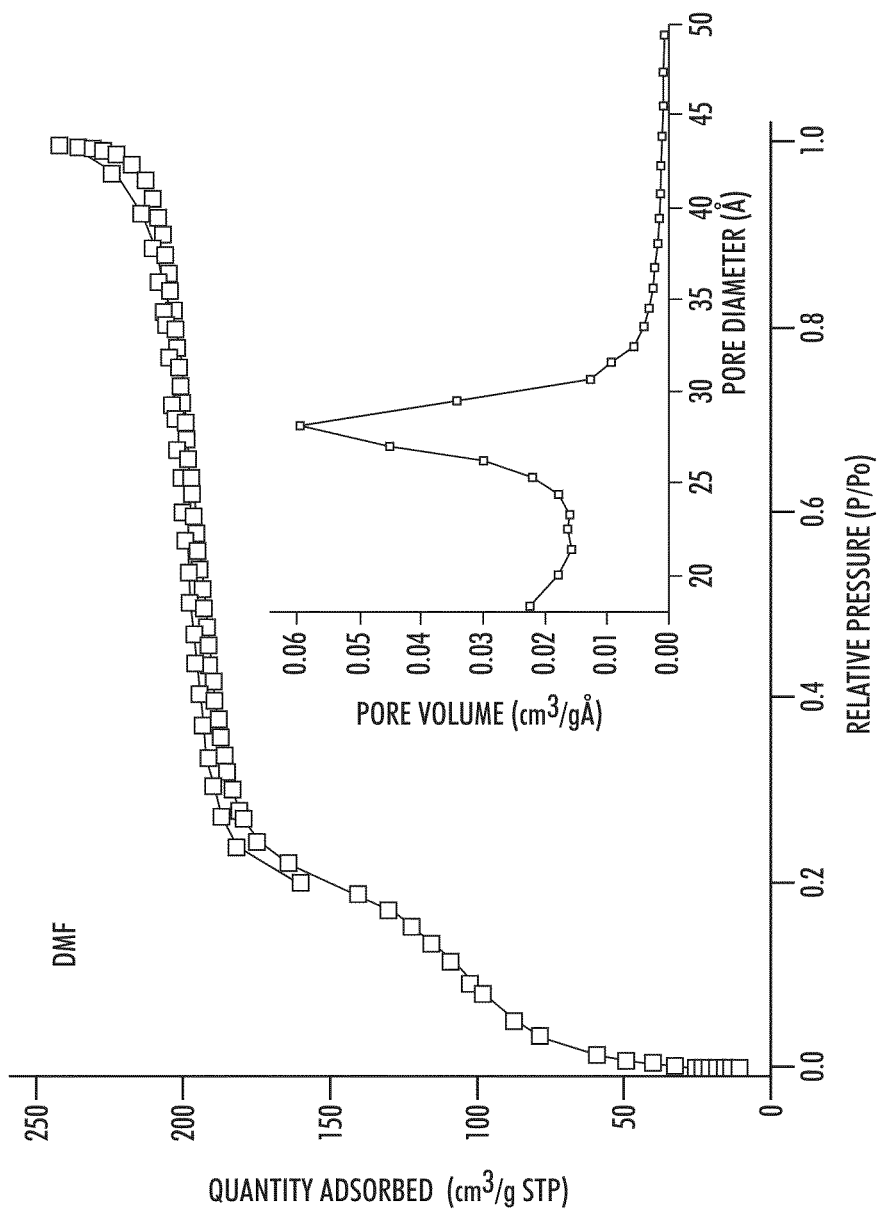
Figure 15E:
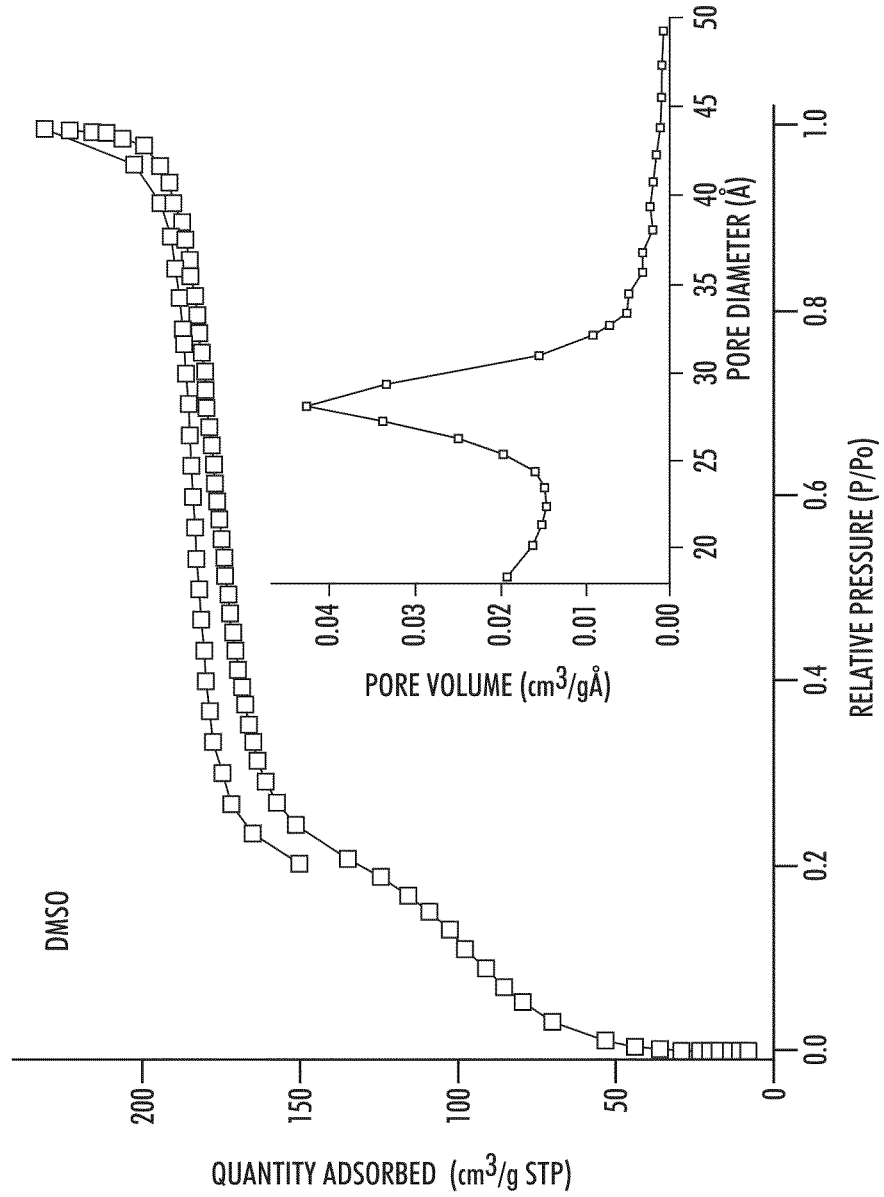
Figure 15F:
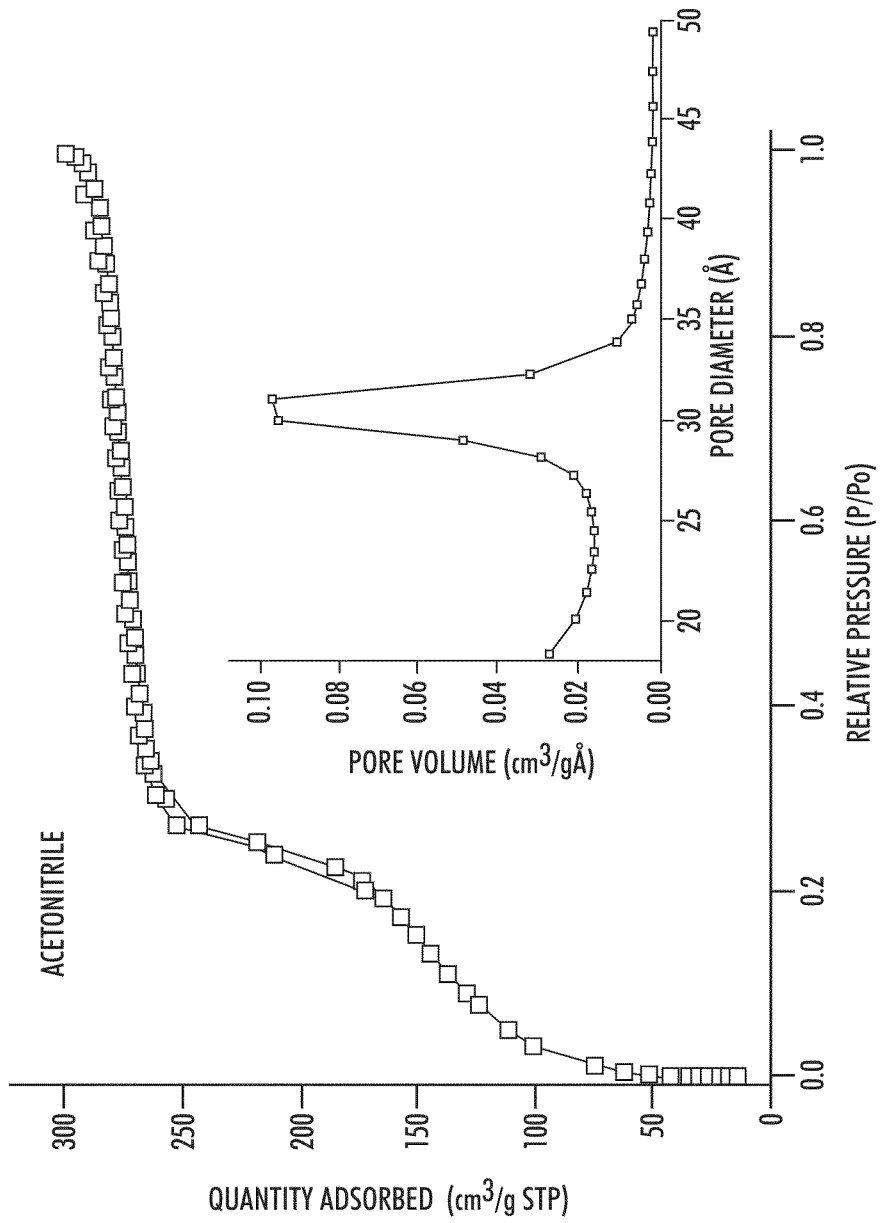
Figure 16A:
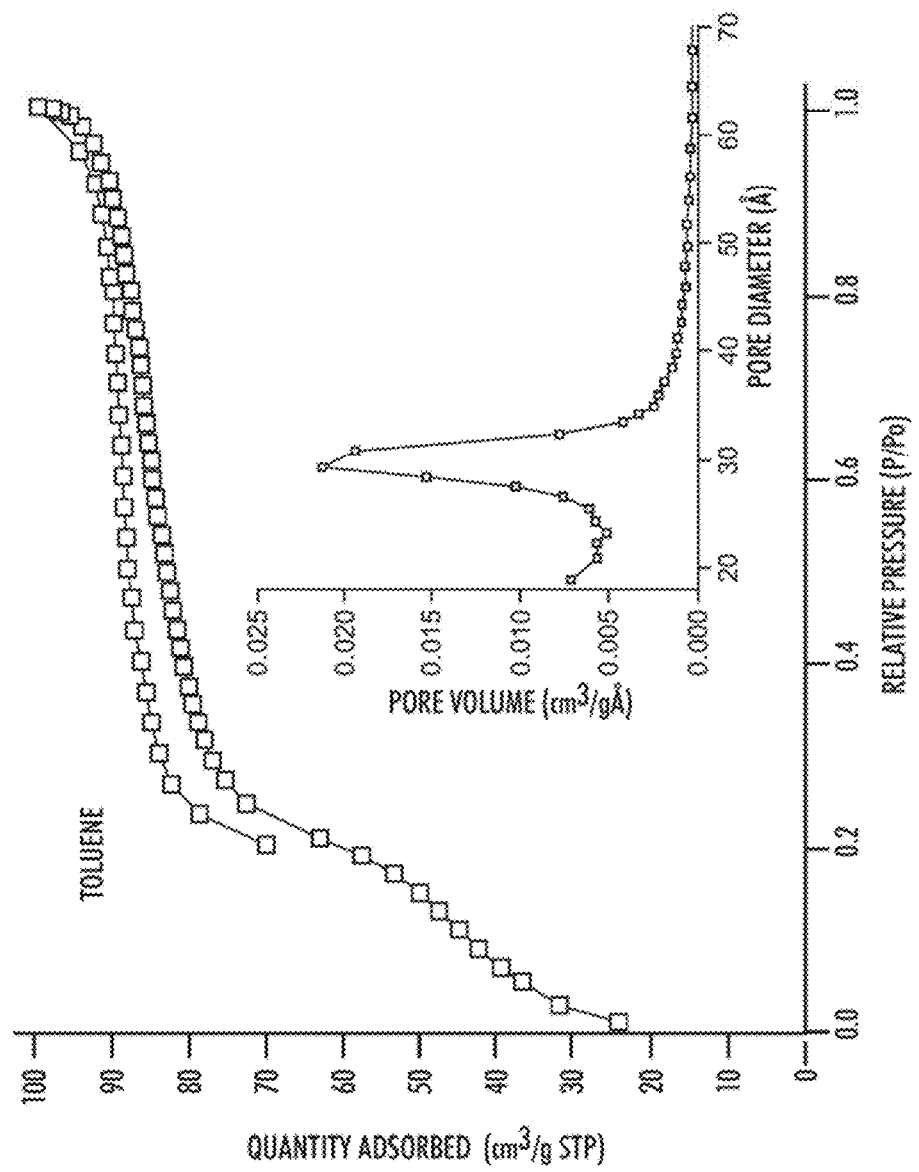
FIGS. 16A-16B are nitrogen gas adsorption isotherms and pore-size distribution data for 3-aminopropyl-grafted mesoporous samples grafted in non-polar solvents.
Figure 16B:
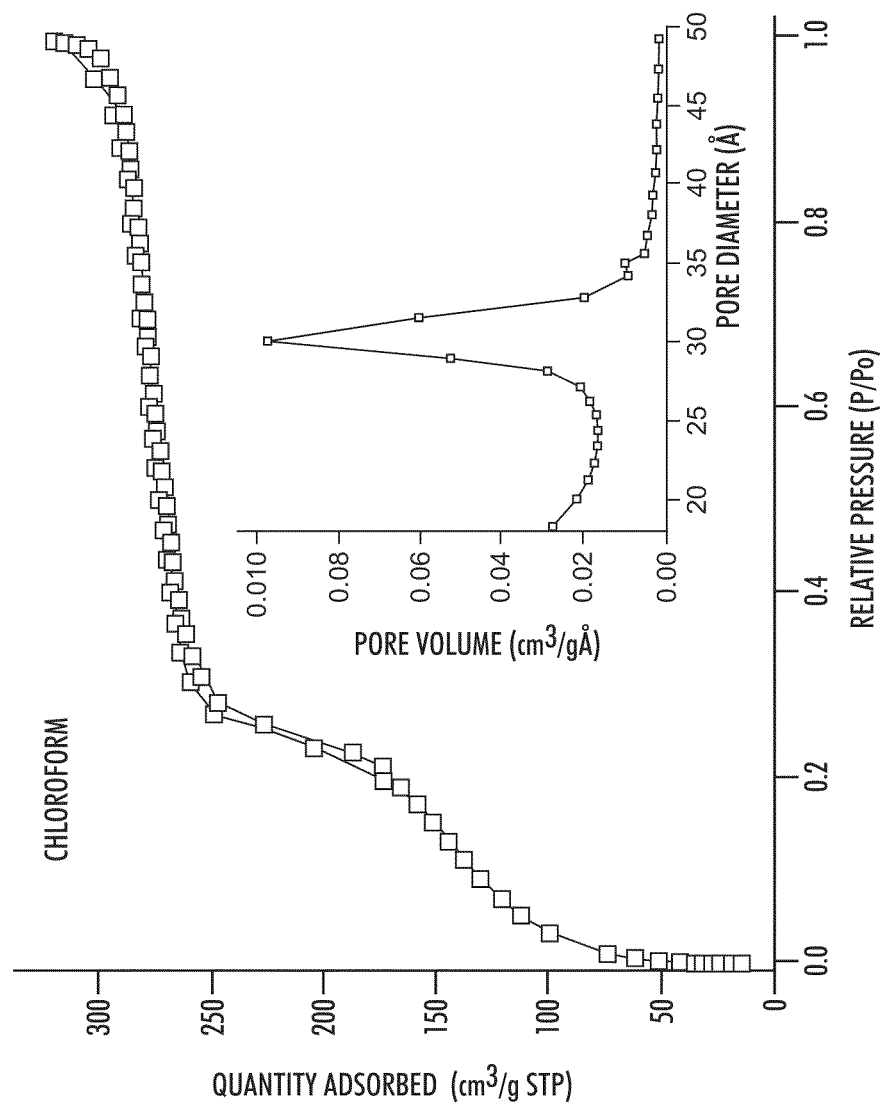

FIG. 12A is a graph of powder X-ray diffraction patterns of catalysts prepared in polar protic solvents; and FIG. 12B is a graph of powder X-ray diffraction patterns of catalysts prepared in dipolar protic solvents or in non-polar solvents. FIG. 13A is a set of transmission electron microscopy images of the MCM-41 starting material, and catalysts prepared in isopropanol and in dimethylformamide; and FIG. 13B is a transmission electron microscopy image of a catalyst prepared in ethyl acetate. $N_2$ gas adsorption isotherms and pore-size distribution data of the parent MCM-41 are shown in FIG. 5B. The corresponding data for the 3-aminopropyl-grafted mesoporous samples grafted in various solvents are shown in FIGS. 14A-14C (polar protic solvents), FIGS. 15A-15F (dipolar aprotic solvents), and FIGS. 16A-16B (non-polar solvents).

The transmission electron microscopy (TEM) images and the X-ray diffraction (XRD) patterns of the samples indicated that all the functionalized samples had highly ordered mesostructures with unit cell dimensions of about 43 Å. Mesopore channels 22 are particularly visible in the TEM image for the sample synthesized in ethyl acetate (FIG. 13B). The TEM and XRD also revealed that grafting of the MCM-41 sample in various polar, dipolar, and non-polar solvents did not cause major structural difference between the samples and when compared to MCM-41. This was further corroborated by $N_2$ gas adsorption data, which showed monodisperse pore size distributions and Type-IV isotherms for all the samples, which are indicative of mesoporous structures. However, the surface areas of the materials varied from 150-900 m$^2$/g while the average pore sizes varied between 28 to 35 Å depending on the solvent used or the percentage of organofunctional groups grafted. The structural data of the MCM-41 starting material and the functionalized samples of this investigation are shown in Table 3.

TABLE 3

Structural data of MCM-41 and 3-aminopropyl-functionalized mesoporous materials grafted in various solvents.

| Sample | Dielectric Constant | Surface Area (m$^2$/g) | Pore Volume (cm$^3$/g) | Unit Cell, $a_0$, (Å)$^a$ | Pore Diameter (Å) | Wall Thickness (Å)$^b$ |
|---|---|---|---|---|---|---|
| Parent Sample | | | | | | |
| MCM-41 | — | 982 ((±6) | 0.81 | 44.3 | 33.8 | 10.5 |
| Polar Solvents | | | | | | |
| Isopropanol | 18 | 902 (±7) | 0.78 | 44.5 | 31.2 | 13.3 |
| Ethanol | 24 | 905 (±3) | 0.71 | 44.4 | 31.4 | 13.0 |
| Methanol | 33 | 864 (±3) | 0.71 | 44.5 | 31.2 | 13.3 |
| Dipolar, Aprotic Solvents | | | | | | |
| Ethyl acetate | 6.0 | 153 (±4) | 0.14 | 45.4 | 34.9 | 10.5 |
| THF | 7.5 | 293 (±7) | | 44.3 | 30.1 | 14.2 |
| Acetone | 21 | 617 (±7) | 0.50 | 44.3 | 30.0 | 14.3 |
| DMF | 38 | 501 (±11) | 0.27 | 44.6 | 29.4 | 15.2 |

TABLE 3-continued

Structural data of MCM-41 and 3-aminopropyl-functionalized mesoporous materials grafted in various solvents.

| Sample | Dielectric Constant | Surface Area ($m^2/g$) | Pore Volume ($cm^3/g$) | Unit Cell, $a_o$, (Å)[a] | Pore Diameter (Å) | Wall Thickness (Å)[b] |
|---|---|---|---|---|---|---|
| DMSO | 47 | 451 (±11) | | 44.4 | 31.1 | 13.3 |
| Acetonitrile | 82 | 618 (±6) | 0.46 | 44.1 | 28.8 | 15.3 |
| Non-polar Solvents | | | | | | |
| Toluene | 2.4 | 259 (±5) | 0.20 | 45.6 | 31.5 | 14.1 |
| Chloroform | 4.8 | 628 (±7) | 0.49 | 44.5 | 29.8 | 14.7 |

[a] $a_o = 2d_{100}/3^{1/2}$ (Å) for 2-D hexagonally ordered materials
[b] Wall thickness is defined as Unit Cell Diameter – Pore Diameter.

Figure 17A:
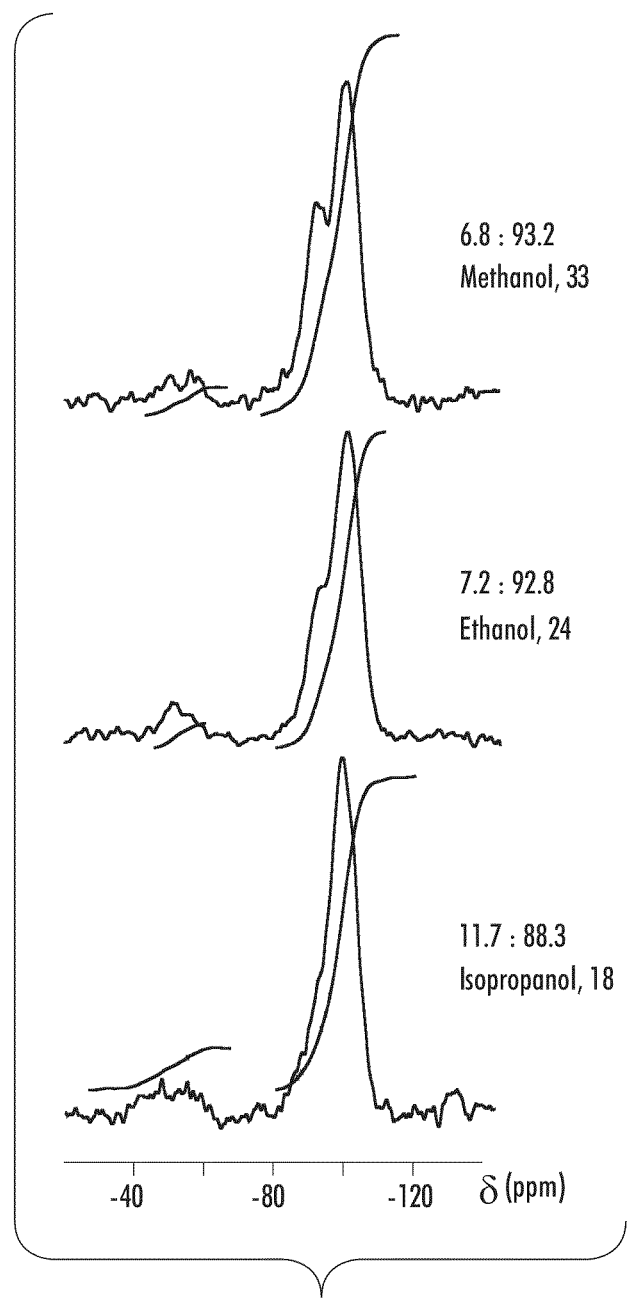
FIGS. 17A-17C are the respective solid-state $^{29}Si$ MAS NMR spectra of 3-aminopropyl-functionalized samples in polar protic solvents, dipolar aprotic solvents, and non-polar solvents.
Figure 17B:
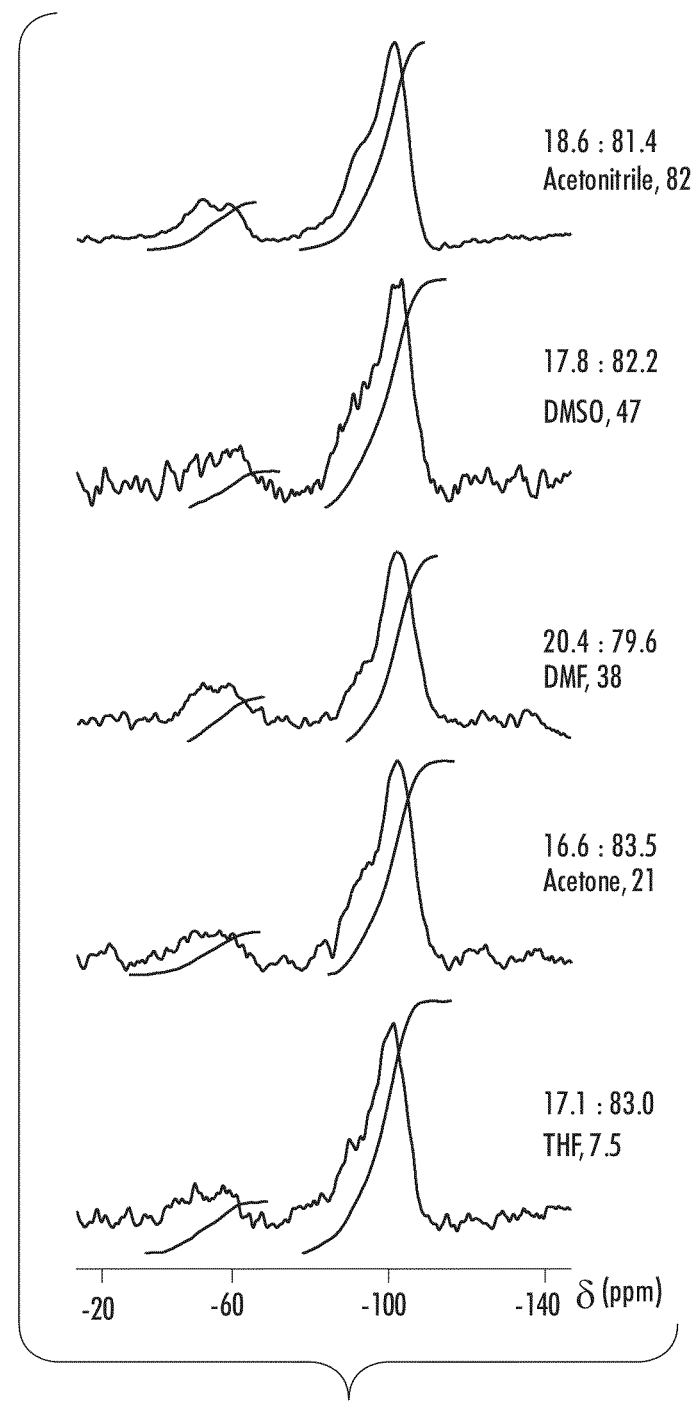
Figure 17C:
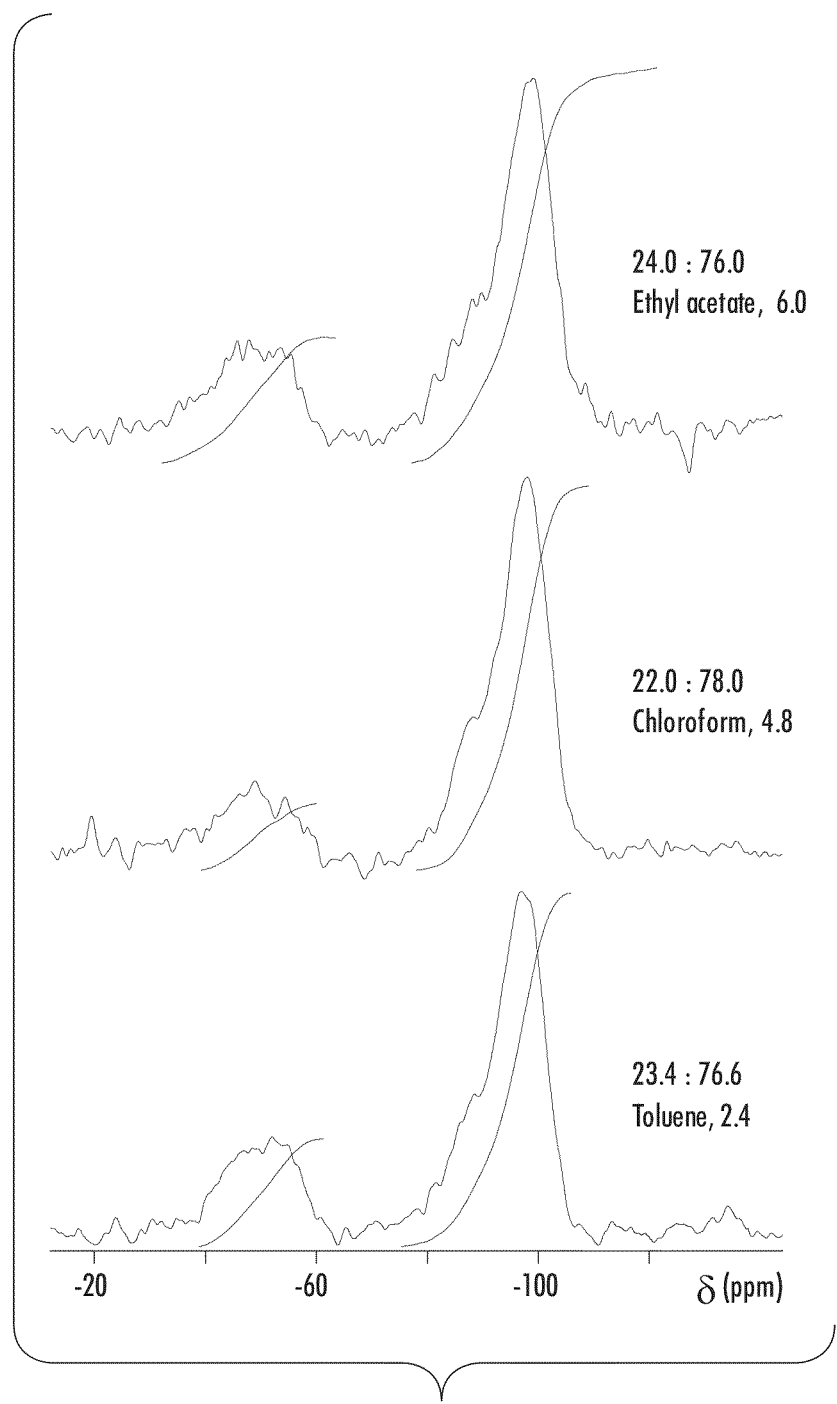
Figure 18A:
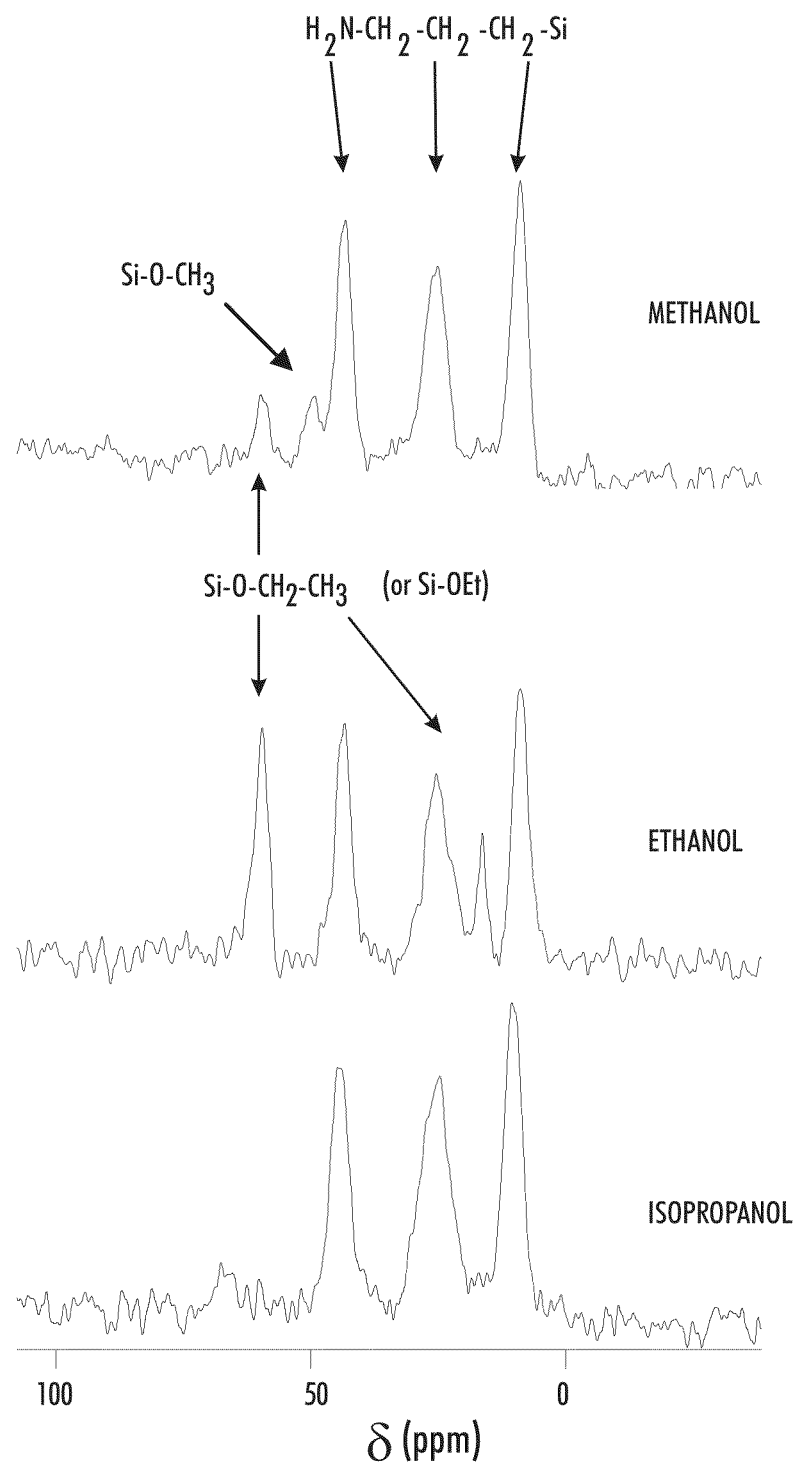
FIGS. 18A-18C are the respective solid-state $^{13}C$ CP MAS NMR of 3-aminopropyl-functionalized samples in polar protic solvents, dipolar aprotic solvents, and non-polar solvents.
Figure 18B:
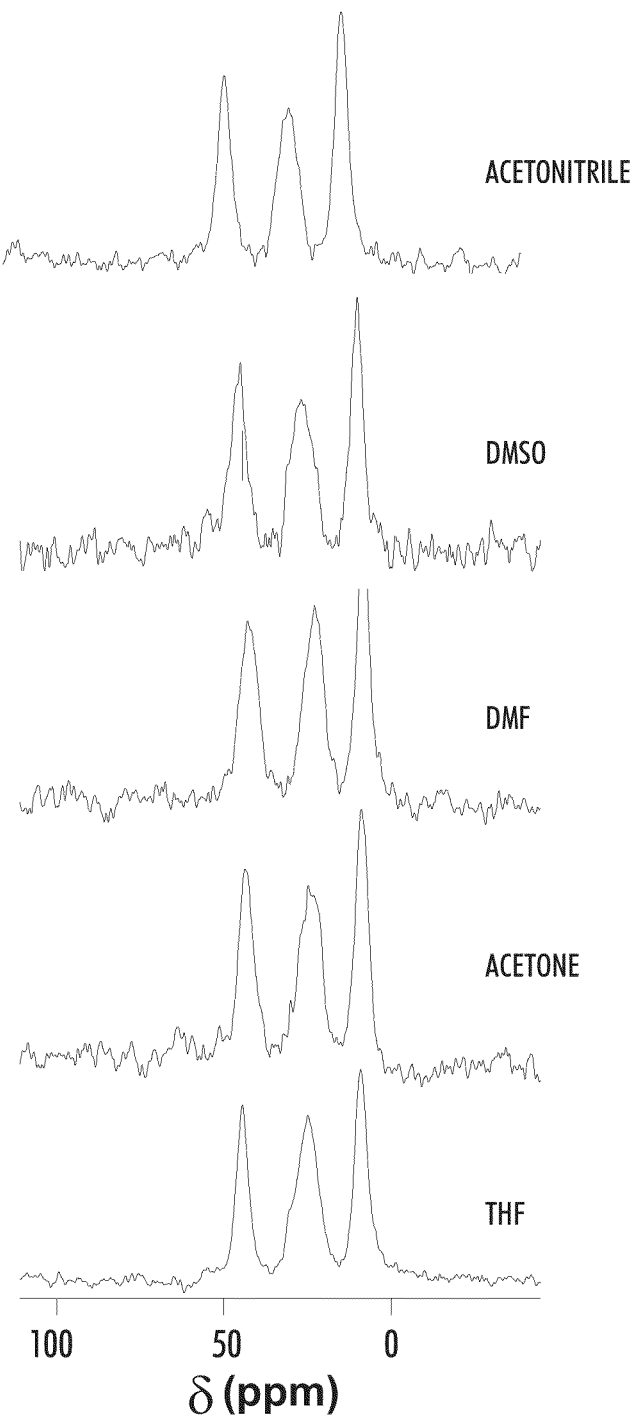
Figure 18C:
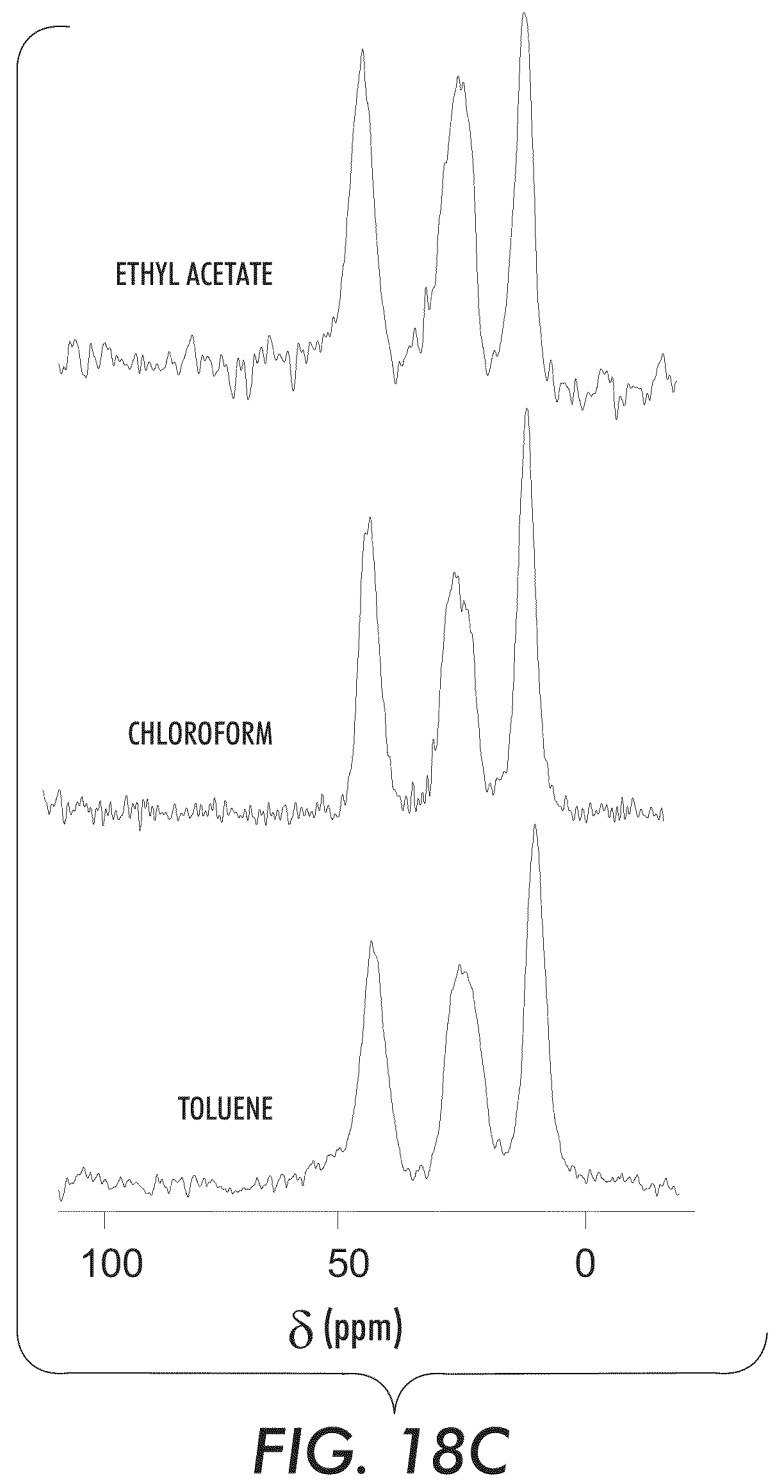
Figure 19A:
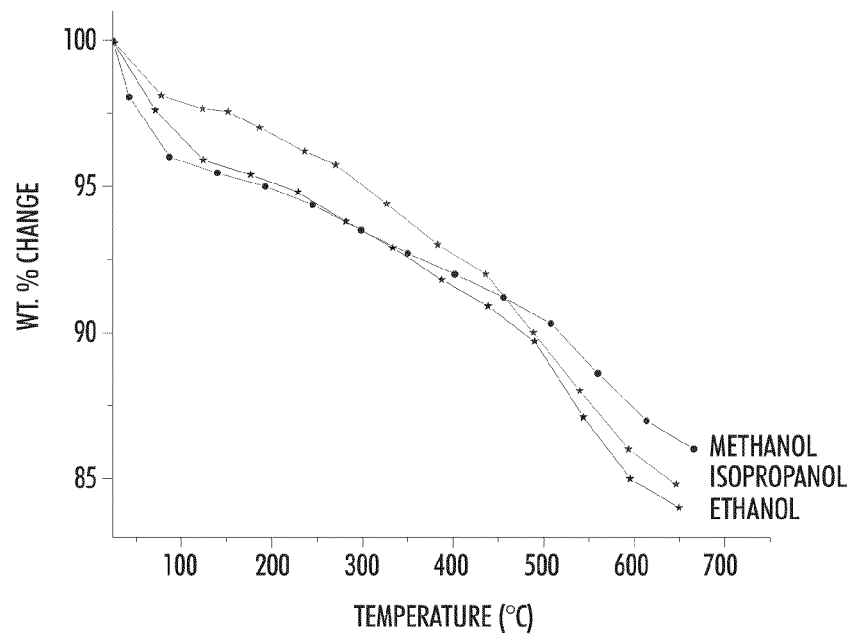
FIGS. 19A-19B are the respective thermogravimetric traces of 3-aminopropyl-functionalized samples in polar protic solvents, dipolar aprotic solvents, and non-polar solvents.
Figure 19B:
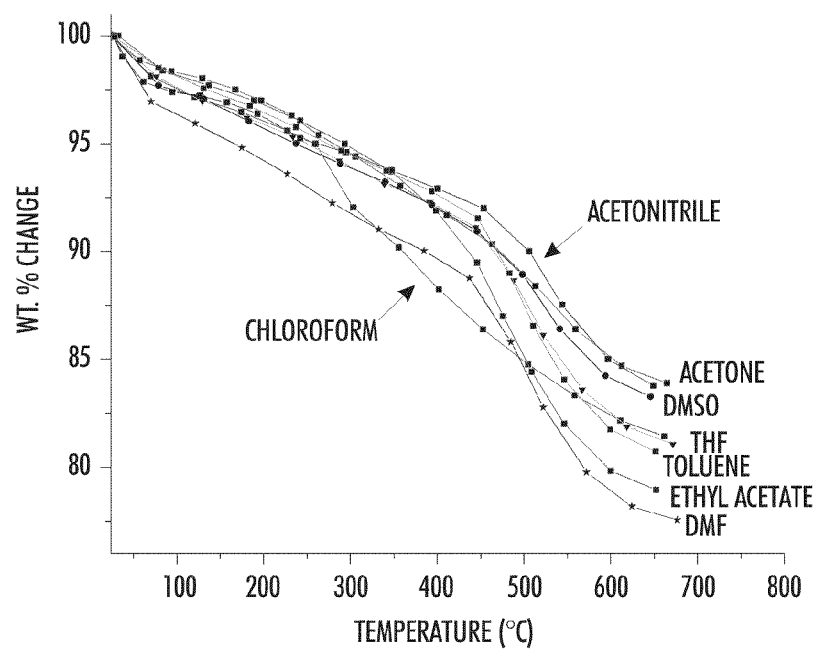

FIGS. 17A-17C are the respective solid-state $^{29}$Si MAS NMR spectra of 3-aminopropyl-functionalized samples in polar protic solvents, dipolar aprotic solvents, and non-polar solvents; FIGS. 18A-18C are the respective solid-state $^{13}$C CP MAS NMR of 3-aminopropyl-functionalized samples in polar protic solvents, dipolar aprotic solvents, and non-polar solvents; and FIGS. 19A-19B are the respective thermogravimetric traces of 3-aminopropyl-functionalized samples in polar protic solvents, dipolar aprotic solvents, and non-polar solvents. Additionally, Table 4 summarizes the results of the grating syntheses in the various solvents.

TABLE 4

Results of grafting synthesis of 3-aminopropyl-functionalized mesoporous materials in various solvents.

| Sample | Dielectric Constant (D) | % T[a] | Wt. % (100-600° C.) | Surface Area ($m^2/g$) | Efficiency (Yield in 12 min)[b] |
|---|---|---|---|---|---|
| Polar Solvents | | | | | |
| Isopropanol | 18 | 11.7 | 12.0 | 902 (±7) | 97.5% |
| Ethanol | 24 | 7.2 | 12.5 | 905 (±3) | 95.0% |
| Methanol | 33 | 6.8 | 8.0 | 864 (±3) | 91.5% |
| Dipolar, Aprotic Solvents | | | | | |
| Ethyl acetate | 6.0 | 24.0 | 18.5 | 153 (±4) | 28.0% |
| THF | 7.5 | 17.1 | 15.4 | 293 (±7) | 38.0% |
| Acetone | 21 | 16.6 | 13.5 | 617 (±7) | 91.5% |
| DMF | 38 | 20.4 | 17.5 | 501 (±11) | 59.0% |
| DMSO | 47 | 17.8 | 13.8 | 451 (±11) | 93.4% |
| Acetonitrile | 82 | 18.6 | 14.0 | 618 (±6) | 95.8% |
| Non-polar Solvents | | | | | |
| Toluene | 2.4 | 23.4 | 17.8 | 259 (±5) | 41.0% |
| Chloroform | 4.8 | 22.0 | 15.2 | 628 (±7) | 85.0% |

[a] % T is the percentage of aminopropylsilica {$(OH)_xO_ySi-(CH_2)_3NH_2$} obtained from the integration of peaks in the $^{29}$Si MAS NMR spectra.
[b] The yield of the reaction between p-hydroxy benzaldehyde and nitromethane at 15 min of reaction time for 20 mg catalyst.
THF: tetrahydrofuran;
DMF: N,N-dimethylformamide; and
DMSO: dimethylsulphoxide.

Figure 20:
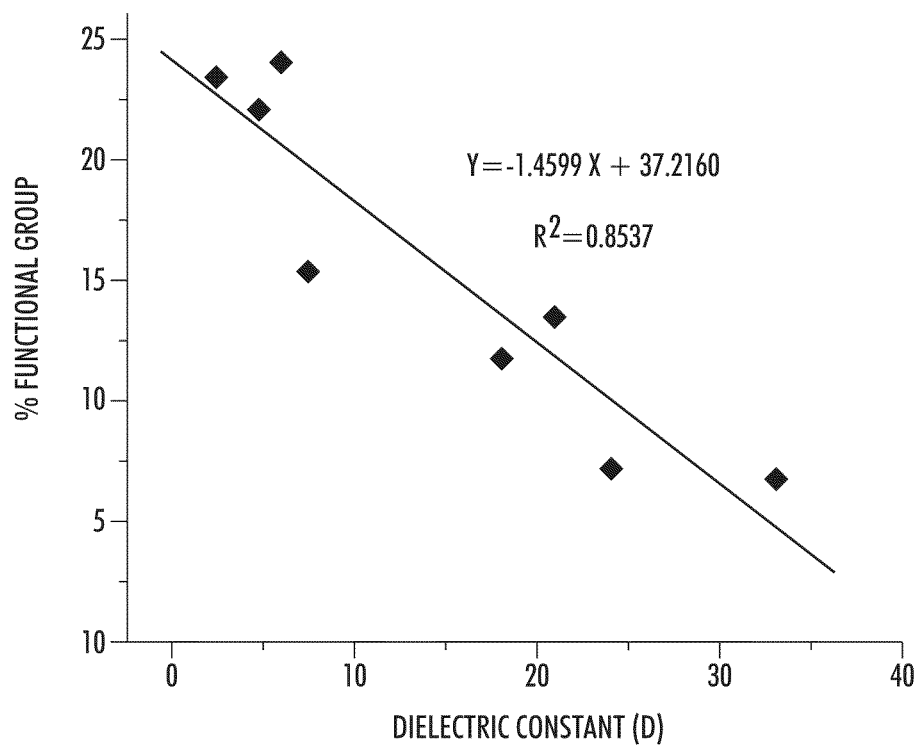
FIG. 20 is a graph showing the correlation between the dielectric constant of reaction medium solvent and the percent of functional groups grafted to available sites in the pores of the MCM-41 substrate.

The percentage of the grafted 3-aminopropyl groups (column 3 in Table 4) was determined from the weight loss in the range of 150-600° C. on thermogravimetric analysis (TGA) traces (FIGS. 19A-19B) and by quantitative solid-state $^{29}$Si MAS NMR spectroscopy (FIGS. 17A-17C). The results indicated that samples grafted in polar, protic solvents to have lower percentages of 3-aminopropyl groups than those grafted in non-polar and dipolar, aprotic solvents. Without wishing to be bound to any particular theory, the applicants believe that this is most likely due to the strong hydrogen bonding between the aminorganosilane and the polar solvents, which lowers the tendency of aminorganosilane to go to the hydrophilic silanol groups to graft. The percentage of the 3-aminopropyl was also correlated with the solvent's dielectric constant as shown in FIG. 20.

For example, for polar, protic solvents, the trend in the percentage of organic group was isopropanol>ethanol>methanol, indicating that solvents with lower dielectric constant grafted more organic groups. A similar dielectric constant dependent trend was exhibited by a series of diprotic, apolar solvents. Generally, the increase in dielectric constant of the solvent resulted in less number of aminopropyl groups (but higher surface areas), which the applicants believe is most likely due to the lower Coulomb's interactive force ($F=kq_1q_2/\epsilon r^2$) between protonated aminopropylsilane cation and deprotonated surface silanol anion. The Coulomb's interactive force is inversely proportional with the dielectric constant of the solvent as expressed by Coulomb's law.

Referring in particular to FIGS. 17A and 19A, the applicants also believe that the observed ethoxy and methoxy groups in samples grafted in methanol and ethanol in indicate possible exchange of alkoxides from the solvents with the surface silanol groups ($Si-OH+EtOH \Leftrightarrow Si-OEt+H_2O$) and the presence of some residual unhydrolyzed alkoxides. The increased weight loss in the TGA (in the range of 150-600° C.) for these samples on the TGA traces could also be due to the additional loss of these alkoxide groups.

Figure 21:
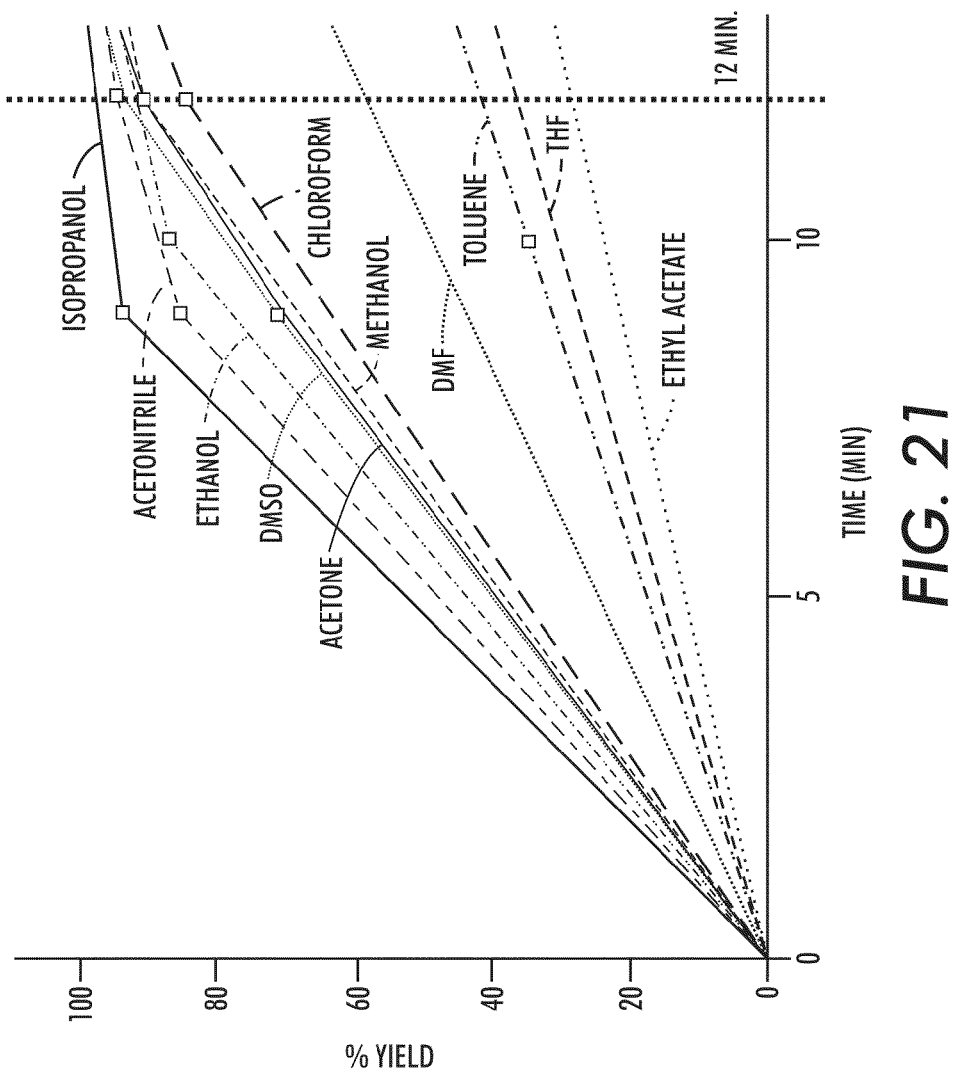
FIG. 21 is a graph of reaction yield versus time for the Henry reaction p-hydroxy benzaldehyde and nitromethane that was catalyzed by 3-aminopropyl-functionalized samples prepared in polar protic solvents, dipolar aprotic solvents, and non-polar solvents.
Figure 22:
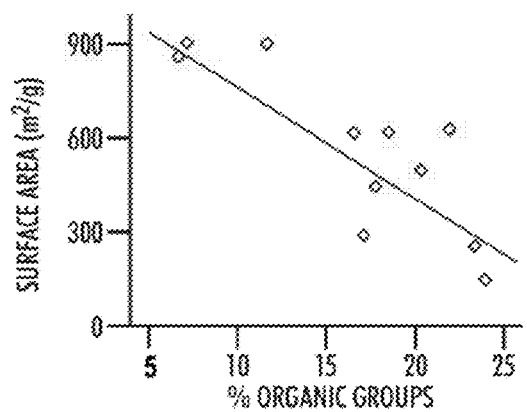
FIG. 22 is a graph of surface area versus percent of functional groups grafted to available sites.
Figure 23:
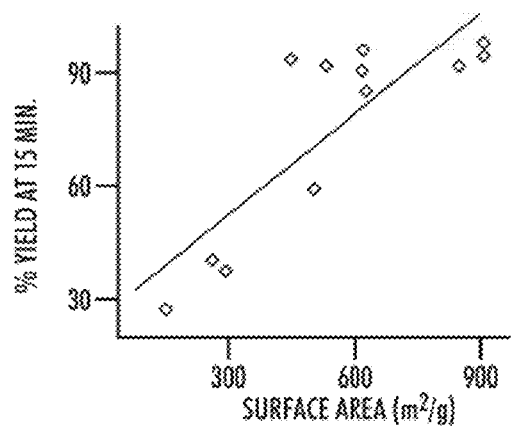
FIG. 23 is a graph of % yield in the Henry reaction at 15 minutes reaction time versus catalyst surface area.
Figure 24:
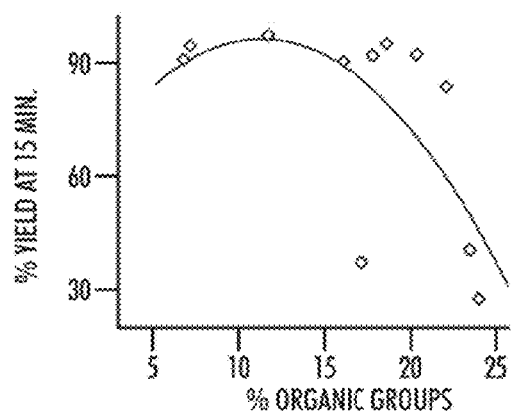
FIG. 24 is a graph of % yield in the Henry reaction at 15 minutes reaction time versus percent of functional groups grafted to available sites.

In this solvent medium investigation, the Henry reaction between p-hydroxy benzaldehyde and nitromethane at 90° C. was carried out, resulting in the formation of nitrostyrene as described previously herein. The results of this reaction study for the various solvents and related data of Table 4 are shown in FIGS. 21-24. FIG. 21 is a graph of reaction yield versus time for this reaction that was carried out in the various solvent media. FIG. 22 is a graph of surface area versus percent of functional groups grafted to available sites. FIG. 23 is a graph of % yield in the Henry reaction at 15 minutes reaction time versus catalyst surface area, and FIG. 24 is a graph of % yield in the Henry reaction at 15 minutes reaction time versus percent of functional groups grafted to available sites.

The efficiency of the 3-aminopropyl-functionalized materials to catalyze this Henry reaction showed an unexpected trend. Referring in particular to FIG. 21 and Table 4, it can be seen that for the polar, protic solvents used for grafting, the catalytic efficiency of the materials decreased in the order of isopropanol>ethanol>methanol. This is inconsistent with the concentrations of grafted organoamines. Unprecedented higher catalytic efficiency by a sample grafted in isopropanol was obtained, even compared to the catalyst AP-E1 prepared in ethanol and previously described in this specification.

Isopropanol resulted in a slightly higher number of grafted organoamines compared to ethanol and methanol. Upon grafting in dipolar, aprotic solvents, the concentration of organoamines increased, but the efficiency decreased except for acetonitrile. Further, the sample grafted in acetone, which likely formed imines as indicated by the obvious yellowish color of the reaction solution, showed an exceptionally higher yield in the series of solvents as well.

The applicants have further found that samples that have higher surface areas also tend to have higher catalytic efficiency (FIG. 23). However, the differences in surface areas alone do not fully explain the observed differences in the catalytic efficiency. For instance, chloroform showed higher surface area than acetonitrile but the latter showed more catalytic efficiency.

Figure 25:
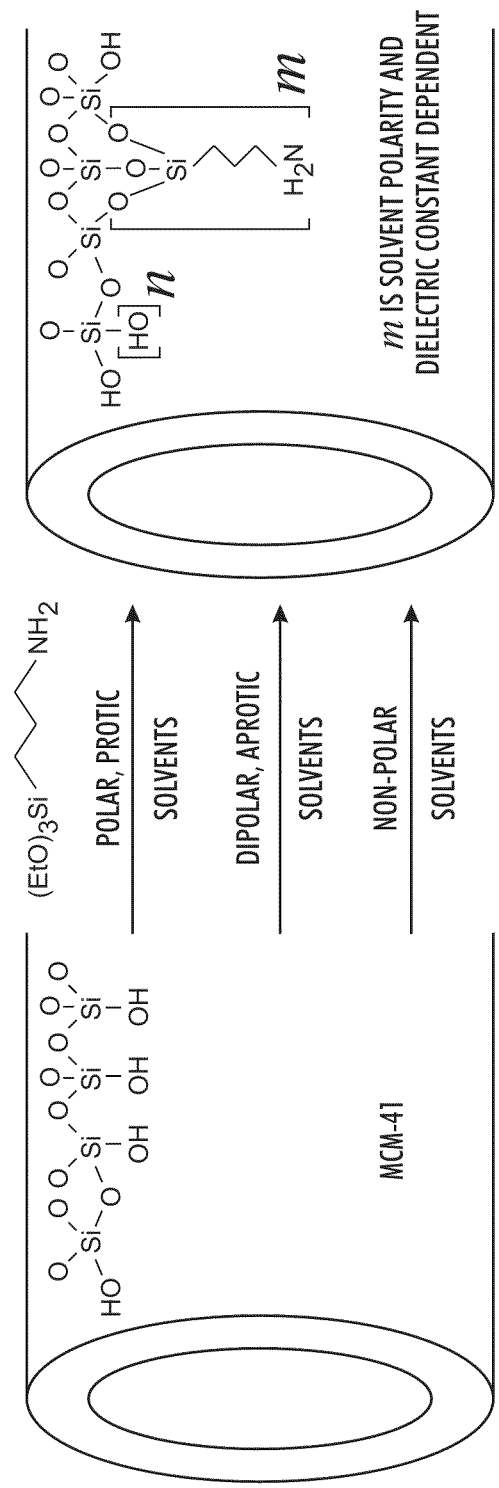
FIG. 25 is an illustration summarizing reaction schemes for converting a mesoporous material into certain catalysts having organoamine functional groups wherein the relative proportions of silanol and postgrafted organoamine are dependent upon the reaction solvent polarity and dielectric constant.

These results reveal that a combination of surface area and site-isolation of the catalytic sites played roles for observed differences in catalytic efficiency. This work also demonstrates that optimum grafting of catalytic sites and enhanced catalytic efficiency can be achieved by proper choice of grafting solvents. Referring to FIG. 25, the relative amount n of silanol groups and the relative amount m of organoamine groups that are present in the mesoporous catalyst material may be optimized to produce a catalyst of high efficiency. Based upon the applicants' discoveries, this may be accomplished in one embodiment by providing postgrafting of organoamine groups at a density of between about 6 and about 15 percent of the available sites. In another embodiment, this may be accomplished by performing the organoamine postgrafting reaction in a polar aprotic solvent. The solvent may be a low molecular weight alcohol, such as methanol, ethanol, and preferably isopropanol. In another embodiment, this may be accomplished by performing the organoamine postgrafting reaction in acetonitrile. In another embodiment, this may be accomplished by performing the organoamine postgrafting reaction in acetone.

Selective, Efficient Trifunctional Nanoporous Catalysts via Co-Placement of Site-Isolated Multifunctional Groups on Mesoporous Materials A synthetic strategy to selective and efficient trifunctional mesoporous catalysts for various p-substituted hydrophilic or hydrophobic reactants in the Henry reaction has been discovered. The synthesis involves the grafting of two site-isolated organofunctional groups simultaneously in polar solvents or by sequential grafting of one group in a polar solvent followed by another in a polar or non-polar solvent. These synthetic conditions allowed the co-placement of two different organic groups in a site-isolated arrangement, along with many residual silanols on the surface of the nanoporous materials.

The applicants have demonstrated this for 3-aminopropyl groups and a secondary functional group, which included ureidopropyl, 3-mercaptopropyl, or methyl groups. By judicious choice of the types and the relative concentrations of the two functional groups and the residual silanols in the materials, the selective catalytic properties for hydrophilic or hydrophobic reactants and the efficiency of the catalysts were tuned. Selectivities for the hydrophilic and hydrophobic reactants, with values as high as 7:1, were achieved by simply changing the loading of secondary organic groups in the materials. Furthermore, the site-isolation grafting of these multiple functional groups enabled a high catalytic efficiency, with typical values of nearly 100% conversion in less than 30 minutes. To the best the applicants' knowledge, there are no examples in the literature of a single functionalized nanoporous material with selectivity for both hydrophilic and hydrophobic reactants over various time intervals with such high efficiency and short conversion time.

The synthesis of the trifunctional catalysts was achieved by extending the synthetic approach previously described herein, in which an efficient bifunctional catalyst for the Henry reaction is produced containing a single type of site-isolated organocatalytic groups. In this invention, the co-placement of judiciously chosen multiple site-isolated functional groups in controlled number is achieved by grafting multiple organosilanes in polar solvents to produce not only efficient but also selective catalysts both for hydrophobic and hydrophilic reactants. This has been demonstrated for 3-aminopropyl organocatalytic groups and a secondary functional group, which included ureidopropyl, 3-mercaptopropyl, or methyl groups, which allowed modifying the materials' surface properties. Furthermore, many residual silanol groups remained on the materials' surface due to polar solvent being used for the grafting. The applicants have discovered that having the silanol groups has proven to be important in order to maximize catalytic efficiency.

The catalytic properties of the resulting materials were investigated in the Henry reaction between various p-substituted benzaldehydes and nitromethane, for each reactant separately, or in 1:1 mole ratio of reactant mixtures. The reactants included p-hydroxybenzaldehyde (p-OH), p-butoxybenzaldehyde (p-But), p-methylbenzaldehyde (p-Me), and p-methoxybenzaldehyde (p-MeO). The samples containing site-isolated 3-aminopropyl groups alone or with ureidopropyl groups preferentially catalyzed a hydrophilic reactant, p-hydroxybenzaldehyde, with a selectivity of 1.6 to 2.8 times over a relatively more hydrophobic reactant p-butoxybenzaldehyde. However, upon introduction of hydrophobic organic groups such as 3-mercaptopropyl and methyl groups along with the 3-aminopropyl groups, the selectivity of the catalysts to hydrophilic benzaldehydes decreased relative to the hydrophobic benzaldehydes. By systematic grafting of site-isolated 3:1 and 9:1 mol ratios of methyl:aminopropyl groups, the selective catalytic property for the hydrophobic reactants increased to as high as 4:1. It is especially noteworthy that these selectivities were accompanied by an extremely small reaction time (typically 15-30 minutes) and relatively high % conversion (very nearly 100% in many cases). This is in contrast to previously reported results, such as the work reported by Huh et al. in *J. Am. Chem. Soc.* 2004, 126, 1010-1011, where only a maximum of 50% yield over 24 hrs was achieved and selectivity only for hydrophobic reagents was possible.

Furthermore, the applicants have performed a study of % yield versus time plots to understand the kinetic progress of the reaction for both individual reactants and for various combination of a mixture of two reactants by mesoporous catalysts. It has been observed that selectivity for hydrophilic or hydrophobic reactants by a single catalyst varied with time, with maximum selectivity reaching at an intermediate time. From a comparative study of MCM-41 and SBA-15 type materials functionalized with similar organic functional groups, it has been found that the size of the nanopores dictates selectivity for our reactants (i.e. it appears that the steric bulk of the reactants or the channel pores of the catalysts plays a definite role in determining selectivity). The presence of residual water in the catalysts was also found to affect the selectivity of the catalysts. Comparative results with respect to homogeneous catalysts were also presented to demonstrate the efficiency of our heterogeneous catalysts. Further, it was found out that reaction yields for p-OH decreased when present in a reaction mixture with relatively non-polar reactants, p-Me and p-But.

Details of the syntheses of the various catalysts will now be provided. It is to be understood that certain aspects of the syntheses, such as the specific sources of reagents, are exemplary and are not to be construed as limiting.

Materials and Reagents: p-Hydroxybenzaldehyde (p-OH), p-butoxybenzaldehyde (p-But), p-tolualdehyde (p-methylbenzaldehyde, p-Me), p-methoxybenzaldehyde (p-MeO), cetyltrimethylammonium bromide (CTAB), tetraethylorthosilicate (TEOS), and 3-aminoproyltrimethoxysilane (APTS), poly(ethylene oxide)-block-poly(butylene oxide)-block-poly(ethylene oxide) (P123), and nitromethane were obtained from Sigma-Aldrich Corporation of St. Louis, Mo. 3-mercaptopropyltri-methoxysilane (MPTS), ureidopropyltriethoxysilane (50% in methanol) (UDPS), and methyltrimethoxysilane (METS) were obtained from Gelest, Inc. of Morrisville, Pa. Anhydrous toluene and isopropanol were purchased from Pharmco-AAPER of Brookfield, Conn. and Shelbyville, Ky.

MCM-41 and SBA-15 were used as the mesoporous silica substrate material. The MCM-41 was synthesized as described previously herein. SBA-15 was synthesized as follows: 4.0 g poly(ethylene oxide)-block-poly(butylene oxide)-block-poly(ethylene oxide) (P123), Pluronic 123, was dissolved in 30 g of water and 120 g of 2 M HCl solution with stirring at about 40° C. Then 8.50 g of TEOS was added into that solution with stirring at about 40° C. for 24 hours. The mixture was kept at 80° C. to age for 12 hours under static condition. Then the solution was cooled to room temperature and filtered. The precipitate was washed with 1:1 ethanol and water three times (3×20 mL). The precipitate was let to dry under ambient condition. The surfactant was extracted via solvent-extraction by stirring the 1 g sample in 100 mL of 1:1 volume ethanol and diethyl ether solution for 5 hours at about 40° C. Then it was filtered and washed with ethanol three times (3×20 mL). Then it was allowed to dry, resulting in the SBA-15 starting material for subsequent postgrafting.

One-pot syntheses of site-isolated trifunctional mesoporous silica by grafting were carried out as follows: Two organic groups consisting of a 3-aminopropyl (AP) and a secondary organic group ureidopropyl (UDP), mercaptopropyl (MP), or methyl (ME) in about 1:1 mole ratio were grafted onto MCM-41 (or SBA-15) by stirring 1:1 mol ratio of APTS with UDPS, MPTS, or METS onto MCM-41 in isopropanol. Briefly, for example, 500 mg of the MCM-41 sample was stirred in a mixture of excess organosilanes containing 1.842 mmol of APTS and 1.842 mmol METS in 325 mL anhydrous isopropanol under reflux at about 80° C. for 6 hours. The solution was filtered and the precipitate was washed with ethanol. This precipitate was dried under ambient condition and it was labeled as APME-1. Similarly other samples were prepared; details are provided in Table 5, and FIG. 26, which depicts the general reaction scheme.

The samples obtained in one-step from the 1:1 mol mixture of the two organosilanes were labeled as: APUD1, APMP1, and APME1, where "AP" stands for 3-aminopropyl, "UD" for ureidopropyl, "MP" for 3-mercaptopropyl, and "ME" for methyl. The subscript "1" was to indicate the synthesis being carried out in one-step grafting. A control sample was also prepared by grafting APTS alone (3.684 mmol) onto MCM-41 under reflux at about 80° C. in isopropanol for 6 hours. The resulting sample was labeled as API1.

TABLE 5

Synthesis and structural data of multifunctional mesoporous materials and the control samples.

| Sample | Substrate/Organosilanes, Solvent | Unit Cell (Å) | Pore Width (Å) | Wall Thickness (Å) | BET Surface Area, m²/g | Pore Volume, cm³/g |
|---|---|---|---|---|---|---|
| MCM-41 | — | 45 | 32 | 13 | 983 | 0.98 |
| APUD1 | MCM-41/1:1 APTS + UDPS, Isopropanol | 44 | 29 | 15 | 833 | 0.64 |
| APMP1 | MCM-41/1:1 APTS + MPTS, Isopropanol | 43 | 28 | 15 | 903 | 0.72 |
| APME1 | MCM-41/1:1 APTS + METS, Isopropanol | 44 | 27 | 17 | 896 | 0.70 |
| APUD2 | MCM-41/APTS, Isopropanol; then UDPS, Isopropanol | 45 | — | — | — | — |
| APMP2 | MCM-41/APTS, Isopropanol; then MPTS, Isopropanol | 44 | 27 | 17 | 834 | 0.56 |
| APME2 | MCM-41/APTS, Isopropanol; then METS, Isopropanol | 46 | 27 | 19 | 866 | 0.64 |
| APUD3 | MCM-41/UDPS, Isopropanol; then APTS, Isopropanol | 46 | 29 | 17 | 928 | 0.69 |
| APMP3 | MCM-41/MPTS, Isopropanol; then APTS, Isopropanol | 44 | 29 | 15 | 906 | 0.66 |
| APME3 | MCM-41/METS, Isopropanol; then APTS, Isopropanol | 46 | 27 | 19 | 907 | 0.70 |
| APME4 | MCM-41/1:3 APTS:METS, Isopropanol | 46 | — | — | — | — |
| APME5 | MCM-41/1:3 APTS:METS, Toluene | 46 | — | — | — | — |
| APME6 | MCM-41/1:9 APTS:METS, Isopropanol | 44 | — | — | — | — |
| API1 | MCM-41/APTS, Isopropanol | 43 | 28 | 15 | 950 | 0.65 |

TABLE 5-continued

Synthesis and structural data of multifunctional mesoporous materials and the control samples.

| Sample | Substrate/Organosilanes, Solvent | Unit Cell (Å) | Pore Width (Å) | Wall Thickness (Å) | BET Surface Area, m²/g | Pore Volume, cm³/g |
|---|---|---|---|---|---|---|
| API1A | MCM-41/APTS, Isopropanol, 12 h | 43 | 27 | 16 | 960 | 0.66 |
| UD1 | MCM-41/UDPS, Isopropanol | 44 | — | — | — | — |
| SBA15 | — | 107 | 61 | 46 | 557 | 0.75 |
| API1-SBA | SBA-15/APTS, Isopropanol | 113 | — | — | — | — |
| APUD1-SBA | SBA-15/1:1 APTS + UDPS, Isopropanol | 108 | 59 | 49 | 372 | 0.63 |
| APME1-SBA | SBA-15/1:1 APTS + METS, Isopropanol | 109 | 60 | 49 | 391 | 0.66 |
| APMP1-SBA | SBA-15/1:1 APTS + MPTS, Isopropanol | 108 | 60 | 48 | 353 | 0.60 |

Two-step synthesis of site-isolated trifunctional mesoporous silica by grafting was carried out as follows: Two series of organoamine functionalized samples were synthesized with two-step sequential grafting of the organosilanes. The first series contained samples grafted with APTS followed by the secondary functional groups. 500 mg MCM-41 and 3.684 mmol of APTS were mixed with 325 mL isopropanol at about 80° C. After stirring for 6 hours, the solution was filtered and the precipitate was washed with ethanol. This precipitate was mixed with 3.684 mmol of one of the secondary organosilanes, UDPS, MPTS, or METS, in 325 mL isopropanol and stirred at about 80° C. for 6 hours. The solution was filtered and the precipitates were washed with ethanol and dried under ambient conditions. The resulting samples were labeled as APUD2, APMP2, and APME2, respectively. Similarly, by changing the sequence of grafting or by stirring the MCM-41, first in UDPS, MPTS, or METS in isopropanol, followed by stirring the resulting samples in APTS in isopropanol, samples APUD3, APMP3, and APME3, respectively were obtained.

Graftings of MCM-41 with APTS:METS in 1:3 and 1:9 mole ratio in isopropanol and toluene were carried out in order to prepare samples containing large concentrations of hydrophobic groups in the following manner: MCM-41 was stirred in 1:3 mol ratio of APTS:METS in isopropanol and in toluene, and in 1:9 mol ratio of APTS:METS in isopropanol at about 80° C. for 6 hours. The solutions were filtered and the precipitates were washed with ethanol. The precipitates were dried under ambient conditions resulting in APME4, APME5, and APME6, respectively.

Grafting of organosilane onto SBA-15 in isopropanol: Additional samples were synthesized by stirring SBA-15 material with only APTS and in 1:1 mol ratio of APTS and METS, UDPS or MPTS. Typically 500 mg of SBA-15 was stirred in 3.684 mmol of APTS in 325 mL isopropanol under reflux at about 80° C. for 6 hours resulting in API1-SBA-15. Stirring of 500 mg of SBA-15 in a mixture of 1.842 mmol of APTS and 1.842 mmol METS in 325 mL isopropanol resulted in APME1-SBA. Similarly, APUD1-SBA and APMP1-SBA were also synthesized (see Table 5).

The parent mesoporous silica and multifunctional mesoporous samples were synthesized and studied using the chemical and physical analysis techniques described previously herein. Additional details are as follows:

The powder X-ray diffraction was measured using a Scintag powder diffractometer. The solid-state $^{13}$C (75.5 MHz) and $^{29}$Si (59.6 MHz) NMR spectra were acquired on a Bruker AVANCE 300 spectrometer. For $^{13}$C CP-MAS NMR experiments, the applicants employed a 7.0 kHz spin rate, 5 s recycle delay, 1 ms contact time, $\pi/2$ pulse width of 5.2 µs, and 1,000-3,000 scans using TPPM 1H decoupling. For the $^{29}$Si CP-MAS NMR experiments, we employed 7.0 kHz spin rate, 10 s recycle delay, 10 ms contact time, $\pi/2$ pulse width of 5.6 µs, and 256-1,024 scans using TPPM $^1$H decoupling. The $^{29}$Si MAS NMR experiments were done with 7.0 kHz spin rate, 100 s recycle delay, $\pi/6$ pulse width of 1.9 µs, and 700-4,000 scans using high power CW $^1$H decoupling. The solution $^1$H NMR was measured by Bruker DPX-300 NMR spectrometer. The BET gas adsorptions were measured with Micromeritics Tristar 3000 adsorption analyzer at 77 K by following previously reported procedures. The TEM images were taken by using a FEI Tecnai T-12 transmission electron microscope working at 120 KeV. The samples for TEM were prepared by sonicating the mesoporous samples in ethanol for 3 minutes, casting a drop of the solution on a formvar-carbon coated copper grid and allowing it to dry under ambient conditions.

Referring in particular to Table 5, the unit cell dimensions were obtained from the sample's d-spacing on XRD (unit cell, $a_o = 2 d_{100}/3^{1/2}$ for hexagonal $P_{6mm}$ mesostructures). Pore width data were obtained from the desorption branch of the $N_2$ gas adsorption isotherm. Wall thickness is defines as unit cell diameter-pore diameter. BET surface areas were obtained from the $N_2$ adsorption isotherm with the BET method.

Figure 26:
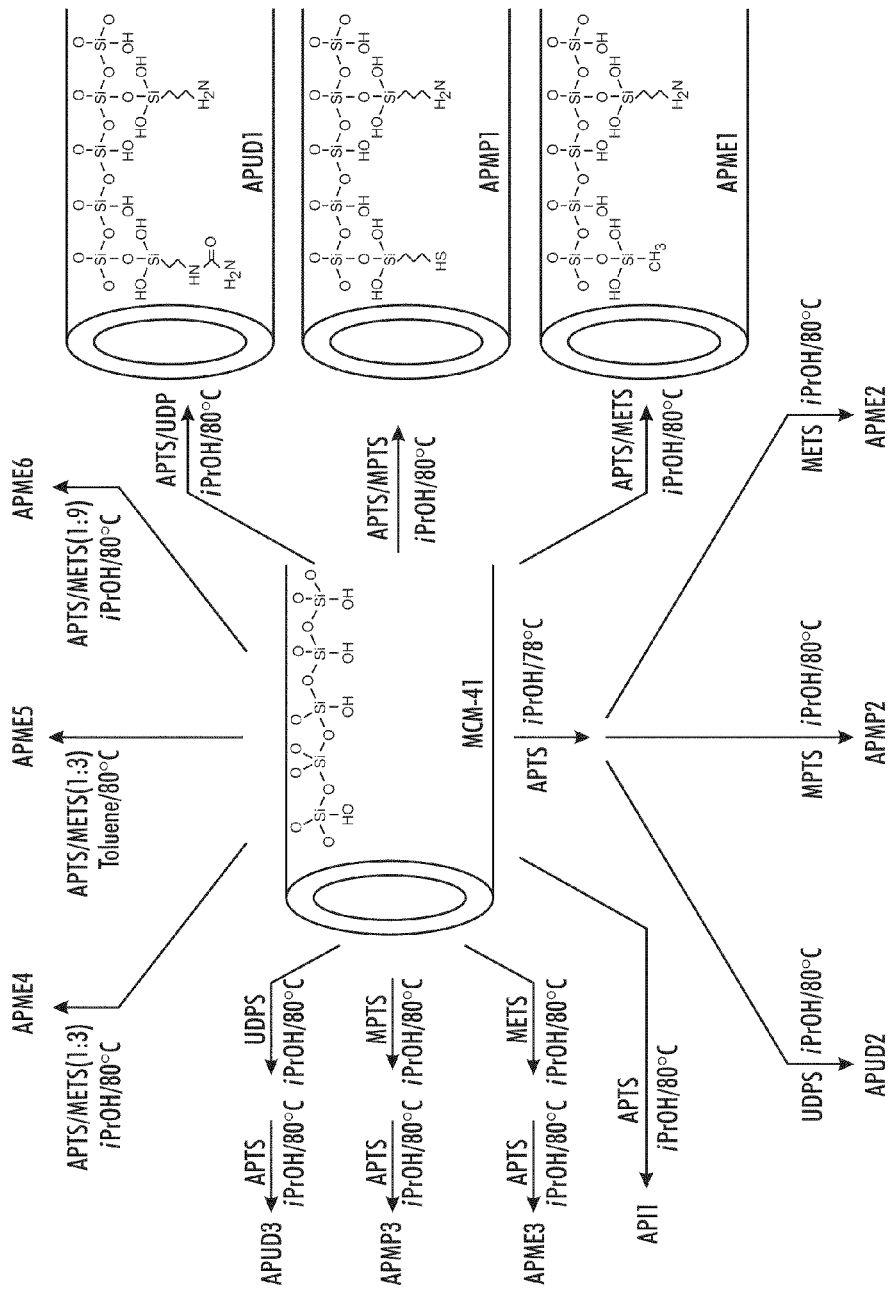
FIG. 26 is an illustration summarizing reaction schemes for converting a mesoporous material into certain mesoporous selective catalysts containing site-isolated 3-aminopropyl groups, many residual silanols, and secondary organic functional groups, including ureidopropyl, 3-mercaptopropyl, or methyl groups.

To briefly summarize, in this embodiment of the invention, a series of multifunctional mesoporous selective catalysts containing site-isolated 3-aminopropyl (AP) groups, many residual silanols, and secondary organic functional groups, including ureidopropyl (UD), 3-mercaptopropyl (MP), or methyl (ME) groups, were synthesized. This was carried out by grafting mixtures of the corresponding organosilanes in various proportions in isopropanol onto the channel walls of a well-ordered mesoporous silica (MCM-41) material in one step or by sequential grafting of one followed by another in isopropanol and/or toluene, as shown in FIG. 26 and Table 5.

Isopropanol was chosen as a solvent for grafting because the applicants have discovered that grafting of organosilanes in isopropanol and polar, protic solvents resulted in the most optimum site-isolated catalytic and the most efficient solid-base mesoporous catalyst for the Henry reaction, as described previously herein. Based on this discovery, the grafting of a mixture of two organosilanes in isopropanol under the same procedure was expected to yield two functional groups in the most optimum site-isolation. Therefore, samples APUD1, APMP1, and APME1, which were synthesized by grafting 1:1 mol ratio of the corresponding two organosilanes in isopropanol, were anticipated to have about a 1:1 mol ratio of site-isolated AP:UD, AP:MP, and AP:ME groups, respectively.

In contrast, the grafting of one functional group in isopropanol followed by the second functional group in the same solvent was expected to result in site-isolated groups in higher concentration of the first, and a relatively lower concentration of the second functional group, especially when the second grafting was done in isopropanol as compared to being done in toluene. The applicants thought this might occur because the number of silanol groups available to enable a second grafting would be fewer after the first grafting compared to that in the original parent material, and because isopropanol grafts less organoamine groups than toluene, as demonstrated by the applicants' previously described experiments.

Control samples, only containing site-isolated 3-aminopropyl groups, were also synthesized by stirring MCM-41 with APTS in isopropanol. For comparative studies of size-dependent selectivity, similarly functionalized samples from SBA-15 material, whose pore diameter is twice greater than MCM-41, were also synthesized. The samples synthesized and studied and the procedures followed to prepare these samples were compiled in the reaction scheme shown in FIG. 26 and in Table 5.

Figure 27A:
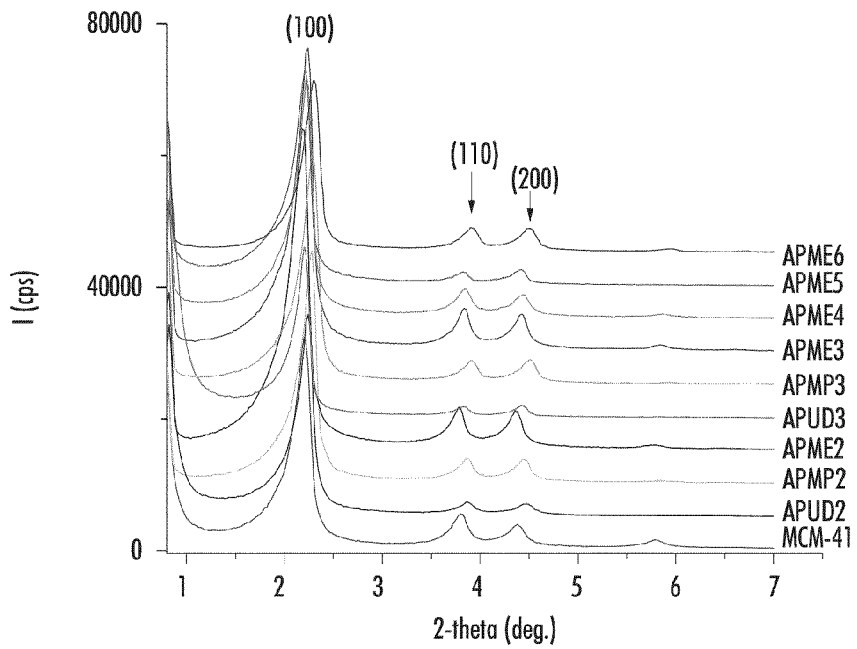
FIG. 27A is a graph of powder X-ray diffraction patterns of certain catalysts prepared on the mesoporous silicate MCM-41 in accordance with the reaction scheme of FIG. 26.
Figure 27B:
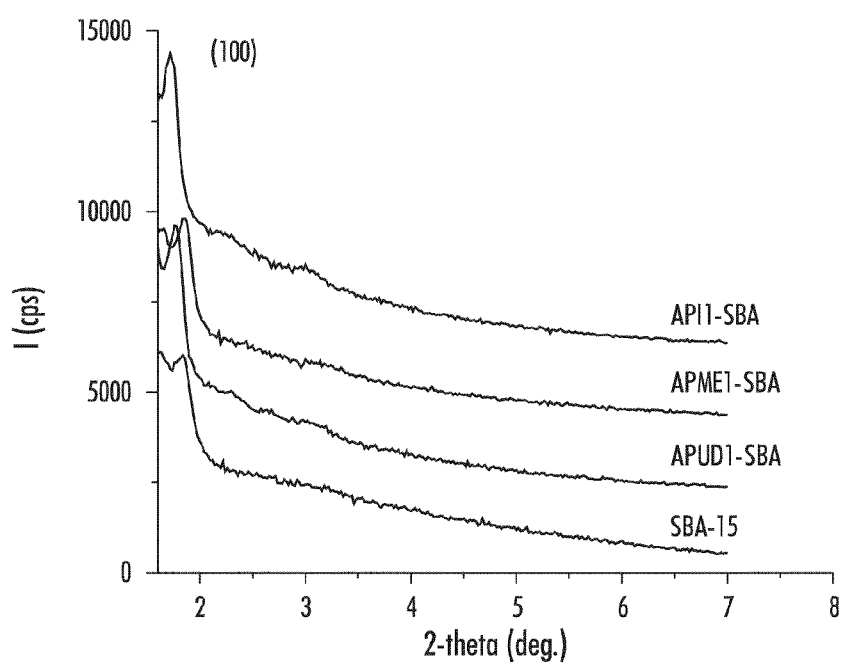
FIG. 27B is a graph of powder X-ray diffraction patterns of certain catalysts prepared on the mesoporous silicate SBA-15.
Figure 28:
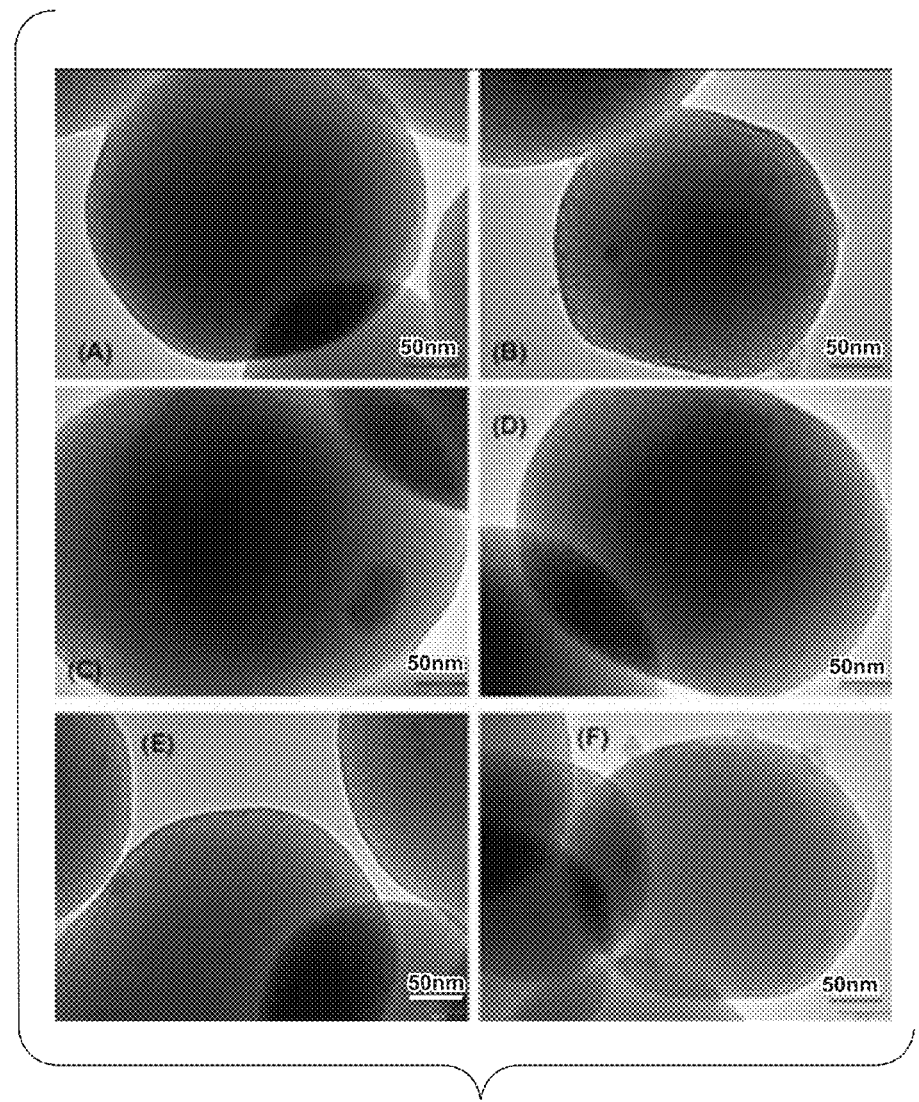
FIG. 28 (A)-(F) are transmission electron microscopy images of (A) MCM-41 mesoporous silicate starting material and selected trifunctional mesoporous catalysts synthesized therefrom, (B) APMP1, (C) APME1, (D) APMP2, (E) APME2 and (F) API1, respectively.
Figure 29:
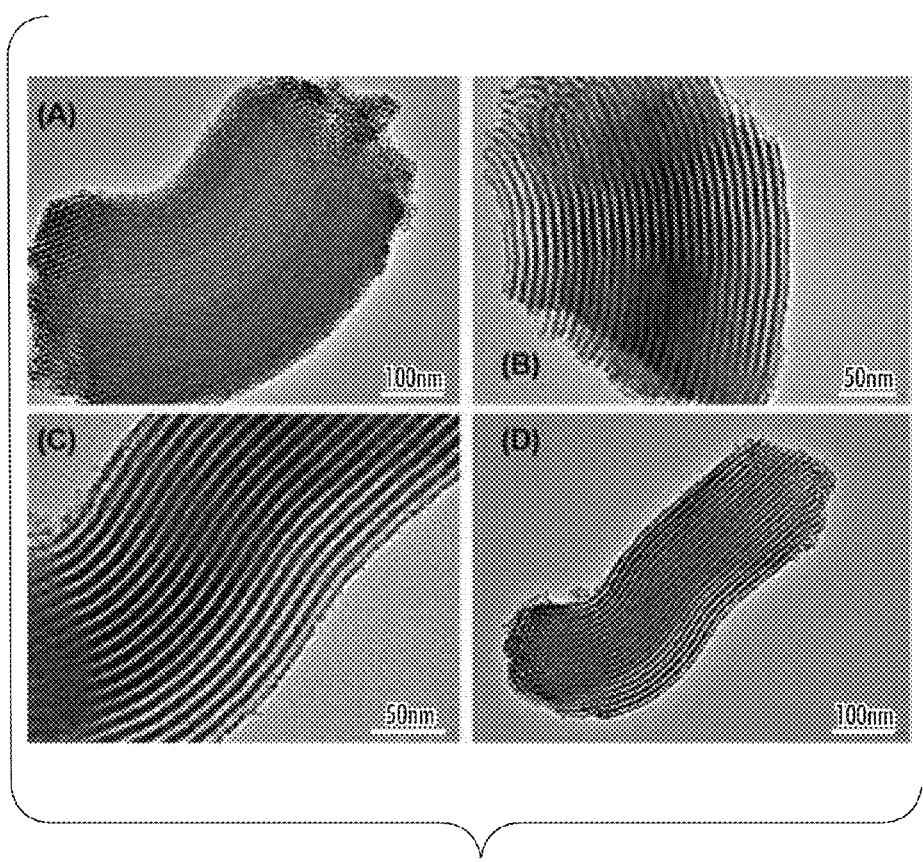
FIG. 29 (A)-(D) are transmission electron microscopy images of (A) MCM-41 mesoporous silicate starting material and selected trifunctional mesoporous catalysts synthesized therefrom, (B) API1-SBA, (B) APUD1-SBA, and APME-1, respectively.
Figure 30A:
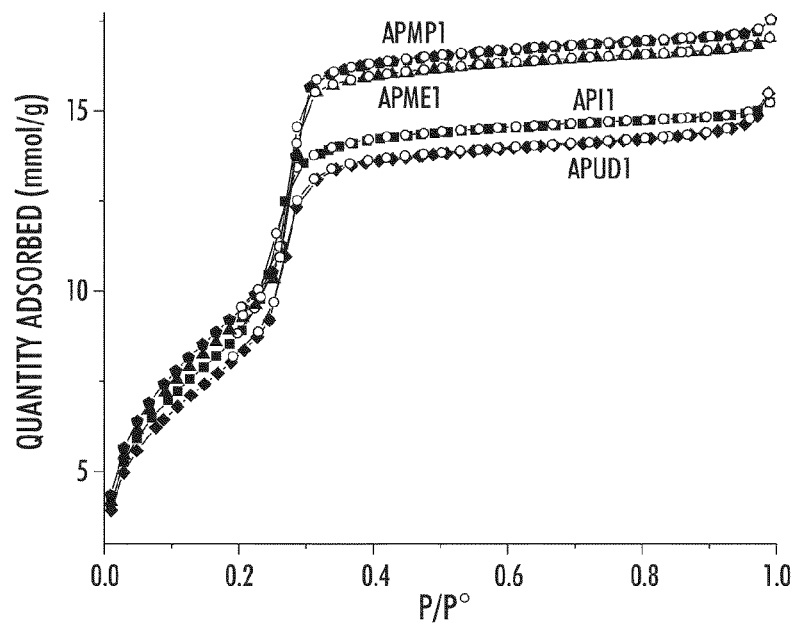
FIGS. 30A-30C are nitrogen gas adsorption isotherms of selected trifunctional mesoporous catalysts synthesized from MCM-41 mesoporous silicate starting material.
Figure 30B:
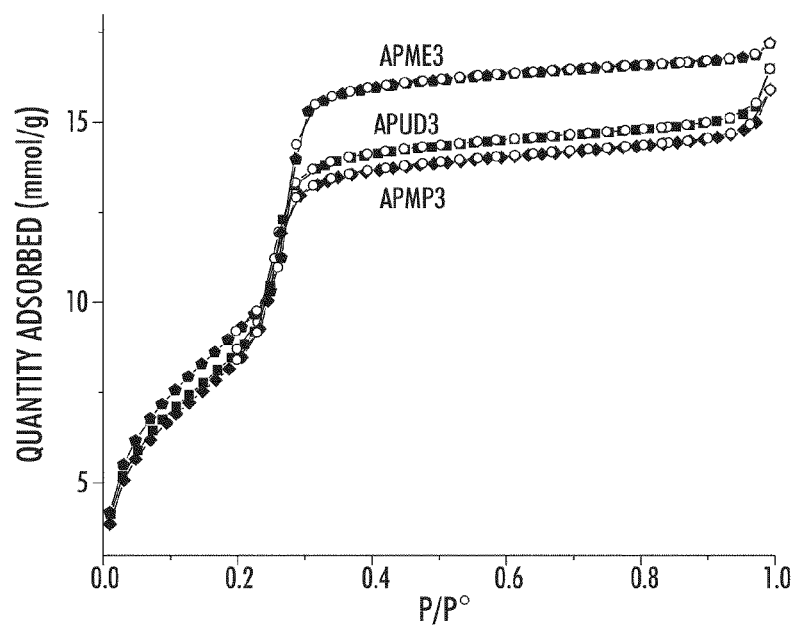
Figure 30C:
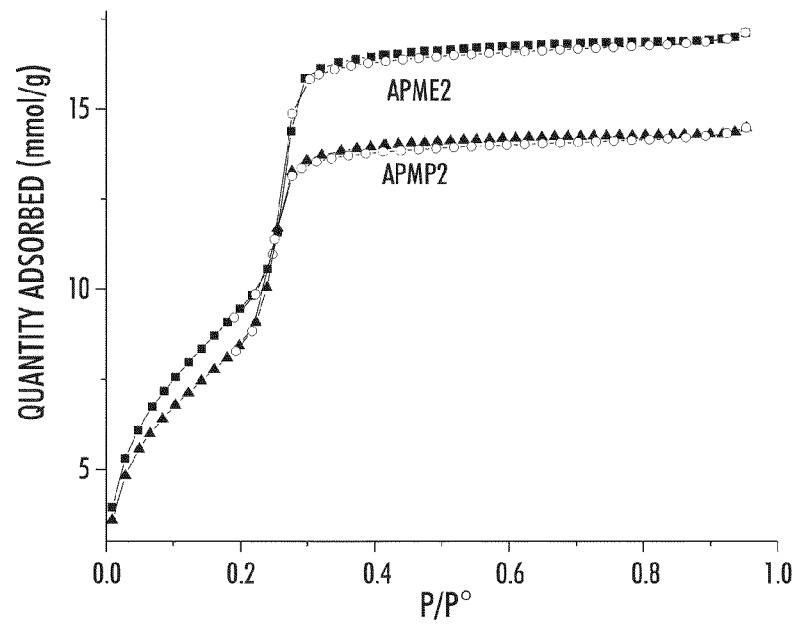
Figure 30D:
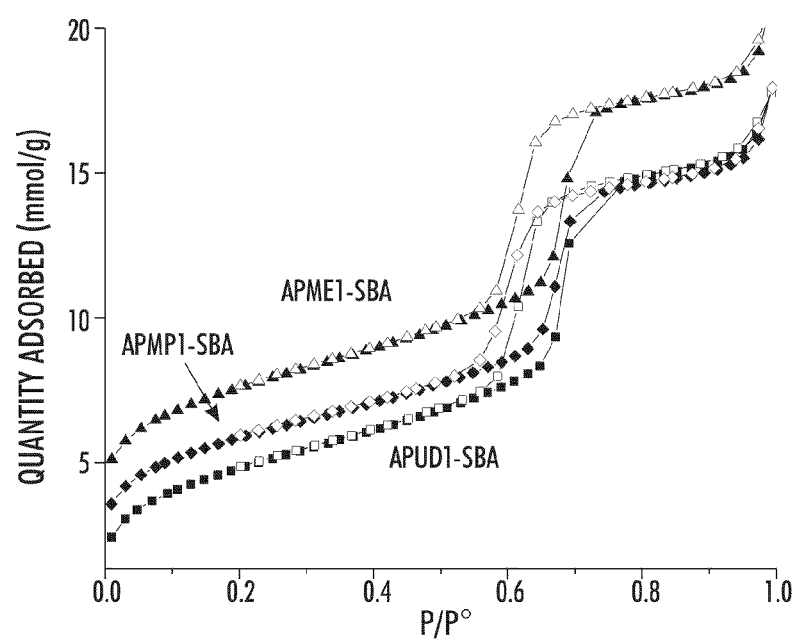
FIG. 30D is a set of nitrogen gas adsorption isotherms of selected trifunctional mesoporous catalysts synthesized from SBA-15 mesoporous silicate starting material.

The original parent mesoporous silica material MCM-41 and SBA-15, and all the functionalized mesoporous materials were characterized by X-ray diffraction (XRD) (FIGS. 27A and 27B), transmission electron microscopy (TEM) (FIGS. 28 and 29), and $N_2$ gas adsorption (FIGS. 30A-30D). The results indicated that all the samples had well-ordered mesoporous structures with unit cell dimensions of about 43-46 Å for those synthesized from MCM-41, and about 107-109 Å for those synthesized from SBA-15, as shown in FIGS. 27A and 27B, respectively. The pore widths were obtained to be between 27-29 Å for the former and 59-61 Å for the latter. The BET surface areas ranged from 833-960 $m^2/g$ for the catalysts synthesized from MCM-41, and from 353-557 $m^2/g$ for the catalysts synthesized from SBA-15 (see Table 5). It is noted that the grafting procedures did not affect the mesoporous structures, the pore diameters or the surface areas in any appreciable manner, as can be seen from the XRD data of FIGS. 27A and 27B, and the data in and Table 5. The presence of well-ordered mesostructures in the samples was also corroborated by TEM images of FIGS. 28 and 29, and the Type IV isotherms obtained on the $N_2$ gas adsorption experiments shown in FIGS. 30A-30D. Structural data for the samples are summarized in Table 5.

FIG. 26 is a schematic illustration of the synthetic pathways for multifunctional mesoporous samples containing various concentrations of 3-aminopropyl (AP) catalytic groups, residual silanols, and a secondary organic group (ureidopropyl (UD), 3-mercaptopropyl (MP), or methyl (ME). The synthesis of the materials was carried out by grafting various mixtures of organosilanes onto MCM-41 in isopropanol. The compositions shown in the scheme were determined based on various characterization results.

Additionally, Table 6 is a compilation of results showing the relative catalytic efficiency of multifunctional mesoporous catalysts synthesized by grafting in the reaction between these p-substituted benzaldehydes and nitromethane. Referring to the column headings of Table 6, the % of T's corresponding to organosilica silicon were obtained from $^{29}Si$ MAS NMR. "% T" as used herein is defined as the percent of silicon atoms that have aminopropyl or organic groups attached.

The weight percent nitrogen was obtained from elemental analysis, EA. The maximum ratio of % yield of the two reactants or the maximum selectivity was determined from the ratio of percent yield versus time of one reactant with that of the other, from the reactions done individually. In the three columns to the right containing percent yield ratios of specific catalyst pairs, the yields shown for the two reactants were taken at the time the maximum ratio of % yields occurred.

Additionally, the yield data for used in calculating the various ratios denoted with superscripts is as follows:
  a The % yield of p-OH was >~90% in 20 minutes.
  b The yield of p-OH was ~75% in 20 minutes.
  c The yield of p-Me was ~≥80% in 20 minutes.
  d The yield of p-Me was ~≥75% in 20 minutes.
  e The yields of p-Me was less than ~<75% in 20 minutes.

It is further noted that catalyst API1 showed a selectivity for p-OH over p-Me with a value of 1.6 times higher at 15 minutes.

TABLE 6

Relative catalytic efficiency of multifunctional mesoporous catalysts synthesized by grafting in the reaction between p-substituted benzaldehydes and nitromethane.

| Sample | % T[b] | Wt. % N, EA[b] | Maximum Ratio of % Yield, % p-OH/% p-But (time, min) | Maximum Ratio of % Yield, % p-Me/% p-OH (time, min) | Maximum Ratio of % Yield, % p-Me/% p-But (time, min) | % Yield p-OH:% Yield p-But at Maximum Ratio | % Yield p-Me:% Yield p-OH at Maximum Ratio | % Yield of p-Me:% p-But at Maximum Ratio |
|---|---|---|---|---|---|---|---|---|
| MCM-41 | — | — | — | — | — | — | — | — |
| APUD1 | 12 | 1.64 | 2.8 (20)[a] | 1.7 (5) | 3.2 (10)[d] | 93:33 | 27:16 | 27:16 |
| APMP1 | 14 | 2.11 | 2.2 (12)[a] | 2.4 (3) | 2.4 (4)[d] | 63:29 | 18:8 | 6:2 |
| APME1 | 18 | 2.50 | 1.7 (22)[a] | 2.0 (3) | 2.2 (5)[d] | 93:55 | 14:7 | 25:11 |
| APUD2 | — | — | 2.3 (10)[a] | 2.3 (5) | 3.7 (10)[d] | 46:20 | 37:16 | 37:16 |
| APMP2 | 17 | — | 2.2 (18)[a] | 1.7 (4) | 2.5 (4)[d] | 87:40 | 18:13 | 18:11 |
| APME2 | 19 | — | 2.5 (5)[b] | 2.0 (5) | 3.8 (5) | 9:4 | 5:3 | 20:5 |
| APUD3 | 13 | — | 1.7 (25)[a] | 3.9 (5) | 7.3 (5)[c] | 99:58 | 76:19 | 76:20 |
| APMP3 | — | — | 1.9 (25)[a] | 3.4 (5) | 5.4 (5)[c] | 99:52 | 72:21 | 72:21 |
| APME3 | 13 | 2.39 | 2.2 (15)[a] | 1.9 (5) | 2.7 (10)[c] | 86:39 | 37:19 | 37:20 |
| APME4 | — | 1.57 | 1.8 (15)[b] | 3.2 (5) | 3.7 (10)[e] | 53:29 | 36:11 | 36:11 |
| APME5 | — | — | 2.6 (20)[b] | 2.4 (5) | 3.8 (10)[e] | 73:28 | 61:12 | 28:12 |
| APME6 | — | 1.46 | 1.8 (25)[b] | 4.0 (5) | 4.0 (5)[d] | 78:43 | 44:11 | 79:20 |
| API1[j] | 15 | — | 2.5 (9)[a] | 1.5 (3) | 2.5 (4) | 61:24 | 17:12 | 23:15 |
| API1A | — | — | 2.1 (10)[a] | 1.8 (5) | 2.6 (5)[c] | 67:32 | 40:22 | 40:22 |

TABLE 6-continued

Relative catalytic efficiency of multifunctional mesoporous catalysts synthesized by grafting in the reaction between p-substituted benzaldehydes and nitromethane.

| Sample | % T[b] | Wt. % N, EA[b] | Maximum Ratio of % Yield, % p-OH/% p-But (time, min) | Maximum Ratio of % Yield, % p-Me/% p-OH (time, min) | Maximum Ratio of % Yield, % p-Me/% p-But (time, min) | % Yield p-OH:% Yield p-But at Maximum Ratio | % Yield p-Me:% Yield p-OH at Maximum Ratio | % Yield of p-Me:% p-But at Maximum Ratio |
|---|---|---|---|---|---|---|---|---|
| API1-SBA | 17 | 3.15 | 2.0 (30) | — | — | 68:34 | — | — |
| APUD1-SBA | 16 | — | 2.1 (20) | — | — | 50:24 | — | — |
| APMP1-SBA | — | — | 2.2 (20) | — | — | 32:15 | — | — |
| APME1-SBA | — | — | 1.9 (30) | — | — | 45:23 | — | — |

Figure 31A:
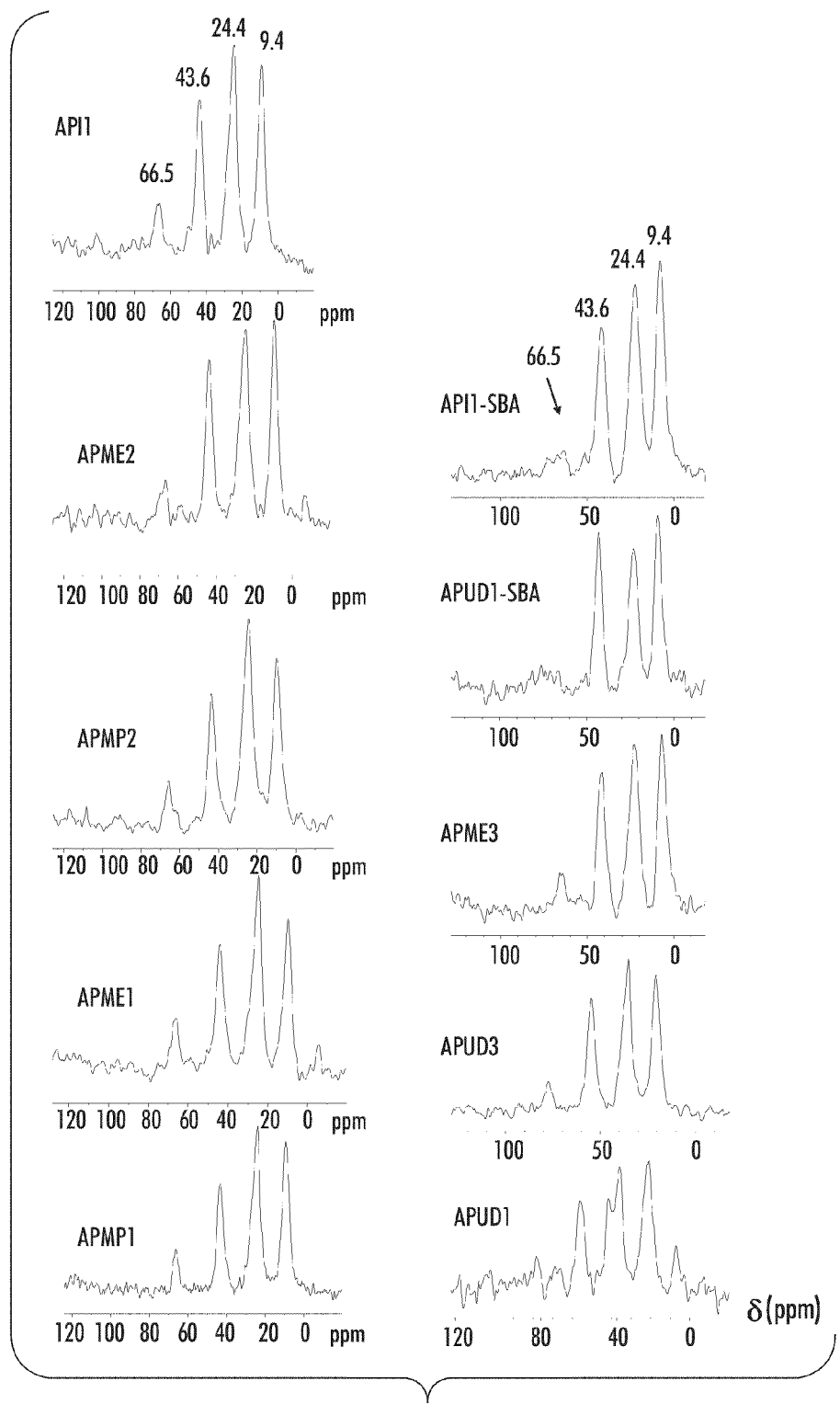
FIG. 31A depicts $^{13}$C CP-MAS solid-state NMR spectra of various trifunctional mesoporous catalysts.
Figure 31B:
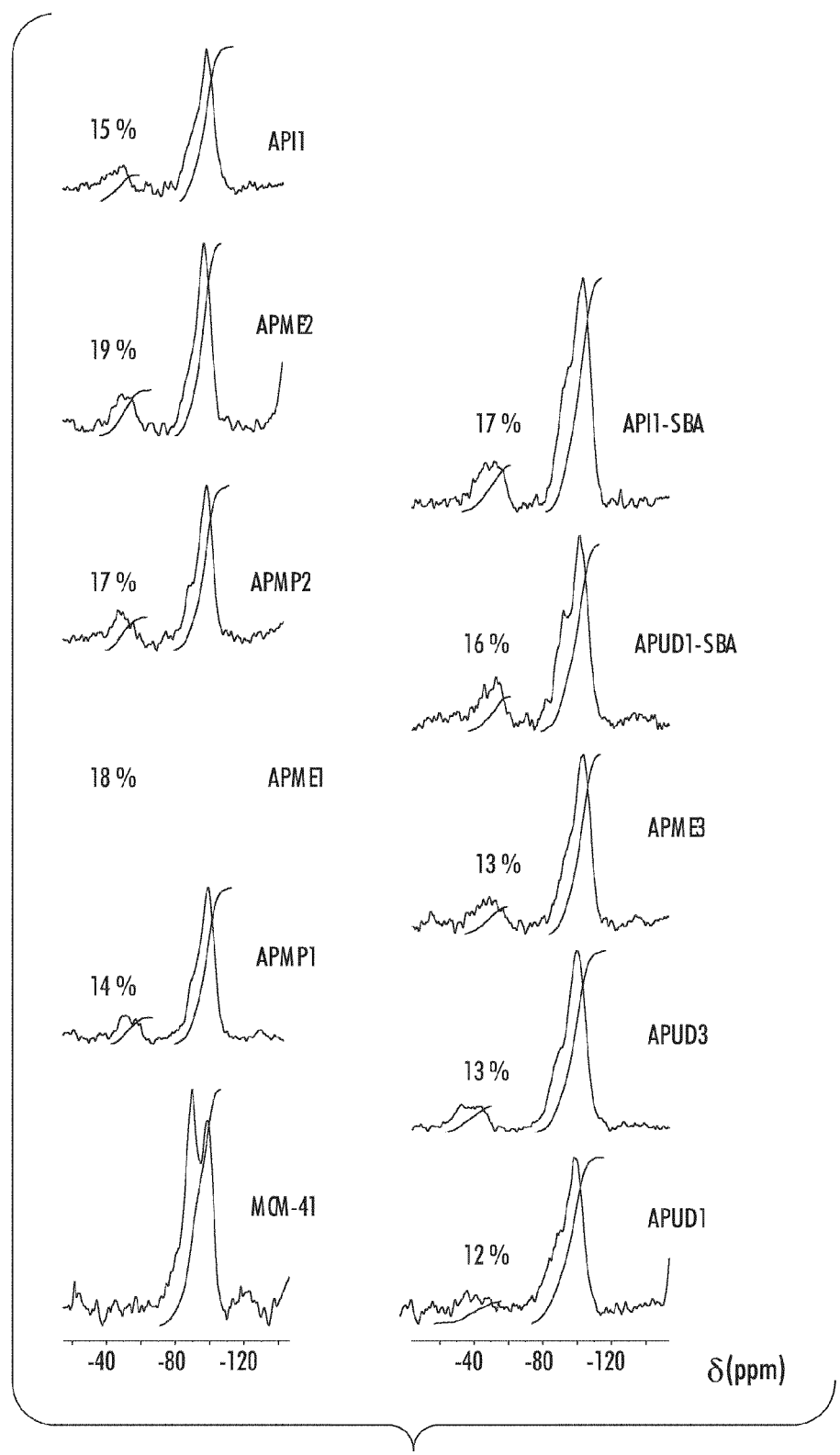
FIG. 31B depicts $^{29}$Si MAS solid-state NMR spectroscopy of MCM-41, and various trifunctional mesoporous catalysts.

By using $^{13}$C and $^{29}$Si solid-state NMR spectroscopy as shown in FIGS. 31A and 31B, and elemental analysis, the presence and the concentrations of the organic groups in the catalyst samples have been analyzed. The $^{13}$C CP-MAS NMR spectra of the samples (FIG. 31A) showed peaks at 9.4, 24.4 and 43.6 ppm. These broad peaks correspond to overlapping peaks of the α, β, γ carbons, respectively, of 3-aminopropyl (AP) group and those of the secondary functional groups, namely UD, or MP groups, or the peak for ME groups depending on the secondary organosilanes grafted (FIG. 31A). The chemical shifts of these functional groups are known to overlap in solid-state NMR spectra. The peak observed at 66 ppm corresponds to isopropoxide carbons (CH$_3$)$_2$CHO— carbons, which have resulted from isopropanol, the solvent used for grafting. Such alkoxide peaks often appear in $^{13}$C solid-state NMR spectra of functionalized mesoporous samples synthesized by grafting, either due to reactions with silanol groups or chemisorption.

After the organosilanes grafting, the Q3 and Q2 peaks corresponding to SiO$_{1.5}$(OH) and SiO(OH)$_2$ groups decreased while the T peaks corresponding to RSi(O)$_x$(OH)$_y$ groups increased, as indicated in FIG. 31B. The "Q" peaks correspond to those silicon atoms containing no organic or aminopropyl groups while the "T" peaks correspond to those silicon atoms containing organic or aminopropyl groups. From the $^{29}$Si MAS NMR spectra of FIG. 31B, it was also observed that the samples grafted in one-step such as APMP1 and APME1 contained about 2% less organic groups compared to the corresponding samples grafted in two steps such as APMP2 and APME2 (Table 6). Also the samples grafted with ME groups appeared to contain about 2-3% higher organic groups than the corresponding samples grafted with UD and MP groups under the same conditions. These indicate that a relatively more hydrophobic and smaller organosilane, such as METS, in a polar solvent, isopropanol, has a higher tendency to graft onto the mesoporous silica surface than to remain in the solvent. Elemental analysis was also used to obtain the weight percent N or weight percent NH$_2$ groups as shown in Table 6. The data also exhibited that grafting of 1:1 mole ratio of APTS and UDPS results in less grafted % N than those corresponding samples grafted with 1:1 mole ratio of APTS and MPTS or METS. The applicants believe that due to the hydrophilic nature of the APTS and UDPS and their tendency to form hydrogen bonding with isopropanol, they have less tendency to go to the silanols to graft. Furthermore, the data indicates that grafting of 1:3 and 1:9 APTS:METS resulted in even lower % N (or less —NH$_2$ groups).

Comparative studies on the selective catalytic properties and efficiency of each material for various p-substituted benzaldehydes including p-OH, p-But, p-Me, and p-MeO, either in individually or in a reaction mixture were performed. For this latter investigation, the reaction scheme for the selective catalysis of different p-substituted benzaldehydes with nitromethane in a mixture of two reactants by a selective multifunctional catalyst of the invention is as follows:

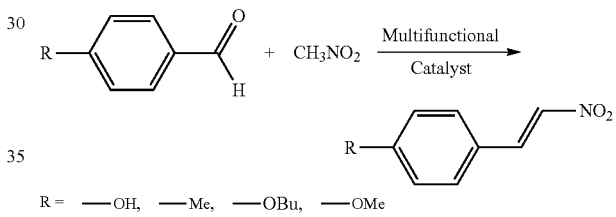

R = ——OH, ——Me, ——OBu, ——OMe

The investigation and resulting discoveries described previously herein indicated that a bifunctional sample containing 3-aminopropyl group and many residual surface silanols catalyzes the Henry reaction between p-hydroxybenzaldehyde and nitromethane effectively. While all of the site-isolated trifunctional mesoporous catalysts described herein also catalyzed the Henry reaction very efficiently, their relative catalytic efficiencies varied with respect to the types and concentrations of the functional groups they contained and the type of the reactants used. By taking advantage of these differences, materials having interesting and useful selective catalytic properties were obtained for reactants in a mixture. The applicants note that that their reactions resulted in exclusively p-substituted nitrostyrene product, unlike some examples in the literature where mixtures of nitroalcohols and nitrostyrene were reported, such as those described by Choudary et al. in *J. Molecular Catal. A.* 1999, 42, 361-365.

The Henry reaction was carried out by using each of the organoamine-functionalized samples obtained above as catalysts for reactions between nitromethane and various p-substituted benzaldehydes. The reactants p-hydroxybenzaldehyde (p-OH), p-butoxybenzaldehyde (p-But), and p-methylbenzaldehyde (p-Me) were used separately and as in 1:1 mol mixture of two reactants in the reaction. Typically, 21 mg of the functionalized mesoporous sample was added into a solution of 1 mmol p-hydroxybenzaldehyde and 10 mL of nitromethane. The reaction was stirred at 90° C. under nitrogen and aliquots of the reaction product were taken with a filter syringe and characterized by solution $^1$H NMR over the course of the reaction. Further characterizations were performed by washing the catalysts to extract any possible reactants and products adsorbed in it. For the 1:1 mol reactant mixtures, a mixture of two reactants (for example, 1 mmol p-OH and 1 mmol p-But) was used and the reaction and characterizations were carried out as above.

With regard to the solution $^1$H NMR measurements, product resonances obtained in acetone-$d_6$ were as follows:

p-hydroxy nitrostyrene ($^1$H NMR): δ 2.95 (1H, br, s), 6.97 (2H, d), 7.72 (2H, d), 7.84(1H, d, J=13.5 Hz), 8.03(1H, d, J=13.5 Hz) and 9.84 (1H, s);

p-butoxy nitrostyrene ($^1$H NMR): δ 7.98 (1H, d, J=13.5 Hz), 7.87 (1H, d, J=13.5 Hz), 7.78 (2H, d), 7.05 (2H, d), 4.13 (2H, t), 1.82 (2H, m), 1.55 (2H, m), 0.98 (3H, t); and p-methyl nitrostyrene ($^1$H NMR): δ 8.07 (1H, d, J=13.5 Hz), 7.93 (1H, d, J=13.5 Hz), 7.72 (2H, d), 7.33 (1H, d), 2.45 (3H, s).

Reactant resonances obtained in acetone-$d_6$ were as follows:

p-hydroxybenzaldehyde ($^1$H NMR): δ 9.85 (1H, s), 7.81 (2H, d), 7.02 (2H, d), 2.95 (1H, br, 5);

p-butoxybenzaldehyde ($^1$H NMR): 9.88 (1H, s), 7.86 (2H, d), 7.10 (2H, d), 4.13 (2H, t), 1.82 (2H, m), 1.55 (2H, m), 0.98 (3H, t);

and p-tolualdehyde 9.99 ($^1$H, s), 7.82 (2H, d), 7.42 (2H, d), 2.44 (3H, s).

Product resonances obtained in acetonitrile-$d_3$ were as follows:

p-hydroxy nitrostyrene ($^1$H NMR): δ 2.19 (1H, br, s), 6.90 (2H, d), 7.57 (2H, d), 7.68 (1H, d, J=13.5 Hz), 8.00 (1H, d, J=13.5) and 9.84 (1H, s);

p-butoxy nitrostyrene ($^1$H NMR): δ 8.10 (1H, d, J=13.5 Hz), 7.77 (2H, d), 7.71 (1H, d, J=13.5 Hz), 6.99 (2H, d), 4.06 (2H, t), 1.77 (2H, m), 1.52 (2H, m), 0.96 (3H, t); and p-methyl nitrostyrene ($^1$H NMR): δ 8.07 (1H, d, J=13.5 Hz), 7.93 (1H, d, J=13.5 Hz), 7.71 (2H, d), 7.32 (1H, d), 2.43 (3H, s).

Reactant resonances obtained in acetonitrile-$d_3$ were as follows:

p-hydroxybenzaldehyde ($^1$H NMR): δ 9.82 (1H, s), 7.63 (2H, d), 7.05 (2H, d), 2.19 (1H, br, s);

p-butoxybenzaldehyde ($^1$H NMR): 9.85 (1H, s), 7.84 (2H, d), 7.05 (2H, d), 4.06 (2H, t), 1.77 (2H, m), 1.52 (2H, m), 0.96 (3H, t); and p-tolualdehyde 9.99 ($^1$H, s), 7.78 (2H, d), 7.39 (2H, d), 2.41 (3H, s).

FIGS. 32A-32N and FIGS. 33A-33C show the percentage yield versus time graph of the Henry reaction of p-OH, p-But, and p-ME. These reactants were chosen so as to allow a systematic study of the dependence of efficiency and selectivity of reactants in the Henry reaction on differences in size, electronic properties, and hydrophobicity. The catalytic tests were carried out for each catalyst listed in Table 5 for the reactants p-OH, p-But and p-ME individually and for different combinations of 1:1 mole ratio of a pair of the reactants. Comparison of the first series of catalysts API1, APUD1, APMP1, and APME1 (Table 6 and FIGS. 32M, 32A, 32B, and 32C, respectively), reveals high catalytic efficiency for individual reactions of p-OH and p-ME with typical yield of about 100% in less than 30 minutes. However, the yield for p-But is slightly lower at 80% in 40 minutes. Despite this, the efficiency of the latter is still much higher than the efficiency obtained previously by Lin et al. in *J. Am. Chem. Soc.* 2004, 126, 1010-1011, which is 50% in 24 hours.

The generally low yield observed for p-But with all the catalysts was found to be due to electronic effects of the butoxy (BuO—) substituent acting via mesomeric deactivation of the carbonyl group and not just because of its steric bulk, since a control experiment performed with p-MeO showed comparative yield in 30 minutes. Further, a similar trend in the relative reactivity of p-OH, p-Me and p-But was observed for homogeneous catalysis using 3-aminopropyltrimethoxysilane as the base in nitromethane. This confirmed the slow reactivity of p-But with respect to p-OH and p-Me being due to the electronic effects. However, the applicants believe that the differences in the efficiency among the various multifunctional mesoporous samples towards p-But with respect to the other benzaldehydes may have to do with the difference in the surface properties the catalysts and the number of catalytic sites available in them. Nevertheless, it is to be understood that the applicants' multifunctional mesoporous heterogeneous catalyst afforded much better yields in smaller reaction time compared to homogenous catalyst for all the p-substituted benzaldehydes.

Figure 32A:
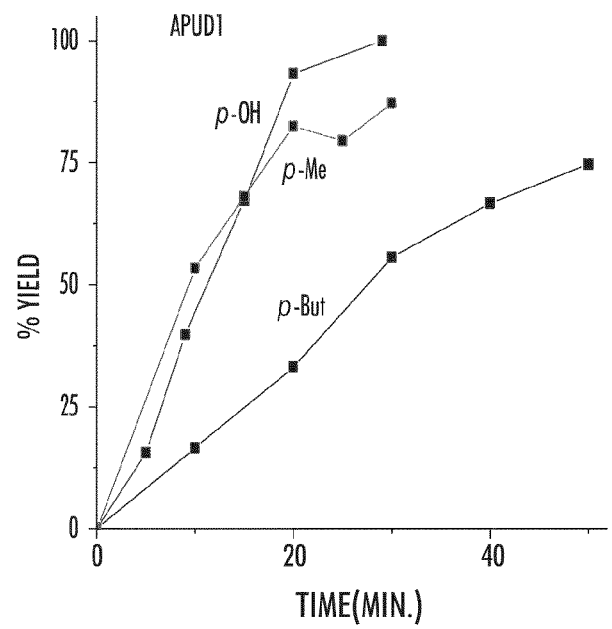
FIGS. 32A-32N are a series of reaction time plots (% yield versus time plots) for the Henry reaction of individual reactants catalyzed by various trifunctional mesoporous catalysts synthesized from parent MCM-41 mesoporous silica.
Figure 32A:
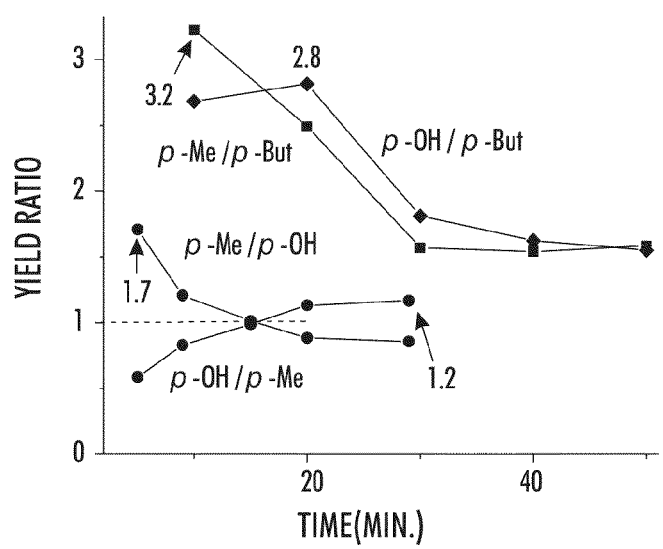
Figure 32B:
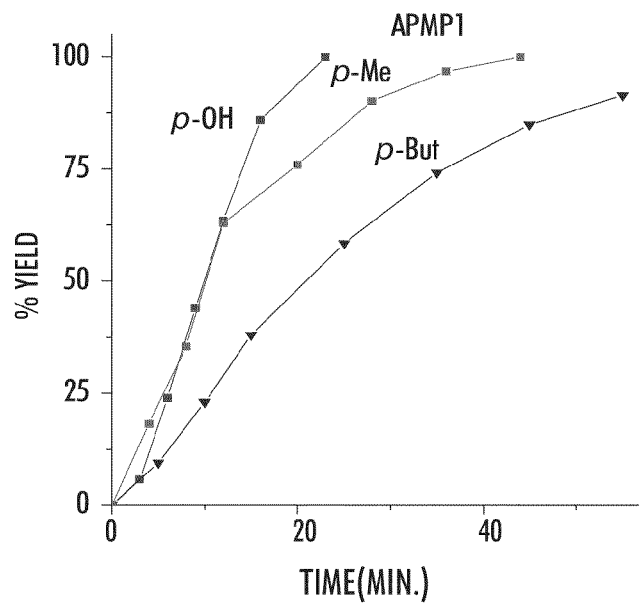
Figure 32B:
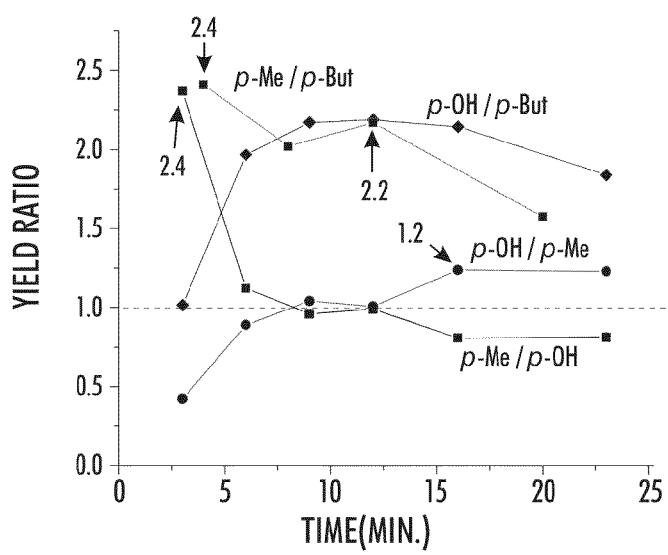
Figure 32C:
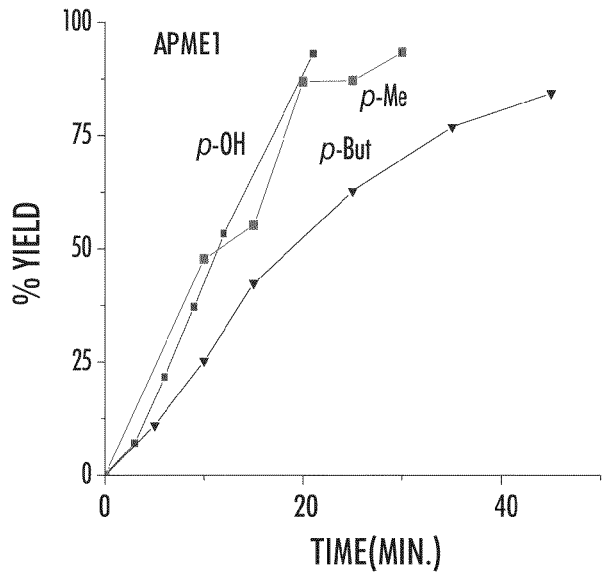
Figure 32C:
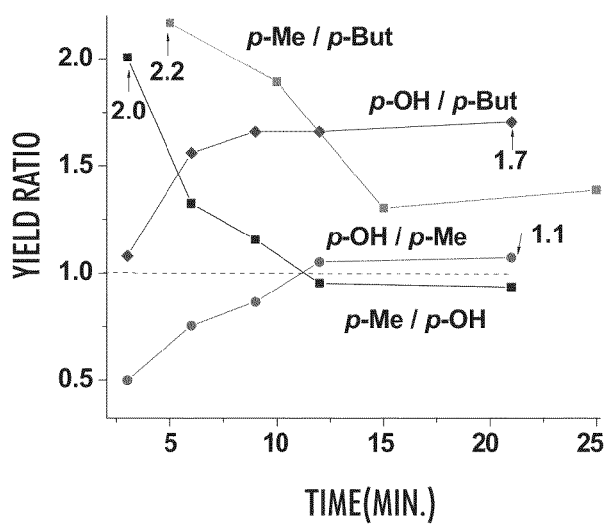
Figure 32D:
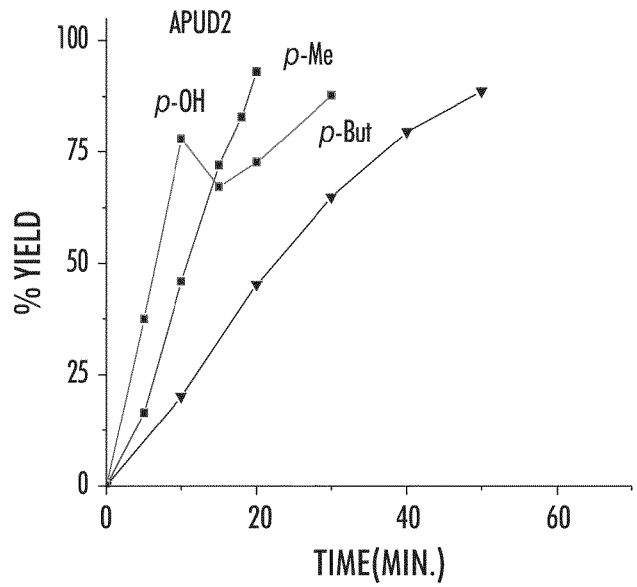
Figure 32D:
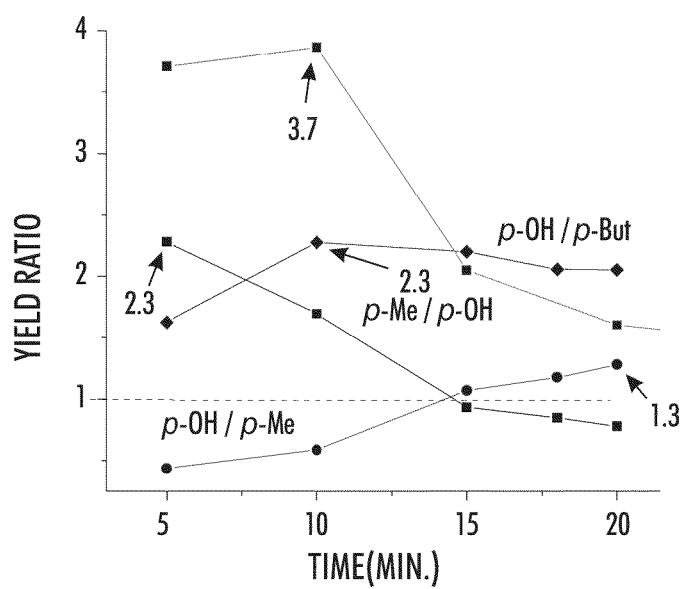
Figure 32E:
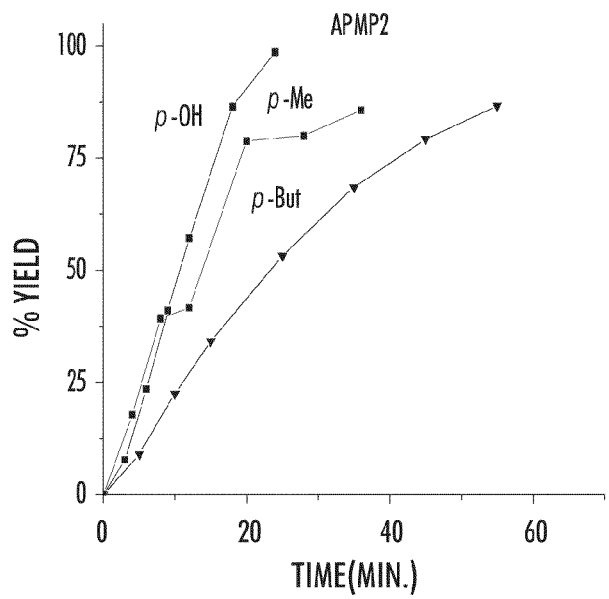
Figure 32E:
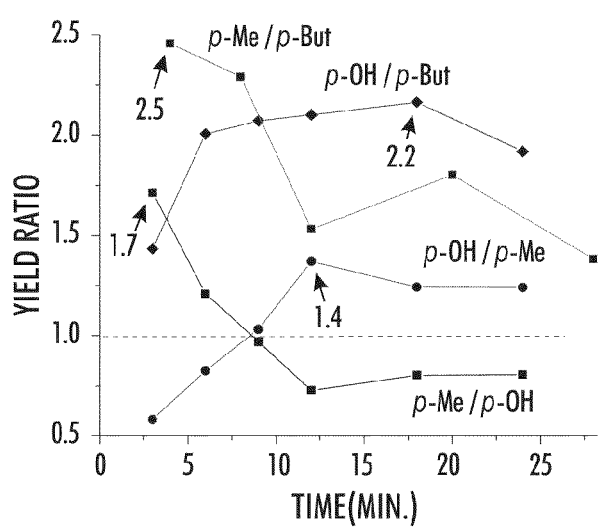
Figure 32F:
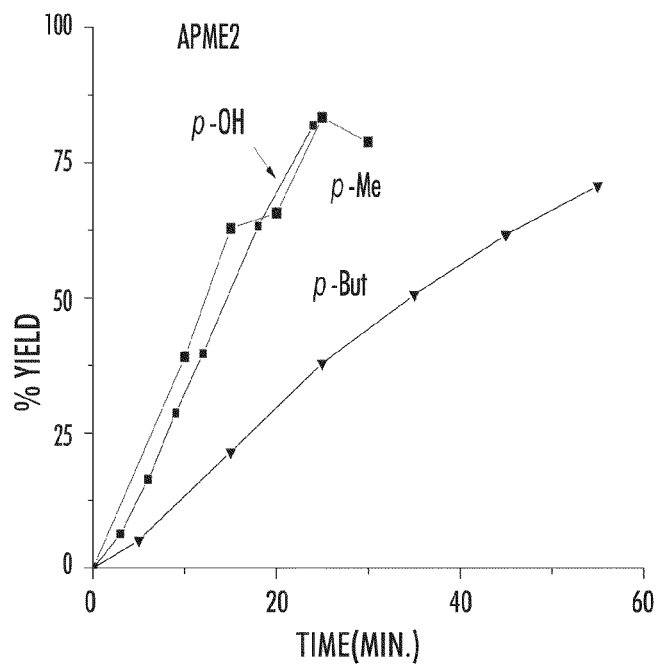
Figure 32F:
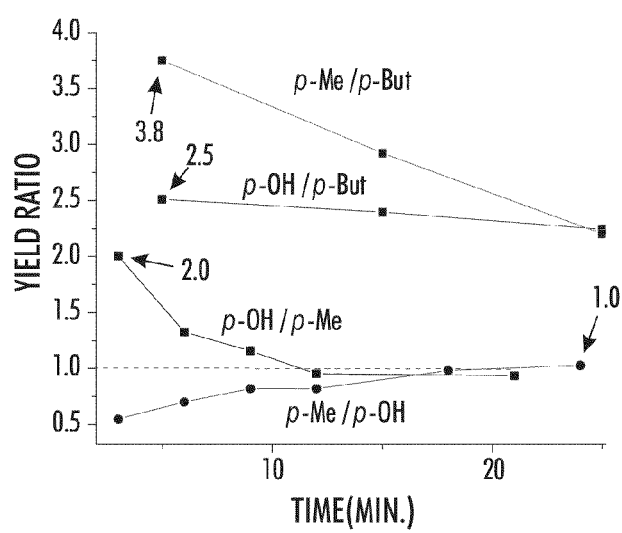
Figure 32G:
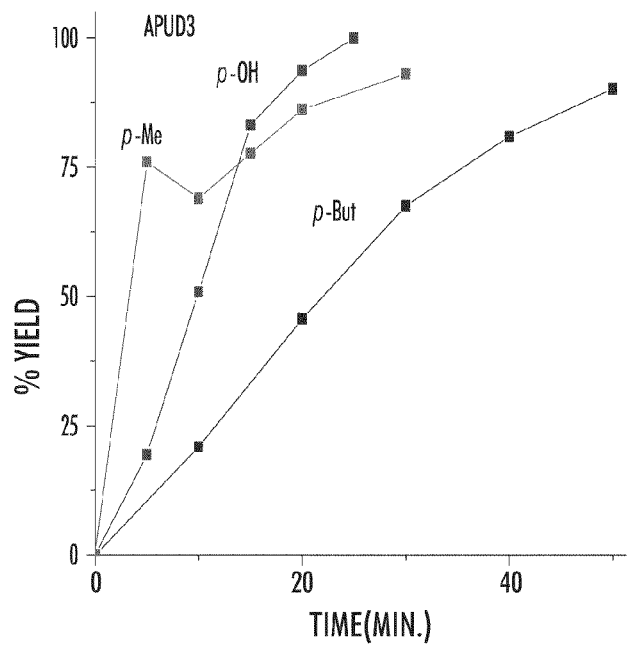
Figure 32G:
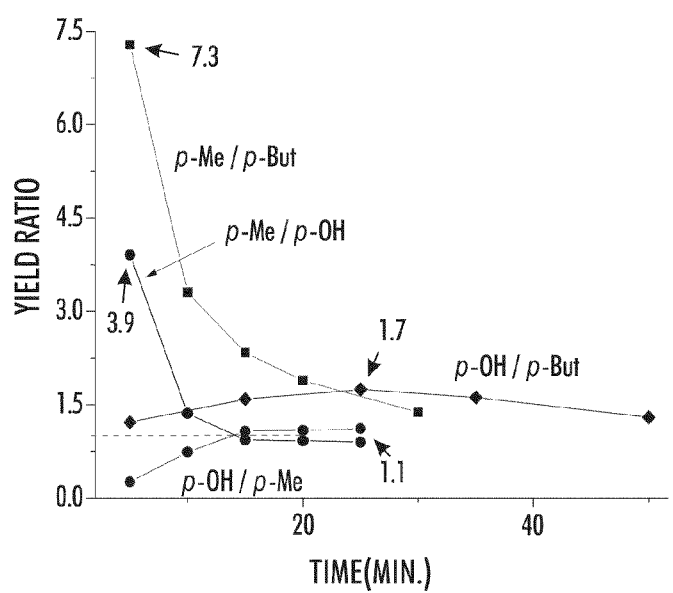
Figure 32H:
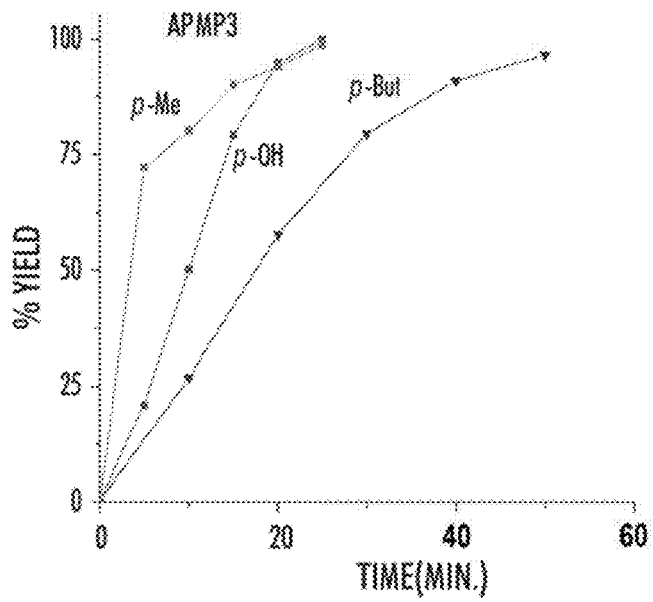
Figure 32H:
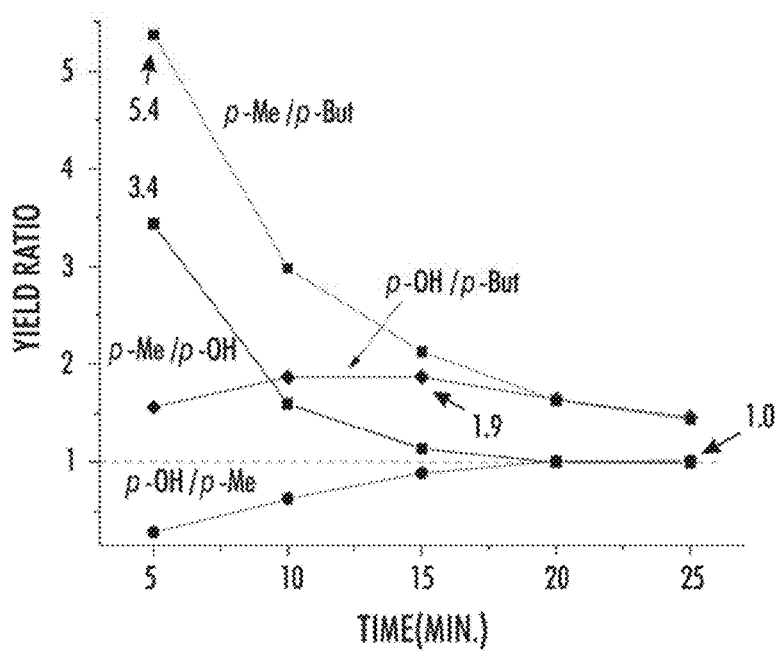
Figure 32I:
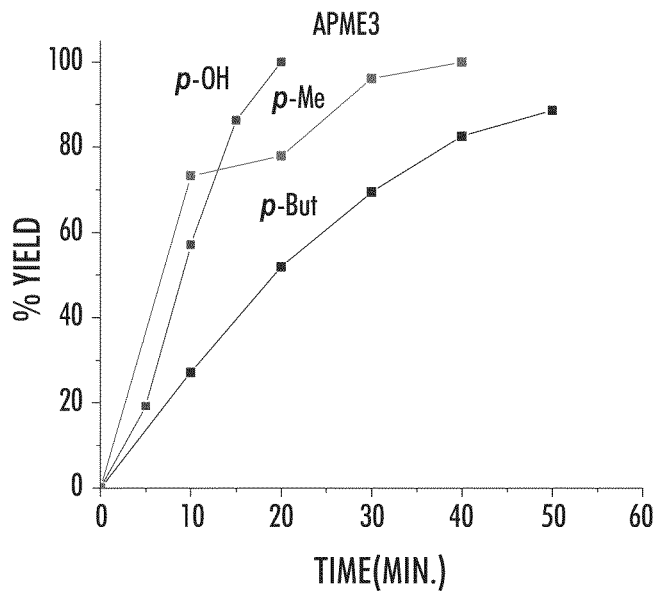
Figure 32I:
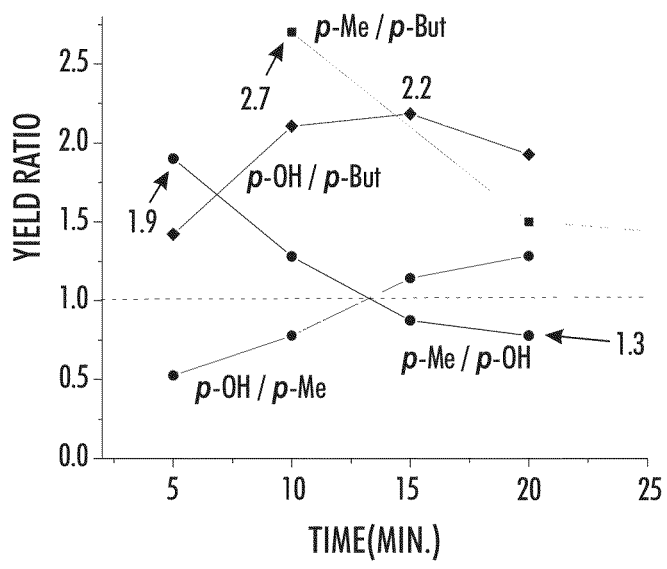
Figure 32J:
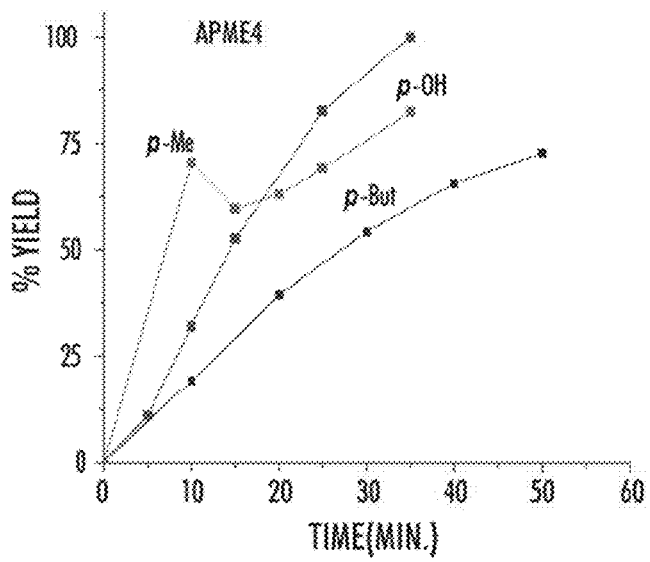
Figure 32J:
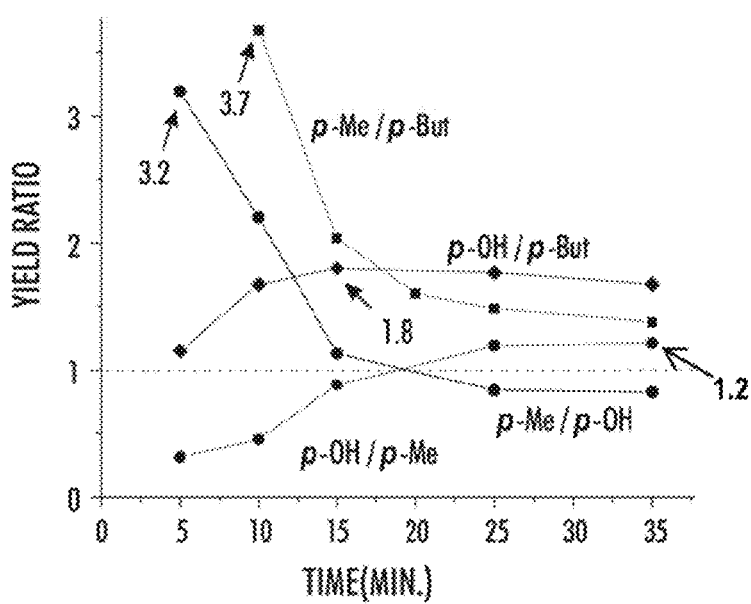
Figure 32K:
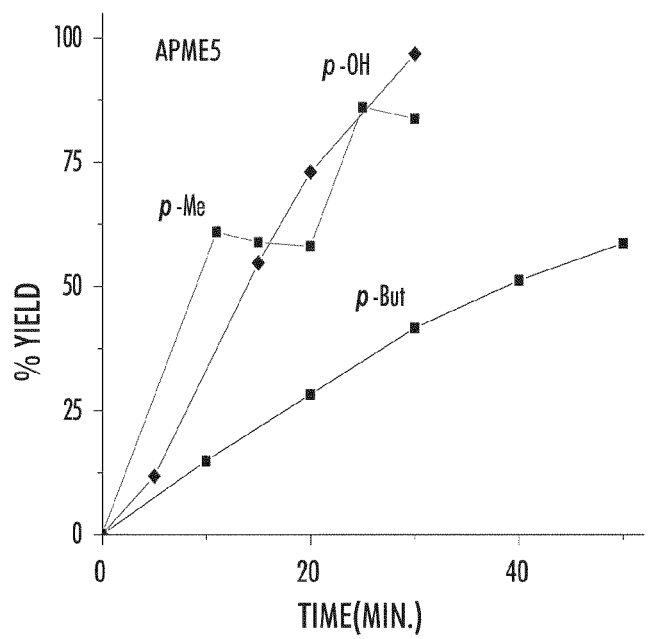
Figure 32K:
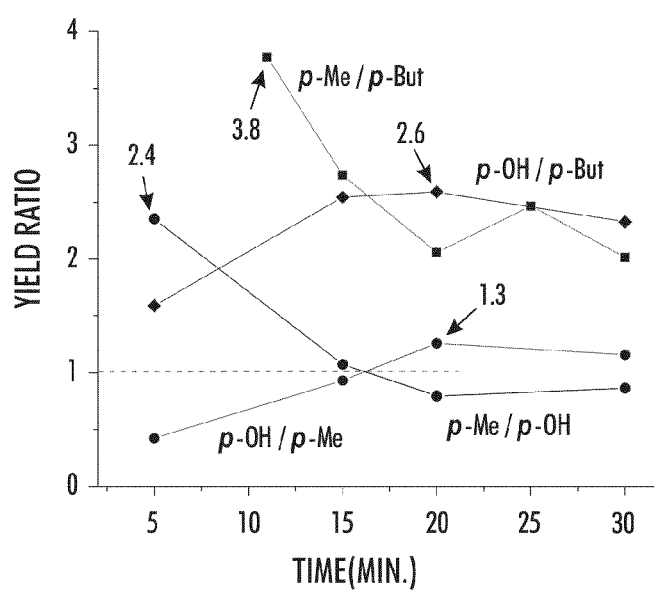
Figure 32L:
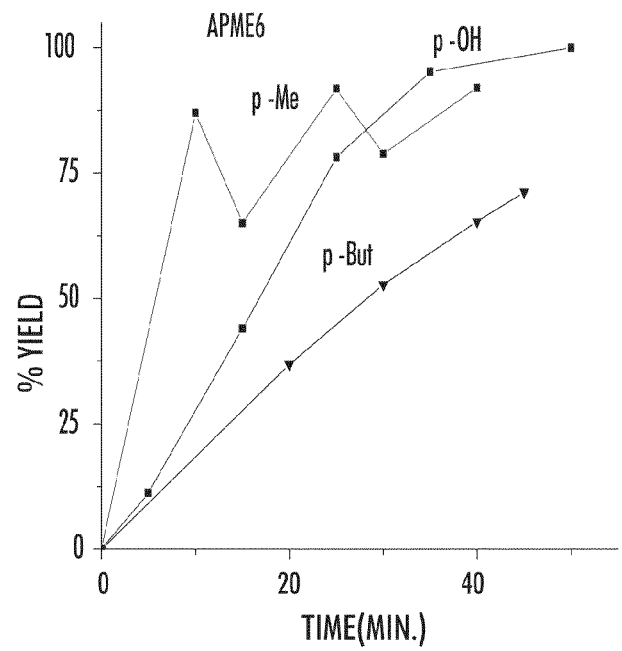
Figure 32I:
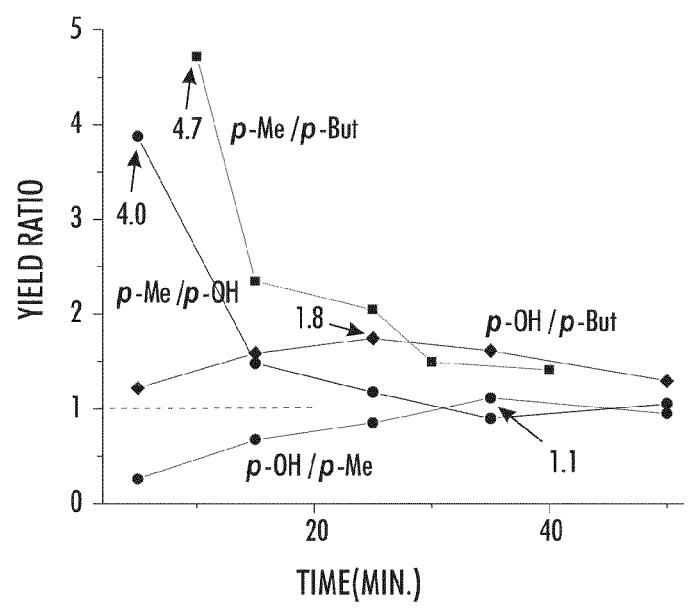
Figure 32M:
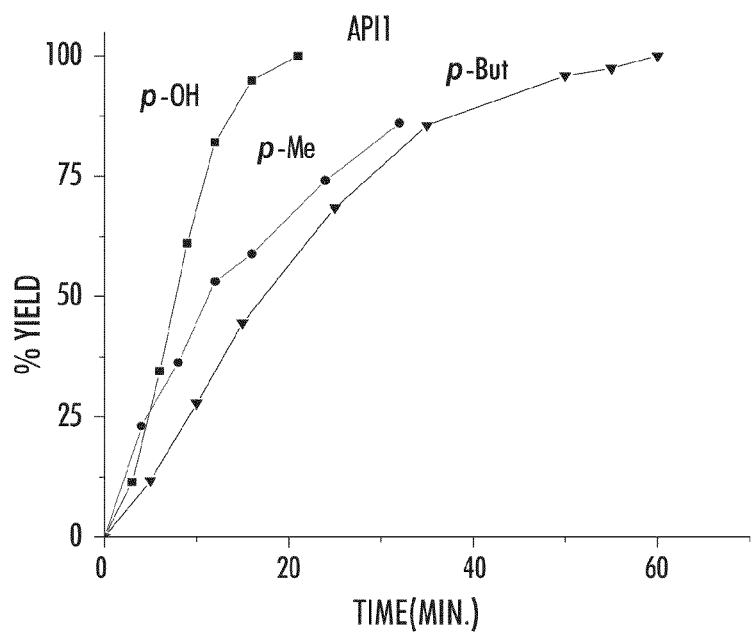
Figure 32M:
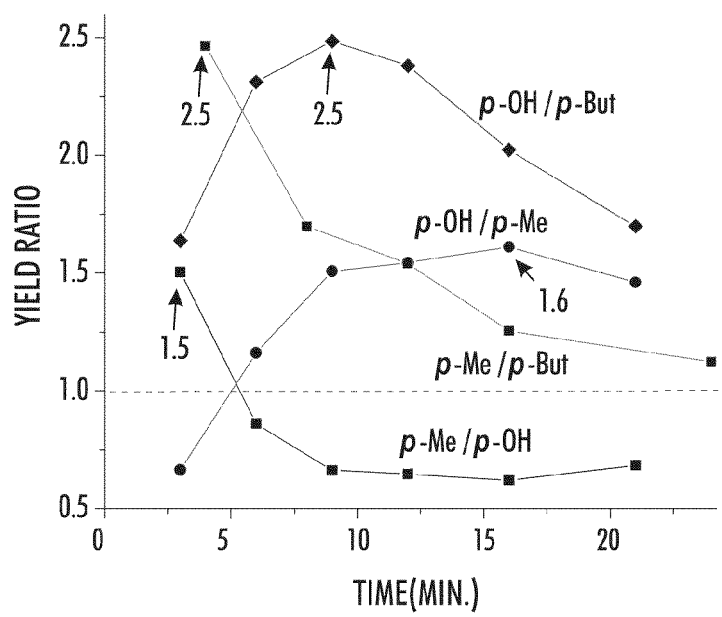
Figure 32N:
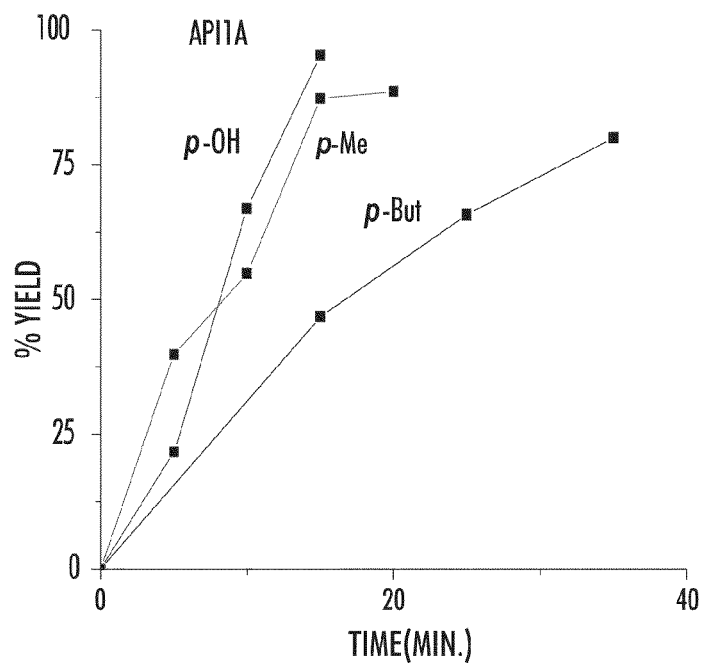
Figure 32N:
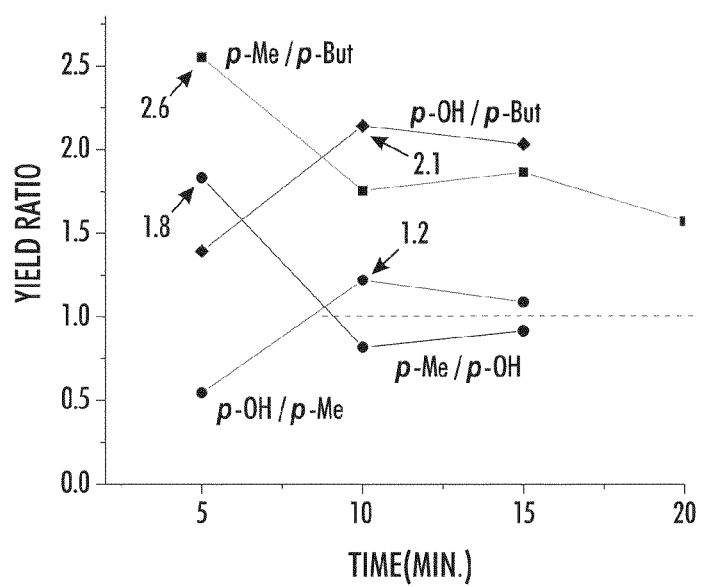
Figure 33A:
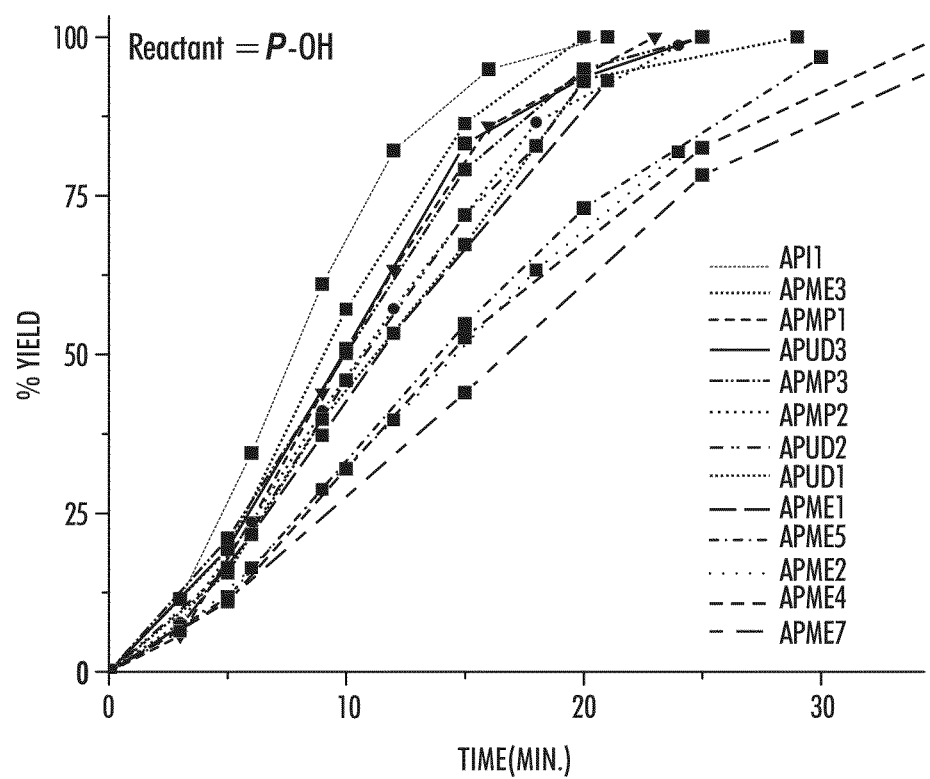
FIGS. 33A-33C are a set of comparative catalysis time plots (% yield versus reaction time) of the Henry reaction compiled for each reactant p-OH, p-But, and p-Me catalyzed by all the catalysts synthesized from the parent MCM-41 mesoporous silica.
Figure 33B:
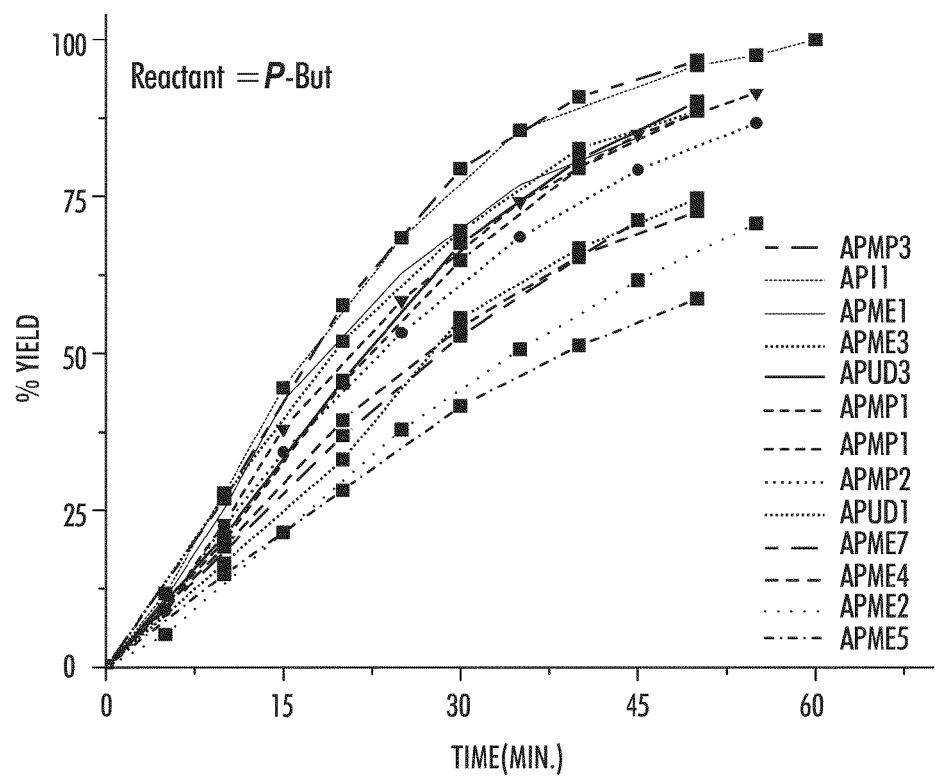
Figure 33C:
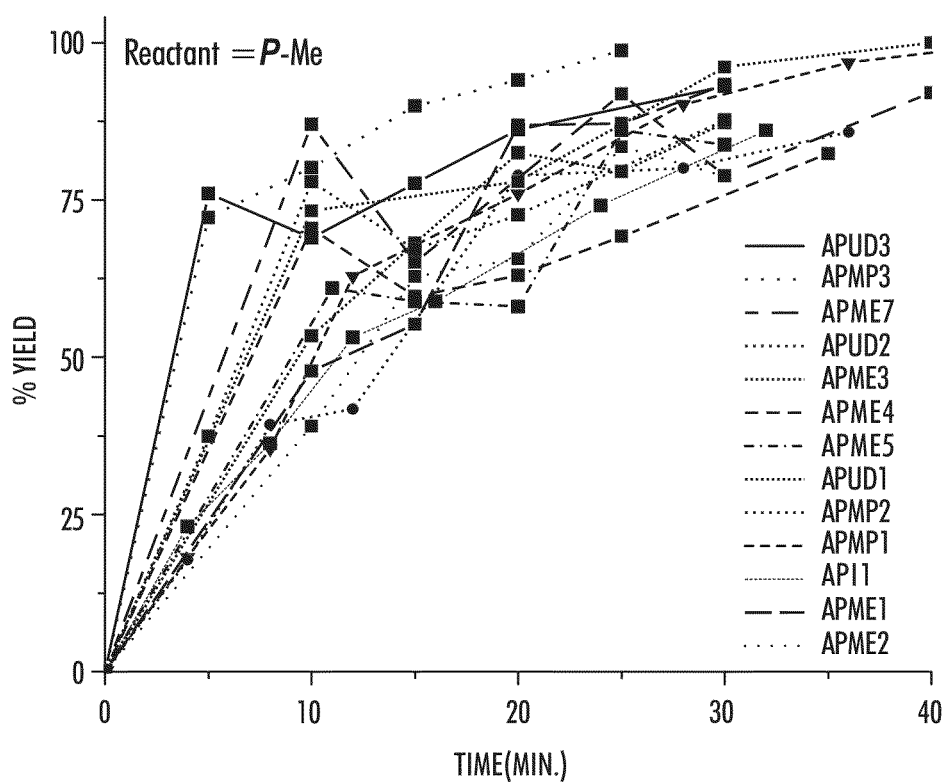
Figure 34A:
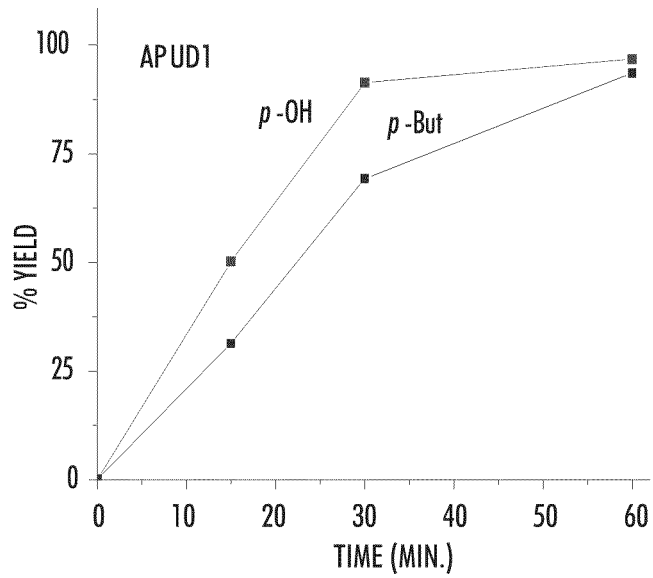
FIGS. 34A-34L are a series of reaction time plots (% yield versus time plots) for the Henry reaction of 1:1 mole mixture of two reactants catalyzed by various selected trifunctional mesoporous catalysts prepared from parent MCM-41 mesoporous silica.
Figure 34A:
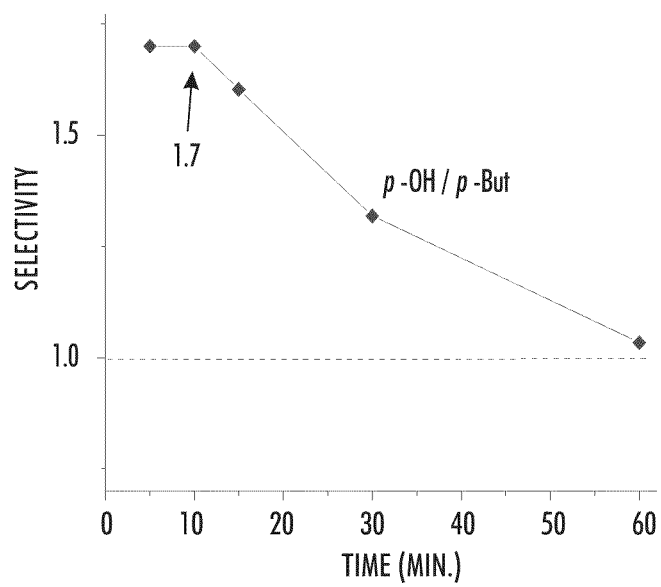
Figure 34B:
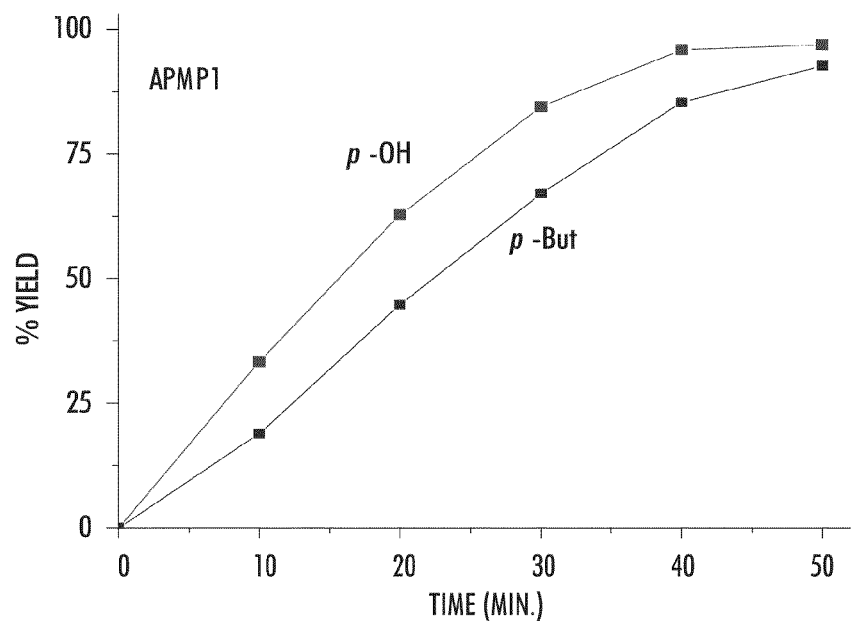
Figure 34B:
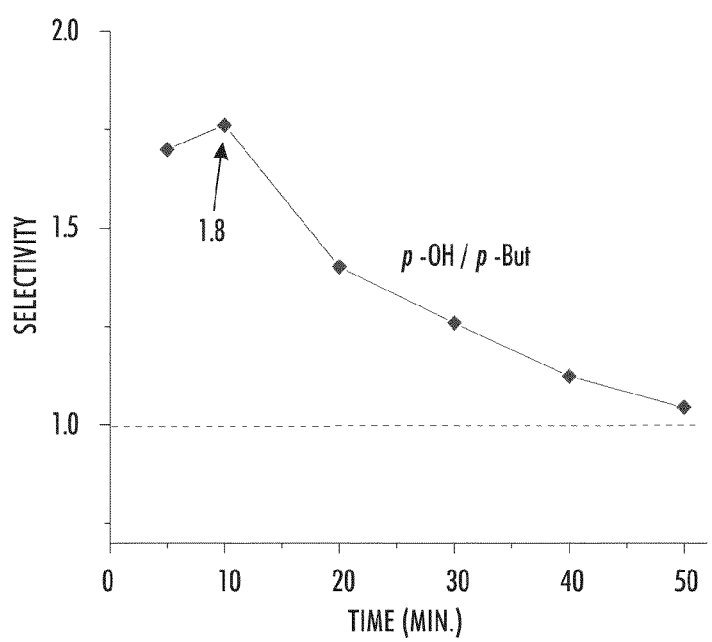
Figure 34C:
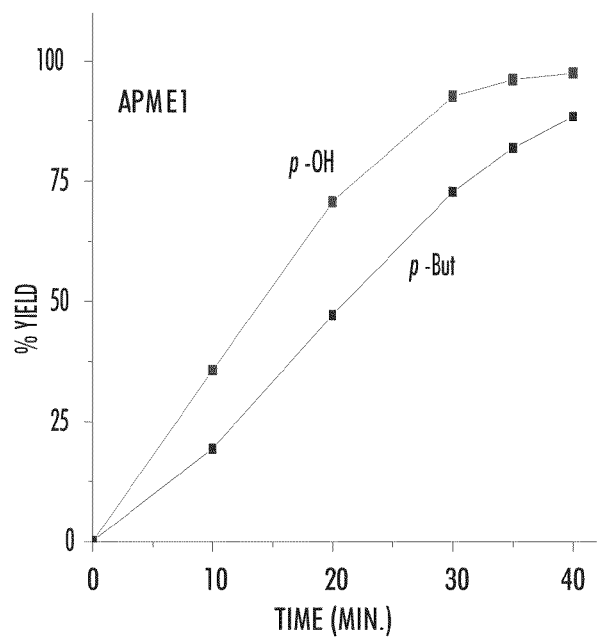
Figure 34C:
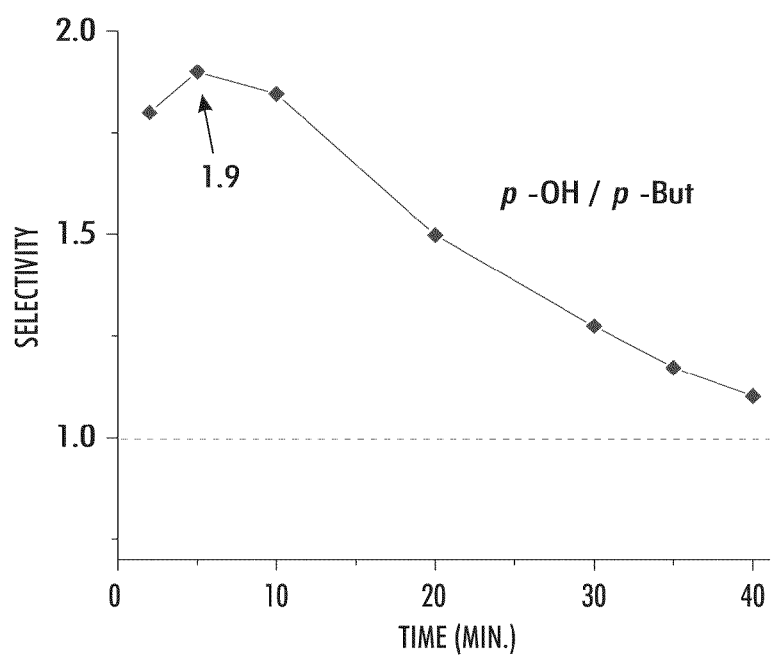
Figure 34D:
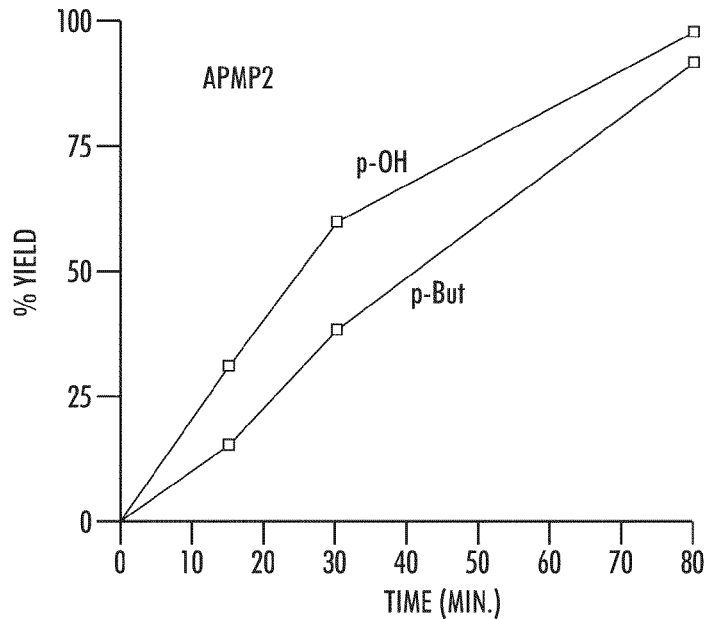
Figure 34D:
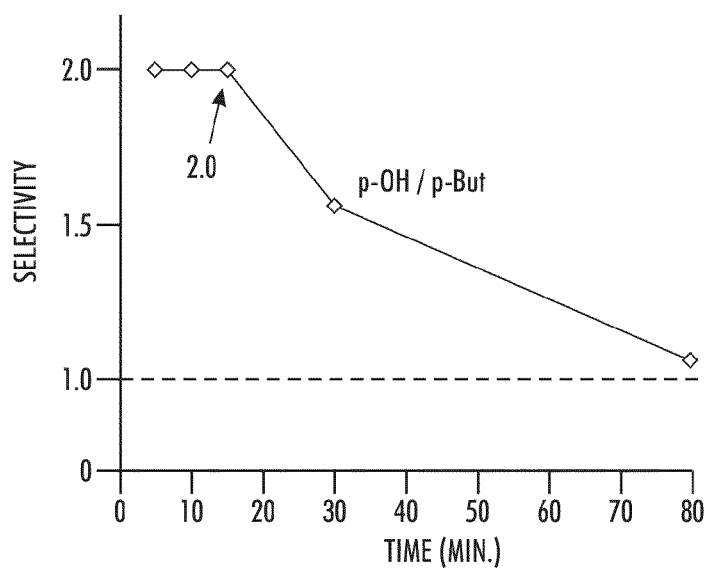
Figure 34E:
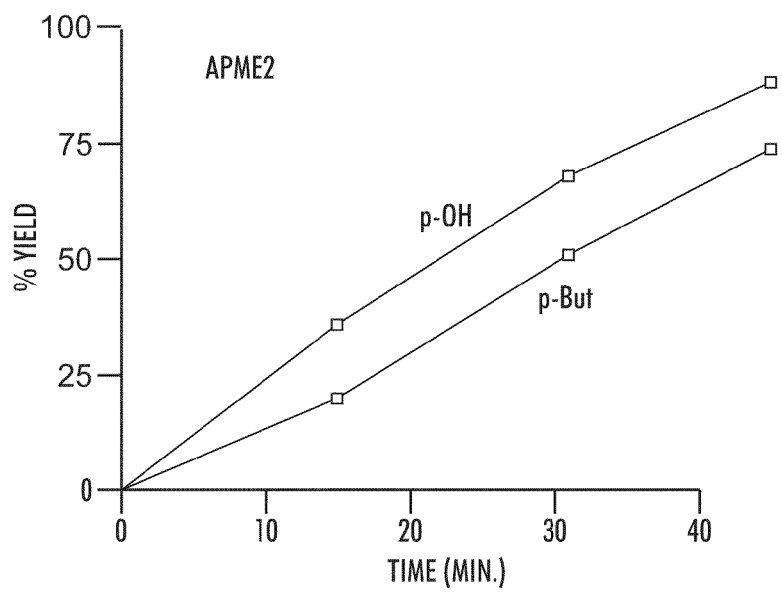
Figure 34E:
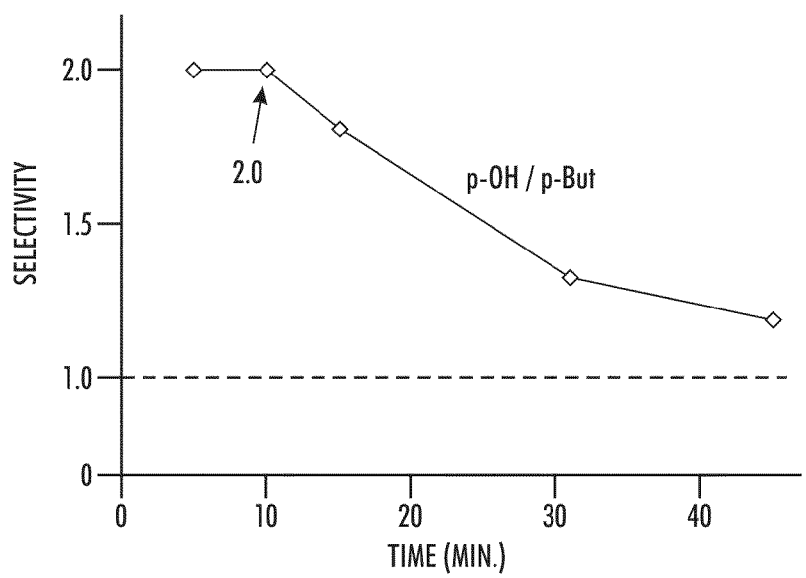
Figure 34F:
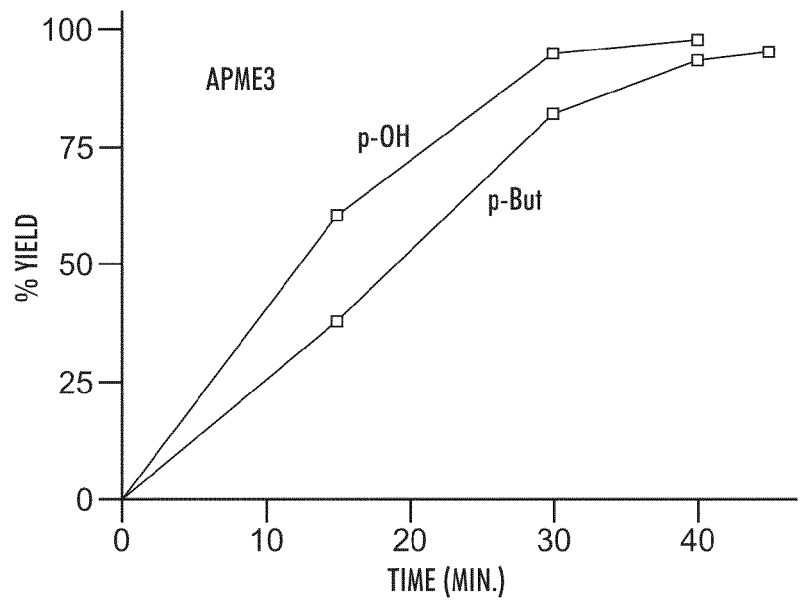
Figure 34F:
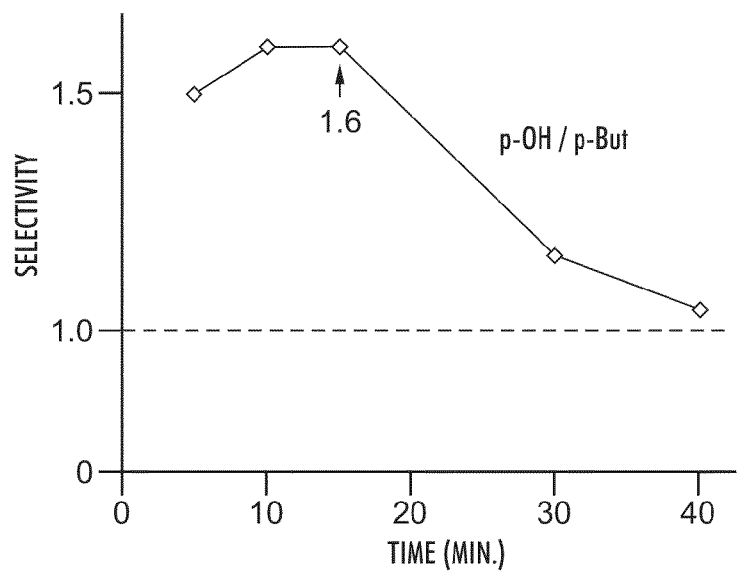
Figure 34G:
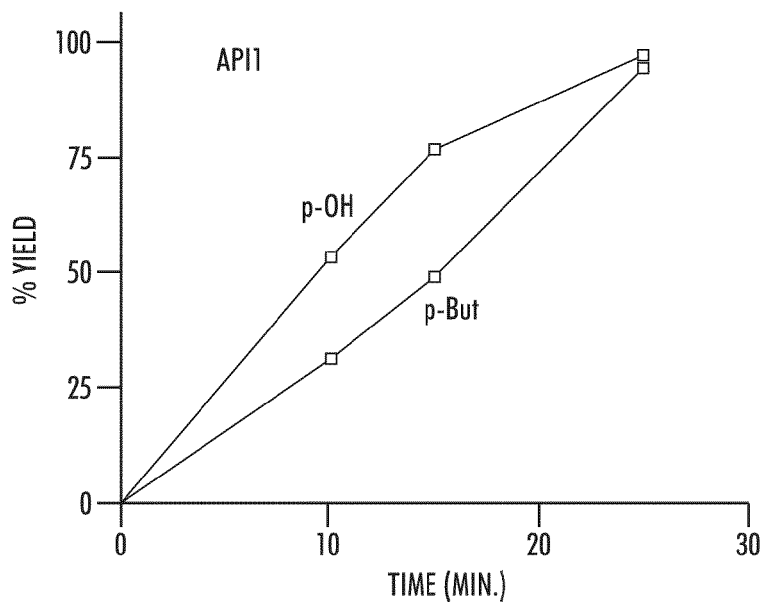
Figure 34G:
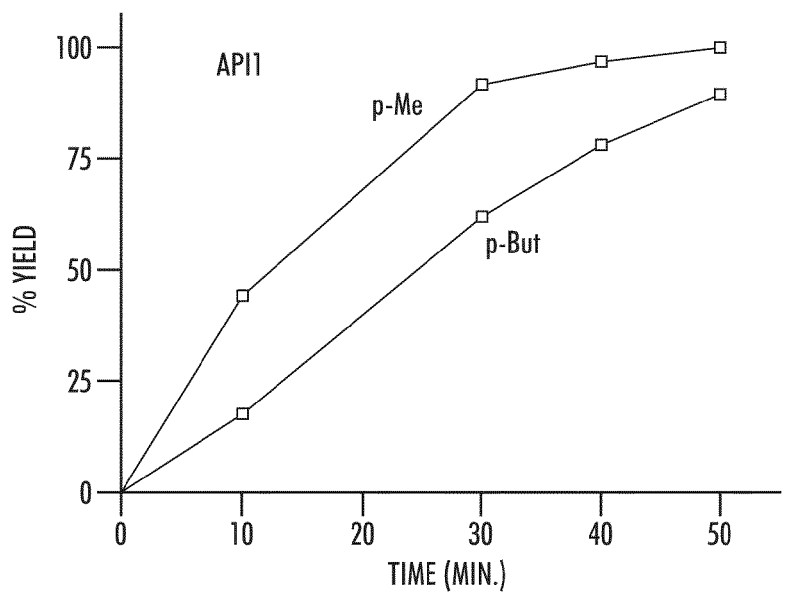
Figure 34H:
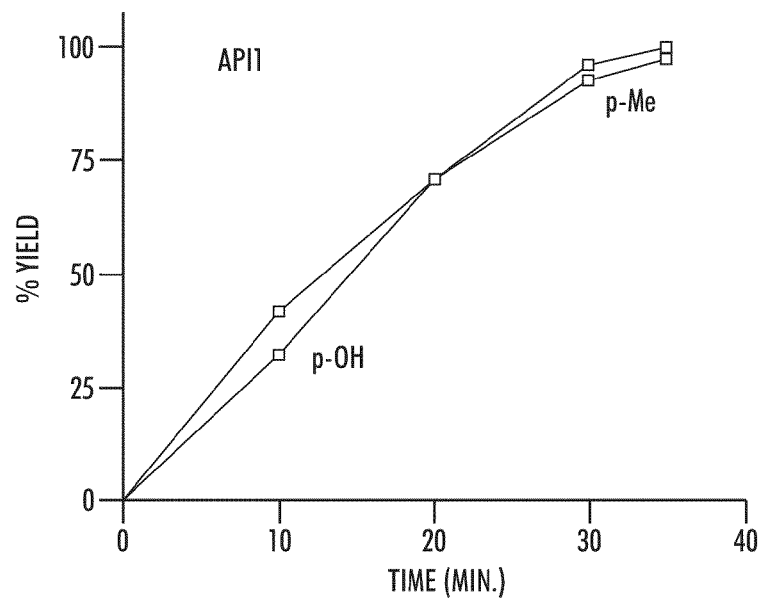
Figure 34H:
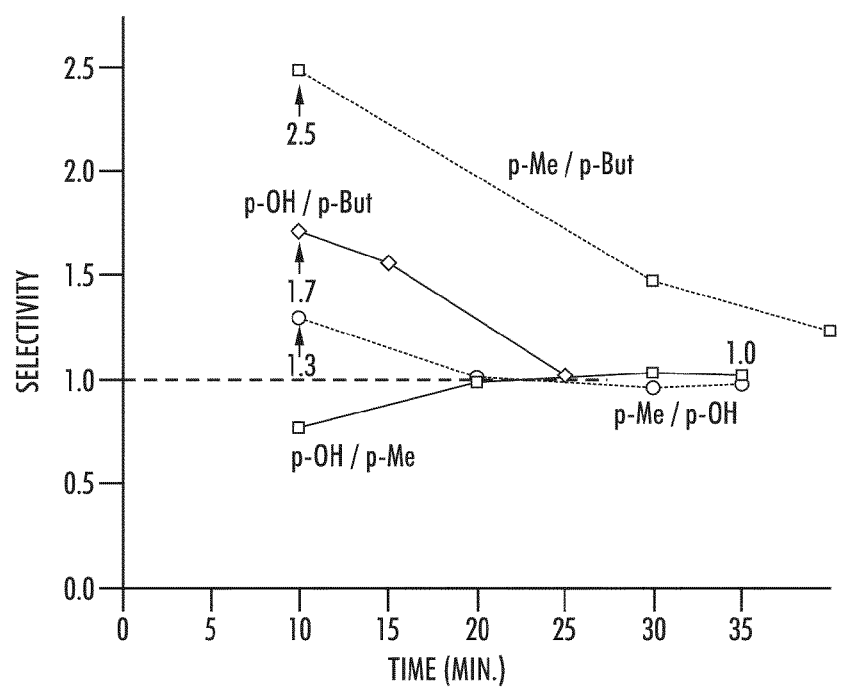
Figure 34I:
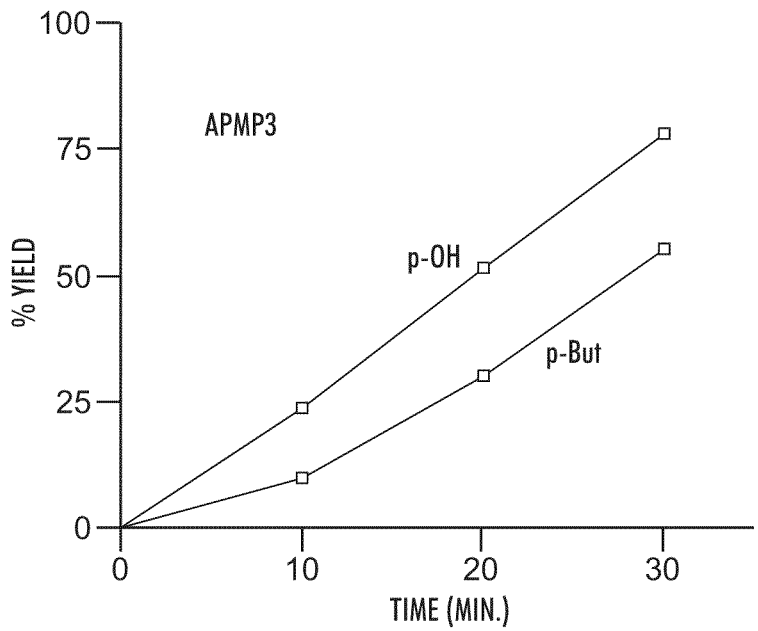
Figure 34I:
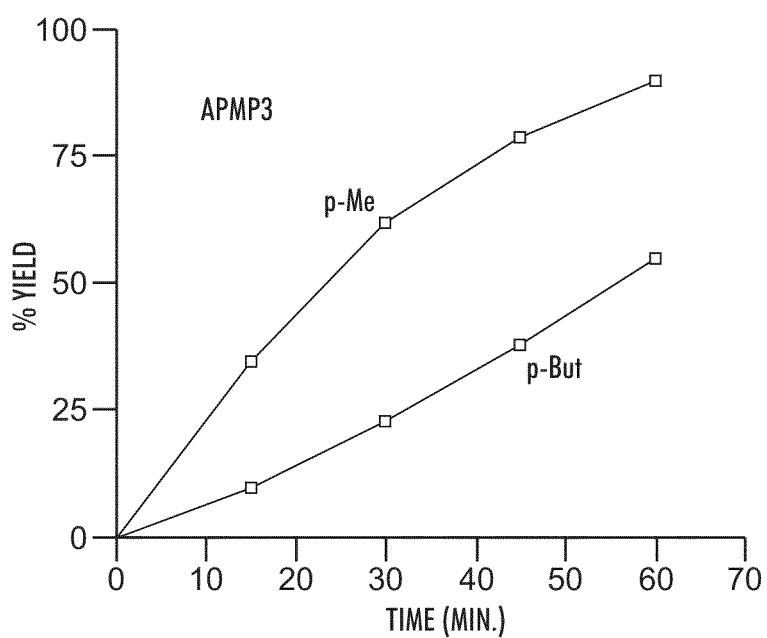
Figure 34J:
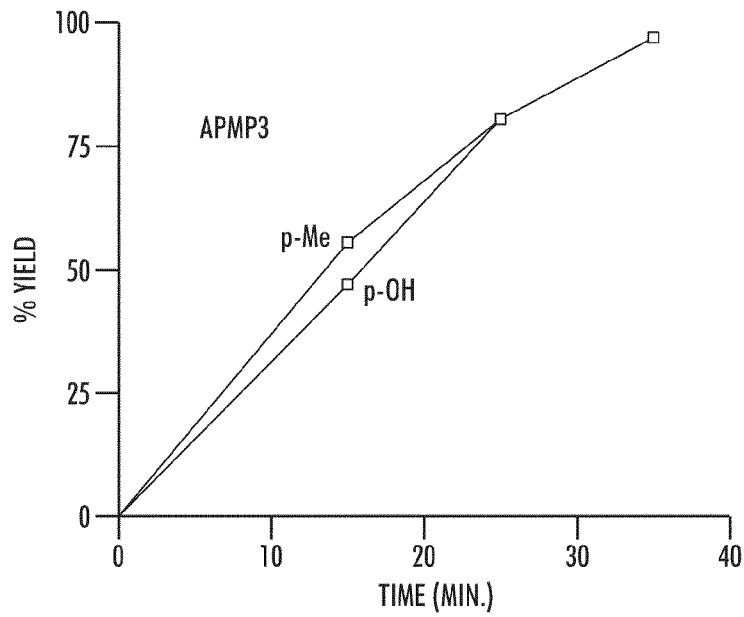
Figure 34J:
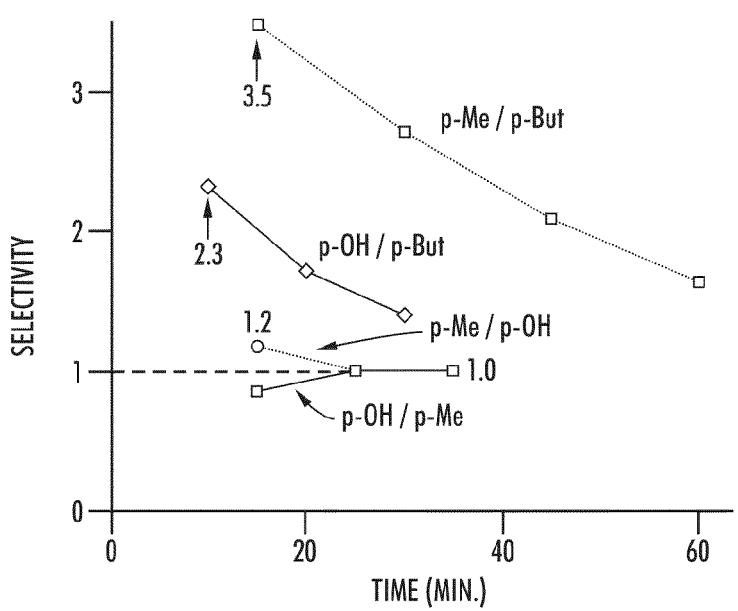
Figure 34K:
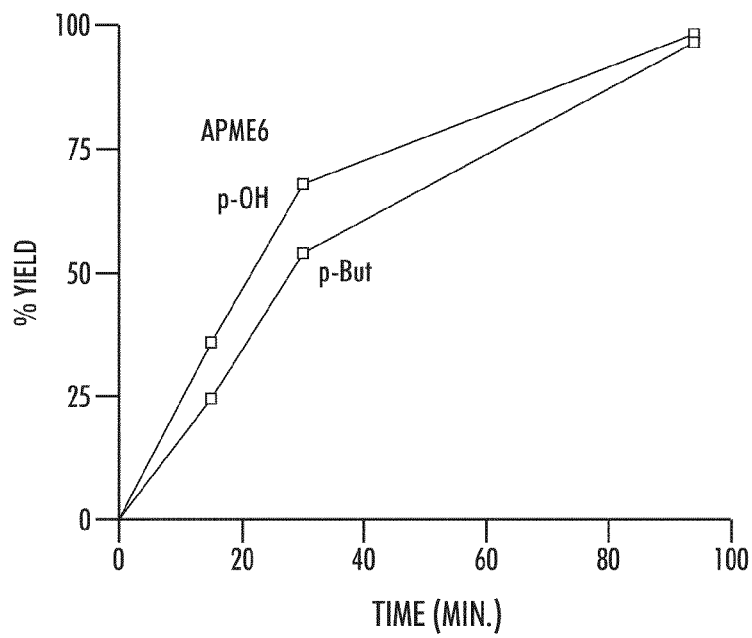
Figure 34K:
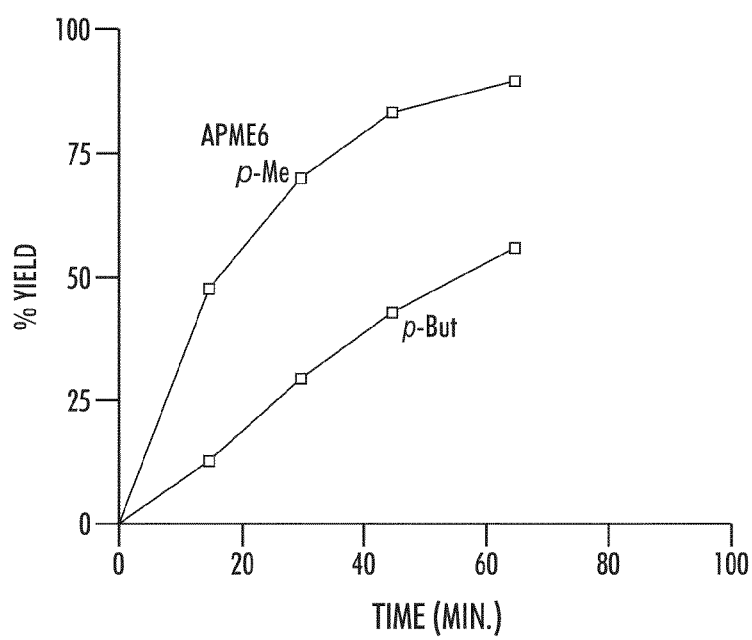
Figure 34L:
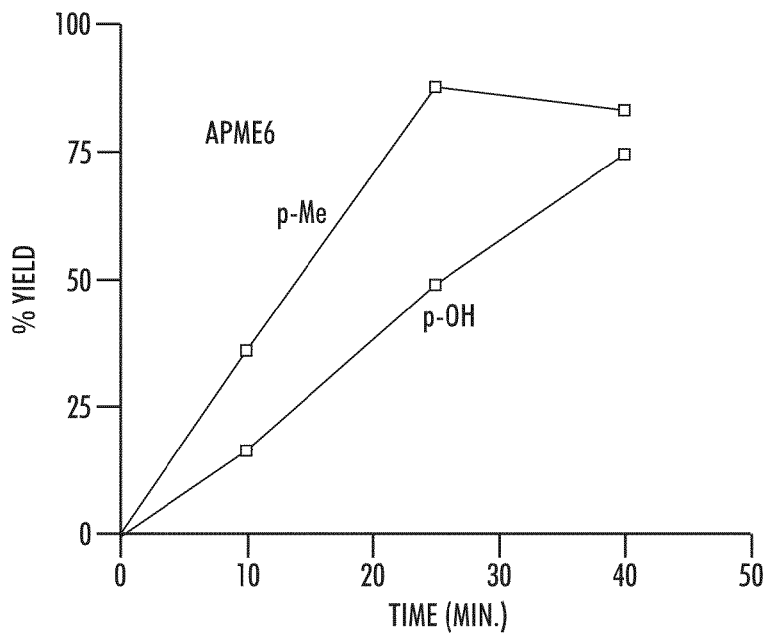
Figure 34I:
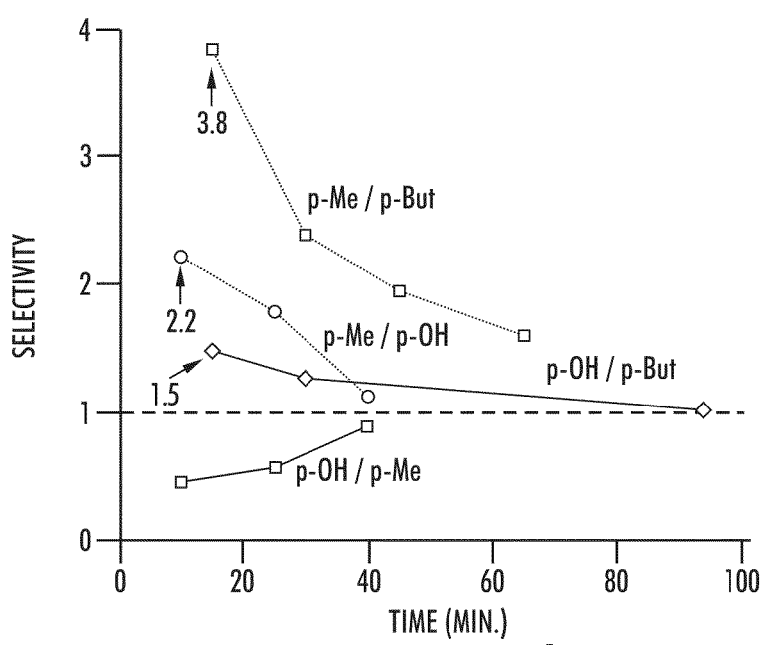
Figure 35A:
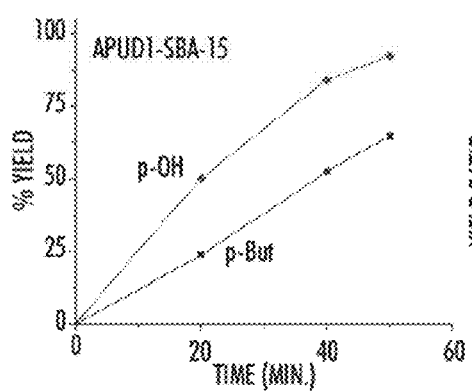
FIGS. 35A-35E are a series of reaction time plots (% yield versus time plots) for the Henry reaction of 1:1 mole mixture of two reactants catalyzed by various selected trifunctional mesoporous catalysts prepared from parent SBA-15 mesoporous silica.
Figure 35A:
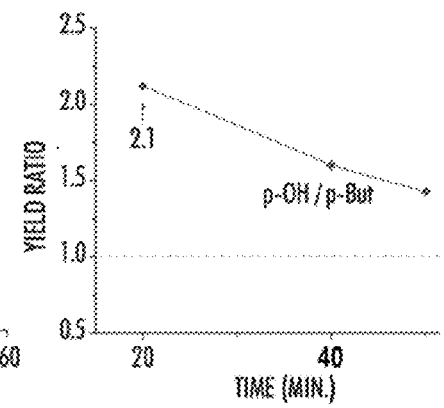
Figure 35B:
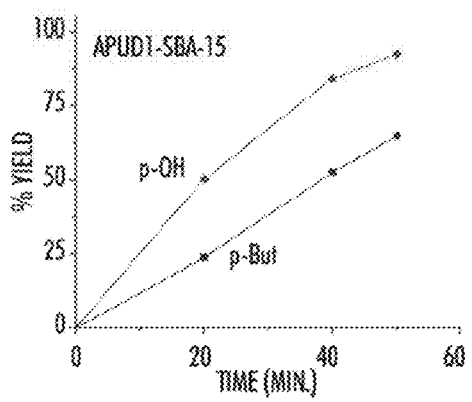
Figure 35B:
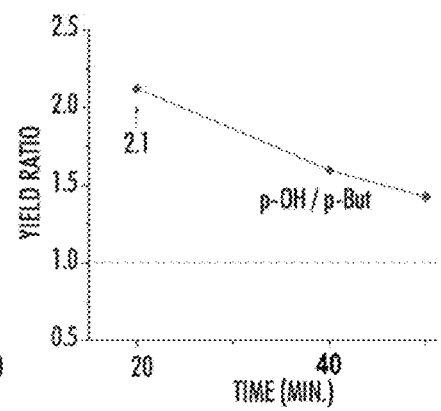
Figure 35C:
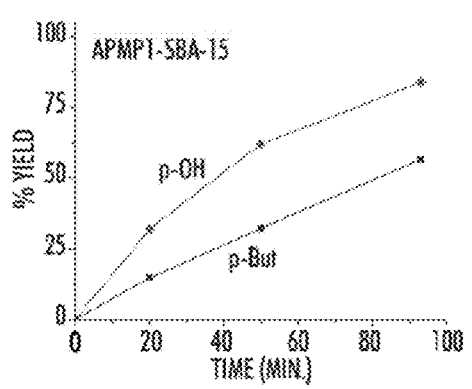
Figure 35C:
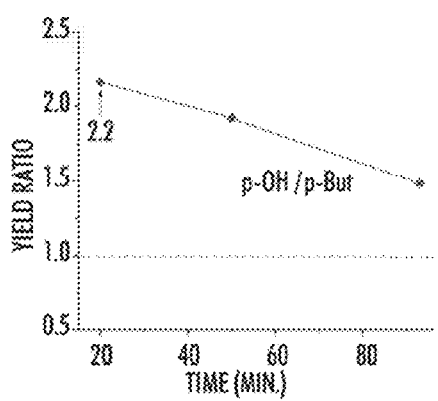
Figure 35D:
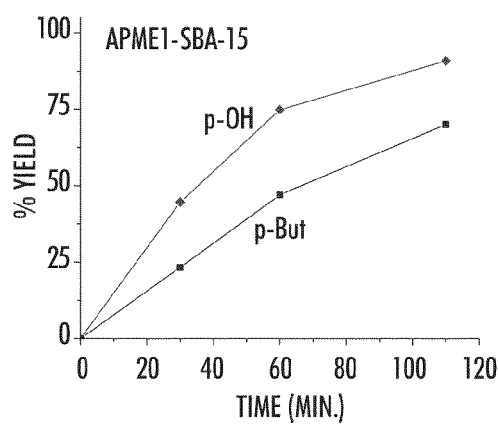
Figure 35D:
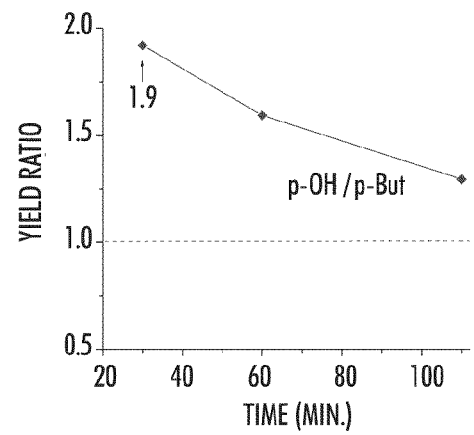
Figure 35E:
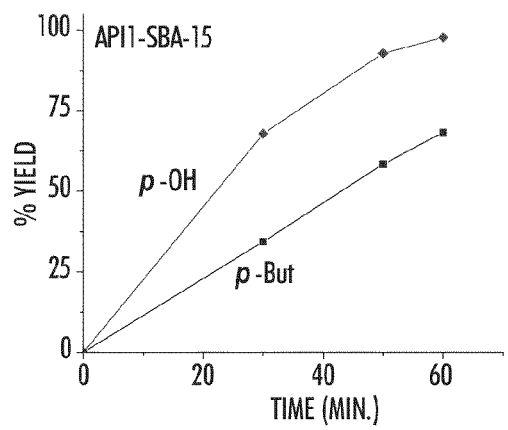
Figure 35E:
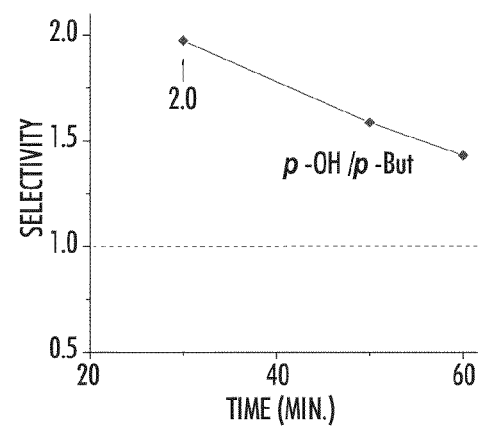

Furthermore, samples that contained a higher loading of organic functional groups generally showed lower efficiency for most of the reactants, which indicates the correlation between catalytic efficiency and relative crowding of the catalytic sites or their site-isolation. Additionally, the catalytic efficiency of one reactant over another (or the relative ratio of yields individually obtained for two reactants by the same catalyst) correlates with the type of functional groups and their concentrations, as indicated in FIGS. 32a-32n and Table 6. For instance, referring to FIGS. 32a, 32d, and 32g, the ratio of % yields of p-OH and p-But for individual reactions was found to be above 2.0 for samples containing UDP and AP groups except for APUD3 (FIG. 32g), which showed a ratio of % yield of 1.7, which could be attributed to the lower concentration of catalytic groups in this sample. Samples such as APME1, APMP3, APME4 and APME6, that contained a large concentration of secondary hydrophobic functional group ME and MP showed a much lower ratio of % yields for p-OH and p-But.

Furthermore, the decrease in the ratio was principally due to the decrease in the % yield of p-OH rather than p-But over time with the latter catalysts. Thus hydrophobic samples allowed relatively more hydrophilic p-OH limited access to the catalytic site. It is also noted that API1 showed the highest % conversion for all the reactants compared to other catalysts. Without wishing to be bound to any particular theory, the applicants believe that this is most likely because it contained the highest concentration of least crowded, most-optimum site-isolated catalytic sites (—$NH_2$ groups) and a higher surface area. It is also worth noting that API1 showed much higher efficiency for hydrophobic reactants compared to 3-aminopropyl containing samples reported by Lin et al., even if both samples have a similar number of —$NH_2$ groups per gram of sample.

For comparative purposes, the applicants have repeated the work of Lin et al. disclosed in *J. Am. Chem. Soc.* 2004, 126, 1010-1011, but with detailed reaction yield versus time plots for mixtures of p-OH, p-But, and p-Me. The applicants carried out the reaction yield versus time study in this case, since our experiments indicated that the selectivity in Henry reaction for a mixture of reactants was time dependent. The applicants have determined that the catalysts of Lin et al. lead to 100% conversion of all the reactants to products within 6 hours, as compared to the maximum of 50% in 24 hours reported by Lin et al. Furthermore, all the catalysts of Lin et al. showed a selectivity towards the p-OH over both p-But and p-Me despite the reported selectivity of p-But over p-OH by Lin. et al. after 24 hours. Additionally, it was found that after the reaction was completed in 6 hours, the nitrostyrene formed started to convert into the Michael product as observed on the $^1$H NMR, as well as possibly polymerize into poly(nitrostyrene) as observed from the waxy residue in the reaction flask. This thus could decrease the true yield of nitrostyrene and introduce error in the data, if the yields were obtained after 24 h based on the NMR peaks of reactants versus products, as performed by Lin et al.

A comparison of the results obtained by the applicants for Lin's catalyst and the applicants' own catalyst shows that the applicants' design of catalysts significantly improves the relative efficiency of all the reactants in the Henry reaction by manifold, and better selectivity is obtained for hydrophilic and hydrophobic reactants both when they are reacted individually (Table 6) and in a mixture, as will be discussed subsequently herein.

Upon comparing p-OH with p-Me, it was clearly observed that graphs of the % yield versus time for most of the catalysts have similar trends (FIGS. 32A-32N). In the initial reaction time, typically before 10 minutes, the rate of reaction of p-Me was higher than that of p-OH in most of the catalysts. The ratio of % yield of p-Me to p-OH during this time (FIGS. 32a-32n) was consistently between 1.4 and 4.0 for all the catalyst indicating the initial preference of the catalysts towards p-Me. In particular, this ratio was found to be the highest in more hydrophobic samples such as APMP3, APME4, APME5, and APME6 (FIGS. 32i, 32j, 32k, and 32l, respectively). After 10 minutes of reaction time, the reaction of p-Me slowed down with respect to that of p-OH and the ratio of % yield of p-Me to p-OH became less than 1.0. Thus, the selectivity values of the catalysts reversed after a certain time and hence a time-dependent study was important to the determination of the exact selectivity.

It is interesting to note that this trend became more pronounced in more hydrophobic samples such as APME5 and APME6, and that homogenous catalysis with APTS precursor in solution does not show this trend. On the contrary, the ratio of % yield of p-Me to p-OH was always less than 1.0 in homogenous catalysis indicating that the phenomenon of selectivity reversal is an exclusive property of the applicants' multifunctional heterogeneous mesoporous materials. Furthermore, since the solution NMR spectra of the reaction did not show any new product peaks corresponding to competitive Michael reaction product, polymerization product, or any other products, the applicants' believe that this fluctuation on the graph of % yield versus time for p-Me may be due to possible differences in the degree of adsorption and desorption of the p-Me reactant and p-methyl nitrostyrene product in the course of the reaction. Furthermore, the presence of hydrogen bonding between the p-OH product and the silanols of the mesoporous catalysts may also have caused this product to become trapped in the initial period of the reactions, making its relative yield smaller in the initial period.

Upon comparing the catalysts' relative yield for p-OH versus p-But, the applicants observed that all the samples showed higher yield for p-OH compared to p-But. In particular, samples APUD1 (FIGS. 32A/32a) and API1 (FIGS. 32M/32m), which contained the most hydrophilic groups, showed the highest selectivity with values of 2.8 and 2.6, respectively, higher for p-OH than for p-But. The other catalysts also showed higher reaction rates for p-OH than for p-But with values ranging from 1.6 to 2.6 times higher.

Control reactions with homogeneous catalysts were also performed. The homogeneous reaction was carried out by using 3-aminoprpyltriethoxysilane (APTS) as the catalyst in nitromethane since the supported 3-aminopropyl group in the mesoporous materials is the active catalyst. We believe that the APTS was the best control homogeneous catalyst. To further reduce the differences between the conditions for the homogeneous and heterogeneous catalysis, we carried out the reaction under nitrogen to avoid any possible hydrolysis and condensation or the triethoxysilyl groups. The homogeneous catalysis experiment also employed similar amounts of reactants and organocatalyst as in the heterogeneous catalysis.

The control reactions showed that p-OH reacted more quickly than the p-But and p-Me, and consequently, this may have contributed to the higher rate of reaction of p-OH compared to p-But inside the mesoporous channels. It is worth noting that the catalysts afforded over 90% yield for p-OH in 20 minutes of reaction time while they afforded a yield of about 50% for p-But in 20 minutes, as indicated in Table 7.

TABLE 7

Percent conversion in the Henry reaction of various p-substituted benzaldehydes and nitromethane in 20 minutes reaction time by the various trifunctional mesoporous catalysts; the reaction was performed at 90° C. using nitromethane as the reactant and the solvent.

| Sample | % Conversion p-OH in 20 min | % Conversion of p-But in 20 min | % Conversion of p-Me in 20 min |
| --- | --- | --- | --- |
| APUD1 | 90 | 30 | 80 |
| APMP1 | 90 | 45 | 75 |
| APME1 | 90 | 50 | 80 |
| APUD2 | 90 | 45 | 75 |
| APMP2 | 90 | 40 | 80 |
| APME2 | 80 | 25 | 70 |
| APUD3 | 90 | 40 | 80 |
| APMP3 | 90 | 60 | 90 |
| APME3 | 90 | 50 | 80 |
| APME4 | 75 | 38 | 70 |
| APME5 | 75 | 25 | 60 |
| APME6 | 75 | 38 | 80 |
| API1 | 90 | 50 | 70 |
| API1A (12 h-dried) | 90 | 50 | 70 |

Catalysts APMP1 (FIG. 32b) and APME1 (FIG. 32c) showed slightly reduced values of 2.2 and 1.7 times, respectively, of higher yields for p-OH than for p-But. This suggests that the hydrophobic groups of MP and ME have reduced the preferential catalysis of p-OH over p-But. Catalysts such as APUD2 (FIG. 32d), APMP2 (FIG. 32e) and APME2 (FIG. 32f) also showed similar high selectivity for p-OH over p-But with values of 2.3, 2.2, and 2.5, respectively. A similar trend was also observed upon comparing the efficiency of p-Me with p-But. Despite the substituents on the aromatic rings of p-Me and p-But having similar hydrophobicity, the catalytic efficiency of all the samples was consistently higher for p-Me than that for p-But and the ratio of % yields of p-Me with that of p-But was much higher when compared to the corresponding values obtained from homogeneous catalysis with APTS precursor in solution. Further, the ratio of % yield for p-Me versus p-But was consistently higher than that observed for % yield of p-Me versus p-OH. Without wishing to be bound to a particular theory, the applicants believe that this could be due to the steric demands imposed by the butoxy (BuO—) substituent of p-But during diffusion inside the pores. In other words, the bigger reactants underwent the reaction less slowly and gave lower yields. These results indicated size selectivity on the part of our functionalized catalysts. Thus our design of the catalyst allowed selectivity based on size as well as hydrophobicity of the reactants.

To design and synthesize more hydrophobic catalysts, the applicants have grafted the METS:APTS in 3:1 and 9:1 mole ratios in isopropanol. These materials (APME4, FIGS. 32J/32j; and APME6, FIGS. 32L/32l, respectively) showed higher selectivity for hydrophobic group, p-Me over p-OH, with values as high as 3.2 and 4.0. The catalytic efficiency of these samples were slightly lower compared to samples synthesized from APTS only (API1) and those synthesized from 1:1 mole mixture of APTS and the secondary organosilanes (APUD1, APMP1, and APME1) because the former (APME4 and APME6) contained less number of organoamine groups. The latter was confirmed by elemental analysis. Besides the AP groups, in some cases, the differences in catalytic efficiency were associated with the second functional group. For instance, sample APUD1 (FIG. 32A/32a) showed slightly higher efficiency than sample API1 (FIG. 32M/32m) for p-OH reactant, with a yield of 42% versus 37% in 15 minutes, despite the fact that APUD1 contained less AP groups than API1. Furthermore, samples APUD2 (FIGS. 32D/32d) and APUD3 (FIGS. 32G/32g) consistently showed a much higher catalytic efficiency for all the reactants. The applicants believe that this is likely due to the cooperative catalytic properties by UD and AP groups compared to the other catalysts, as reported by Huh et al. in *Angew. Chem., Int. Ed.* 2005, 44, 1826-1830.

Selectivity of the catalysts for mixture of reactants indicated a similar trend as those results obtained for reactions performed for the reactants individually. Reactions of 1:1 mol mixture of different pair of reactants were investigated with a number of catalysts. Results of this investigation are summarized in Table 8, and FIGS. 34A-34K, FIGS. 34a-34k, FIGS. 35A-35E, and FIGS. 35a-35e. The reactions were performed at 90° C. using nitromethane as the reactant and the solvent. The data in each of the columns of Table 8 are based on the maximum ratio of % yield of one reactant versus the other with respect to time, in a reaction mixture containing 1:1 mol ratio of both reactants.

The samples grafted with 1:1 mole ratio of AP and the secondary functional groups showed little selectivity for p-Me compared to p-OH, with values of about 1.0 being obtained in all cases. However, the highly hydrophobic catalyst, APME6, showed a selectivity of 2.2 for p-Me over p-OH. Since these two reactants have similar sizes, this supports the premise that the catalyst does not discriminate between p-Me and p-OH on the basis of size, but instead, hydrophobicity. However, comparing p-Me with p-But, all the samples showed higher selectivity for p-Me than p-But. These values, however, varied corresponding to the hydrophobicity of the samples, with the more hydrophobic sample having the highest value. For instance, the values obtained were 3.8, 3.5, and 2.5 for catalysts APME6, APMP3, and API1, respectively. Thus, apart from the intrinsic differences in the reactivity, the size selectivity of the pores results in higher reaction rate for p-Me over p-OH.

The effect of water on the materials or drying the catalysts on the catalytic efficiency was also investigated. The results of this investigation are summarized in FIG. 36 and Table 9.

TABLE 9

Effects of drying bifunctional mesoporous catalysts and its effect on the catalytic efficiency of the materials in the Henry reaction demonstrated by catalyst API1 samples dried at different times.

| Sample | % Conversion of p-OH in 15 min | % Conversion of p-But in 25 min | % Conversion of p-Me in 15 min |
|---|---|---|---|
| API1 (1 hour drying) | 80 | 48 | 57 |
| API1 (3 hours drying) | 94 | 68 | 56 |
| API1 (12 hours drying) | 95 | 66 | 87 |

TABLE 8

Mesoporous catalysts and control samples synthesized by grafting in various solvents and their catalytic efficiency in a reaction containing 1:1 mol mixtures of various p-substituted benzaldehyde with nitromethane.

| Sample | Maximum Selectivity or % p-OH/% p-But (time, min)[b] | Maximum Selectivity or % p-Me/% p-OH (time, min)[b] | Maximum Selectivity or % p-Me/% p-But (time, min)[b] | % Yield p-Me:% Yield p-But at maximum selectivity[b] | % Yield p-Me:% Yield p-OH at maximum selectivity[b] | % Yield of p-Me:% p-But at maximum selectivity[b] |
|---|---|---|---|---|---|---|
| APUD1 | 1.7 (10) | — | — | 34:21 | — | — |
| APMP1 | 1.8 (10) | — | — | 36:19 | — | — |
| APME1 | 1.9 (10) | — | — | 21:10 | — | — |
| APMP2 | 2.0 (15) | — | — | 48:32 | — | — |
| APME2 | 2.0 (10) | — | — | 25:13 | — | — |
| APME3 | 1.6 (15) | — | — | 60:38 | — | — |
| APMP3 | 2.3 (5)[e] | 1.2 (15) | 3.5 (15) | 12:5 | 56:47 | 35:10 |
| APME6 | 1.5 (15)[f] | 2.2 (15) | 3.8 (15) | 36:24 | 36:16 | 48:13 |
| API1 | 1.7 (10) | 1.3 (10) | 2.5 (10) | 54:31 | 42:32 | 44:18 |

All of the catalysts showed a selectivity of about 2 for p-OH over p-But, with no significant differences among the catalysts. This selectivity was obtained in about 10-15 minutes of reaction time. Typical yield was found to be 70% in 10 minutes for more selectively reacted reactant, p-OH, with the highest being 90% and 60% at 30 minutes for p-OH and p-But, respectively. The slight decrease in efficiency in case of 1:1 reaction is indicative of the competition between the reactants to access the catalytic sites on the basis of their steric bulk and hydrophobicity. Hydrophobic catalysts, such as APME6, showed a decreased selectivity of 1.6 for p-OH compared to p-But.

Figure 36:
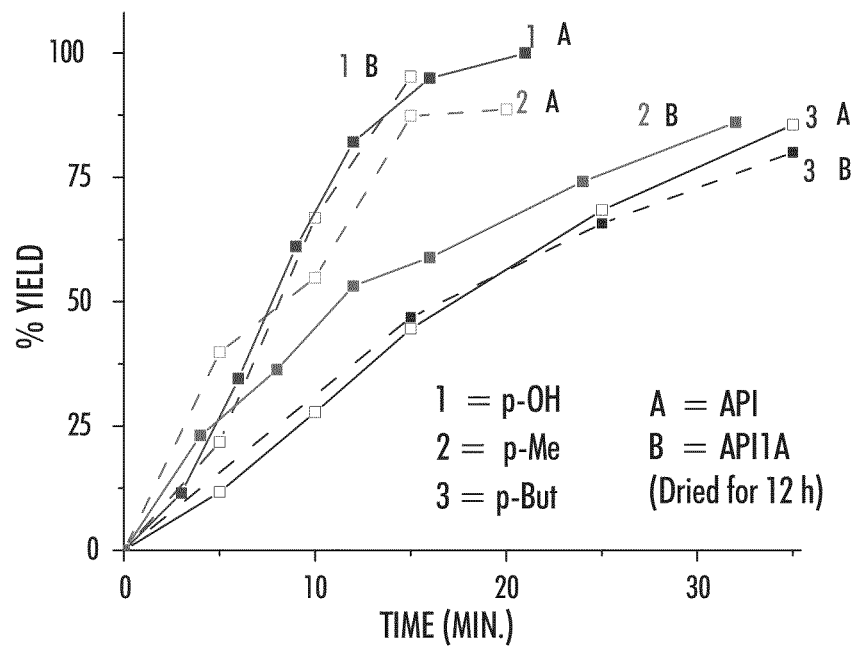
FIG. 36 is a graph of the effect of drying of the trifunctional mesoporous catalysts in the Henry reaction, as demonstrated by the API1 sample, which was dried under ambient condition 1 hour and in an oven at 80° C. for 12 hours.

Heating of the catalyst before reactions was found to be preferable for obtaining a good yield. For example, referring to Table 9, for catalyst API1 the optimum heating time was found to be 3 hours for p-OH and p-But at 80° C. While further heating of the catalysts to 12 hours increased the yield of p-Me appreciably, it did not cause additional change on the yields of p-OH and p-But (FIG. 36). Removal of $H_2O$ and $CO_2$ by heating has been reported to increase the strength of basic sites of solid-base catalysts for nitroaldol condensation by Hattori in *Appl. Catal. A*. 2001, 222, 247-259. The applicants believe that this may be the reason for increased catalytic efficiency of the dried samples.

Figure 37:
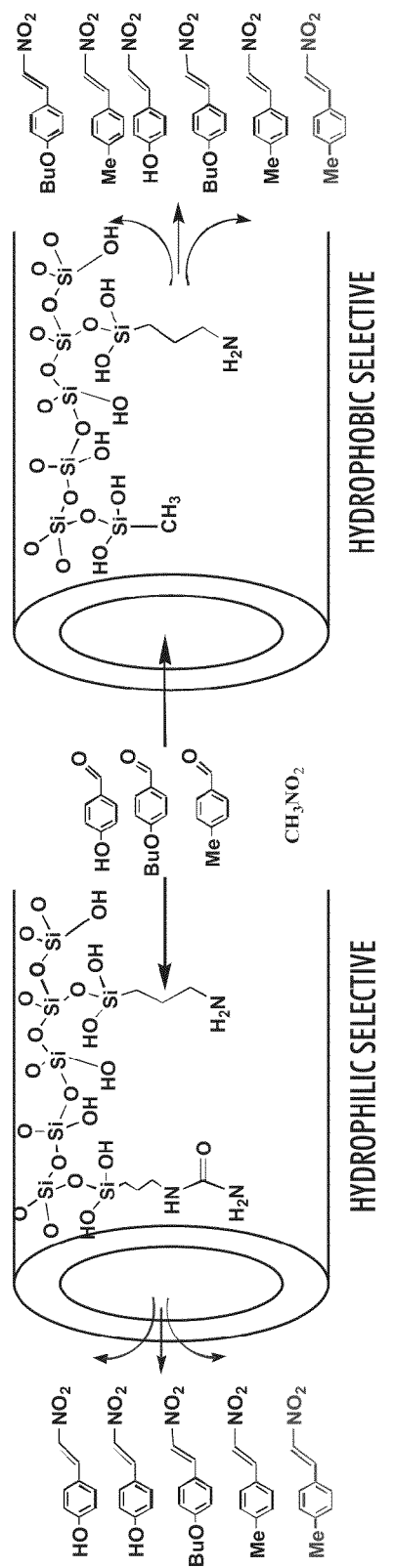
FIG. 37 is a schematic illustration of the applicants' synthesis of selective, efficient trifunctional mesoporous catalysts containing multiple site-isolated functional groups for selective catalysis of either hydrophilic or hydrophobic reactants in the Henry reaction.

In summary, we have disclosed the synthesis of selective, efficient trifunctional mesoporous catalysts containing multiple site-isolated functional groups for selective catalysis of either hydrophilic or hydrophobic reactants in the Henry reaction, as illustrated schematically in FIG. 37. This was demonstrated in the reaction between nitromethane and various p-substituted benzaldehydes having different size, hydrophobicity, and electronic properties. While the site-isolation of organoamine and silanol functional groups on the trifunctional mesoporous materials rendered high efficiency in the reaction, the judiciously chosen secondary organic functional groups inside the mesoporous channels have provided the materials with suitable surface properties to allow the preferential reaction of hydrophilic or hydrophobic reactants to the other one. Further, the selective catalytic properties for a mixture of some of the reactants were found to be time dependent. It is noted that the reaction products by these catalysts were exclusively p-substituted nitrostyrenes. By stopping the reaction at a specific time and by removing the catalyst, higher concentration of selective reaction product from one reactant could be achieved. The synthetic approach employed here is simple and versatile and can be adapted to a number of other catalytic reactions and mixtures of reactants. To the best of the applicants' knowledge, this is the first time that a grafting synthesis method for efficient trifunctional mesoporous selective, efficient catalysts for both hydrophilic and hydrophobic reactants has been reported. The resulting materials should potentially be useful for many reactions that are commonly employed for the synthesis of various fine and pharmaceutical chemicals.

Optimizing Cooperative Acid-Base Bifunctional Mesoporous Catalysts for the Henry Reaction: Effects of Site-Isolation, Concentration, and Separation of Functional Groups The effects of site-isolation, relative concentrations and separation distance between bifunctional groups in acid-base bifunctional mesoporous materials on the cooperative catalytic properties and efficiency of the materials in the base-catalyzed Henry reaction have also been studied. The applicants have discovered that the site-isolation and relative concentrations of the bifunctional groups can be controlled by simple, one-step, facile grafting of organoamines on mesoporous silica at various temperatures using ethanol and toluene as solvents; and that the separation distances between the functional groups can be controlled by using shorter and longer organoamines, i.e. grafting organoamines of specifically chosen lengths.

The grafting of a minororganosilanes in ethanol has resulted in site-isolated organoamine and organodiamine groups with an organoamine:silanol ratio of about 0.2 and high surface area materials. In contrast, grafting in toluene resulted in densely populated organoamines with an organoamine:silanol ratio of about 1.0 and low surface area materials. The monoamine- and diamine-functionalized samples from ethanol afforded nearly 100% yield in 15 and 30 minutes, respectively, in the Henry reaction between p-hydroxybenzaldehyde and nitromethane, while the corresponding samples grafted in toluene gave nearly 100% yield in more than 1 and 2.5 hours, respectively. The importance of grafting in ethanol and many residual silanols to enhance the catalytic efficiency of the materials were further confirmed by grafting additional organosilanes onto the bifunctional catalyst. The resulting materials from ethanol exhibited only a slightly reduced catalytic efficiency, while those from toluene again showed significantly reduced efficiency. The cooperative catalytic effect by the bifunctional groups was higher for 3-aminopropyl-functionalized samples, whose primary amines were in close proximity with silanols, compared to 3-aminoethyl(3-aminopropyl)-functionalized samples.

A comprehensive study of the effects of site-isolation, relative concentrations and separation distance between bifunctional groups in acid-base bifunctional mesoporous materials on the cooperative catalytic properties and efficiency of the materials in base-catalyzed Henry reaction was performed, and is described herein. In accordance with the invention, a series of organomonoamine- and organodiamine-functionalized samples with various degrees of site-isolation, relative concentrations of the bifunctional groups, and separation distances were synthesized via a simple, one-step, facile grafting of organosilanes on mesoporous silica at various temperatures using ethanol and toluene solvents. The applicants have performed investigations of the resulting materials' cooperative catalytic properties and efficiency in the Henry reaction. The cooperative effect by the acid and base functional groups and the surface areas in the materials have been found to be dependent on the degree of site-isolation, the silanol:organoamine ratio, and the separation distance between the functional groups.

The applicants have carried out the study by preparing a series of samples containing various concentrations of organomonoamine, organodiamine and cyanopropyl functional groups via grafting organosilanes onto mesoporous silica in ethanol and toluene at various temperatures, and by investigating the materials' catalytic properties in the Henry reaction. The applicants have discovered that organoamine- and organodiamine-functionalized samples from ethanol contain site-isolated organoamines and silanols and an organoamine:silanol ratio of about 0.2; and that these samples provide the highest efficiency (a yield of very nearly 100% in and 30 minutes, respectively) for the Henry reaction between p-hydroxybenzaldehyde and nitromethane. As noted previously, the corresponding samples grafted in toluene gave densely populated organoamines and silanols, an organoamine:silanol ratio of about 1.0, and lower catalytic efficiency.

By further comparative studies, the applicants have discovered that the cooperative catalysis by the bifunctional groups to be distance dependent, as shorter 3-aminopropyl-functionalized samples afforded very nearly 100% yield in 15 minutes, while longer 3-aminoethyl(2-amniopropyl)propydiamine-functionalized samples afforded very nearly 100% yield in 30 minutes. The applicants believe that this longer time to approach 100% yield is presumably due to the closer distances between the organoamine and silanol groups in the former. Grafting of more organosilanes in ethanol onto the silanols of the bifunctional acid-base catalysts resulted in only slight reduction in silanol concentration and insignificant decrease in catalytic efficiency, while grafting of the same organosilanes in toluene resulted in large decrease in silanol concentration, poor cooperative catalysis, and significant decrease in yield. Over one hour was required to approach 100% yield in the latter instance.

Details of the syntheses of the various catalysts in this investigation will now be provided. As noted previously, it is to be understood that certain aspects of the syntheses, such as the specific sources of reagents, are exemplary and are not to be construed as limiting.

Materials and Reagents: Nitromethane, p-hydroxybenzaldehyde, cetyltrimethylammonium bromide (CTAB), tetraethoxysilane, 3-aminoproyltrimethoxysilane, 2-amino(3-aminopropyl)trimethoxysilane, and 3-cyanopropyltriethoxysilane were all obtained from Sigma-Aldrich Corporation of St. Louis, Mo., and they were used as received without further purification. Anhydrous toluene and ethanol were obtained from BDH Chemicals Ltd. of Dorset UK and were also used as received.

MCM-41 was used as the mesoporous silica substrate material, and was synthesized as described previously herein.

Figure 38:
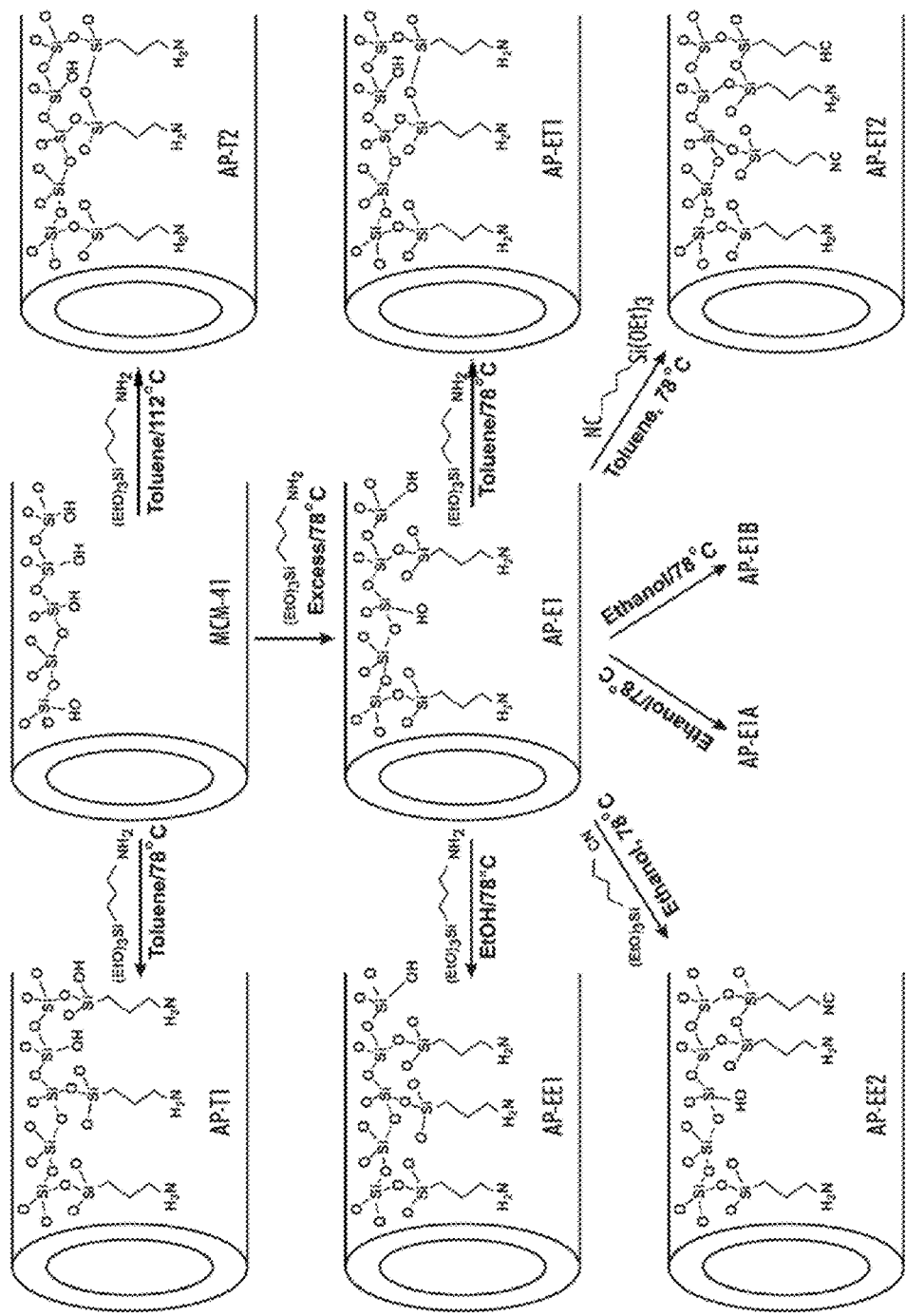
FIG. 38 is an illustration summarizing reaction schemes for converting the mesoporous material MCM-41 into catalysts containing various concentrations of organomonoamine via grafting of aminopropyltrimethoxysilane onto MCM-41 in ethanol and toluene at various temperatures.

FIG. 38 is an illustration summarizing reaction schemes for converting the mesoporous material MCM-41 into catalysts containing various concentrations of organomonoamine via grafting of aminopropyltrimethoxysilane onto MCM-41 in ethanol and toluene at various temperatures. Details of the various syntheses are as follows:

Synthesis of Monoamine-Functionalized Mesoporous Silica in Ethanol: A monoamine functionalized mesoporous material was synthesized by grafting 3-aminopropyltrimethoxysilane (APTS) onto MCM-41. Briefly, 500 mg of the MCM-41 sample was stirred in excess amount, 0.27 g (1.51 mmol), of APTMS and 200 mL anhydrous ethanol under reflux at about 78° C. for 6 hours. The solution was filtered and the precipitate was washed with dichloromethane, then with ethanol. The precipitate was allowed to dry under ambient conditions and it was labeled as AP-E1.

Synthesis of Monoamine-Functionalized Mesoporous Silica in Toluene: Two organoamine samples were prepared by grafting 3-aminpropyltrimethoxysilane (APTS) onto MCM-41 in toluene. Briefly, 500 mg of the MCM-41 sample was stirred in excess amount, 0.66 g (3.68 mmol), of APTS and 200 mL toluene at about 78° C. The solution was filtered and the precipitate was washed with dichloromethane, and then with ethanol. The precipitate was allowed to dry under ambient conditions and it was referred to as AP-T1. A second sample was prepared in the same manner, but under reflux at about 112° C. for 6 hours. This sample was referred to as AP-T2.

Grafting of More Organosilane onto AP-E1 in Ethanol and Toluene: Further grafting of two different organosilanes on sample AP-E1 in ethanol and toluene was carried out. Typically, 300 mg of the AP-E1 prepared above was placed in a small flask and was stirred in an excess amount, 0.40 g (2.23 mmol) of 3-aminopropyltrimethoxysilane (APTS) under reflux at about 78° C. for 6 hours in 200 mL ethanol. The solution was filtered and the precipitate was washed with dichloromethane and ethanol. The precipitate was allowed to dry under ambient conditions and it was named AP-EE1. A second sample was prepared with the same procedure, but in 200 mL of toluene at about 78° C., and this sample was named AP-ET1.

Similarly, 3-cyanopropyltriethoxysilane (OPTS) was grafted on sample AP-E1 in ethanol and toluene. Typically, 300 mg of sample AP-E1 was stirred in an excess amount, 0.40 g (2.23 mmol), of OPTS under reflux at about 78° C. for 6 hours in ethanol. The solution was filtered and the precipitate was washed with dichloromethane and ethanol and it was allowed to dry under ambient conditions. The resulting precipitate was denoted as AP-EE2. A second sample was prepared in the same way, but in toluene at about 78° C. and this sample was denoted as AP-ET2.

Control Samples (Treatment of AP-E1 in Ethanol and Toluene): To prepare control samples, AP-E1 was stirred in ethanol and toluene without organosilanes. Typically, 300 mg of sample AP-E1 was stirred under reflux at about 78° C. for 3 hours in ethanol. The solution was filtered and the precipitate was washed with dichloromethane and ethanol and allowed to dry under ambient conditions. The resulting precipitate was denoted as AP-E1A. A second sample was prepared the same way, but in toluene at about 78° C., and the resulting sample was named AP-E1B.

Additional reactions were also performed to convert the mesoporous material into a series of organodiamine-functionalized catalysts containing various concentrations of organodiamine via grafting onto MCM-41 in ethanol and toluene at various temperatures. Details of these syntheses are as follows:

Synthesis of Diamine-Functionalized Mesoporous Silica by Grafting in Ethanol and Toluene: Two mesoporous samples functionalized with organodiamine groups were prepared by grafting [3-(2-aminoethylamino)propyl]trimethoxysilane (AAPTS) in ethanol and toluene. Briefly, 500 mg of the MCM-41 sample was stirred in excess amount, 0.50 g (2.23 mmol), of AAPTS and 200 mL ethanol under reflux at about 78° C. for 6 hours. The solution was filtered and the precipitate was filtered with dichloromethane, and then with ethanol. The precipitate was allowed to dry under ambient conditions and it was denoted as AAP-E1.

Similarly, grafting of excess amount, 0.50 g (2.23 mmol), of AAPTS on MCM-41 in 200 mL toluene under reflux at about 112° C. for 6 hours was carried out. The solution was filtered and the precipitate was washed the same way as above. The resulting sample was referred to as AAP-T1.

The parent mesoporous silica and the series of organomonoamine- and organodiamine-functionalized samples were synthesized and studied using the chemical and physical analysis techniques described previously herein, or techniques/instruments similar thereto. Additional details are as follows:

The powder X-ray diffraction was measured using a Scintag powder diffractometer. Small angle X-ray scattering was measured with Synchrotron radiation at the Cornell High Energy Synchrotron Source (CHESS) as well as by using a Bruker-Axs Nanostar System. The solid-state $^{13}$C (75.5 MHz) and $^{29}$Si (59.6 MHz) NMR spectra were acquired on a Bruker AVANCE 300 spectrometer. For $^{13}$C CP-MAS NMR experiments, the applicants employed 7.0 kHz spin rate, 5 s recycle delay, 1 ms contact time, $\pi/2$ pulse width of 5.2 µs, and 1000-3000 scans using TPPM $^1$H decoupling. For the $^{29}$Si CP-MAS NMR experiments, we employed 7.0 kHz spin rate, 10 s recycle delay, 10 ms contact time, $\pi/2$ pulse width of 5.6 µs, and 256-1024 scans using TPPM $^1$H decoupling. The $^{29}$Si MAS NMR Experiments were done with 7.0 kHz spin rate, 100 s recycle delay, $\pi/6$ pulse width of 1.9 µs, and 700-4000 scans using high power CW $^1$H decoupling. The thermogravimetric analysis was carried out with a Q-500 Quantachrome Analyzer (TA-Instruments). The GC-MS was measured with HP-5971 GC-MS spectrometer. The solution $^1$H NMR was measured by Bruker DPX-300 NMR spectrometer. The BET gas adsorptions were measured with Micromeritics ASAP 2020 volumetric adsorption analyzer at 77 K by following previously reported procedure. The TEM images were obtained with a JEOL 1200 EX TEM instrument.

The above syntheses are summarized as follows. A series of monoamine- and diamine-functionalized mesoporous acid-base bifunctionalized materials with various concentrations of organoamine and silanol groups were synthesized by grafting 3-aminopropyltrimethoxysilane (APTS), 2-aminoethyl(3-aminopropyl)trimethoxysilane (AAPTS) and 3-cyanopropyltriethoxysilane (OPTS) onto mesoporous silica (MCM-41) using ethanol as a solvent, as shown in FIG. 38 and Table 10. Referring to Table 10, the unit cell data were obtained from the sample's d-spacing on XRD (unit cell, $a_0=2d_{100}/3^{1/2}$ for hexagonal $P_{6mm}$ mesostructures). The BJH pore diameters were obtained from the adsorption branch on the $N_2$ gas adsorption isotherm. Wall thickness is defined as Unit Cell Diameter-Pore Diameter.

TABLE 10

Synthesis and structural and composition data for monoamine- and diamine-functionalized mesoporous materials and other control samples prepared by grafting organosilanes onto MCM-41 in ethanol and toluene.

| Sample | Substrate + Organosilane, Solvent (Grafting Temperature)[b] | Unit Cell (Å) | BET Surface Area (m²/g) | BJH Pore Diameter (Å) | Wall Thickness (Å) |
|---|---|---|---|---|---|
| MCM-41 | — | 44.3 | 1030 | 34.1 | 10.2 |
| AP-E1 | MCM-41 + APTS, Ethanol (78° C.) | 44.4 | 906 | 31.4 | 13.0 |
| AP-T1 | MCM-41 + APTS, Toluene (78° C.) | 45.6 | 259 | 31.5 | 14.1 |
| AP-T2 | MCM-41 + APTS, Toluene (112° C.) | 44.4 | 60 | 30.6 | 13.8 |
| AP-EE1 | AP-E1 + APTS, Ethanol (78° C.) | 44.2 | 990 | 29.4 | 14.8 |
| AP-ET1 | AP-E1 + APTS, Toluene (78° C.) | 44.0 | 73 | 21 | |
| AP-EE2 | AP-E1 + CPTS, Ethanol (78° C.) | 44.5 | 1100 | 30.0 | 14.5 |
| AP-ET2 | AP-E1 + CPTS, Toluene (78° C.) | 44.1 | 872 | 28.5 | 15.6 |
| AP-E1A | AP-E1 + Ethanol (78° C.) | 44.0 | 1202 | 29.3 | 14.7 |
| AP-E1B | AP-E1 + Toluene (78° C.) | 43.8 | 1888 | 29.6 | 14.2 |
| AAP-E1 | AAPTS, Ethanol (78° C.) | 44.2 | 1021 | 32.3 | 9.8 |
| AAP-T1 | AAPTS, Toluene (112° C.) | 43.6 | 85 | 29.0 | 14.6 |

The MCM-41 material was synthesized as reported previously herein. The surfactant template was extracted by stirring the as-synthesized MCM-41 in a dilute acid/methanol solution to leave more surface silanol groups. The grafting of site-isolated organoamine groups onto the surface silanols of the materials was carried out by stirring APTS and AAPTS in ethanol at 78° C., which resulted in samples AP-E1 and AAP-E1, respectively. The grafting of densely populated organomonoamine were obtained by grafting APTS on MCM-41 in toluene at 78° C. and in reflux at 112° C. to provide samples AP-T1 and AP-T2, respectively. Similarly, densely populated organodiamine were formed by grafting of AAPTS in toluene on MCM-41 at 78° C. to result in sample AAP-T1. Furthermore, control samples were prepared by grafting more APTS onto AP-E1 using ethanol and toluene to afford samples AP-EE1 and AP-ET1, respectively. Similarly, 3-cyanopropyltriethoxysilane (CPTMS) was grafted onto AP-E1 in ethanol and toluene to result in AP-EE2 and AP-ET2, respectively. Additional control samples were obtained by stirring AP-E1 in ethanol and toluene without organosilanes to result in AP-E1A and AP-E1B, respectively.

Figure 39A:
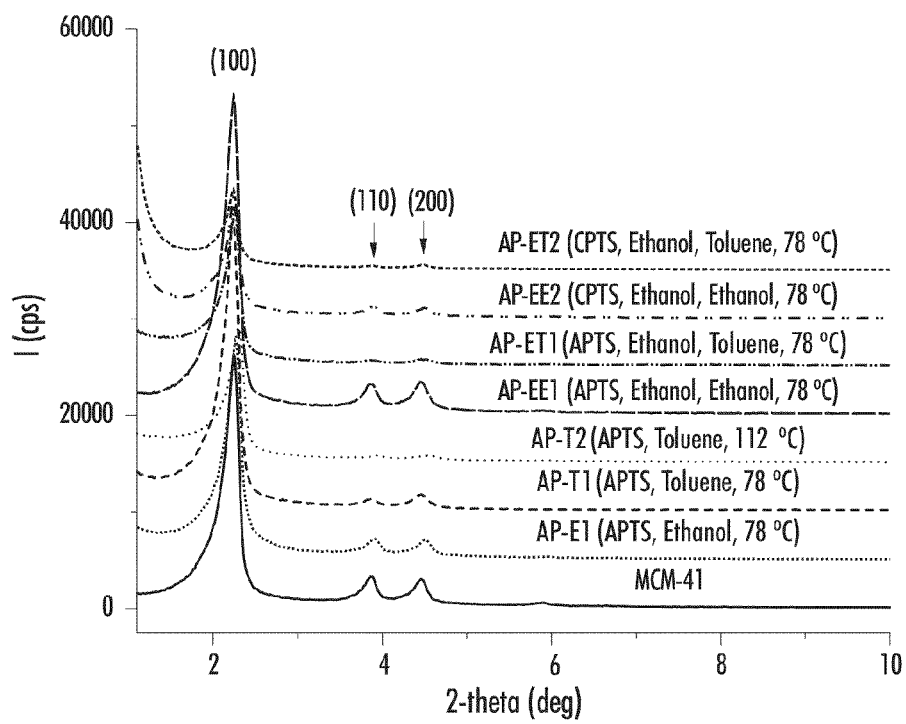
FIG. 39A depicts the powder X-ray diffraction patterns of MCM-41 compared with the certain organomonoamine functionalized mesoporous catalyst samples prepared by grafting in ethanol and toluene.
Figure 39B:
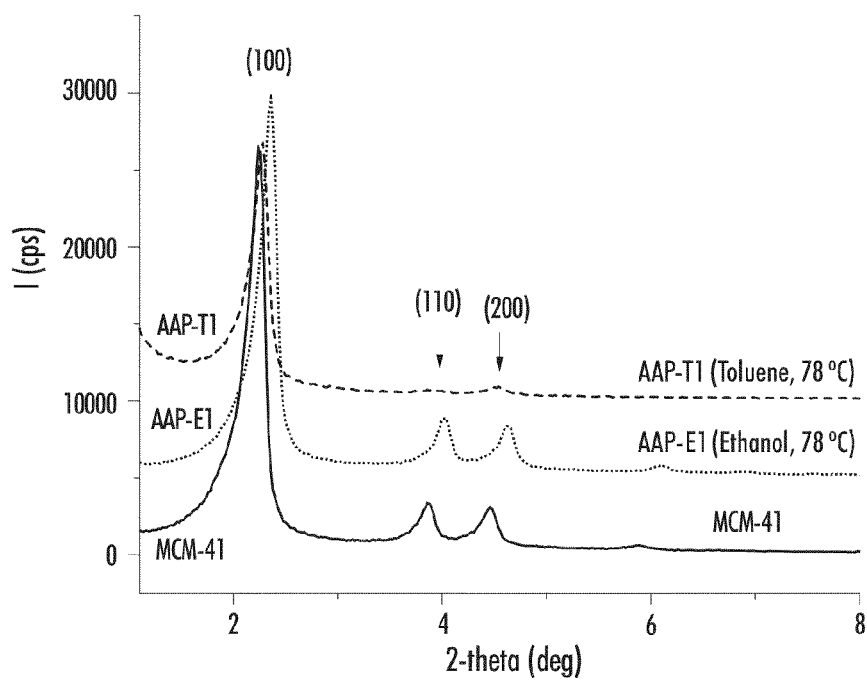
FIG. 39B depicts the powder X-ray diffraction patterns of MCM-41 compared with certain organodiamine functionalized catalyst samples.

The structures of the pre-made mesoporous sample (MCM-41) and the resulting organoamine-functionalized mesoporous samples were characterized by powder X-ray diffraction (XRD) and small angle X-ray scattering (SAXS). FIG. 39A depicts the powder X-ray diffraction patterns of MCM-41 compared with the following organomonoamine functionalized mesoporous samples prepared by grafting in ethanol and toluene: AP-E1, AP-T1, AP-T2, AP-EE1, AP-ET1, AP-EE2, and AP-ET2. FIG. 39B depicts the powder X-ray diffraction patterns of MCM-41 compared with organodiamine functionalized samples AAP-E1 and AAP-T1.

Referring first to FIG. 39A, the XRD patterns of the MCM-41 and all the organoamine grafted samples showed a sharp (100) Bragg reflection and at least two additional peaks corresponding to (110) and (200) Bragg reflections, which indicated that all the samples have highly ordered hexagonal, $P_{6mm}$, mesostructures. From the d-spacing on XRD, the unit cell dimensions of the materials were calculated to be about 43.8-45.6 Å (Table 10). As can also be seen in FIG. 39A, only a minor reduction in the intensities of their Bragg reflections was observed in the organoamine-functionalized samples compared to MCM-41, which indicated that the grafting of organosilanes onto the MCM-41, both in ethanol and toluene, did not cause major changes in the mesostructures.

Figure 39C:
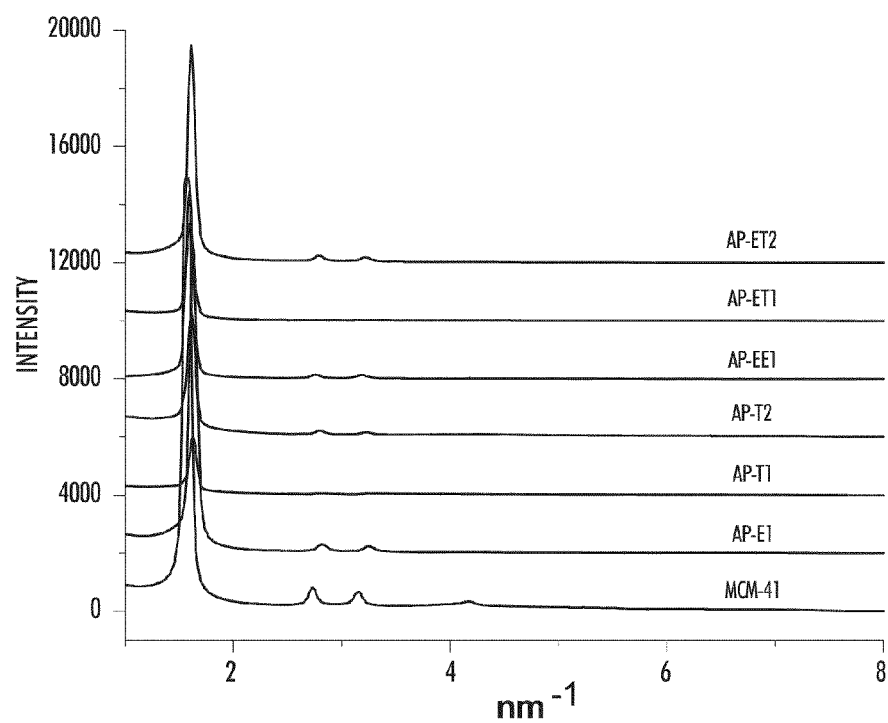
FIG. 39C depicts small angle X-ray scattering (SAXS) of MCM-41 compared with the certain organomonoamine functionalized mesoporous catalyst samples prepared by grafting in ethanol and toluene.
Figure 39D:
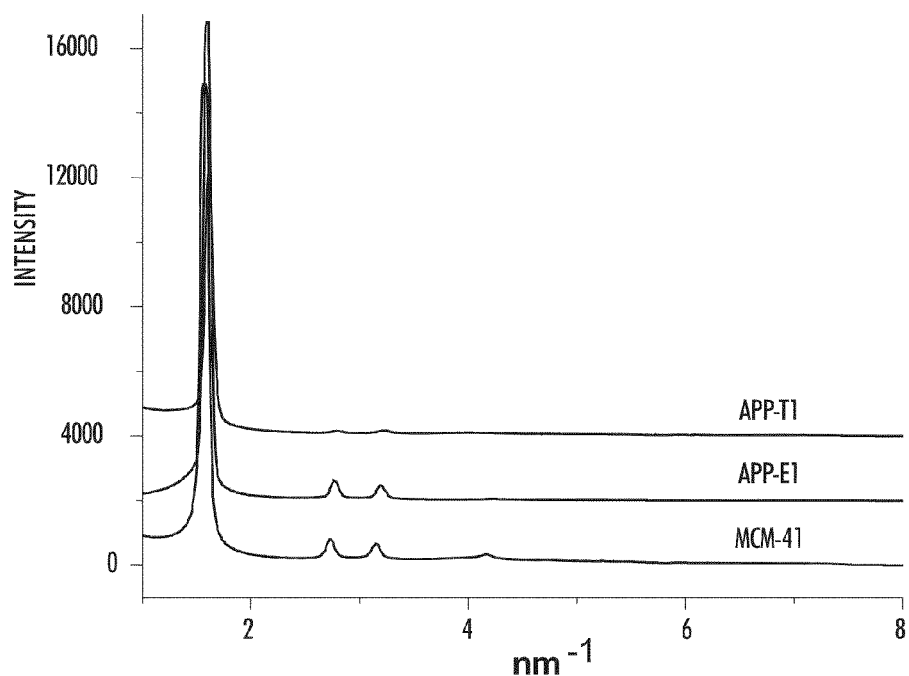
FIG. 39D depicts small angle X-ray scattering of MCM-41 compared with certain organodiamine functionalized catalyst samples.

Without wishing to be bound to any particular theory, the applicants believe that the slight decrease in the Bragg reflections in samples grafted in toluene, such as in AP-T1 and AP-T2, compared to samples grafted in ethanol, such as in AP-E1 and AP-EE1, were possibly due to the slight reduction in electron contrast caused by the grafting of more organoamine groups in the former than in the latter. The slight noticeable reduction in unit cell dimension of AP-T2 compared to AP-T1 and AP-E1 was probably due to the slight shrinkage of the mesostructures caused by the condensation of residual surface silanols in the materials at higher temperatures, under which AP-T2 was prepared. The well-ordered mesostructures in these materials were also further confirmed by small angle X-ray scattering (SAXS) measurements (see FIGS. 39C and 39D), which exhibited four or more Bragg reflections.

Figure 40:
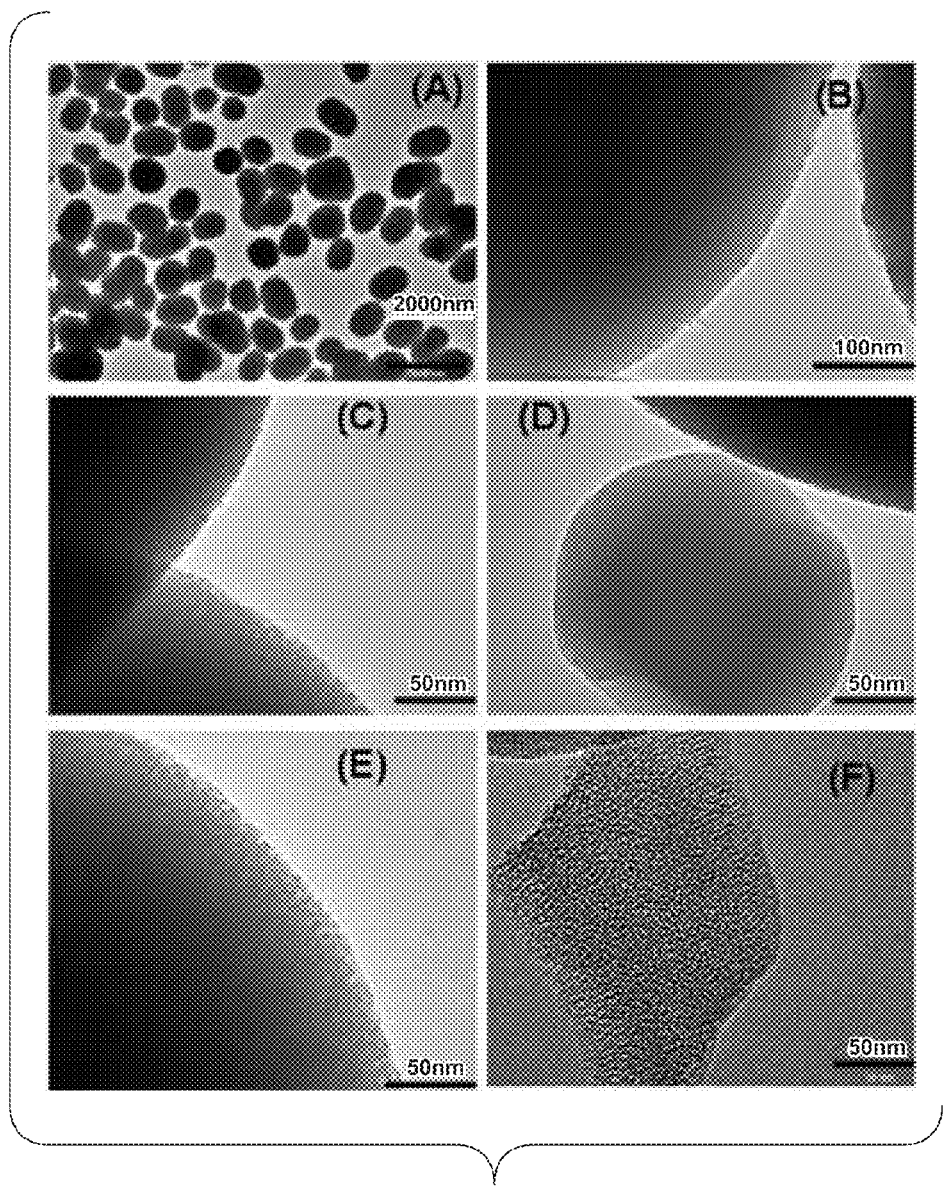
FIG. 40 (A)-(F) are transmission electron microscopy images of MCM-41 mesoporous silicate starting material, and selected organomonoamine and organodiamine mesoporous catalysts synthesized therefrom.

FIG. 40 (A)-(F) are transmission electron microscopy images of (A) MCM-41 mesoporous silicate starting material, and selected organomonoamine and organodiamine mesoporous catalysts synthesized therefrom, (B) AP-E1, (C) AP-T1 (D) AP-T2, (E) AAP-E1 and (F) a high resolution TEM image of AP-E1, respectively. The structures of the materials were further confirmed by these TEM images, which showed nanorod shaped particles having mesoporous structures. Supramolecular synthesis in basic solution from pure tetraalkoxysilanes has been reported by Huh et al. in *Chem. Mater.* 2003, 15, 4247-4256 to form such nanorod shaped mesoporous particles while the presence of a few mmol of organosilanes leads to spherical mesoporous particles.

Figure 41A:
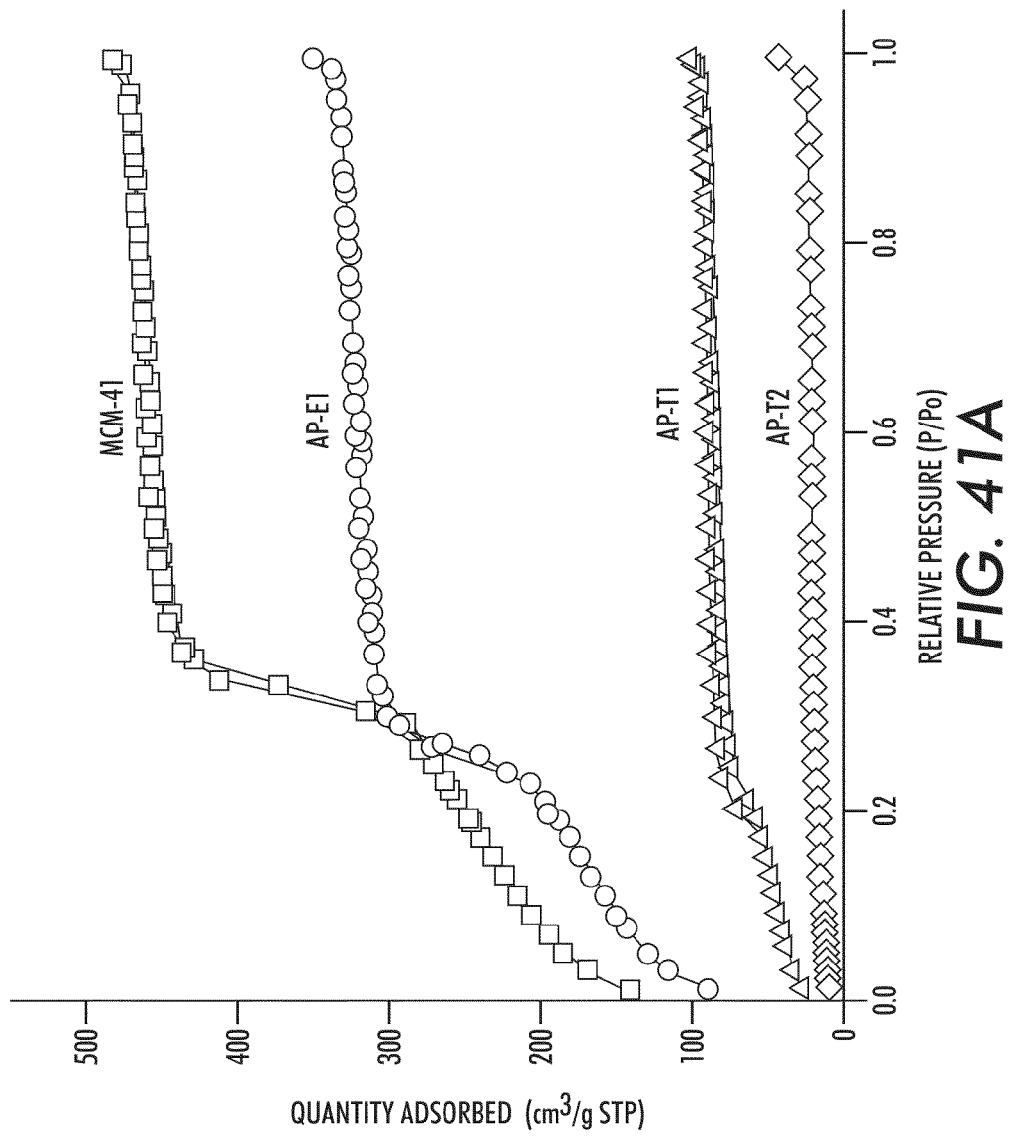
FIGS. 41A and 41B are nitrogen gas adsorption isotherms of MCM-41 mesoporous silicate starting material, and selected organomonoamine and organodiamine mesoporous catalysts synthesized therefrom.
Figure 41B:
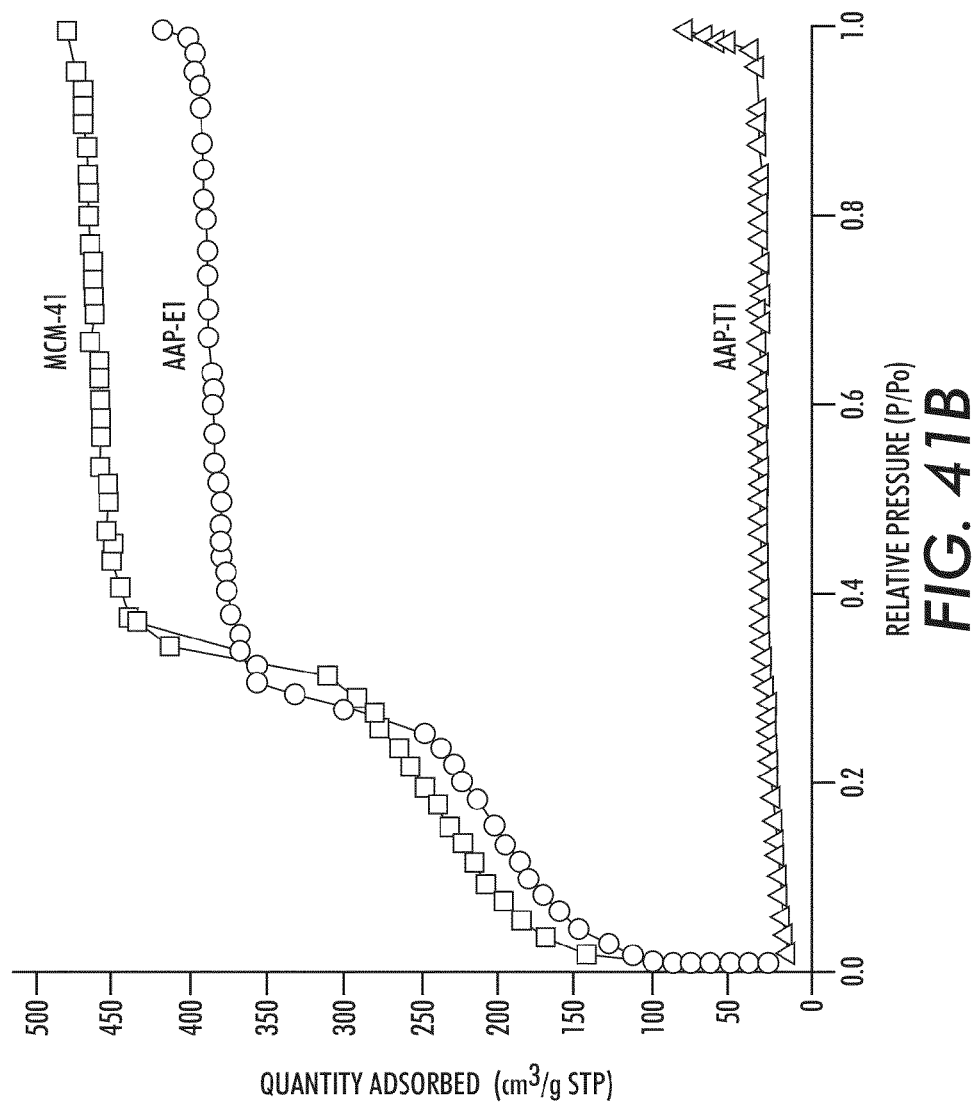
Figure 41C:
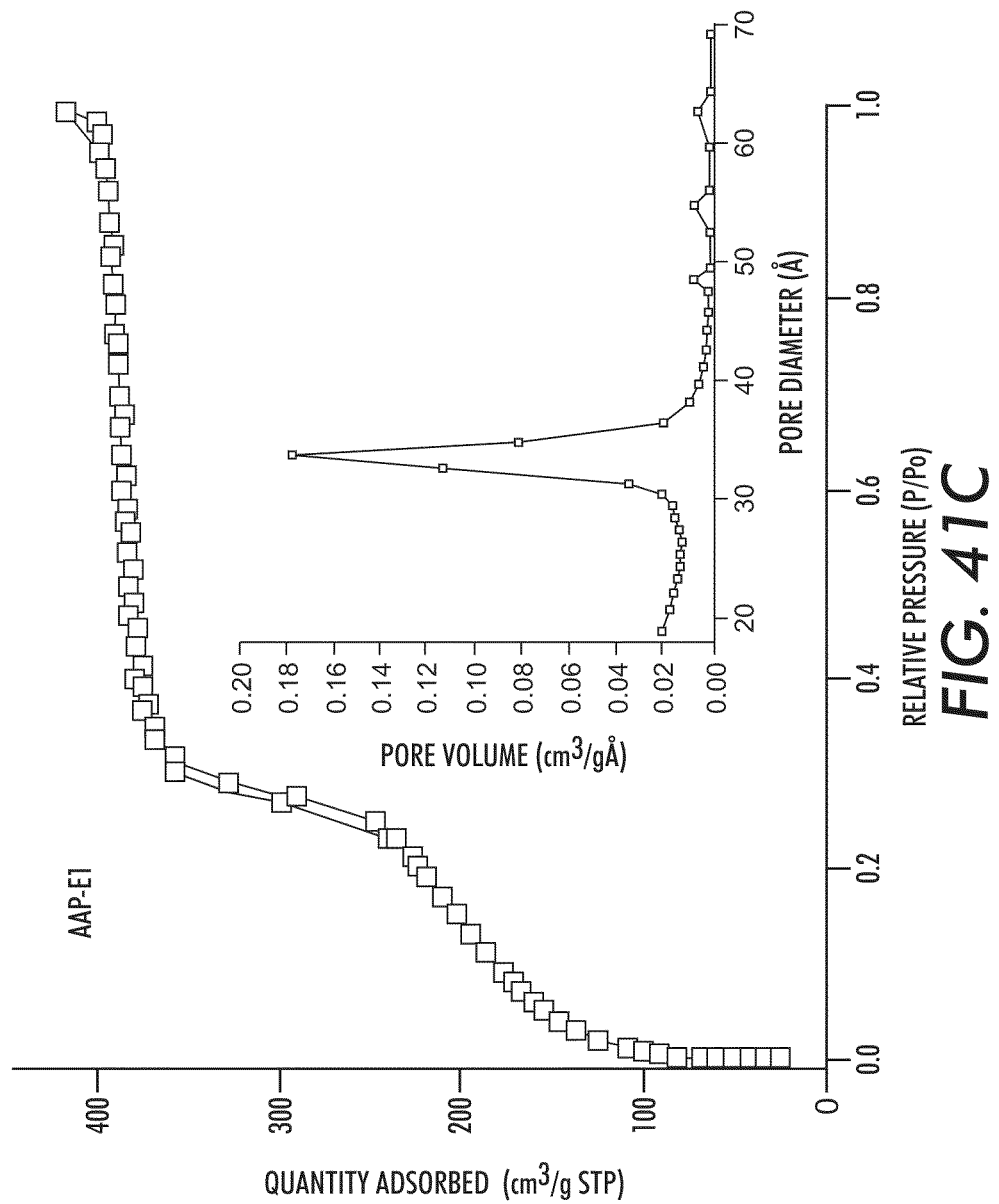
Figure 41D:
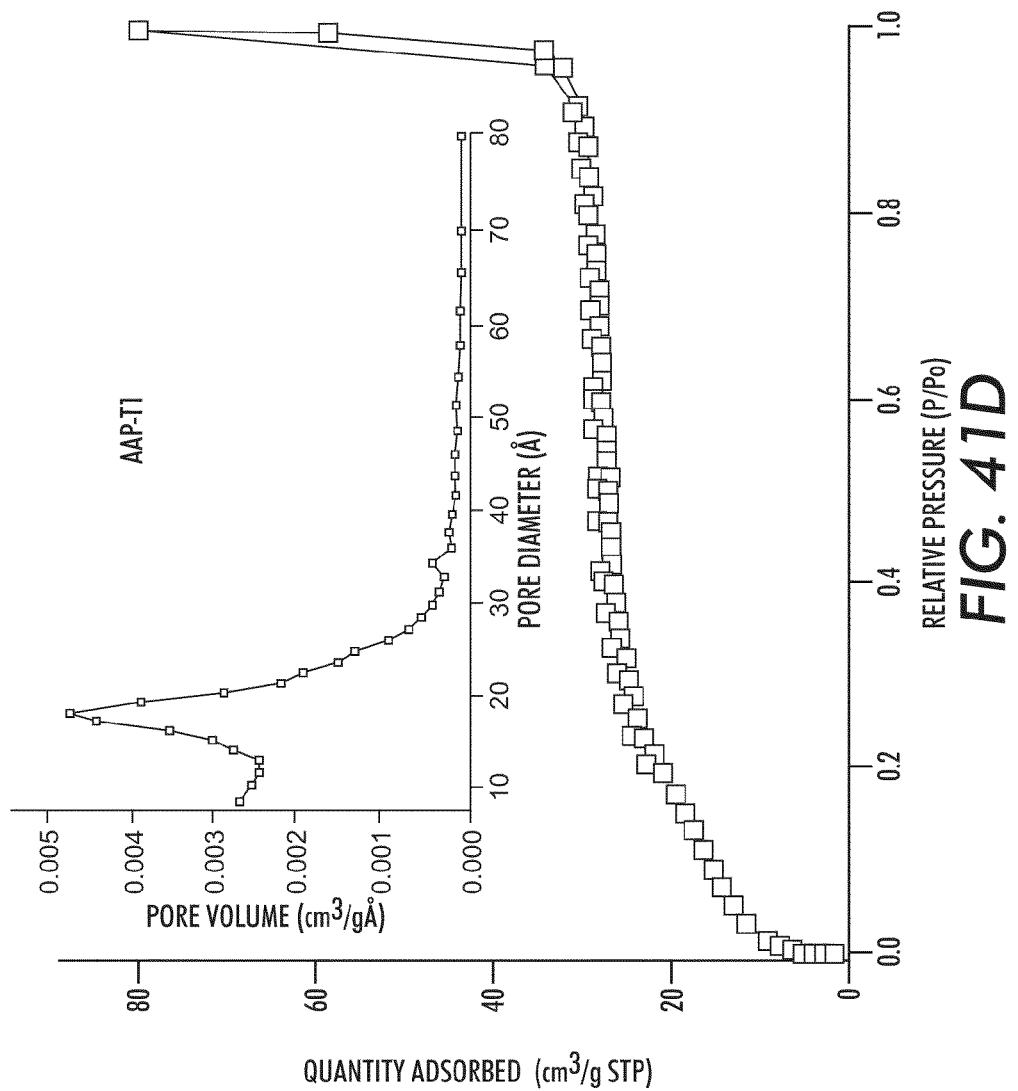
Figure 41E:
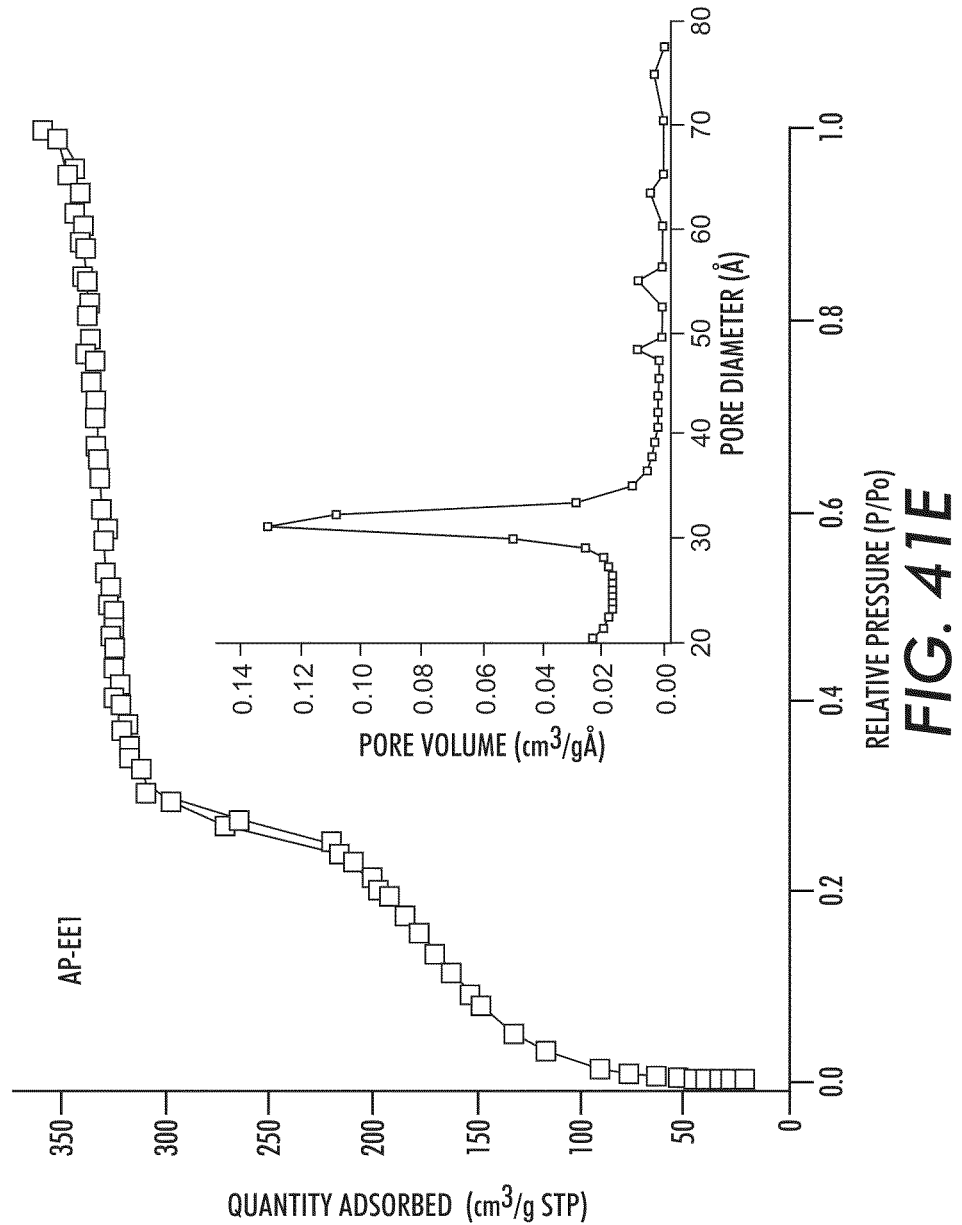
Figure 41F:
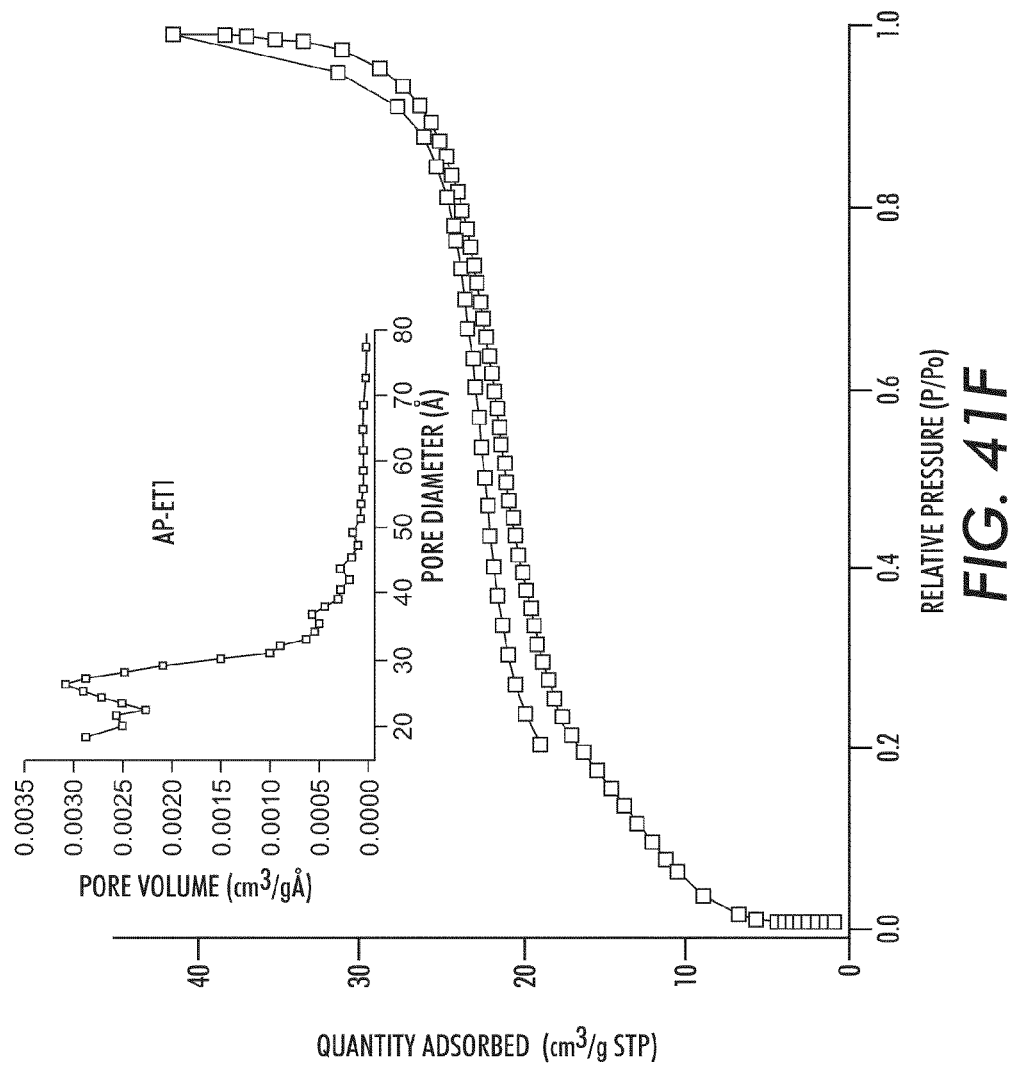
Figure 41G:
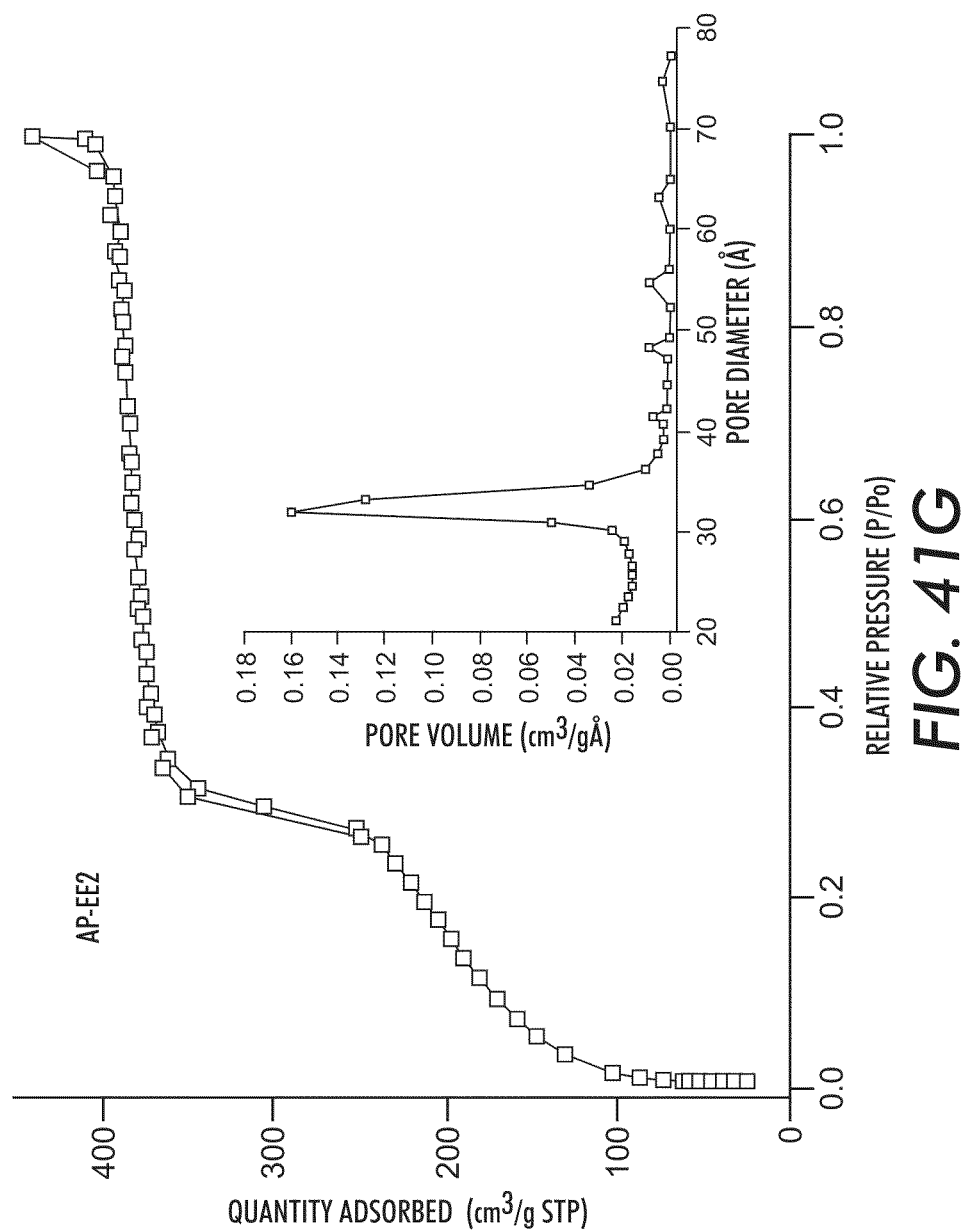
Figure 41H:
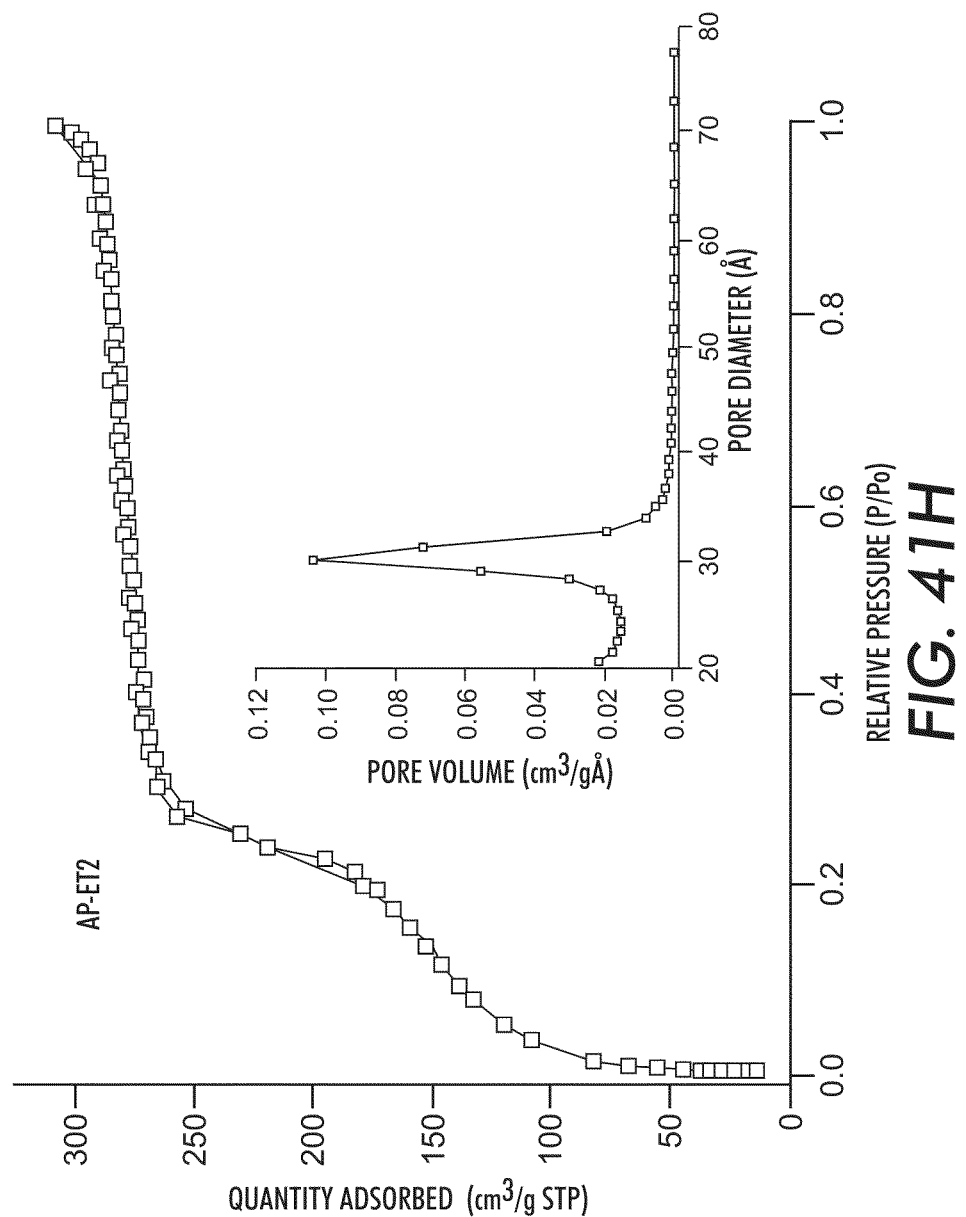
Figure 41I:
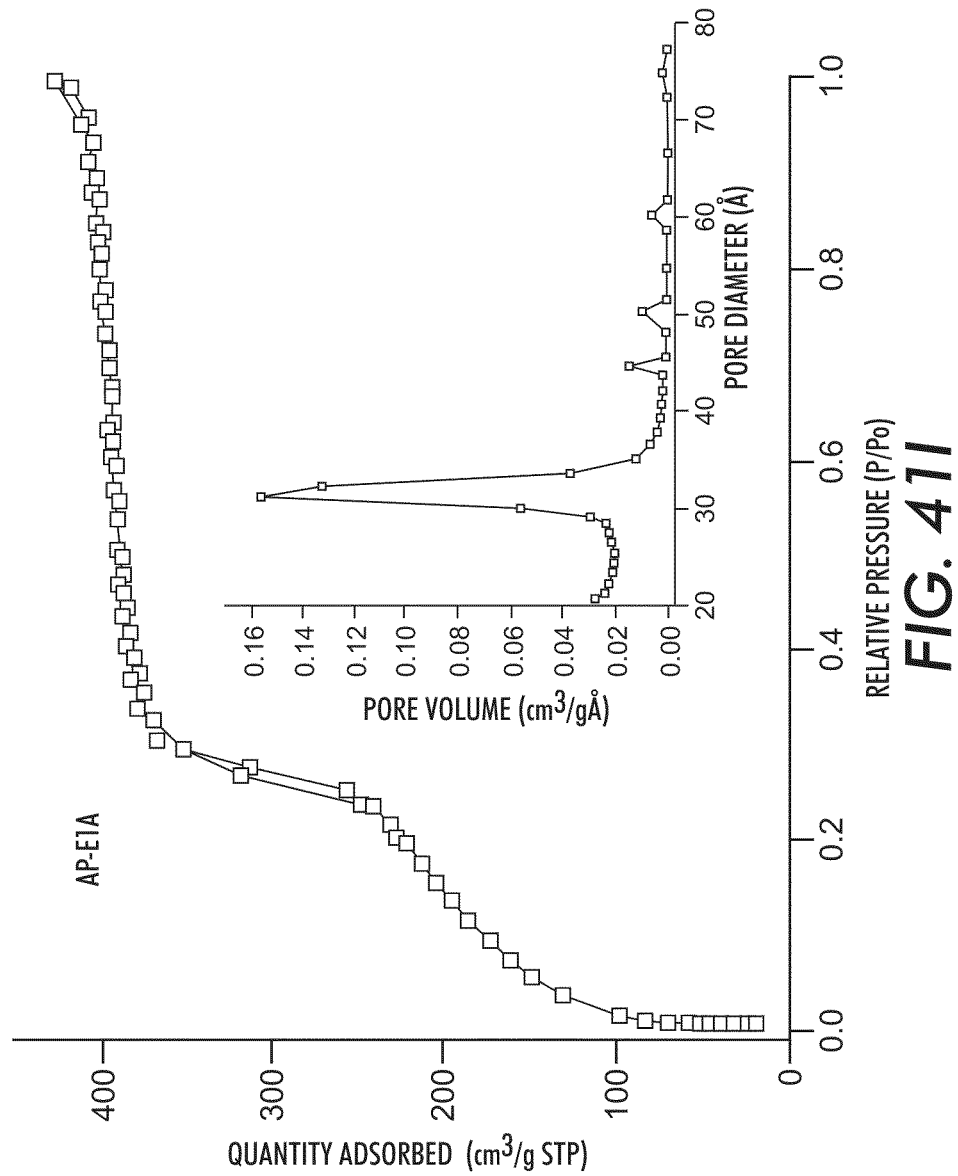
Figure 41J:
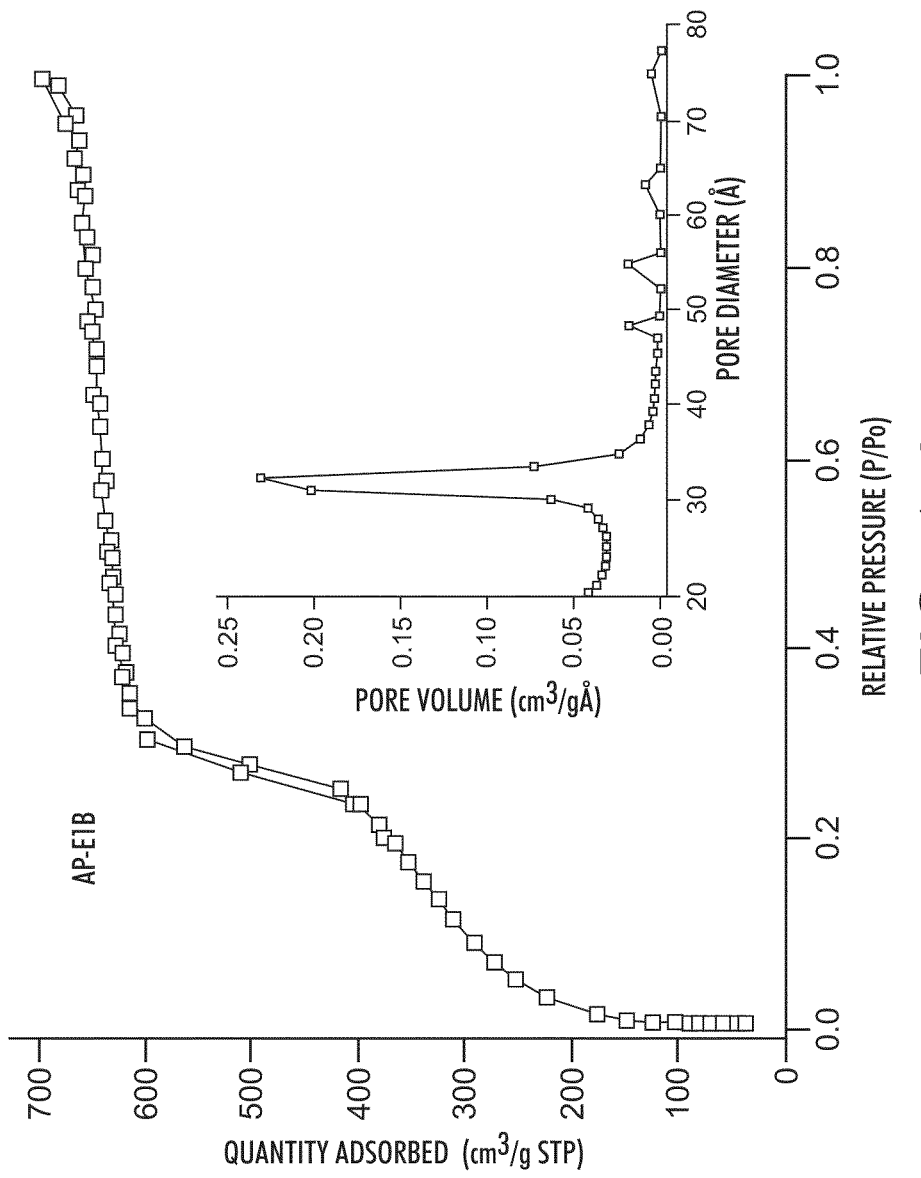

FIG. 41A depicts nitrogen gas adsorption isotherms of MCM-41 compared with those for organomonoamine mesoporous catalysts AP-E1, AP-T1, and AP-T2; and FIG. 41B depicts nitrogen gas adsorption isotherms of MCM-41 compared with those for organodiamine mesoporous catalysts AAP-E1 and AAP-T1. FIGS. 41C-4J are the individual isotherms and pore-size distribution data for the AAP-E1, AAP-T1, AP-EE1, AP-ET1, AP-EE2, AP-ET2, AP-E1A, and AP-E1B materials; and FIGS. 5B-5E are the individual isotherms and pore-size distribution data for the MCM-41, AP-E1, AP-T1, and AP-T2 materials. These $N_2$ gas adsorption measurements of the samples showed Type IV isotherms with no significant hysteresis for all of the samples, which was characteristic of the presence of well-ordered mesoporous structures in the materials. The BET surface areas of the samples, however, varied very significantly depending on the synthesis conditions employed. The surface areas of MCM- 41, AP-E1, AP-T1, and AP-T2 were 1030, 906, 260, and 60 m²/g, respectively, while the surface areas of AAP-E1 and AAP-T1 were 905 and 80 m²/g, respectively. Since all of the materials showed ordered mesoporous structures, the applicants believe that the decrease in surface area of the organoamine-grafted samples compared to MCM-41 was likely caused exclusively by the density of the organoamines in the mesopores.

Similar trends in lower surface areas were also observed for the control samples AP-EE1, AP-ET1, AP-EE2 and AP-ET2 (see Table 10). The samples grafted in toluene and at atoms than the corresponding samples grafted in ethanol, AP-E1 and AAP-E1. In fact, the T peaks on $^{29}$Si MAS NMR for AP-E1 and AAP-E1 samples were barely observable. However, these peaks were clearly observable on $^{29}$Si $\{^1H\}$ CP-MAS NMR spectra. The results indicated that the samples grafted in ethanol resulted in very few organoamines but many residual silanols compared to the corresponding samples grafted in toluene. From the relative peaks on the $^{29}$Si MAS NMR spectra, the relative composition of the 3-aminopropyl groups and silanol groups in each material was determined. These compositions are summarized in Table 11.

TABLE 11

Data of concentrations of organoamine and silanol groups in organoamine-functionalized samples obtained from solid-state NMR and TGA results.

| Sample | mmol Si—R—NH₂/g sample | mmol Si—OH/g sample | [Si—OH]/[Si—R—NH₂] (or [Si—R—NH₂]/[Si—OH]) | Wt. % of Organoamine from $^{29}$Si MAS NMR | Wt. % change between 100-600° C. |
|---|---|---|---|---|---|
| AP-E1 | 1.32 | 6.8 | 5.1 (0.2) | 7.8 | 10.7 |
| AP-T1 | 4.2 | 3.8 | 0.9 (1.1) | 15.5 | 14.8 |
| AP-T2 | 4.3 | 3.0 | 0.7 (1.4) | 25.0 | 16.8 |
| AAP-E1 | 1.5 | 9.4 | 6.2 (0.2) | 15.4 | 12.4 |
| AAP-T1 | 2.4 | 4.1 | 1.7 (0.6) | 24.0 | 21.5 | higher temperatures showed significant decrease in surface areas compared to samples grafted in ethanol. This indicates that grafting in toluene and at higher temperatures favored immobilization of higher concentration of organoamine groups in the materials. While the BJH pore size distribution of the samples exhibited a monodisperse pore size distribution, the pore diameters decreased more significantly for samples containing more organoamines and organic groups, particularly those grafted in toluene. For instance, the pore diameter of the MCM-41 was 34.1 Å while the pore diameters of AP-E1, AP-T1, and AP-T2 were 31.4, 31.6, and 30.6 Å, respectively. Similarly, the pore diameters of the AAP-E1 and AAP-T1 were 34.4, and 29.0 Å, respectively. Similarly, the wall thickness was higher for samples grafted in toluene than samples grafted in ethanol. It is also worth noting that the pore volume reduction was higher in samples grafted in toluene than in ethanol.

Figure 42A:
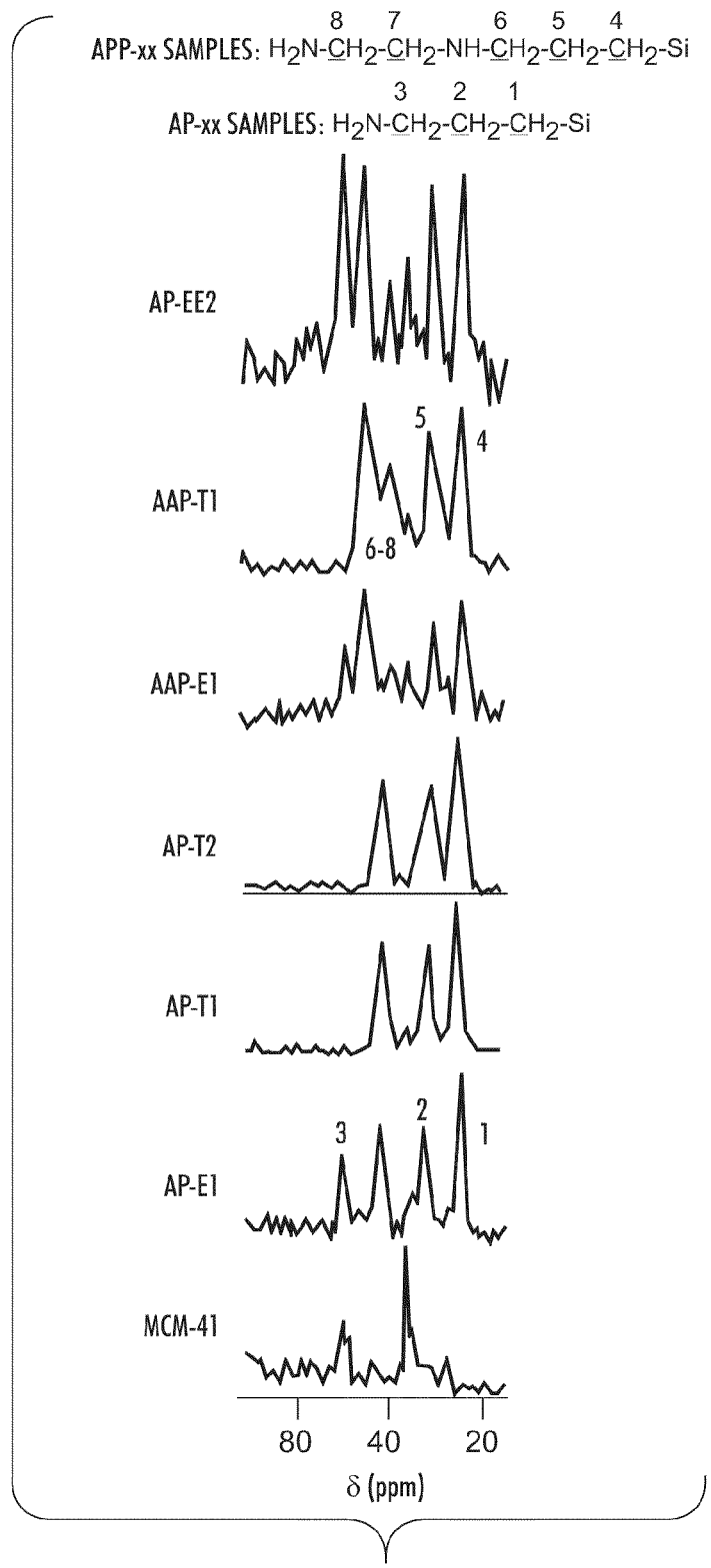
FIG. 42A depicts $^{13}$C CP-MAS solid-state NMR spectra of MCM-41 and various organomonoamine and organodiamine mesoporous catalysts.
Figure 42B:
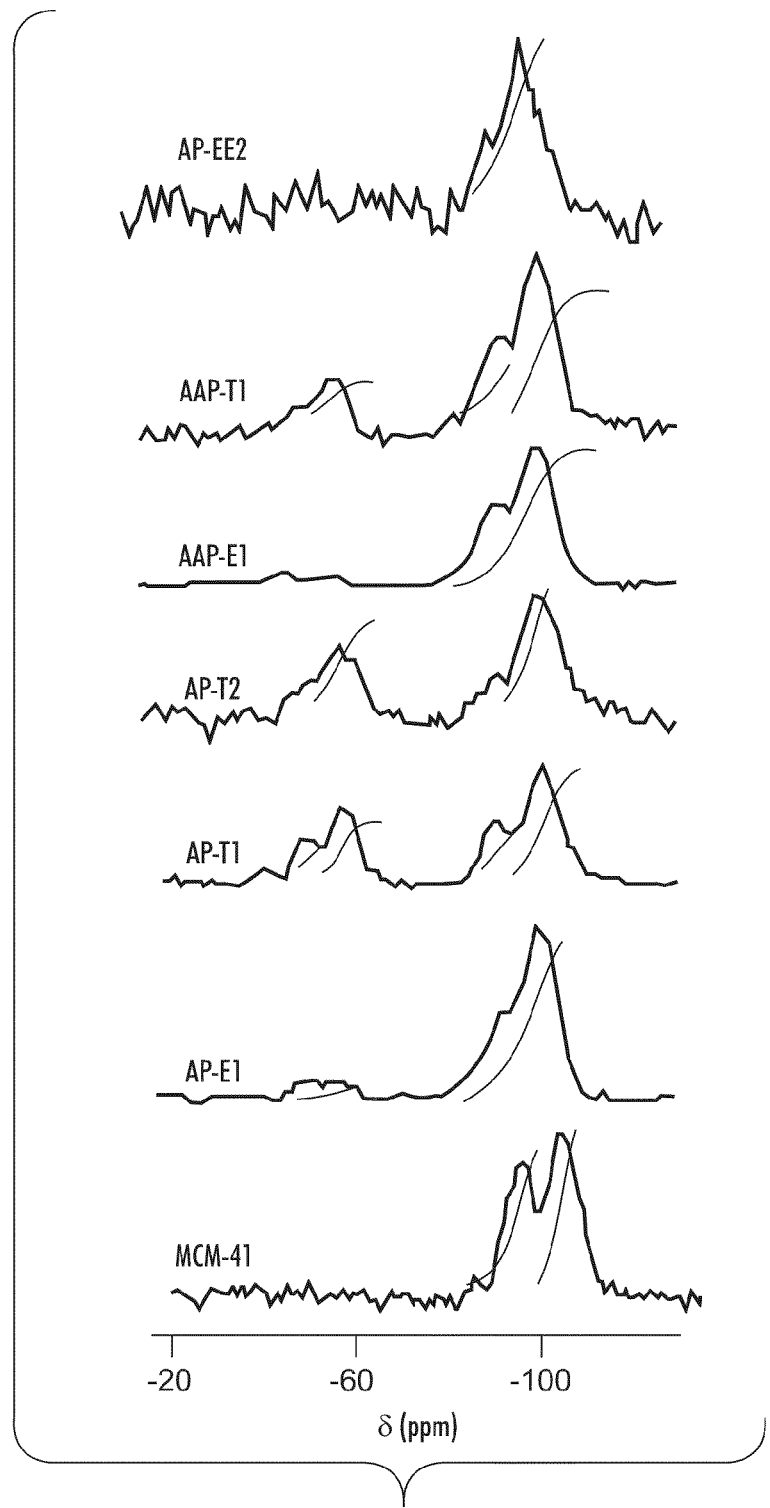
FIG. 42B depicts $^{29}$Si MAS solid-state NMR spectroscopy of MCM-41 and various organomonoamine and organodiamine mesoporous catalysts.
Figure 42C:
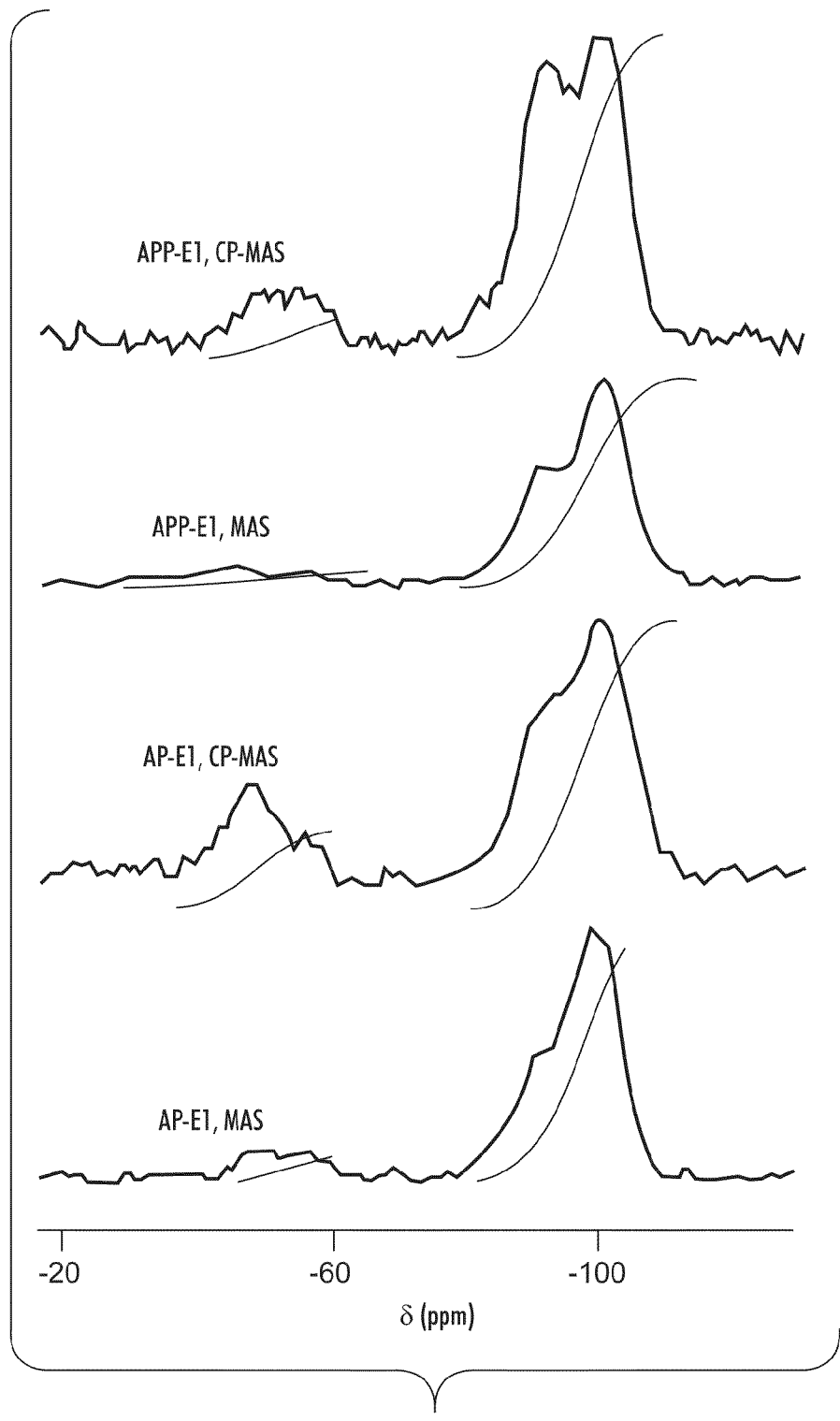
FIG. 42C depicts a comparison of the $^{29}$Si CP MAS compared with $^{29}$Si MAS NMR spectra for the monoamine and diamine functionalized mesoporous samples.

The presence and concentrations of the organic functional groups in the materials after grafting were characterized by combinations of solid-state NMR spectroscopy and thermogravimetric analysis. FIG. 42A depicts $^{13}$C CP-MAS solid-state NMR spectra of MCM-41, AP-E1, AP-T1, AP-T2, AAP-E1, AAP-T1; and FIG. 42B depicts $^{29}$Si MAS and CP MAS solid-state NMR spectroscopy of MCM-41, AP-E1, AP-T1, AP-T2, AAP-E1, AAP-T1, and AP-EE2. FIG. 42C depicts a comparison of the $^{29}$Si CP MAS compared with $^{29}$Si MAS NMR spectra for the monoamine and diamine functionalized mesoporous samples. The $^{13}$C CP-MAS NMR of FIG. 42A confirmed the presence of 3-aminopropyl, 2-aminoethyl (3-aminopropyl), and 3-cyanopropyl groups in APTS, AAPTS, and CPTS-functionalized samples. The intensity of the peaks corresponding to these functional groups was higher in samples grafted in toluene than corresponding samples grafted in ethanol, indicating the grafting of more organic groups in toluene than in ethanol.

These were further confirmed by $^{29}$Si MAS and $^{29}$Si CP-MAS NMR spectra of FIG. 42B. The $^{29}$Si MAS NMR spectra indicated that the APTS and AAPTS functionalized samples grafted in toluene, AP-T1, AP-T2 and AAP-T1, showed more T peaks corresponding to Si(Organic)(O)$_x$(OH)$_{1.5-x}$ silicon With regard to the data in Table 11, the mmol of Si—R—NH₂ per unit gram of organoamine-functionalized sample was obtained by integrating the T peaks on $^{29}$Si MAS NMR, i.e. [Si—R—NH₂]=T3+T2+T1. The mmol of Si—OH in unit gram of organoamine-functionalized sample was obtained by integrating the T and Q peaks on $^{29}$Si MAS NMR, i.e. total [Si—OH]=Q3+2(Q2)+3(Q1)+T2+2(T1). The ratio of the number of Si—OH and Si-organoamine ([Si—OH]/[Si—R—NH₂]) group was calculated by obtaining the total number of [Si—OH]=[silanols]=Q3+2(Q2)+3(Q1)+T2+2(T1) and the total number of organoamine groups=[Si—R—NH₂]=T3+T2+T1. The weight percent of organoamine was obtained by integrating the T peaks (T1+T2+T3) on $^{29}$Si MAS NMR. The weight percent change was obtained from TGA in the range of 100-600° C.

In studying these NMR data, the applicants have discovered an interesting relationship between the percent of silanol and organoamine groups as summarized in Table 11. By integrating the Q and T peaks, the total number of silanol groups per unit mass of material was obtained from Q3+2(Q2)+3(Q1)+T2+2(T1), while the overall numbers of Si—R—NH₂ groups per unit mass of material was obtained from T3+T2+T1. Similarly, the weight percent of the organoamine groups and mmol NH₂ catalytic sites per unit mass of sample were calculated.

Figure 43A:
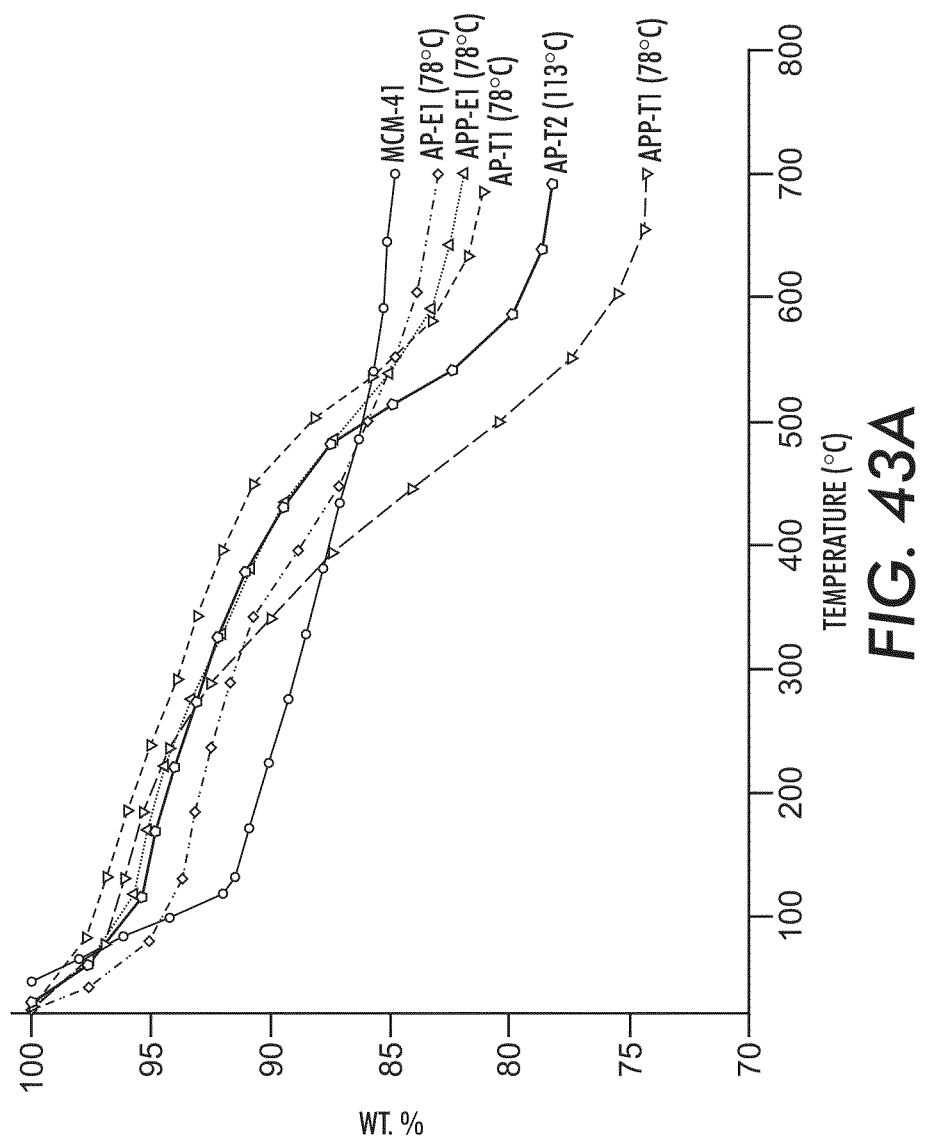
FIGS. 43A and 43B depict thermogravimetric analyses of the MCM-41 sample compared with monoamine and diamine functionalized samples grafted in ethanol and toluene.

Thermogravimetric analysis was further used to confirm the solid-state NMR results. FIG. 43A shows the thermogravimetric analyses of the MCM-41 sample compared with the monoamine and diamine functionalized samples grafted in ethanol and toluene: AP-E1, AP-T1, AP-T2, AAP-E1, and AAP-T1. These TGA traces showed a weight loss below 100° C. by all the samples, which was due to evaporation of physisorbed water from the samples. Most importantly, the TGA traces showed a weight reduction in the range of 100-600° C., which is mainly due to the loss of organoamine groups as well as due to some loss of chemisorbed water and water of condensation of the silanols. The latter two were confirmed from the TGA trace of the pure MCM-41, which has no organoamine group and which showed a weight loss of about 7% in the range of 100-600° C. Despite the 7 weight loss due to condensation of silanols in the range of 100-600° C. for MCM-41, the weight loss in the corresponding organofunctionalized samples would be significantly less than that for MCM-41, as the latter contained less number of surface silanols.

Analysis of the TGA traces in the range of 100-600° C. exhibited sample AP-E1 to have a weight loss of 10.7% while AP-T1 and AP-T2 to have weight losses of 14.6 and 16.6%, respectively. Similarly, AAP-E1 showed weight loss of 12.4 while AAP-T1 showed a weight loss of 21.5% as indicated in Table 11. From these results, it was again clear that the mesoporous samples grafted in ethanol to have significantly less number of organoamines than corresponding samples grafted in toluene and at higher temperatures. Further analysis revealed AP-T2 to have 2.0 more weight loss in the range of 100-600° C. than AP-T1, and AP-T1 in turn to have 4% more weight loss than AP-E1. This indicates that the grafting density depends more on the type of the solvent used than the grafting temperature. Further comparative TGA analysis indicated AP-E1 and AP-T1 to have ~1.7 and 6.7 less weight losses than AAP-E1 and AAP-T1 in the range of 100-600° C. This was clearly mainly due to the lower molecular weight of the organoamine compared to organodiamine (or by the additional aminoethylene group, —NHCH$_2$CH$_2$—, in the organodiamines), as the mmol Si—R—NH$_2$ in the two materials were similar.

The applicants note that such comparative studies of weight losses due to organoamine groups in these samples based on TGA traces requires careful analysis because the weight loss in the range of 100-600° C. is not only caused by the loss of organoamine groups but also by loss of water from condensation of silanols. Additionally, the relative numbers these two groups in the materials are inversely related. For instance, based on solid-state NMR results, samples AP-T1 and AP-T2 have larger numbers of organoamine groups but fewer number of silanol groups compared to sample AP-E1. Consequently, the percentage of weight loss due to condensation of silanol groups in AP-T1 and AP-T2 in the range of 100-600° C. should be smaller than that in AP-E1. This implies that the actual difference in percentage of weight losses due to the organoamine groups between AP-E1 and AP-T1 as well as AAP-E1 and AAP-T1 should, in fact, be higher than what was obtained from the TGA analysis and could parallel those obtained from the solid-state NMR analysis. For instance, the weight loss by sample AP-T1 from the TGA traces in the range of 100-600° C. was 4.1% higher than that for AP-E1 without taking silanols into account while the value obtained from solid-state NMR was 7.7% higher, as shown in Table 11. From combinations of the NMR and TGA results, the mmol of silanols Si—R—NH$_2$ catalytic sites in the samples were determined, and possible compositions of the materials were compiled in the reaction scheme shown in FIG. 38.

Previously in this specification, the applicants disclosed mesoporous samples with site-isolated 3-aminopropyl groups that are much more efficient catalysts in base-catalyzed reactions than corresponding samples with densely populated 3-aminopropyl groups due to the higher surface area and the cooperative effects of bifunctional groups in the former. In this section of the specification, we now report comprehensive effects of site isolations, concentrations and separation distances between organomonoamine (organodiamine) and silanol bifunctional groups on the cooperative catalytic properties and efficiency of the materials in base-catalyzed reactions.

The applicants performed the Henry reaction between p-hydroxybenzaldehyde and nitromethane by using all the organoamine-functionalized catalyst samples of the invention prepared as described herein and listed in Table 12 as catalysts. The reaction scheme was as follows:

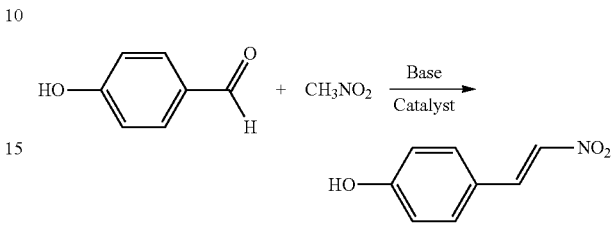

Typically, 20 mg of the aminofunctionalized mesoporous sample was added into a solution of 122 mg (1 mmol) p-hydroxybenzaldehyde and 10 mL of nitromethane. The reaction was stirred at 90° C. (or at 50° C.) under nitrogen and aliquots of the reaction product were taken with a filter syringe and characterized by solution $^1$H NMR and GC-MS over the course of the reactions. The percent yield and conversion were determined by using $^1$H NMR (Bruker DPX-300 MHz) spectra. Resonances in acetone-d$_6$ were as follows:

p-hydroxy nitrostyrene ($^1$H NMR): δ 2.85 (1H, br, s), 6.96 (2H, d), 7.71 (2H, d), 7.83 (1H, d, J=13.5 Hz), and 8.04 (1H, d, J=13.5 Hz); and p-hydroxybenzaldehyde ($^1$H NMR): δ 2.95 (1H, br, s), 7.05 (2H, d), 7.8 (2H, d), and 9.84 (1H, s).

Figure 44A:
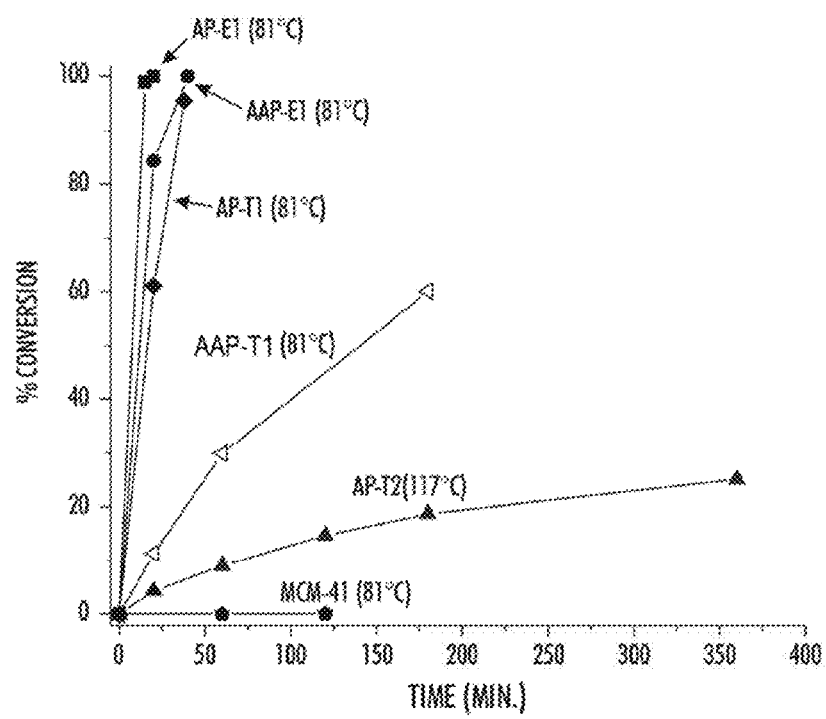
FIGS. 44A and 44B are catalysis time plots of certain monoamine and diamine functionalized samples grafted in ethanol and toluene.
Figure 44B:
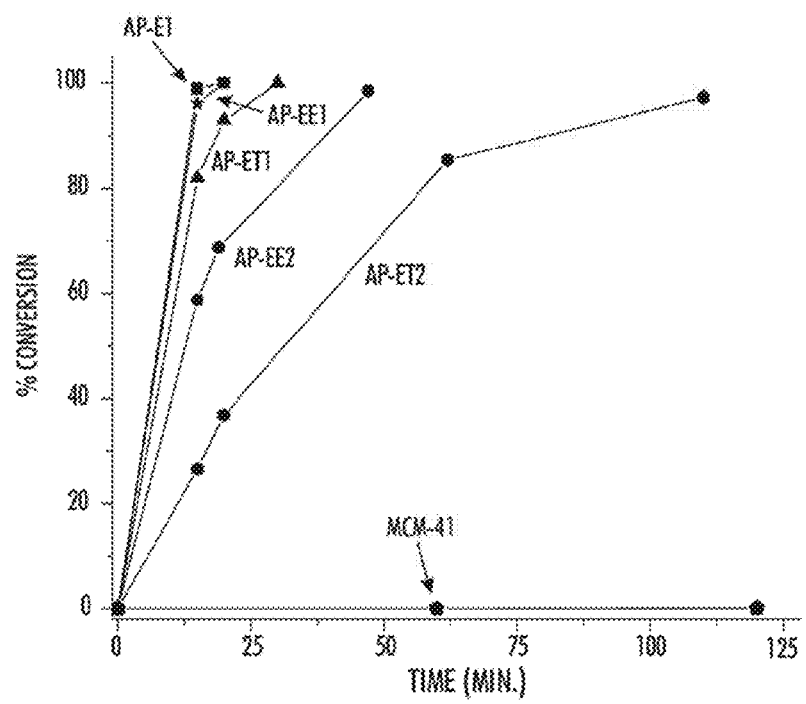

FIG. 44A depicts the catalysis time plots of AP-E1, AP-T1, AP-T2, AAP-E1, AAP-T1 and control sample MCM-41; and FIG. 44B depicts the catalysis time plots of sample AP-E1 compared with AP-EE1, AP-ET1, AP-EE2, and AP-ET2. Table 12 summarizes the applicants' mesoporous catalysts and control samples synthesized by grafting in various solvents and their catalytic efficiency in a reaction between p-hydroxybenzaldehyde and nitromethane. With regard to the data in Table 12, the Henry reaction was performed at 90° C. using nitromethane as the reactant and the solvent unless mentioned otherwise. The mmol NH$_2$/g sample data were obtained from $^{29}$Si MAS NMR. TON is defined as the turn-over number, i.e. mmol product/mmol catalyst. For samples AAP-E1 and AAP-T1, the reaction was done at 50° C. in nitromethane. For sample AP-E1, the reaction was performed at 90° C. using toluene as a solvent in the presence of a stoichiometric amount of nitromethane.

The yields of the reaction were monitored over a course of reaction time by solution $^1$H NMR and GC-MS. For comparison purposes, the same amount of catalysts and reagents were used in the reactions. As can be seen in FIGS. 44A and 44B, both the monoamine- and diamine-functionalized samples synthesized in ethanol, AP-E1 and AAP-E1, were much more efficient than the corresponding samples grafted in toluene, AP-T1, AP-T2, and AP-T3, despite the former samples having about four times lower numbers of organoamine groups than the latter. The AP-E1 and AAP-E1 gave very nearly 100% yield in 15 and 30 minutes; corresponding turn-over-numbers (TON) of 37.5 and 7.6; and turn-over-frequencies of 150.0/h and 30.4/h, respectively. To the best of the applicants' knowledge, these values indicate these materials to be the most efficient catalysts of all mesoporous materials reported for Henry reactions in the literature to date.

TABLE 12

Mesoporous catalysts and control samples synthesized by grafting in various solvents and their catalytic efficiency in a reaction between p-hydroxybenzaldehyde and nitromethane.

| Sample | mmol NH$_2$/g sample | [Si—OH]/[—R] | Yield (%) in 15 min | Yields (%) in various times | TON in 15 min | TOF in 15 min (TON/h) |
|---|---|---|---|---|---|---|
| MCM-41 | — | 6.4 | 0 | 0 | — | — |
| AP-E1 | 1.3 | 5.1 | 99.0 | 100 (16 min) | 37.5 | 150.0 |
| AP-T1 | 4.2 | 0.9 | 52.5 | 95.5 (39 min) | 6.2 | 24.8 |
| AP-T2 | 4.3 | 0.7 | 3.1 | 11.7 (1 h) | 0.6 | 2.4 |
| AAP-E1 | 1.5 | 6.2 | 64.5 | 100 (30 min) | 7.6 | 30.4 |
| AAP-T1 | 2.4 | 1.7 | 10.6 | 29.9 (1 h) | 2.3 | 9.2 |
| AP-EE1 | — | — | 90.5 | 90.5 (15 min) | — | — |
| AP-ET1 | — | — | 82.0 | 98 (30 min) | — | — |
| AP-EE2 | — | — | 58.8 | 68.7 (19 min) | — | — |
| AP-ET2 | — | — | 26.8 | 98.4 (2 h) | — | — |
| AP-E1A | — | — | 82.0 | 93 (20 min) | — | — |
| AP-E1B | — | — | 96.2 | 100 (20 min) | — | — |
| AAP-E1 | — | — | 81.0 | 100 (30 min) | — | — |
| AAP-E1 | — | — | 9.7 | 61 (1 h) | — | — |
| AAP-T1 | — | — | 9.2 | 45 (1 h) | — | — |
| AP-E1 | — | — | 98 | 100 (18 min) | — | — |

Figure 45A:
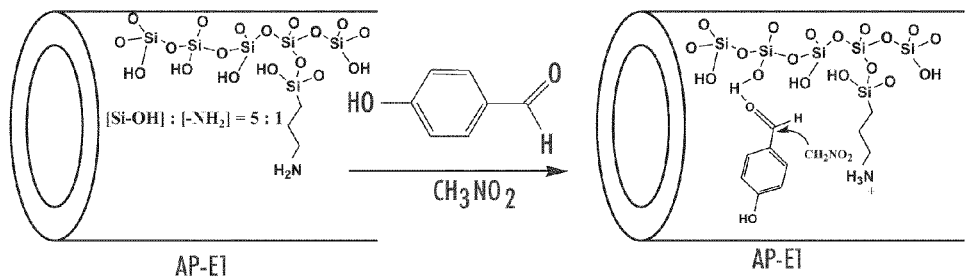
FIG. 45 is a schematic illustration of the mechanisms and differences of cooperative catalysis by amines and silanols groups in certain monoamine and diamine functionalized samples grafted in ethanol and toluene samples in the Henry reaction between p-hydroxybenzaldehyde and nitromethane.
Figure 45B:
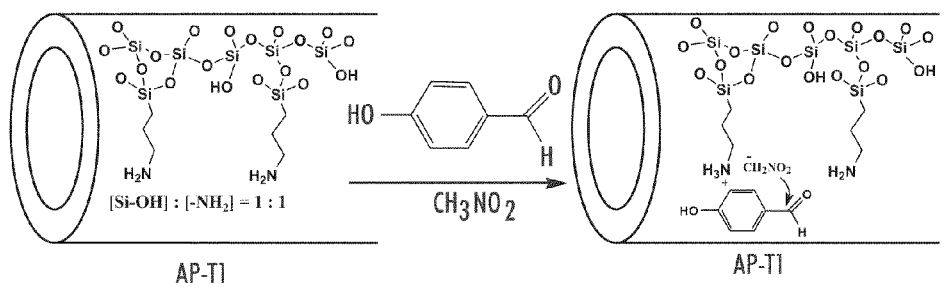

For comparison, the control samples that the applicants prepared by grafting aminorganosilanes in toluene at 78° C., AP-T1 and AAP-T1, gave a 12.0% and 29.9% yield in about 1 hour, while in contrast, catalyst reported by Demicheli et al. in *Tetrahedron Lett.* 2001, 42, 2401-2403 using toluene gave 96% in 1 hour. The applicants believe that the differences in efficiency between these five catalysts can be explained by the differences in site-isolation, the organoamine:silanol ratio, and the surface areas of the materials. For instance, samples AP-E1 and AAP-E1 contained higher surface areas and more silanol groups than samples AP-T1, AP-T2, and AAP-T1, and consequently, the former resulted in better cooperative and efficient catalysis. The presence of large number of residual silanols, the formation of site-isolated organoamines and silanol groups and the higher surface areas in AP-E1 and AAP-E1 materials would be responsible for the increased cooperative catalytic efficiency in these samples. Related mechanisms and differences of cooperative catalysis by the amines and silanol groups in AP-E1, AP-T1, and AAP-E1 samples in the selected Henry reaction are shown in FIG. 45. The silanol:organoamine ratio obtained from solid-state NMR for each material is also shown therein.

The applicants believe that the higher efficiency of sample AP-E1 compared to sample AAP-E1 is also noteworthy. The concentration of primary amines (—NH$_2$ groups) in AP-E1 and AAP-E1 was 1.3 and 1.5 mmol/g, respectively, which were similar, while their respective silanols were 6.8 and 9.4 mmol/g. These would give a [Si—OH]: [Si-Organoamine] ratio of 5:1 and 6:1 in AP-E1 and AAP-E1 samples, respectively. The surface areas of AP-E1 and AAP-E1 were 906 and 889 m$^2$/g, respectively, which were also comparable. Based on these results and considering the presence of additional 1.5 mmol/g secondary amine groups in the diamine functionalized sample, AAP-E1, one would expect AAP-E1 to be a more efficient catalyst. However, AP-E1 unexpectedly showed a higher catalytic efficiency or turn-over-number (37.5) than AAP-E1, which showed a turn-over-number of 7.6.

Figure 45C:
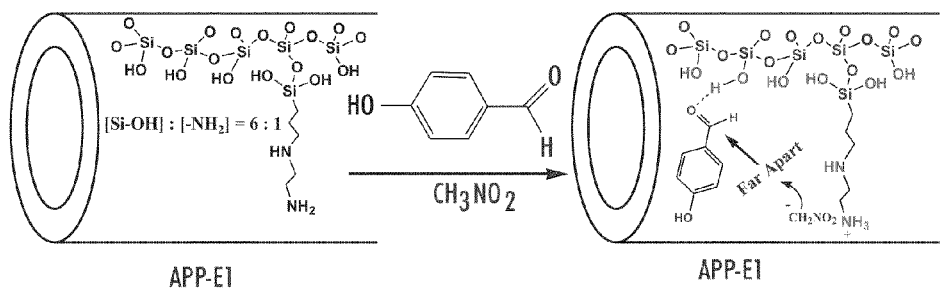

This indicates the importance of the shorter distance between the primary amine and the surface silanol groups in the AP-E1, which allowed better cooperative effects by the amine group and the silanols, as compared to that in AAP-E1, whose primary amine is farther from the surface silanols (FIG. 45C). Despite that the secondary amine groups in AAP-E1 are close to silanols, they were much less efficient catalysts for the Henry reaction compared to primary amines, as reported by Shimizu et al. in *Tetrahedron Lett.* 2002, 43, 9073-9075. In the proposed cooperative catalytic mechanism shown in FIG. 45A, a nitromethyl anion would remain close to the primary amine group, which becomes ammonium ion. The nitromethyl anion can attack the silanol-activated carbonyl carbon of benzaldehyde more easily if the amine and silanols are close to each other as in AP-E1 compared to in AAP-E1. A similar ion-pair catalytic mechanism was also proposed recently by Katz et al. in *J. Am. Chem. Soc.* 2006, 128, 3737-3747.

Further analysis of the relationships between the ratio of [Si—OH]:[Si—R] and the efficiency of the catalysts also revealed another interesting discovery. From the data in Table 12, it was clear that sample AP-E1 with a [Si—OH]:[Si—Pr—NH$_2$] ratio of 5:1 gave more efficient catalysis compared to samples AP-T1 and AP-T2 whose [Si—OH]:[Si—Pr—NH$_2$] was 1:1. Similarly, AAP-E1 with [Si—OH]:[Si—Pr—NH$_2$] of 6:1 is a much better catalyst than AAP-T1, which has a [Si—OH]/[Si—Pr—NH$_2$] of about 2:1. These results indicated that a significantly higher number of silanols with respect to organoamine groups would be needed to result in effective cooperative catalysis and to leave the materials with higher surface areas. From the applicants' studies, the materials with a [Si—OH]:[Si—Pr—NH$_2$] ratio close to ~5:1, which consists of 5 silanols for every organoamine group, have resulted in the highest efficiency known to us. Interestingly, a [Si—OH]:[Si—Pr—NH$_2$] ratio of 1:1, as in AP-T2, does not give an ideal cooperative effect. The applicants believe that this is possibly due to the lower surface area as well as the steric hindrance caused by the densely populated, longer organoamines around surface silanols in AP-T2, which inhibit the activation of benzaldehyde carbonyl groups by silanols for the Henry reaction.

The cooperative effects by the organoamine and silanol groups and the increased catalytic efficiency occurred better in samples grafted in ethanol. These samples contained less organoamines, more silanols and high surface areas. On the other hand, more densely populated organoamine, less silanols and less surface areas occurred when the grafting was done in toluene. In ethanol, which is a polar solvent, the aminorganosilanes form hydrogen bonding with the solvent. This reduces their grafting tendency onto the surface silanol groups of the mesoporous materials, whereas in non-polar solvents such as toluene, the hydrophilic aminorganosilanes have a strong tendency to go to and graft onto the hydrophilic mesoporous silica surfaces. The various dielectric constants used in the analysis are provided in Table 13.

TABLE 13

Dielectric constants and boiling points of the solvents used in various catalyst syntheses.

| Solvent | Chemical formula | Dielectric constant | Boiling point |
|---|---|---|---|
| Ethanol | $CH_3CH_2OH$ | 24 | 78° C. |
| Toluene | $C_6H_5CH_3$ | 2.4 | 111° C. |

Moreover, aminorganosilanes tend to aggregate through hydrogen bonding in toluene and result in densely populated, aggregated organoamines. The formation of organoamine clustering and grafting of organoamines as aggregates on the surface inhibit cooperative effects by organoamines and silanols. Furthermore, a significant reverse reaction between grafted organoamine groups and ethanol could take place in ethanol, which reduces the number of organoamine grafted in ethanol.

In order to further prove the effects of the solvents in grafting of different concentrations of organoamine groups and the cooperative effects by the organoamine and residual silanol groups to catalyze the Henry reaction, additional experiments involving grafting of additional organosilanes in ethanol and toluene onto AP-E1 were carried out as shown in FIG. 38. The AP-E1 sample was chosen because it contained a significant number of silanol groups and its catalytic efficiency was the highest. First, 3-aminopropyltrimethoxysilane (APTS) was grafted onto AP-E1 in ethanol and toluene to result in AP-EE1 and AP-ET1, respectively. This grafting procedure decreased the number of silanol groups in the materials but increased the organoamine groups.

Figure 43B:
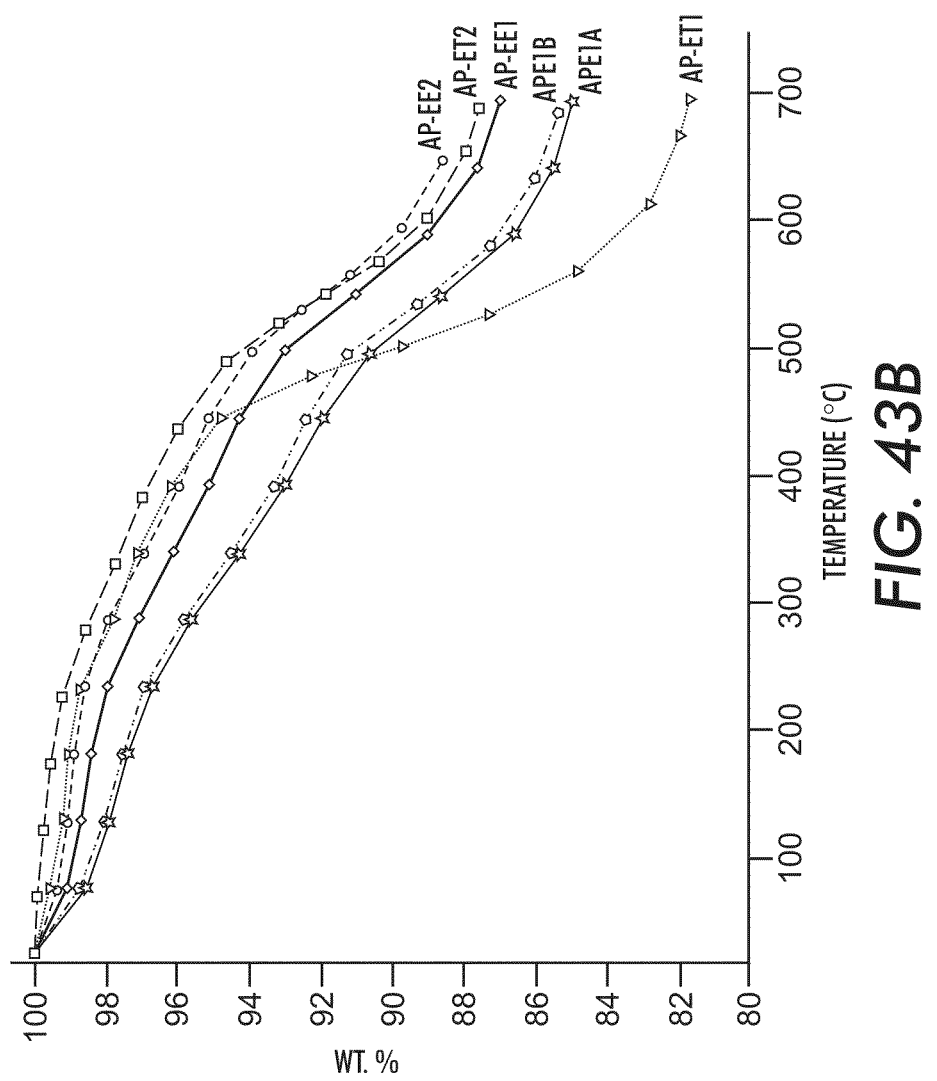
Figure 46A:
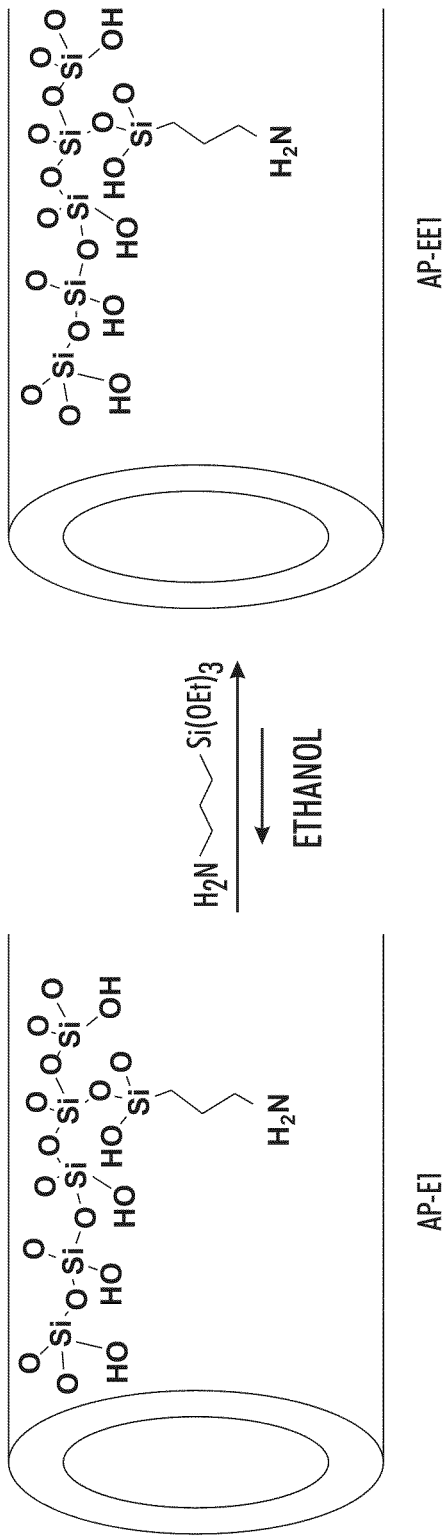
FIGS. 46A and 46B are a schematic illustrations of the grafting functionalization of one organoamine functionalized catalyst sample of the invention with additional organosilanes in ethanol and toluene, respectively.

Secondly, a 3-cyanopropyltriethoxysilane in ethanol and toluene was also grafted onto AP-E1 to result in AP-EE2 and AP-ET2. This procedure could only decrease the residual silanol groups and it did not increase the organoamine concentration in the samples. Furthermore, the 3-cyanopropyl groups do not significantly change the hydrophilicity of the materials to catalyze the Henry reaction in nitromethane. These grafting of additional 3-aminopropyl and 3-cyanopropyl groups in the AP-E1 was determined by TGA analysis. For instance, the TGA analysis indicated weight losses in the range of 100-600° C. for sample AP-EE1 and AP-ET1 to be 10.8 and 16.0%, respectively, whereas those for AP-EE2 and AP-ET2 were, 10.1 and 10.6, respectively, as shown in FIG. 43B. Compared with weight loss for AP-E1 (10.7%), these results revealed that additional grafting organic groups on AP-E1 barely occurred in ethanol, while some grafting did take place in toluene, as shown schematically in FIGS. 46A and 46B. Further analysis by XRD for these materials indicated that their well-ordered mesoporous structures remained intact.

Figure 46B:
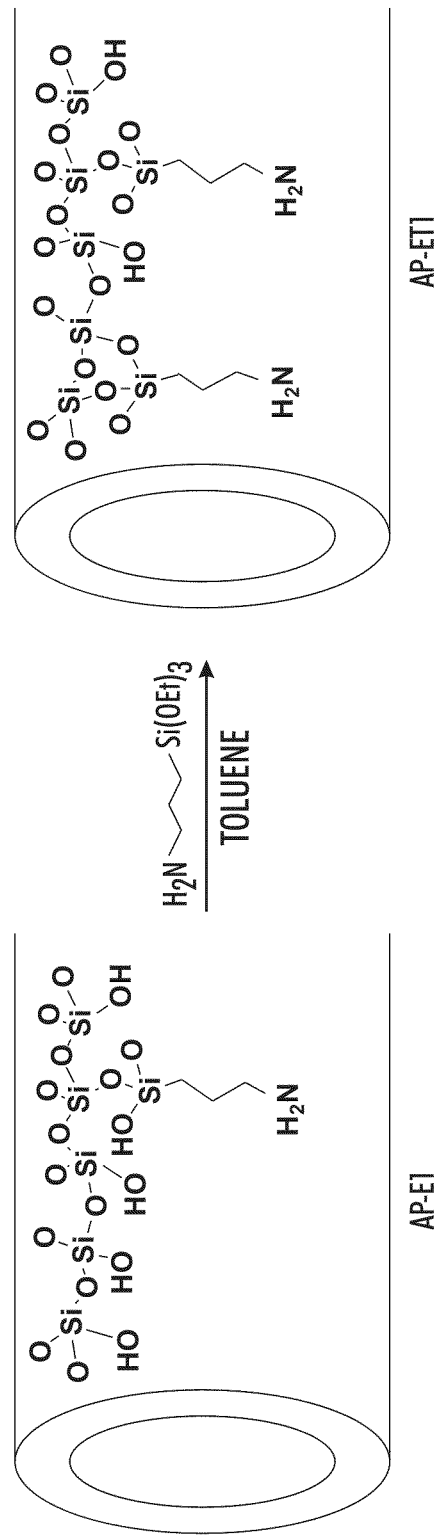

Comparative investigations of the efficiency of these samples in catalysis revealed the importance of the silanol groups and ethanol as a solvent for grafting again. While AP-EE1 and AP-EE2 showed only little reduction in their catalytic efficiency and surface areas, samples AP-ET1 and AP-ET2 showed significant reduction in their catalytic efficiencies and surface areas, as shown in FIG. 46B and Table 12. Furthermore, sample AP-ET2, which contained 3-cyanopropyl groups at the expense of silanols, showed even significantly lower efficiency compared to AP-ET1, which contained a corresponding number of 3-aminopropyl at the expense of the silanols.

The applicants believe that the reduction of the catalytic efficiency in AP-ET1 and AP-ET2 is due to significant decrease in their silanol groups compared to the AP-EE1 and AP-EE2, and an indication of the importance of silanol groups and high surface areas for enhanced catalytic efficiency. The slightly higher catalytic efficiency of AP-EE1 compared to AP-EE2 was due to the additional organic groups in the former being catalytically active 3-organoamine sites, while the additional organic groups in the latter being inactive 3-cyanopropyl groups. Consequently, there would be more chances of cooperative interaction by organoamines and silanols in AP-EE1 than in AP-EE2 (also in AP-ET1 than AP-ET2). These results further corroborated the importance of less number of organoamines, more silanols, higher surface areas and the involvement of silanols and organoamines in the materials to cooperatively catalyze the Henry reaction as a bifunctional catalyst.

In order to understand the cooperative effects by the bifunctional groups, it is also worth comparing the number of catalytic sites with other materials in the literature. to the best of the applicants' knowledge, our catalysts AP-E1 and AAP-E1 have shown the highest efficiency for the Henry reaction compared to any mesoporous material reported either by grafting or co-assembly methods. The most efficient catalyst previously reported by Diamicheli et al. in *Tetrahedron Lett.* 2001, 42, 2401-2403 involved grafting of excess organosilanes in toluene onto calcined mesoporous silica, and it had about 1.36 mmol-$NH_2$/g, which is a comparable value to our most efficient catalyst, AP-E1.

The number of Si—OH groups in the Diamicheli catalyst was not reported. Since the grafting was done on a calcined MCM-41 and in toluene under reflux, we believe that the number of Si—OH must be presumably much lower than our AP-E1 sample. On the other hand, organoamine functionalized samples synthesized by Lin et al. in *J. Am. Chem. Soc.* 2004, 126, 1010-1011 via co-assembly method contained triamine groups. We believe that the co-assembly synthesis would result in large number of silanol groups and consequently significant cooperative effect; however, these issues have been overlooked previously by Lin et al. Despite the possible presence of such cooperative effects in the materials reported by them, their catalysts still have much lower efficiency compared to the applicants' acid-base bifunctional catalysts. The applicants believe that this may be due to their relatively inferior mesostructures, as can be inferred from their XRD patterns as well as possible weak cooperative interaction due to the longer separation distance between the silanols and the primary amines of these triamine-functionalized materials.

Figure 47:
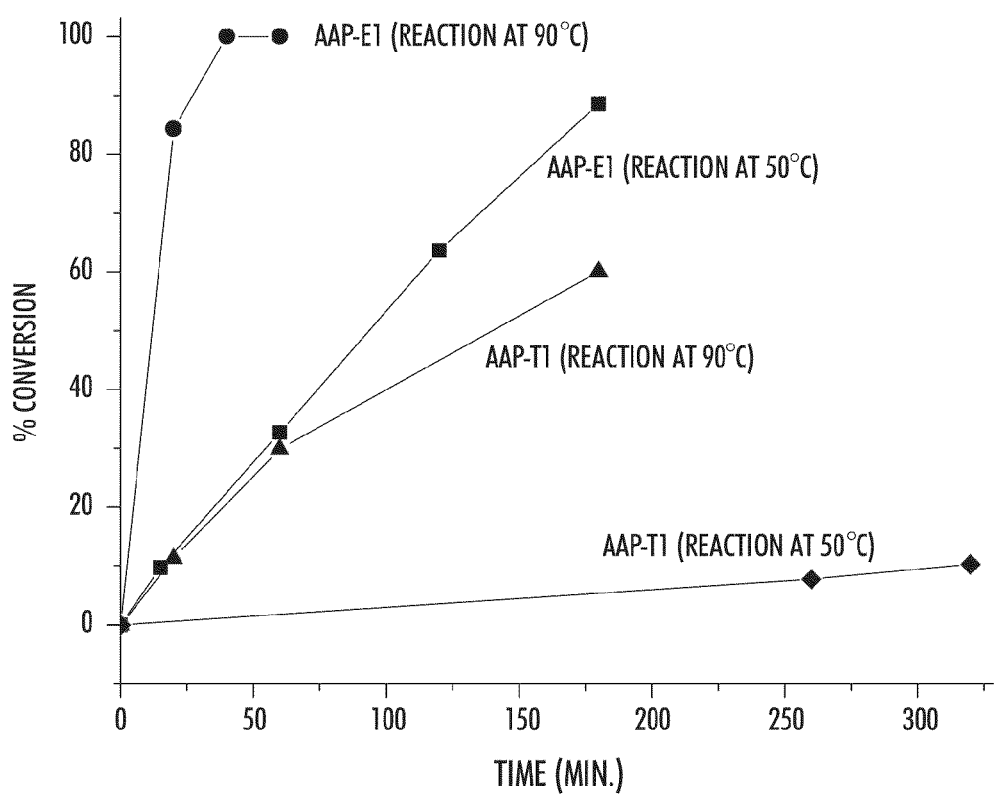
FIG. 47 is a temperature dependent catalysis time plot of certain organodiamine-functionalized mesoporous catalyst materials of the invention.

In the Henry reaction catalyzed by these acid-base bifunctional catalysts, an appropriate solvent such as nitromethane and a higher temperature were also found to increase the catalytic efficiency, as indicated in Table 12. Additionally, FIG. 47 is a temperature dependent catalysis time plot of the organodiamine-functionalized mesoporous materials AAP-E1 at 90° C., AAP-T1 at 90° C., AAP-E1 at 50° C., and AAP-T1 at 50° C. By way of example, it can be seen that the reaction performed at 50° C. resulted in three times less yield in the same reaction time compared to the reaction performed at 90° C. To the best of the applicants' knowledge, this is the first time detailed temperature and time plot studies for Henry reaction catalyzed by organoamine-functionalized mesoporous materials have been studied. This study allows the rational design and synthesis of optimized cooperative and efficient recyclable catalysts. For instance, studies of recyclability of our acid-base bifunctional catalyst, AP-E1 have indicated an efficiency of about 100, 98.2, 97.5, and 97.4% in 15 min reaction time.

In summary, the applicants have discovered certain effects of site-isolation, concentrations and separation distances of functional groups in bifunctional acid-base catalysts on the cooperative catalytic properties and efficiencies of the materials in base-catalyzed Henry reaction. This was achieved by comparative studies of a series of organoamine functionalized samples containing various concentrations of organomonoamine (or organodiamine) and silanol groups synthesized by simple grafting of organomonosilane onto mesoporous silica using ethanol and toluene as solvents. The organoamine-functionalized materials synthesized in ethanol have resulted site-isolated organoamine groups or less number of organoamine groups and large numbers of residual silanol groups (organoamine:silanol ratio of 1:4-5). The resulting 3-aminopropyl and 3-aminoethyl(3-aminopropyl) functionalized samples cooperatively catalyzed the Henry reaction between p-hydroxybenzaldehyde and nitromethane to completion within ~15 and 20 min and with a TON value of 37.5 and 7.6, respectively, in 15 min reaction time.

To the best of the applicants' knowledge, the catalytic efficiencies of these materials have been the highest ever to be reported with at least 3-6 times more turnover numbers than the corresponding control samples synthesized in toluene. Control catalytic experiments by MCM-41 sample, which contain no organoamines resulted in no Henry reaction. Further grafting of organosilanes onto the residual silanol groups of the ethanol product resulted in little additional organic groups when the grafting was done in ethanol again but a significant increase of organic groups in toluene.

Figure 48:
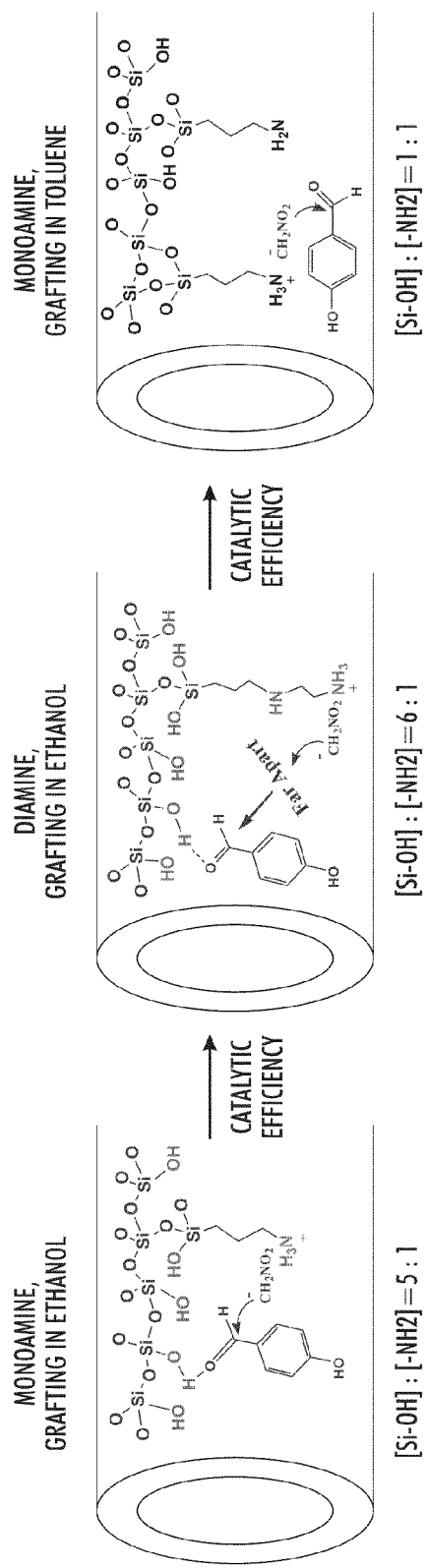
FIG. 48 is a schematic representation of the relative efficiencies in catalysis of the Henry reaction by the applicants' monoamine and diamine functionalized mesoporous catalyst samples grafted in ethanol and toluene.

FIG. 48 is a schematic representation of the relative efficiencies in catalysis of the Henry reaction by the applicants' monoamine and diamine functionalized mesoporous catalyst samples grafted in ethanol and toluene. From our studies, we have determined that a ratio of silanol:organoamine of 5:1 results in the highest acid-base cooperative effect and the highest catalytic efficiency in Henry reaction. Furthermore, this cooperative effect by the organoamine and the silanol groups and the efficiency of the catalysts was found to increase when the distances between the two functional groups is shorter. The catalysts were also found to be highly recyclable with only a very slight decrease in the efficiency of the materials after four cycles. To the best of our knowledge, this is the first time that ethanol has been used for grafting organoamines (and organosilanes) on the surfaces of mesoporous silica materials. Our detailed time plot studies for Henry reaction by mesoporous materials have also been disclosed herein.

This simple synthetic approach is expected to allow the synthesis of other efficient bifunctional materials and nanoporous solid catalysts via a low temperature (78° C.) facile synthesis in a more environmentally friendly solvent, ethanol, as compared to the traditionally and more commonly used toluene solvent at 110° C. This synthetic approach can be adapted to the synthesis of highly efficient catalysts with optimized cooperative and synergistic properties and that are suitable for a number of industrial applications.

It is, therefore, apparent that there has been provided, in accordance with the present invention, multifunctional mesoporous catalyst compositions and methods of preparation therefor. While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. A method of making a catalyst, the method comprising:
   a) providing a solid particulate silicate MCM-41 mesoporous substrate having surface silanol groups that define available sites for postgrafting with catalytic functional groups;
   b) stirring a weight of the solid particulate silicate MCM-41 mesoporous substrate in ethanol in a first vessel;
   c) heating the weight of the solid particulate silicate MCM-41 mesoporous substrate in ethanol in the first vessel to a reflux temperature of 78° C. and adding a weight of 3-aminopropylsilane with stirring;
   d) maintaining the first vessel at the reflux temperature of 78° C. for a refluxing duration to cause postgrafting of 3-aminopropyl groups onto a portion of the available sites of the solid particulate silicate MCM-41 mesoporous substrate to form first solid particulate catalyst in the ethanol, the postgrafted 3-aminopropyl groups replacing between 6 and 15 percent of the surface silanol groups defining the available sites, and the remainder of surface silanol groups remaining as available sites.

2. The method of claim 1, further comprising filtering the first solid particulate catalyst from the ethanol, and recovering first solid particulate catalyst precipitate.

3. The method of claim 2, further comprising washing the first solid particulate catalyst precipitate with a solvent, and drying the first solid particulate catalyst precipitate to produce a first dry particulate catalyst.

4. The method of claim 2, further comprising:
   a) mixing a weight of the first solid particulate catalyst precipitate with a weight of ureidopropyltriethoxysilane into isopropanol in a second vessel;
   b) stirring the first solid particulate catalyst precipitate and the ureidopropyltriethoxysilane in the second vessel at a temperature of 80° C. for a duration to cause postgrafting of ureidopropyl groups onto a portion of the remainder of surface silanol groups remaining as available sites on the first solid particulate catalyst to form second solid particulate catalyst in the isopropanol.

5. The method of claim 2, further comprising:
   a) mixing a weight of the first solid particulate catalyst precipitate with a weight of 3-mercaptopropyltriethoxysilane into isopropanol in a second vessel;
   b) stirring the first solid particulate catalyst precipitate and the 3-mercaptopropyltriethoxysilane in the second vessel at a temperature of 80° C. for a duration to cause postgrafting of 3-mercaptopropyl groups onto a portion of the remainder of surface silanol groups remaining as available sites on the first solid particulate catalyst to form second solid particulate catalyst in the isopropanol.

6. The method of claim 2, further comprising:
   a) mixing a weight of the first solid particulate catalyst precipitate with a weight of methyltrimethoxysilane into isopropanol in a second vessel;
   b) stirring the first solid particulate catalyst precipitate and the methyltrimethoxysilane in the second vessel at a temperature of 80° C. for a duration to cause postgrafting of methyl groups onto a portion of the remainder of surface silanol groups remaining as available sites on the first solid particulate catalyst to form second solid particulate catalyst in the isopropanol.

7. The method of claim 2, further comprising:
a) mixing a weight of the first solid particulate catalyst precipitate with a weight of 3-cyanopropyltriethoxysilane into ethanol in a second vessel;
b) stirring the first solid particulate catalyst precipitate and the 3-cyanopropyltriethoxysilane in the second vessel at a temperature of 78° C. for a duration to cause postgrafting of 3-cyanopropyl groups onto a portion of the remainder of surface silanol groups remaining as available sites on the first solid particulate catalyst to form second solid particulate catalyst in the ethanol.

* * * * *